US010344305B2

(12) United States Patent
Franklin et al.

(10) Patent No.: US 10,344,305 B2
(45) Date of Patent: Jul. 9, 2019

(54) MICROBIAL OILS WITH LOWERED POUR POINTS, DIELECTRIC FLUIDS PRODUCED THEREFROM, AND RELATED METHODS

(71) Applicant: Corbion Biotech, Inc., South San Francisco, CA (US)

(72) Inventors: Scott Franklin, Woodside, CA (US); Walter Rakitsky, San Diego, CA (US); George Rudenko, Mountain View, CA (US); Xinhua Zhao, Dublin, CA (US); Felipe Arana Rodriguez, San Mateo, CA (US); Wenhua Lu, Pacifica, CA (US); Janice Wee, San Mateo, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 16/186,316

(22) Filed: Nov. 9, 2018

(65) Prior Publication Data

US 2019/0136273 A1 May 9, 2019

Related U.S. Application Data

(60) Division of application No. 15/179,253, filed on Jun. 10, 2016, now Pat. No. 10,167,489, which is a continuation of application No. 14/730,671, filed on Jun. 4, 2015, now Pat. No. 9,388,435, which is a continuation of application No. 13/288,815, filed on Nov. 3, 2011, now Pat. No. 9,066,527.

(60) Provisional application No. 61/546,932, filed on Oct. 13, 2011, provisional application No. 61/522,231, filed on Aug. 10, 2011, provisional application No. 61/438,966, filed on Feb. 2, 2011, provisional application No. 61/409,902, filed on Nov. 3, 2010.

(51) Int. Cl.

| C12N 1/20 | (2006.01) |
|---|---|
| C12P 7/64 | (2006.01) |
| A23D 9/007 | (2006.01) |
| C11B 3/00 | (2006.01) |
| C10M 169/04 | (2006.01) |
| H01F 27/32 | (2006.01) |
| C12N 15/79 | (2006.01) |
| C12N 9/42 | (2006.01) |
| A23D 9/02 | (2006.01) |
| H01B 3/20 | (2006.01) |
| C11B 3/14 | (2006.01) |
| C11B 3/10 | (2006.01) |
| C11B 3/06 | (2006.01) |
| C11B 1/10 | (2006.01) |
| C11B 1/06 | (2006.01) |
| C11B 1/02 | (2006.01) |
| H01F 27/10 | (2006.01) |

(52) U.S. Cl.
CPC ............ *C12P 7/6463* (2013.01); *A23D 9/007* (2013.01); *A23D 9/02* (2013.01); *C10M 169/041* (2013.01); *C11B 1/025* (2013.01); *C11B 1/06* (2013.01); *C11B 1/10* (2013.01); *C11B 3/001* (2013.01); *C11B 3/006* (2013.01); *C11B 3/008* (2013.01); *C11B 3/06* (2013.01); *C11B 3/10* (2013.01); *C11B 3/14* (2013.01); *C12N 9/2442* (2013.01); *C12N 15/79* (2013.01); *C12P 7/6409* (2013.01); *C12Y 301/02014* (2013.01); *H01B 3/20* (2013.01); *H01F 27/321* (2013.01); *H01F 27/105* (2013.01)

(58) Field of Classification Search
CPC ............................... C12N 15/52; C12P 7/6463
USPC ....................................................... 435/257.2
See application file for complete search history.

(56) References Cited

U.S. PATENT DOCUMENTS

| 2,235,056 A | 3/1941 | Walmesley |
|---|---|---|
| 2,383,602 A | 8/1945 | Gerald et al. |
| 2,967,700 A | 1/1961 | Lee et al. |
| 3,142,135 A | 7/1964 | Kathrein |
| 3,280,502 A | 10/1966 | Farrow et al. |
| 3,320,693 A | 5/1967 | Shirota et al. |
| 3,475,274 A | 10/1969 | Harned |
| 3,957,578 A | 5/1976 | Narita et al. |
| 3,962,466 A | 6/1976 | Nakabayashi |
| 3,983,008 A | 9/1976 | Shinozaki et al. |
| 4,005,062 A | 1/1977 | Schnell |

(Continued)

FOREIGN PATENT DOCUMENTS

| AU | 2011323288 B2 | 9/2016 |
|---|---|---|
| CN | 1251108 A | 4/2000 |

(Continued)

OTHER PUBLICATIONS

"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].

(Continued)

*Primary Examiner* — Tekchand Saidha
(74) *Attorney, Agent, or Firm* — Weaver Austin Villeneuve & Sampson LLP

(57) ABSTRACT

Methods and compositions for the production of dielectric fluids from lipids produced by microorganisms are provided, including oil-bearing microorganisms and methods of low cost cultivation of such microorganisms. Microalgal cells containing exogenous genes encoding, for example, a sucrose transporter, a sucrose invertase, a fructokinase, a polysaccharide-degrading enzyme, a lipid pathway modification enzyme, a fatty acyl-ACP thioesterase, a desaturase, a fatty acyl-CoA/aldehyde reductase, and/or an acyl carrier protein are useful in manufacturing dielectric fluids.

7 Claims, 3 Drawing Sheets

Specification includes a Sequence Listing.

(56) References Cited

U.S. PATENT DOCUMENTS

| | | |
|---|---|---|
| 4,103,039 A | 7/1978 | Mandai et al. |
| 4,182,777 A | 1/1980 | Saunders |
| 4,273,790 A | 6/1981 | Bosco et al. |
| 4,341,038 A | 7/1982 | Bloch et al. |
| 4,373,434 A | 2/1983 | Alexander et al. |
| 4,390,561 A | 6/1983 | Blair et al. |
| 4,519,845 A | 5/1985 | Ou |
| 4,627,192 A | 12/1986 | Fick |
| 4,673,490 A | 6/1987 | Subramanian et al. |
| 4,755,467 A | 7/1988 | Scopes et al. |
| 4,901,635 A | 2/1990 | Williams |
| 4,992,605 A | 2/1991 | Craig et al. |
| 5,001,059 A | 3/1991 | Skatrud et al. |
| 5,091,116 A | 2/1992 | Krishnamurthy et al. |
| 5,130,242 A | 7/1992 | Barclay |
| 5,212,087 A | 5/1993 | Fournier et al. |
| 5,252,198 A | 10/1993 | Harrison et al. |
| 5,270,175 A | 12/1993 | Moll et al. |
| 5,270,177 A | 12/1993 | Ramos Lazcano et al. |
| 5,304,481 A | 4/1994 | Davies et al. |
| 5,330,913 A | 7/1994 | Nakayama |
| 5,338,673 A | 8/1994 | Thepenier et al. |
| 5,354,878 A | 10/1994 | Connemann et al. |
| 5,360,730 A | 11/1994 | Orndorff et al. |
| 5,391,724 A | 2/1995 | Kindl et al. |
| 5,395,455 A | 3/1995 | Scott et al. |
| 5,436,394 A | 7/1995 | Willmitzer et al. |
| 5,455,167 A | 10/1995 | Voelker et al. |
| 5,460,870 A | 10/1995 | Arthurs |
| 5,492,938 A | 2/1996 | Kyle et al. |
| 5,518,918 A | 5/1996 | Barclay |
| 5,547,699 A | 8/1996 | Lizuka et al. |
| 5,563,058 A | 10/1996 | Davies et al. |
| 5,595,965 A | 1/1997 | Wiggins |
| 5,597,400 A | 1/1997 | Nonomura et al. |
| 5,680,812 A | 10/1997 | Linsgeseder |
| 5,685,218 A | 11/1997 | Kemper |
| 5,693,507 A | 12/1997 | Daniell et al. |
| 5,711,983 A | 1/1998 | Kyle et al. |
| 5,723,761 A | 3/1998 | Voelker et al. |
| 5,756,135 A | 5/1998 | Seeley |
| 5,826,500 A | 10/1998 | Kemper |
| 5,888,947 A | 3/1999 | Lambert et al. |
| 5,900,370 A | 5/1999 | Running |
| 5,910,630 A | 6/1999 | Davies et al. |
| 5,945,585 A | 8/1999 | Hitz et al. |
| 5,968,791 A | 10/1999 | Davis et al. |
| 6,139,897 A | 10/2000 | Goto et al. |
| 6,166,231 A | 12/2000 | Hoeksema |
| 6,255,505 B1 | 7/2001 | Bijl et al. |
| 6,338,866 B1 | 1/2002 | Criggall et al. |
| 6,344,231 B1 | 2/2002 | Nakajo et al. |
| 6,355,861 B1 | 3/2002 | Thomas |
| 6,372,460 B1 | 4/2002 | Gladue et al. |
| 6,410,281 B1 | 6/2002 | Barclay |
| 6,441,208 B2 | 8/2002 | Bijl et al. |
| 6,534,261 B1 | 3/2003 | Cox, III et al. |
| 6,620,427 B2 | 9/2003 | Lasekan et al. |
| 6,680,426 B2 | 1/2004 | Daniell et al. |
| 6,727,373 B2 | 4/2004 | Bijl et al. |
| 6,750,048 B2 | 6/2004 | Ruecker et al. |
| 6,762,345 B1 | 7/2004 | Cahoon et al. |
| 6,763,345 B1 | 7/2004 | Hempleman et al. |
| 6,867,308 B2 | 3/2005 | Bartok et al. |
| 7,053,267 B2 | 5/2006 | Knauf et al. |
| 7,063,957 B2 | 6/2006 | Chen |
| 7,081,567 B2 | 7/2006 | Xue et al. |
| 7,109,392 B1 | 9/2006 | Broglie et al. |
| 7,135,620 B2 | 11/2006 | Daniell et al. |
| 7,214,297 B2 | 5/2007 | Wang et al. |
| 7,268,276 B2 | 9/2007 | Ruezinsky et al. |
| 7,309,602 B2 | 12/2007 | David |
| 7,351,558 B2 | 4/2008 | Ruecker et al. |
| 7,468,267 B2 | 12/2008 | Monod et al. |
| 7,504,259 B2 | 3/2009 | Yadav et al. |
| 7,588,931 B2 | 9/2009 | Damude et al. |
| 7,622,570 B2 | 11/2009 | Oswald et al. |
| 7,652,156 B2 | 1/2010 | Hillion et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 7,851,199 B2 | 12/2010 | Bailey et al. |
| 7,879,591 B2 | 2/2011 | Damude et al. |
| 7,883,822 B2 | 2/2011 | Burgess et al. |
| 7,883,882 B2 | 2/2011 | Franklin et al. |
| 7,914,832 B2 | 3/2011 | Uchino |
| 7,935,515 B2 | 5/2011 | Franklin et al. |
| 7,939,710 B1 | 5/2011 | Apt et al. |
| 8,003,365 B2 | 8/2011 | Yoshikuni et al. |
| 8,029,579 B2 | 10/2011 | Knuth et al. |
| 8,043,496 B1 | 10/2011 | Schuh et al. |
| 8,088,718 B2 | 1/2012 | Bicerano et al. |
| 8,119,583 B2 | 2/2012 | Day et al. |
| 8,163,675 B2 | 4/2012 | Navarrete et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,278,261 B2 | 10/2012 | Day et al. |
| 8,283,483 B2 | 10/2012 | Williams et al. |
| 8,435,767 B2 | 5/2013 | Franklin et al. |
| 8,450,083 B2 | 5/2013 | Day et al. |
| 8,476,059 B2 | 7/2013 | Trimbur et al. |
| 8,497,116 B2 | 7/2013 | Trimbur et al. |
| 8,512,999 B2 | 8/2013 | Trimbur et al. |
| 8,518,689 B2 | 8/2013 | Trimbur et al. |
| 8,530,207 B2 | 9/2013 | Watts et al. |
| 8,592,188 B2 | 11/2013 | Franklin et al. |
| 8,633,012 B2 | 1/2014 | Franklin et al. |
| 8,647,397 B2 | 2/2014 | Trimbur et al. |
| 8,674,180 B2 | 3/2014 | Franklin et al. |
| 8,697,402 B2 | 4/2014 | Trimbur et al. |
| 8,697,427 B2 | 4/2014 | Franklin et al. |
| 8,765,424 B2 | 7/2014 | Franklin et al. |
| 8,772,575 B2 | 7/2014 | Franklin et al. |
| 8,790,914 B2 | 7/2014 | Trimbur et al. |
| 8,802,422 B2 | 8/2014 | Trimbur et al. |
| 8,822,176 B2 | 9/2014 | Day et al. |
| 8,822,177 B2 | 9/2014 | Day et al. |
| 8,846,352 B2 | 9/2014 | Chua et al. |
| 8,846,375 B2 | 9/2014 | Franklin et al. |
| 8,852,885 B2 | 10/2014 | Franklin et al. |
| 8,889,401 B2 | 11/2014 | Trimbur et al. |
| 8,889,402 B2 | 11/2014 | Trimbur et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,102,973 B2 | 8/2015 | Franklin et al. |
| 9,109,239 B2 | 8/2015 | Franklin et al. |
| 9,068,213 B2 | 9/2015 | Franklin et al. |
| 9,200,307 B2 | 12/2015 | Franklin et al. |
| 9,249,252 B2 | 2/2016 | Ngantung et al. |
| 9,249,436 B2 | 2/2016 | Franklin et al. |
| 9,249,441 B2 | 2/2016 | Franklin et al. |
| 9,255,282 B2 | 2/2016 | Franklin et al. |
| 9,279,136 B2 | 3/2016 | Franklin et al. |
| 9,353,389 B2 | 5/2016 | Franklin et al. |
| 9,388,435 B2 | 7/2016 | Franklin et al. |
| 9,434,909 B2 | 9/2016 | Trimbur et al. |
| 9,464,304 B2 | 10/2016 | Franklin et al. |
| 9,551,017 B2 | 1/2017 | Franklin et al. |
| 9,593,351 B2 | 3/2017 | Franklin et al. |
| 9,657,299 B2 | 5/2017 | Franklin et al. |
| 9,719,114 B2 | 8/2017 | Franklin et al. |
| 9,909,155 B2 | 3/2018 | Franklin et al. |
| 9,969,990 B2 | 5/2018 | Davis et al. |
| 10,006,034 B2 | 6/2018 | Franklin et al. |
| 10,053,715 B2 | 8/2018 | Franklin et al. |
| 10,167,489 B2 | 1/2019 | Franklin et al. |
| 2002/0012979 A1 | 1/2002 | Berry |
| 2002/0059661 A1 | 5/2002 | Dehesh |
| 2002/0122868 A1 | 9/2002 | Floeter et al. |
| 2002/0144455 A1 | 10/2002 | Bertrand et al. |
| 2002/0178467 A1 | 11/2002 | Dehesh |

(56) References Cited

U.S. PATENT DOCUMENTS

| | | |
|---|---|---|
| 2003/0054524 A1 | 3/2003 | Spener et al. |
| 2003/0079249 A1 | 4/2003 | Shanklin et al. |
| 2003/0082595 A1 | 5/2003 | Jiang et al. |
| 2003/0097686 A1 | 5/2003 | Knauf et al. |
| 2003/0145350 A1 | 7/2003 | Spener et al. |
| 2003/0211594 A1 | 11/2003 | Rosebrook |
| 2003/0229237 A1 | 12/2003 | Haas et al. |
| 2004/0033557 A1 | 2/2004 | Scott et al. |
| 2004/0053235 A1 | 3/2004 | Smirnoff et al. |
| 2004/0074760 A1 | 4/2004 | Portnoff et al. |
| 2004/0230085 A1 | 11/2004 | Jakkula et al. |
| 2004/0235123 A1 | 11/2004 | Liao et al. |
| 2005/0005333 A1 | 1/2005 | Ruezinsky et al. |
| 2005/0102716 A1 | 5/2005 | Venkatramesh et al. |
| 2005/0112735 A1 | 5/2005 | Zappi et al. |
| 2005/0153002 A1 | 7/2005 | Socia Rosales et al. |
| 2005/0170479 A1 | 8/2005 | Weaver et al. |
| 2005/0262588 A1 | 11/2005 | Dehesh et al. |
| 2005/0266537 A1 | 12/2005 | Chen |
| 2005/0272611 A1 | 12/2005 | Lord et al. |
| 2006/0048240 A1 | 3/2006 | Alexandrov et al. |
| 2006/0075522 A1 | 4/2006 | Cleveland et al. |
| 2006/0094088 A1 | 5/2006 | Picataggio et al. |
| 2006/0094089 A1 | 5/2006 | Barclay |
| 2006/0094090 A1 | 5/2006 | Damude et al. |
| 2006/0107346 A1 | 5/2006 | Schneeberger et al. |
| 2006/0122410 A1 | 6/2006 | Fichtali et al. |
| 2006/0130182 A1 | 6/2006 | Heim et al. |
| 2006/0153826 A1 | 7/2006 | Arnould et al. |
| 2006/0156436 A1 | 7/2006 | Nakamura et al. |
| 2006/0162006 A9 | 7/2006 | Sherman et al. |
| 2006/0199984 A1 | 9/2006 | Kuechler et al. |
| 2006/0225341 A1 | 10/2006 | Rohr et al. |
| 2006/0286205 A1 | 12/2006 | Fichtali et al. |
| 2007/0004016 A1 | 1/2007 | Picataggio et al. |
| 2007/0009988 A1 | 1/2007 | Monod et al. |
| 2007/0048848 A1 | 3/2007 | Sears |
| 2007/0099280 A1 | 5/2007 | Barclay |
| 2007/0118916 A1 | 5/2007 | Puzio et al. |
| 2007/0167396 A1 | 7/2007 | Dillon et al. |
| 2007/0218183 A1 | 9/2007 | Nakhasi et al. |
| 2007/0248531 A1 | 10/2007 | Debryun et al. |
| 2007/0254354 A1 | 11/2007 | Millis et al. |
| 2007/0261138 A1 | 11/2007 | Graham et al. |
| 2007/0275438 A1 | 11/2007 | David |
| 2008/0014620 A1 | 1/2008 | Op Den Camp et al. |
| 2008/0038804 A1 | 2/2008 | Du et al. |
| 2008/0040822 A1 | 2/2008 | Metz et al. |
| 2008/0107776 A1 | 5/2008 | Prakash et al. |
| 2008/0160593 A1 | 7/2008 | Oyler |
| 2008/0194029 A1 | 8/2008 | Hegemann et al. |
| 2008/0206379 A1 | 8/2008 | Fabritius et al. |
| 2008/0229451 A1 | 9/2008 | Cao et al. |
| 2008/0256666 A1 | 10/2008 | Zhu et al. |
| 2008/0283803 A1 | 11/2008 | Rapp et al. |
| 2009/0004715 A1 | 1/2009 | Trimbur et al. |
| 2009/0011480 A1 | 1/2009 | Trimbur et al. |
| 2009/0018300 A1 | 1/2009 | Bloom et al. |
| 2009/0035842 A1 | 2/2009 | Trimbur et al. |
| 2009/0047721 A1 | 2/2009 | Trimbur et al. |
| 2009/0061493 A1 | 3/2009 | Trimbur et al. |
| 2009/0064567 A1 | 3/2009 | Lippmeier et al. |
| 2009/0099260 A1 | 4/2009 | Namal Senanayake et al. |
| 2009/0117253 A1 | 5/2009 | Hong et al. |
| 2009/0142322 A1 | 6/2009 | Ye |
| 2009/0145392 A1 | 6/2009 | Clark et al. |
| 2009/0148918 A1 | 6/2009 | Trimbur et al. |
| 2009/0176272 A1 | 7/2009 | Champagne et al. |
| 2009/0211150 A1 | 8/2009 | Wu et al. |
| 2009/0234146 A1 | 9/2009 | Cooney et al. |
| 2009/0271892 A1 | 10/2009 | Thomasset et al. |
| 2009/0274736 A1 | 11/2009 | Dillon et al. |
| 2009/0298143 A1 | 12/2009 | Roessler et al. |
| 2009/0298159 A1 | 12/2009 | Wu et al. |
| 2009/0305942 A1 | 12/2009 | Day et al. |
| 2009/0317878 A1 | 12/2009 | Champagne et al. |
| 2010/0010088 A1 | 1/2010 | Chilton et al. |
| 2010/0021912 A1 | 1/2010 | Farese et al. |
| 2010/0035320 A1 | 2/2010 | Blanchard et al. |
| 2010/0058651 A1 | 3/2010 | Knuth et al. |
| 2010/0093031 A1 | 4/2010 | Kobayashi et al. |
| 2010/0105955 A1 | 4/2010 | Alibhai et al. |
| 2010/0120643 A1 | 5/2010 | Brown et al. |
| 2010/0137647 A1 | 6/2010 | Bradin |
| 2010/0151112 A1 | 6/2010 | Franklin et al. |
| 2010/0151535 A1 | 6/2010 | Franklin et al. |
| 2010/0151538 A1 | 6/2010 | Franklin et al. |
| 2010/0151539 A1 | 6/2010 | Franklin et al. |
| 2010/0151567 A1 | 6/2010 | Franklin et al. |
| 2010/0154293 A1 | 6/2010 | Hom et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0228068 A1 | 9/2010 | O'Connor et al. |
| 2010/0237279 A1 | 9/2010 | Hulse et al. |
| 2010/0239712 A1 | 9/2010 | Brooks et al. |
| 2010/0248322 A1 | 9/2010 | Pfeiffer et al. |
| 2010/0249260 A1 | 9/2010 | Casati et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0035309 A1 | 12/2010 | Havemen et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0047863 A1 | 3/2011 | Trimbur et al. |
| 2011/0065821 A1 | 3/2011 | Abraham et al. |
| 2011/0072714 A1 | 3/2011 | Gaertner et al. |
| 2011/0111470 A1 | 5/2011 | Berry et al. |
| 2011/0165634 A1 | 7/2011 | Franklin et al. |
| 2011/0190522 A1 | 8/2011 | Trimbur et al. |
| 2011/0203168 A1 | 8/2011 | Franklin et al. |
| 2011/0250658 A1 | 10/2011 | Franklin et al. |
| 2011/0252696 A1 | 10/2011 | Franklin et al. |
| 2011/0256268 A1 | 10/2011 | Franklin et al. |
| 2011/0256282 A1 | 10/2011 | Piechocki et al. |
| 2011/0270001 A1 | 11/2011 | Ishihara et al. |
| 2011/0284215 A1 | 11/2011 | Pfeiffer et al. |
| 2011/0293785 A1 | 12/2011 | Franklin et al. |
| 2011/0294174 A1 | 12/2011 | Franklin et al. |
| 2012/0009636 A1 | 1/2012 | Berry et al. |
| 2012/0021495 A1 | 1/2012 | Vanzin |
| 2012/0028319 A1 | 2/2012 | Trimbur et al. |
| 2012/0034662 A1 | 2/2012 | Hu et al. |
| 2012/0060242 A1 | 3/2012 | Senger et al. |
| 2012/0119862 A1 | 5/2012 | Franklin et al. |
| 2012/0122192 A1 | 5/2012 | Trimbur et al. |
| 2012/0128851 A1 | 5/2012 | Brooks et al. |
| 2012/0156717 A1 | 6/2012 | Allnutt et al. |
| 2012/0164701 A1 | 6/2012 | Trimbur et al. |
| 2012/0203018 A1 | 8/2012 | Franklin et al. |
| 2012/0277452 A1 | 11/2012 | Franklin et al. |
| 2012/0277453 A1 | 11/2012 | Franklin et al. |
| 2012/0283460 A1 | 11/2012 | Franklin et al. |
| 2012/0288930 A1 | 11/2012 | Trimbur et al. |
| 2012/0324784 A1 | 12/2012 | Franklin et al. |
| 2012/0329109 A1 | 12/2012 | Chua et al. |
| 2013/0004646 A1 | 1/2013 | Franklin et al. |
| 2013/0006006 A1 | 1/2013 | Day et al. |
| 2013/0031678 A1 | 1/2013 | Zheng et al. |
| 2013/0034887 A1 | 2/2013 | Franklin et al. |
| 2013/0078709 A1 | 3/2013 | Franklin et al. |
| 2013/0089916 A1 | 4/2013 | Franklin et al. |
| 2013/0096211 A1 | 4/2013 | Franklin et al. |
| 2013/0102039 A1 | 4/2013 | Franklin et al. |
| 2013/0116462 A1 | 5/2013 | Durrett et al. |

(56) References Cited

U.S. PATENT DOCUMENTS

| | | |
|---|---|---|
| 2013/0122180 A1 | 5/2013 | Brooks et al. |
| 2013/0157917 A1 | 6/2013 | Fluck |
| 2013/0165677 A1 | 6/2013 | Franklin et al. |
| 2013/0197247 A1 | 8/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0316410 A1 | 11/2013 | Franklin et al. |
| 2013/0317240 A1 | 11/2013 | Franklin et al. |
| 2013/0323382 A1 | 12/2013 | Franklin et al. |
| 2013/0323823 A1 | 12/2013 | Franklin et al. |
| 2013/0330790 A1 | 12/2013 | Trimbur et al. |
| 2013/0331584 A1 | 12/2013 | Franklin et al. |
| 2013/0338385 A1 | 12/2013 | Franklin et al. |
| 2014/0170716 A1 | 6/2014 | Trimbur et al. |
| 2014/0249342 A1 | 9/2014 | Franklin et al. |
| 2014/0256024 A1 | 9/2014 | Franklin et al. |
| 2014/0256600 A1 | 9/2014 | Dillon et al. |
| 2014/0305031 A1 | 10/2014 | Day et al. |
| 2014/0315267 A1 | 10/2014 | Franklin et al. |
| 2014/0336100 A1 | 11/2014 | Day et al. |
| 2014/0357746 A1 | 12/2014 | Ngantung et al. |
| 2014/0377847 A1 | 12/2014 | Franklin et al. |
| 2015/0073163 A1 | 3/2015 | Chua et al. |
| 2015/0125914 A1 | 5/2015 | Franklin et al. |
| 2015/0218604 A1 | 8/2015 | Franklin et al. |
| 2015/0275149 A1 | 10/2015 | Dummer et al. |
| 2015/0344917 A1 | 12/2015 | Franklin et al. |
| 2016/0010066 A1 | 1/2016 | Davis et al. |
| 2016/0024538 A1 | 1/2016 | Franklin et al. |
| 2016/0032332 A1 | 2/2016 | Davis et al. |
| 2016/0186191 A1 | 6/2016 | Franklin et al. |
| 2016/0186219 A1 | 6/2016 | Franklin et al. |
| 2016/0194672 A1 | 7/2016 | Franklin et al. |
| 2016/0237448 A1 | 8/2016 | Cahoon et al. |
| 2016/0348119 A1 | 12/2016 | Franklin et al. |
| 2016/0376617 A1 | 12/2016 | Franklin et al. |
| 2017/0022436 A1 | 1/2017 | Trimbur et al. |
| 2017/0145450 A1 | 5/2017 | Franklin et al. |
| 2017/0314048 A1 | 11/2017 | Franklin et al. |
| 2018/0142218 A1 | 5/2018 | Moseley et al. |
| 2018/0216144 A1 | 8/2018 | Rakitsky |
| 2018/0237811 A1 | 8/2018 | Franklin et al. |

FOREIGN PATENT DOCUMENTS

| | | |
|---|---|---|
| CN | 1852986 A | 10/2006 |
| CN | 101037639 A | 9/2007 |
| CN | 101092353 A | 12/2007 |
| CN | 101108997 A | 1/2008 |
| CN | 101130513 A | 2/2008 |
| CN | 101611125 A | 12/2009 |
| CN | 101765661 A | 6/2010 |
| CN | 101824440 A | 9/2010 |
| DE | 2756977 A1 | 6/1978 |
| EP | 0 562 504 B1 | 11/1995 |
| EP | 1 178 118 A1 | 2/2002 |
| EP | 1 642 959 A1 | 4/2006 |
| EP | 1 681 337 A1 | 7/2006 |
| EP | 1 741 767 A1 | 1/2007 |
| EP | 1947189 A2 | 7/2008 |
| EP | 2 327 776 A1 | 6/2011 |
| EP | 2152849 B1 | 2/2013 |
| EP | 2 370 555 B1 | 4/2016 |
| FR | 2924126 A1 | 5/2009 |
| GB | 824151 | 11/1959 |
| JP | 57-150379 | 9/1982 |
| JP | 60006799 A | 1/1985 |
| JP | 06-253872 A | 9/1994 |
| JP | 07-008217 | 1/1995 |
| JP | 07-075557 | 3/1995 |
| JP | H09-511650 A | 11/1997 |
| JP | H10-46181 A | 2/1998 |
| JP | 2000-136199 | 5/2000 |
| JP | 2000-175696 A | 6/2000 |
| JP | 2002-125601 | 5/2002 |
| JP | 2002-161294 | 6/2002 |
| JP | 2002-523864 A | 7/2002 |
| JP | 2003-102467 A | 4/2003 |
| JP | 2003-325067 A | 11/2003 |
| JP | 2004-500839 | 1/2004 |
| JP | 2007-314549 A | 12/2007 |
| JP | 2008-081559 | 4/2008 |
| JP | 2008-514221 | 5/2008 |
| JP | 2008-148663 | 7/2008 |
| JP | 2008-178871 | 8/2008 |
| JP | 2010-514446 | 5/2010 |
| JP | 2010-528627 | 8/2010 |
| JP | 2015-500009 A | 1/2015 |
| JP | 6071904 | 2/2017 |
| KR | 10-2007-00085649 A | 8/2007 |
| KR | 10-2010-0022473 | 3/2010 |
| WO | WO 91/018105 A1 | 11/1991 |
| WO | WO 92/011373 A1 | 7/1992 |
| WO | WO 93/006712 A1 | 4/1993 |
| WO | WO 94/010288 A1 | 5/1994 |
| WO | WO 95/13390 A2 | 5/1995 |
| WO | WO 95/031553 A1 | 11/1995 |
| WO | WO 97/040698 A1 | 11/1997 |
| WO | WO 98/032770 A1 | 7/1998 |
| WO | WO 99/037166 A1 | 7/1999 |
| WO | WO 99/64618 A1 | 11/1999 |
| WO | WO 00/011682 A1 | 3/2000 |
| WO | WO 00/061740 A1 | 10/2000 |
| WO | WO 00/066750 A2 | 11/2000 |
| WO | WO 00/74471 A1 | 12/2000 |
| WO | WO 02/008403 A2 | 1/2002 |
| WO | WO 02/085293 A2 | 10/2002 |
| WO | WO 04/101753 A2 | 11/2004 |
| WO | WO 05/003310 A2 | 1/2005 |
| WO | WO 2005/035693 A2 | 4/2005 |
| WO | WO 06/055322 A2 | 5/2006 |
| WO | WO 2006/052807 A2 | 5/2006 |
| WO | WO 2006/122299 A2 | 11/2006 |
| WO | WO 2007/027669 A1 | 3/2007 |
| WO | WO 07/38566 A2 | 4/2007 |
| WO | WO 07/106903 A2 | 9/2007 |
| WO | WO 07/117511 A2 | 10/2007 |
| WO | WO 07/121100 A2 | 10/2007 |
| WO | WO 07/134294 A2 | 11/2007 |
| WO | WO 2007/141257 A2 | 12/2007 |
| WO | WO 08/002643 A2 | 1/2008 |
| WO | WO 2008/011811 A1 | 1/2008 |
| WO | WO 08/060571 A2 | 5/2008 |
| WO | WO 2008/058664 A1 | 5/2008 |
| WO | WO 08/083352 A1 | 7/2008 |
| WO | WO 08/130372 A2 | 10/2008 |
| WO | WO 2008/134836 A2 | 11/2008 |
| WO | WO 08/151149 A2 | 12/2008 |
| WO | WO 2008/150461 A2 | 12/2008 |
| WO | WO 09/076559 A1 | 6/2009 |
| WO | WO 09/105620 A1 | 8/2009 |
| WO | WO 09/126843 A2 | 10/2009 |
| WO | WO 2009/124070 A1 | 10/2009 |
| WO | WO 10/019813 A2 | 2/2010 |
| WO | WO 2010/017346 A2 | 2/2010 |
| WO | WO 10/045368 A2 | 4/2010 |
| WO | WO 2010/037209 A1 | 4/2010 |
| WO | WO 10/063031 A2 | 6/2010 |
| WO | WO 10/063032 A2 | 6/2010 |
| WO | WO 10/111698 A2 | 9/2010 |
| WO | WO 10/120923 A1 | 10/2010 |
| WO | WO 10/120939 A2 | 10/2010 |
| WO | WO 11/026008 A1 | 3/2011 |
| WO | WO 11/096891 A1 | 6/2011 |
| WO | WO 2011/075716 A1 | 6/2011 |
| WO | WO 11/090730 A1 | 7/2011 |
| WO | WO 11/130573 A1 | 10/2011 |
| WO | WO 11/130576 A1 | 10/2011 |
| WO | WO 11/130578 A2 | 10/2011 |
| WO | WO 11/150410 A2 | 12/2011 |
| WO | WO 11/150411 A1 | 12/2011 |
| WO | WO 12/061647 A2 | 5/2012 |
| WO | WO 12/106560 A1 | 8/2012 |

(56) References Cited

FOREIGN PATENT DOCUMENTS

| WO | WO 12/154626 A1 | 11/2012 |
|---|---|---|
| WO | WO 13/082186 A2 | 6/2013 |
| WO | WO 13/096891 | 6/2013 |
| WO | WO 13/158938 | 10/2013 |
| WO | WO 14/176515 A2 | 10/2014 |
| WO | WO 15/051319 A2 | 4/2015 |
| WO | WO 2016/007862 A2 | 1/2016 |
| WO | WO 2016/164495 A1 | 10/2016 |
| WO | WO 2017/058802 A1 | 4/2017 |

OTHER PUBLICATIONS

"Codex Standard for Named Vegetable Oils," Codex Alimentarius, Codex Stan 210-1999, pp. 1-16, (1999).
"Enzymatic Assay of Invertase (EC 3.2.1.26)," Sigma-Aldrich Co. LLC., (1999). [Retrieved from the Internet Aug. 21, 2012: < http://www.sigmaaldrich.com/etc/medialib/docs/Sigma/General_Information/invertase_temp_25.Par.0001.File.tmp/invertase_temp_25.pdf>] (Author is not Available).
Aggelis et al., "Enhancement of single cell oil production by Yarrowia lipolytica growing in the presence of Teucrium polium L. aqueous extract," Biotechnology Letters, 21:747-749, (1999).
Aguirre et al., "Engineering challenges in biodiesel production from microalgae," Critical Reviews in Biotechnology, 33(3): 293-308, (2013).
Alberto et al., "Crystal structure of inactivated Thermotoga maritima invertase in complex with the trisaccharide substrate raffinose," Biochem. J., 395:457-462 (2006).
Altschul et al., "Basic local alignment search tool," J Mol Biol, 215(3):403-410, (1990).
Amaro et al., "Advances and perspectives in using microalgae to produce biodiesel," Applied Energy, 88:3402-3410, (2011).
Andersen, "Biology and Systematics of Heterokont and Haptophyte Algae," American Journal of Botany, 91(10):1508-1522, (2004).
Appel et al., "A multicopy vector system for genetic studies in Mucor circinelloides and other zygomycetes," Molecular Genetics and Genomics, 271(5):595-602, (2004).
Apt et al., "Stable nuclear transformation of the diatom Phaeodactylum tricornutum," Mol Gen Genet, 252(5):572-579, (1996).
Barnes et al., "Contribution of 5'- and 3'-untranslated regions of plastid mRNAs to the expression of Chlamydomonas reinhardtii chloroplast genes," Mol Genet Genomics, 274(6):625-636, (2005).
Beale et al., "Chlorophyll Synthesis in Chlorella: Regulation by Degree of Light Limitation of Growth," Plant Physiol., 47:230-235, (1971).
Bergh et al., "Expression of the *Saccharomyces cerevisiae* glycoprotein invertase in mouse fibroblasts: Glycosylation, secretion, and enzymatic activity," Proc. Natl. Acad. Sci. USA, 84:3570-3574, (1987).
Bhunia et al., "Algal Biodiesel Production: Challenges and Opportunities," Bioenergy and Biofuel from Biowastes and Biomass, American Society of Civil Engineers, pp. 313-345, (2010).
Bigogno et al., "Biosynthesis of arachidonic acid in the oleaginous microalga *Parietochloris incisa* (Cholorphyceae): Radiolabeling studies," Lipids 37(2):209-216 (2002); Abstract Only.
Bigogno et al., "Lipid and fatty acid composition of the green oleaginous alga *Parietochloris incisa*, the richest plant source of arachidonic acid," Pytochemistry, 60:497-503, (2002).
Blowers et al., "Studies on Chlamydomonas chloroplast transformation: foreign DNA can be stably maintained in the chromosome," Plant Cell, 1(1):123-132, (1989).
Bonaventure et al., "Disruption of the FATB Gene in *Arabidopsis dethonstrates* an Essential Role of Saturated Fatty Acudes in Plant Growth," The Plant Cell 15:1020-1033, (2003).
Bordes et al., "A new recombinant protein expression system for high-throughput screening in the yeast *Yarrowia lipolytica*," Journal of Microbiological Methods, 70(3):493-502, (2007).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).

Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga *Prototheca wickerhamii*," Eukaryotic Cell, 4(2):253-261, (2005).
Boutry et al., "Targeting of bacterial chloramphenicol acetyltransferase to mitochondria in ransgenic plants," Nature, 328(6128):340-2, (1987).
Boynton et al., "Chloroplast Transformation in Chlamydomonas with High Velocity Microprojectiles," Science, 240(4858):1534-1538, (1988).
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Canam, "An Investigation of the Physiological Roles and Enzymatic Properties of Invertases in Tobacco and Hybrid Poplar," Thomas Benjamin Canam, 165 pages, (2008).
Carlson et al., "The Secreted Form of Invertase in *Saccharomyces cerevisiae* Is Synthesized from mRNA Encoding a Signal Sequence," Molecular and Cellular Biology,3(3):439-447, (1983).
Cartens et al,. "Eicosapentaenoic Acid (20:5n-3) from the Marine Microalga *Phaeodactylum ricornutum*," Journal of the American Oil Chemists' Society, 73(8):1025-1031, (1996).
Chasan, "Engineering Fatty Acids—The Long and Short of It," Plant Cell, 7:235-237, (1995).
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Effect of C/N ratio and aeration on the fatty acid composition of heterotrophic Chlorella sorokiniana," Journal of Applied Phycology, 3:203-209, (1991).
Chen et al., "High cell density culture of microalgae in heterotrophic growth," Trends in Biotechnology, 14:421-426, (1996).
Chen et al., "Highly Effective Exresion of Rabbit Neutrophil Peptide-1 Gene in Chlorella Ellipsoidea Cells," Current Genetics 39:365-370, (2001).
Cheng et al., "Sugars modulate an unusual mode of control of the cell-wall invertase gene (Incw1) through its 3' untranslated region in a cell suspension culture of maize," Proc. Natl. Acad. Sci. USA, 96:10512-10517, (1999 ).
Chica et al., "Semi-rational approaches to engineering enzyme activity: combining the benefits of directed evolution and rationa; design ," Current Opinion in Biotechnology, 16:378-384, (2005).
Cho et al., "Molecular cloning and expression analysis of the cell-wall invertase gene family in rice (*Oryza sativa* L.)," Plant Cell Rep , 24:225-236 , (2005).
Chow et al., "Electrotranformation of Chlorella Vulgaris," Plant Cell Reports, 18:778-780, (1999).
Ciferri, "Thiamine-deficiency of *Prototheca*, a Yeast-like Achloric Alga," Nature, 178:1475-1476, (1956).
Co et al., "Matching the Functionality of Single-Cell Algal Oils with Different Molecular Compositions," J Am Oil Chem Soc, doi: 10.1007/s11746-013-2405-y, 16 pages, (2014).
Cobley et al., "CpeR is an activator required for expression of the phycoerythrin operon (cpeBA) in the cyanobacterium *Fremyella diplosiphon* and is encoded in the phycoerythrin linker-polypeptide operon (cpeCDESTR)," Molecular Microbiology, 44(6):1517-153.

(56) References Cited

OTHER PUBLICATIONS

Cobley et al., Construction of Shuttle Plasmids Which Can Be Efficiently Mobilized From *Escherichia coli* Into the Chromatically Adapting Cyanobacterium, Plasmid, 30:90-105, (1993).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Coles et al., "Synthetic Mimicking of Plant Oils and Comparison with Naturally Grown Products in Polyurethane Synthesis," Macromol. Biosci., 8:526-532, (2008).
Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemis.
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-2):31-41, (2009).
Da Silva et al., "Effect of n-dodecane on Crypthecodinium cohnii fermentations and DHA production," J Ind Microbiol Biotechnol, DOI 10.1007/s10295-006-0081-8, 9 pages, (2006).
Davies et al., "Expression of the Arylsulfatase Gene from the Beta 2-Tubulin Promoter in Chlamydomonas reinhardtii," Nucleic Acids Research, 20(12):2959-2965, (1992).
Dawson et al., "Stable Transformation of Chlorella: Rescue of Nitrate Reductase-Deficient Mutants with the Nitrate Reductase Gene," Current Microbiology, 35:356-362, (1997).
Day, AL. et al., "Safety evaluation of a high-lipid algal biomass from Chlorella protorhecoides," Rego!. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
De Coninck et al., "*Arabidopsis* AtcwINV3 and 6 are not invertases but are fructan exohydrolases (FEHs) with different substrate specificities," Plant, Cell and Environment , 28,:432-443, (2005).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Dehesh et al., "KAS IV: a 3-ketoacyl-ACP synthase from *Cuphea* sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).
Deshnium et al., "Transformation of Synechococcus with a gene for choline oxidase enhances tolerance to salt stress," Plant Mol Biol, 29(5):897-907, (1995).
Devos et al., "Practical Limits of Function Prediction," Proteins: Structure, Function, and Genetics, 41:98-107, (2000).
Dimou et al., "Genes coding for a putative cell-wall invertase and two putative monosaccharide/H+ transporters are expressed in roots of etiolated Glycine max seedlings," Plant Science , 169:798-804, (2005).
Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, (1995).
Dugar et al., "Relative potential of biosynthetic pathways for biofuels and bio-based products," Nature Biotechnology, 29(12):1074-1078, (2011).
Dunahay et al., "Genetic Engineering of Microalgae for Fuel Production," Applied Biochemistry and Biotechnology, 34/35:331-339 (1992).

Dunahay et al., "Manipulation of Microalgal Lipid Production Using Genetic Engineering," Applied Biochemistry and Biotechnology, 57/58:223-231, (1996).
Eccleston et al., "Medium-chain Fatty Acid Biosynthesis and Utilization in Brassica Mapus Plants Expressing Lauroyl-Acyl Carrier Protein Thioesterase," Planta 198:46-53, (1996).
Ehneβ et al., "Co-ordinated induction of mRNAs for extracellular invertase and a glucose transporter in Chenopodium rubrum by cytokinins," The Plant Journal , 11(3):539-548, (1997).
El-Fadaly et al., "Single Cell Oil Production by an Oleaginous Yeast Strain in a Low Cost Cultivation Medium," Research Journal of Microbiology, 4(8):301-313, (2009).
El-Sheekh, MM., "Stable Transformation of the Intact Cells of Chlorella Kessleri With High Velocity Microprojectiles," Biologia Plantarium 42(2): 209-216, (1999).
EPO Supplementary European Search Report and European Search Opinion for application EP 12782478.7 dated Oct. 22, 2014.
EPO Supplementary European Search Report and European Search Opinion for application EP08769988.0 dated Jul. 1, 2011.
EPO Supplementary European Search Report and European Search Opinion for application EP11158642.6 dated Jul. 1, 2011.
EPO Supplementary European Search Report and European Search Opinion for application EP 09829850.8 dated May 16, 2014.
EPO Supplementary European Search Report and European Search Opinion for application EP09729658 dated Jan. 3, 2013.
Erhan, "Vegetable Oils as Lubricants, Hydraulic Fluids, and Inks," Baileys Industrial Oil and Fat Products, 6:259-278, (2005).
Evans et al., "A comparison of the oleaginous yeast, *Candida curvata*, grown on different carbon sources in continuous and batch culture," Lipids, 18(09):623-629, (1983).
Facciotti et al., "Improved stearate phenotype in transgenic canola expressing a modified acyl-acyl carrier protein thioesterase," Nat Biotechnol., 17(6):593-597, (1999).
Falciatore et al., "Transformation of Nonselectable Reporter Genes in Marine Diatoms," Marine Biotechnology; 1:239-251, (1999).
Fall et al., "Bioconversion of Xylan to Triglycerides by Oil-Rich Yeasts," Applied and Environmental Microbiology, 47(5):1130-1134, (1984).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Ferrentino, "Microalgal oil extraction and in situ transesterification," University of New Hampshire, Pub. No. MT 1447885, 8 pages, (2007).
Ferrentino, et al., "Microalgal Oil Extraction and In-situ Transesterification," AIChE Annual Mtg, San Francisco, CA, Nov. 11-13, 2006. Abstract.
Forster et al., "Citric acid production from sucrose using a recombinant strain of the yeast *Yarrowia lipolyticae*," Appl Microbiol Biotechnol, 75:1409-1417 , (2007).
Foyer et al., "Sucrose and Invertase, an Uneasy Alliance," Iger Innovations, pp. 18-21, (1997).
Franklin et al., "Prospects for molecular farming in the green alga *Chlamydomonas reinhardtii*," Current Opinion in Plant Biology, 7:159-165, (2004).
Franzen et al., "Chloroplast transit peptides from the green alga *Chlamydomonas reinhardtii* share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of Botryococcus braunii," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).

(56) References Cited

OTHER PUBLICATIONS

Gallagher et al., "Isolation and characterization of a cDNA clone from *Lolium temulentum* L. encoding for a sucrose hydrolytic enzyme which shows alkaline/neutral invertase activity," Journal of Experimental Bota, 49(322.):789-795, (1998).

Gascon et al., "Comparative Study of the Properties of the Purified Internal and External invertases from Yeast," The Journal of Biological Chemistry, 243(7):1573-1577, (1968).

GenBank: Accession No. AAC49001.1, May 1995. [Retrieved from the Internet Oct. 14, 2014: <URL: http://www.ncbi.nlrrtnih.gov/protein/595955?sat=13&satkey=6522409>].

Gill et al., "Lipid Accumulation in an Oleaginous Yeast (Candida 107) Growing on Glucose in Single-Stage Continuous Culture," Applied and Environmental Microbiology, 33(02):231-239, (1977).

Giuffrida et al., "Formation and hydrolysis of triacylglycerol and sterols epoxides: role of unsaturated triacylglycerol peroxyl radicals," Free Radical Biology and Medicine, 37(1):104-114, (2004).

Godt et al., "Regulation and Tissue-Specific Distribution of mRNAs for Three Extracellular Invertase Isoenzymes of Tomato Suggests an Important Function in Establishing and Maintaining Sink Metabolism," Plant Physiol, 115:273-282, (1997).

Goetz et al., "The different pH optima and substrate specificities of extracellular and vacuolar invertases from plants are determined by a single amino-acid substitution," The Plant Journal, 20(6):707-711, (1999)

Gouveia et al., "Microalgae in Novel Food Products," Food Chemistry Research Developments, Chapter 2, Nova Science Publishers, Inc., ISBN 978-1-60456-262-0, 37 pages, (2008).

Graves et al., "Hyaluronan synthesis in virus PBCV-1-infected chlorella-like green algae," Virology, 257(1):15-23, (1999).

Grima et al., "Recovery of microalgal biomass and metabolites: process options and economics," Biotechnology Advances, 20:491-515, (2003).

Grinna et al., "Size Distribution and General Structual Features of N-Linked Oligosaccharides from the Methylotrophic Yeast, *Pichia pastoris*," Yeast, 5:107-115, (1989).

Gruber et al., "*Escherichia coli*-Anacystis nidulans plasmid shuttle vectors containing the PL promoter from bacteriophage lambda," Current Microbiology, 22(1):15-19, (1991).

Guiry et al., "How Many Species of Algae are There?," J. Phycol., 48:1057-1063, (2012).

Gul et al., "Sterols and the Phytosterol Content in Oilseed Rape (*Brassica napus* L.)," Journal of Cell and Molecular Biology, 5:71-79 (2006).

Gunstone, "Enzymes as biocatalysts in the modification of natural lipids," Journal of the Science of Food and Agriculture, 79:1535-1549, (1999).

Guo-Zhong et al., "The Actin Gene Promoter-driven Bar as a Dominant Selectable Marker for Nuclear Transformation of Dunaliella Salina," Acta Genetica Sinica, 32(4): 424-433, (2005).

Guschina et al., "Lipids and lipid metabolism in eukaryotic algae," Progress in Lipid Research, 45:160-186, (2006).

Hajirezaeil et al., "Impact of elevated cytosolic and apoplastic invertase activity on carbon metabolism during potato tuber development," Journal of Experimental Botany, GMP Special Issue, 51:439-445, (2000).

Hall et al., "Expression of a foreign gene in Chlamydomonas reinhardtii," Gene, 124(1):75-81, (1993).

Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).

Hallmann et al., "Reporter Genes and Highly Regulated Promoters as Tools for Transformation Experiements in Volvox Carteri," Proc Natl Acad Sci U S A., 91(24):11562-11566, (1994).

Hanley-Bowdoin et al., "Chloroplast promoters," Trends in Biochemical Sciences, 12:67-70, (1987).

Hawkins et al., "Expression of Human Growth Hormone by the Eukaryotic Alga, Chlorella," Current Microbiology, 38:335-341, (1999).

Heifetz, "Genetic Engineering of the Chloroplast," Biochimie, 82:655-666, (2000).

Heise et al., "Factors Controlling Medium-Chain Fatty Acid Synthesis In Plastids From Cuphea Embryos," Prog. Lipid Res., 33(1/2):87-95, (1994).

Henderson et al., "Lipid Composition and Biosynthesis in the Marine Dinoflagellate Crypthecodznzum Cohnii," Phytochem. 27(6):1679-1683 (1988).

Henikoff et al., "Amino Acid Substitution Matrices from Protein Blocks," Proc Natl Acad of Sci, 89(22):10915-10919, (1992).

Heredia et al., "Simultaneous utilization of glucose and xylose by Candida curvata D in continuous culture," Biotechnology Letters, 10(01):25-30, (1988).

Heredia-Arroyo et al., "Oil Accumulation via Heterotrophic/Mixotrophic Chlorella protothecoides," Appl Biochem Biotechnol, 162:1978-1995, (2010).

Hillen et al., "Hydrocracking of the Oils of Botryococcus braunii to Transport Fuels," Biotechnology and Bioengineering, 24(1):193-205, (1982).

Hiramatsu et al., "Expression of a chitinase gene and lysis of the host cell wall during Chlorella virus CVK2 infection," Virology, 260(2):308-315, (1999).

Hitz et al., "Cloning of a Higher-Plant Plastid Omega-6 Fatty Acid Desaturase cDNA and Its Expression in a Cyanobacterium," Plant Physiology, 105(2):635-641, (1994).

Hong et al., "Engineering Yarrowia lipolytica to express secretory invertase with strong FBAIIN promoter," Yeast, 29:59-72, (2012). Published online Dec. 29, 2011 in Wiley Online Library (wileyonlinelibrary.com).

Hossain et al., "The effect of the sugar source on citric acid production by Aspergillus niger," Appl Microbiol Biotechnol , 19:393-397, (1984).

Hu et al., "Microalgal Triacylglycerols as Feedstocks for Biofuel Production: Perspectives and Advances," The Plant Journal 54:621-639, (2008).

Huang et al., "Expression of Mercuric Reductase From Bacillus Megaterium MB1 in Eukaryotic Microalga *Chlorella* sp. DT: An Approach for Mercury Phytoremediation," Appl. Microbiol. Biotechnol., 72:197-205, (2006).

Inoue et al., "Analysis of oil derived from liquefaction of Botryococcus Braunii," Biomass and Bioenergy, 6(4):269-274, (1994).

Isbell et al., "Acid-catalyzed condensation of oleic acid into estolides and polyestolides," Journal of the American Oil Chemists' Society, 71(2):169-174, (1994).

Isbell et al., "Synthesis of Triglyceride Estolides from Lesquerella and Castor Oils," JAOCS, vol. 79(12):1227-1233, (2002).

Iturriaga et al. "Heterologous transformation of Mucor circinelloides with the Phycomyces blakesleeanus leu1 gene," Current Genetics, 21(3):215-223, (1992).

Jakobiak et al., "The Bacterial Paromomycin Resistance Gene, aphH, as a Dominant Selectable Marker in Volvox carteri," Protist, 55: 381-393, (2004).

Jarvis et al. "Transient Expression of Firefly Luciferase in Protoplasts of the Green Alga *Chlorella ellipsoidea*," Current Genet., 19: 317-322, (1991).

Jaworski et al., "Industrial oils from transgenic plants," Current Opinion in Plant Biology, 6:178-184, (2003).

Jha et al., "Cloning and functional expression of an acyl-ACP thioesterase FatB type from Diploknema (Madhuca) butyracea seeds in *Escherichia coli*," Plant Physiology and Biochemistry, 44:645-655, (2006).

Ji et al., "The rice genome encodes two vacuolar invertases with fructan exohydrolase activity but lacks the related fructan biosynthesis genes of the Pooideae," New Phytologist, 173:50-62, (2007).

Jiang et al., "The actin gene promoter-driven bar as a dominant selectable marker for nuclear transformation of Dunaliella salina," Yi Chuan Xue Bao, 32(4):424-433, (2005).

Jones et al., "Palmitoyl-Acyl Carrier Protein (ACP) Thioesterase and the Evolutionary Origin of Plant Acyl-ACP Thioesterases," Plant Cell, 7:359-371, (1995).

Kalscheuer et al., "Establishment of a Gene Transfer System for Rhodococcus Opacus PD630 Based on Electroporation and its

(56) References Cited

OTHER PUBLICATIONS

Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of Chlorella," Plant Celll Physiol., 30(4):513-521, (1989).
Kang et al., "Genetic diversity in chlorella viruses flanking kcv, a gene that encodes a potassium ion channel protein," Virology, 326(1):150-159, (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kern et al., "Stability, quaternary structure, and folding of internal, external, and core-glycosylated invertase from yeast," Protein Sci., 1:120-131, (1992).
Kim et al. "Stable Integraion and Functional Expression of Flounder Growth Hormone Gene in Tranformed Microalga, *Chlorella ellipsoidea*," Mar. Biotechnol. 4:63-73 (2002).
Kimchi-Sarfaty et al., "A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Kong et al., "Microbial production of lipids by cofermentation of glucose and xylose with Lipomyces starkeyi 2#," Chinese Journal of Bioprocess Engineering, 05(02):36, (2007). Abstract.
Krebbers et al., "The maize chloroplast genes for the beta and epsilon subunits of the photosynthetic coupling factor CF1 are fused," Nucleic Acids Res, 10(16): 4985-5002, (1982).
Kris-Etherton et al., "Monounsaturated Fatty Acids and Risk of Cardiovascular Disease," Circulation, 100:1253-1258, (1999).
La Scala et al., "The effect of fatty acid composition on the acrylation kinetics of epoxidized riacylglycerols," Journal of the American Oil Chemists' Society, 79(1):59-63, (2002).
Lalonde et al., "The Dual Function of Sugar Carriers: Transport and Sugar Sensing," The Plant Cell 11:707-726, (1999).
Lammens et al., "Arabidopsis thaliana cell wall invertase in complex with ligands," HASYLAB, Annual Report 2006, Part II, Scientific User Contributions Part II, Protein Crystallography at EMBL Beamlines, pp. 61-62, (2006). [Retrieved from the Internet Aug. 21, 2012: <http://hasyweb.desy.de/science/annual_reports/2006_report/part2/contrib/72/17730.pdf>].
Lapidot et al., "Stable Chloroplast Transformation of the Unicellular Red Alga *Porphyridium* Species," Plant Physiol, 129:7-12, (2002).
Lara et al., "Extracellular Invertase Is an Essential Component of Cytokinin-Mediated Delay of Senescence," The Plant Cell, 16:1276-1287, (2004).
Larson et al., "Acyl CoA profilesoftransgenic plants that accumulate medium-chain fatty acids indicate inefficient storage lipid synthesis in developing oilseeds," The Plant Journal, 32(4):519-527, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).
Le Roy et al., "Unraveling the Difference between Invertases and Fructan Exohydrolases: A Single Amino Acid (Asp-239) Substitution Transforms *Arabidopsis* Cell Wall Invertasel into a Fructan 1-Exohydrolase," Plant Physiology, 145:616-625, (2007).
Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
Leon-Banares et al., "Transgenic microalgae as green cell-factories," Trends in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Li et al., "Broad-spectrum oil-producing yeast carbon filter," China Biotechnology, 25(12):39-44 (2005), and machine translation.
Li et al., "Crude Glycerin into Polyurethane Foam and Biopolyols," Ohio State University, Agriculture and Natural Resources Fact Sheet, 4 pages, (2011).
Li et al., "DNA variation at the invertase locus invGE/GF is associated with tuber quality traits in populations of potato breeding clones," Genetics, 40 pages, (2005). Published on Mar. 31, 2005 as 10.1534/genetics.104.040006.
Li et al., "High-density cultivation of oleaginous yeast *Rhodosporidium toruloides* Y4 in fed-batch culture," Enzyme and Microbial Technology, 41:312-317, (2007).
Lindley, "The impact of food processing antioxidants in vegetable oils, fruits, and vegetables," Trends in Food Science & Technology. 9:336-340, (1998).
Liras et al., "Biosynthesis and Secretion of Yeast Invertase Effect of Cycloheximide and 2-Deoxy-D-glucose," Eur. J. Biochem., 23:160-165, (1971).
List et al., "Melting properties of some structured lipids native to high stearic acid soybean oil," Grasas y Aceites, 55(Fasc. 2):135-137, (2004).
Lu, "Biosynthesis and Gene Engineering of Plant Fatty Acids," Chinese Bulletin of Botany, 17(6):481-491, (2000). Abstract only.
Lubitz, "The Protein Quality, Digestibility, and Composition of Algae, Chlorella 71105," J. Food Sci. 28(2):229-232 (1963).
Lumbreras et al., "Efficient Foreign Gene Expression in Chlamydomonas Reinhardtii Mediated by an Endogenous Intron," Plant Journal, 14(4):441-447, (1998).
Madzak et al., "Functional analysis of upstream regulating regions from Yarrowia lipolytica XPR2 promoter," Microbiology, 145:75-87, (1999).
Manuell et al., "Robust expression of a bioactive mammalian protein in Chlamydomonas chloroplast," Plant Biotech J, 5(3):402-412, (2007).
Maruyama et al., "Introduction of Foreign DNA Into Chlorella Saccharophila by Electroporation," Biotechnology Techniques, 8:821-826, (1994).
Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," The Journal of Biological Chemistry, 280(5):3621-3627, (2005).
Mayer et al., "Identification of amino acid residues involved in substrate specificity of plant acyl-ACP thioesterases using a bioinformatics-guided approach," BMC Plant Biology, 7(1):1-11, (2007).
Mayfield et al., "Expression and Assembly of a Fully Active Antibody in Algae," Proc Natl Acad Sci, 100(2):438-442, (2003).

(56) References Cited

OTHER PUBLICATIONS

Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meesters et al., "High-cell-density cultivation of the lipid accumulating yeast *Cryptococcus curvatus* using glycerol as a carbon source," Applied Microbiology and Biotechnology, 45:575-579, (1996).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide Extraction of Compounds With Pharmaceutical Importance from Microalgae," Inorganica Chimica Acta, 356:328-334, (2003).
Meng et al., "Biodiesel production from oleaginous microorganisms," Renewable Energy, 34:1-5, (2009).
Metzger et al., "Botryococcus braunii: A Rich Source for Hydrocarbons and Related Ether Lipids," Applied Microbiology and Biotechnology, 66(5):486-496, (2005).
Miao et al., "High Yield Bio-Oil Production from Fast Pyrolysis by Metabolic Controlling of Chlorella Protothecoides," J. Biotech., 110:85-93, (2004).
Minowa et al., "Oil Production from Algal Cells of Dunaliella tertiolecta by Direct Thermochemical Liquefaction," Fuel, 74(12):1735-1738, (1995).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
Mitsljhashi et al., "Differential Expression of Acid Invertase Genes during Seed Germination in *Arabidopsis thaliana*," Biosci. Biotechnol. Biochem, 68(3):602-608, (2004).
Moreno-Perez et al., "Reduced expression of FatA thioesterases in *Arabidopsis* affects the oil content and fatty acid composition of the seeds," Planta, 235:629-639, (2012).
Morris, "Effect of Growth Temperature on the Cryopreservation of Prototheca," Journal of General Microbiology, 94:395-399, (1976).
Mullet et al., "Multiple transcripts for higher plantrbcL andatpB genes and localization of the transcription initiation site of therbcL gene," Plant Molecular Biology, 4(1):39-54, (1985).
Murakami et al., "Lipid Composition of Commercial Bakers' Yeasts Having Different Freeze-tolerance in Frozen Dough," Biosci. Biotechnol. Biochem., 60(11)1874-1876, (1996).
Murakami et al., "Lipids and Fatty Acid Custipvsi lions of Chlorella," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Nahm, "Quality Characteristics of West African Shea Butter (*Vitellaria paradoxa*) and Approaches to Extend Shelf-Life," Master Thesis, Master of Science in Food Service, Rutgers, The State University of New Jersey, 133 pages, (2011).
Napier et al., "Tailoring plant lipid composition: designer oilseeds come of age," Current Opinion in Plant Biology, 13:330-337, (2010).
Nazaruddin et al., "The Effect of Enzymatic Alcoholysis on the Physicochemical Properties of Commercial Cocoa Butter Substitutes," Pakistan Journal of Nutrition, 10(8):718-723, (2011).
Needleman et al., "A general method applicable to the search for similarities in the amino acid sequence of two proteins," Journal of Molecular Biology, 48(3):443-453, (1970).
Neigeborn et al., "Genes Affecting the Regulation of Suc2 Gene Expression by Glucose Repression in *Saccharomyces cerevisiae*," Genetics, 108:845-858, (1984).
Neigeborn et al., "Mutations Causing Constitutive Invertase Synthesis in Yeast: Genetic Interactions with snf Mutations," Genetics, 115:247-253, (1987).
Nguyen-Quoc et al., "A role for 'futile cycles' involving invertase and sucrose synthase in sucrose metabolism of tomato fruit," Journal of Experimental Botany, 52(358):881-889, (2001).
Oda et al., "Degradation of Polylactide by Commercial Proteases," Journal of Polymers and the Environment, 8(1):29-32, (2000).
O'Mullan et al., "Purification and some properties of extracellular invertase B from Zymomonas rrtobiris," Appl Microbiol Biotechnol, 38:341-346, (1992).
Onai et al., "Natural Tranformation of the Termophillic Cyanbacterium Thermosynechococcus Elongatus BP-1: A Simple and Efficicent Method for Gene Transfer," Mol Genet Genomics, 271(1):50-9, (2004).
Pagny et al., "Fusion with HDEL Protects Cell Wall Invertase from Early Degradation when N-glycosylation is Inhinited," Plant Cell Physiol., 44(2):173-182 , (2003).
Papanikolaou et al., "Single cell oil production by Yarrowia lipolytica growing on and industrial derivative of animal fat in batch cultures," Appl. Microbiol. Biotechnol., 58:308-312, (2002).
Papanilolaou et al., "Lipid production by Yarrowia lipolytica growing on industrial glycerol in a single-stage continuous culture," Bioresource Technology, 82:43-49, (2002).
Papanikolaou et al., "Yarrowia lipolytica as a potential producer of citric acid from raw glycerol," Journal of Applied Microbiology , 92:737-744, (2002).
Park et al., "Isolation and Characterization of Chlorella Virus From Fresh Water in Korea and Application in Chlorella Transformation System," Plant Pathol. J., 21(1):13-20, (2005).
Patil et al., "Fatty acid composition of 12 microalgae for possible use in aquaculture feed," Aquacult Int , 15:1-9, (2007).
PCT International Preliminary Report on Patentability (Chapter I) dated May 31, 2011 for application PCT/US09/066142.
PCT International Preliminary Report on Patentability (Chapter I) dated Aug. 13, 2012 for application PCT/US11/38463.
PCT International Preliminary Report on Patentability (Chapter I) dated Dec. 7, 2009 for application PCT/US08/65563.
PCT International Preliminary Report on Patentability for application PCT/US2011/059224 dated May 16, 2013.
PCT International Search Report and Written Opinion of the International Searching Authority for Aapplication PCT/US2013/037261 dated Aug. 23, 2013.
PCT International Search Report and Written Opinion of the International Searching Authority for application PCT/US2014/035476 dated Feb. 18, 2015.
PCT International Search Reort and Written Opinion of the International Searching Authority for application PCT/US2014/059161 dated Jun. 1, 2015.
PCT International Search Reort and Written Opinion of the International Searching Authority for application PCT/US2015/023181 dated Jul. 28, 2015.
PCT International Search Report for application PCT/US2011/032582 dated Aug. 9, 2011.
PCT International Search Report for application PCT/US2011/038463 dated Jan. 18, 2012.
PCT International Search Report for application PCT/US2011/059224 dated Jun. 27, 2012.
PCT International Search Report for application PCT/US2012/023696 dated May 23, 2012.
PCT International Search Report for application PCT/US2012/036690 dated Aug. 30, 2012.
PCT International Search Report dated Aug. 20, 2010 for application PCT/US2009/066142.
PCT International Search Report dated Nov. 5, 2010 for application PCT/US2009/066141.
PCT International Search Report dated Nov. 6, 2008 for application PCT/US2008/065563.
PCT Invitation to Pay Additional Fees for application PCT/US2014/059161 dated Mar. 9, 2015.
PCT Invitation to Pay Additional Fees from the International Searching Authority for application PCT/US2014/035476 dated Dec. 1, 2014.
PCT Written Opinion of the International Search Authority dated Aug. 20, 2010 for application PCT/US2009/066142.

(56) References Cited

OTHER PUBLICATIONS

PCT Written Opinion of the International Searching Authority for application PCT/US2011/032582 dated Aug. 9, 2011.
PCT Written Opinion of the International Searching Authority for application PCT/US2011/038463 dated Jan. 18, 2012.
PCT Written Opinion of the International Searching Authority for application PCT/US2012/023696 dated May 23, 2012.
PCT Written Opinion of the International Searching Authority for application PCT/US2012/036690 dated Aug. 30, 2012.
PCT Written Opinion of the International Searching Authority dated Nov. 5, 2010 for application PCT/US2009/066141.
PCT Written Opinion of the International Searching Authority dated Nov. 6, 2008 for application PCT/US2008/065563.
Pearson et al., "Improved tools for biological sequence comparison," Proc Natl Acad Sci, 85(8):2444-2448, (1988).
Perlman et al., "Mutations affecting the signal sequence alter synthesis and secretion of yeast invertase," Proc. Natl. Acad. Sci. USA, 83:5033-5037, (1986).
Petkov et al., "Which are fatty acids of the green alga *Chlorella*?," Biochemical Systematics and Ecology, 35:281-285, (2007).
Phippen et al., "Total seed oil and fatty acid methyl ester contents of Cuphea accessions," Industrial Crops and Products, 24:52-59, (2006).
Pons et al., "Three Acidic Residues Are at the Active Site of a β-Propeller Architecture in Glycoside Hydrolase Families 32, 43, 62, and 68," Proteins: Structure, Function, and Bioinformatics , 54:424-432, (2004).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proels et al., "Novel mode of hormone induction of tandem tomato invertase genes in floral issues," Plant Molecular Bioingy , 52:191-201, (2003).
Proschold et al., "Portrait of a Species: *Chlamydomonas reinhardtii*," Genetics, 170(4):1601-1610, (2005).
Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (1993). Abstract.
Radakovits et al., "Genetic Engineering of Algae for Enhance Biofuel Production," Eukaryotic Cell, 9(4): 486-501, (2010).
Radmer et al., "Commercial applications of algae: opportunities and contraints," Journal of Applied Phycology, 6:93-98, (1984).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Reddy et al., "Characterization of the Glycosylation Sites in Yeast External Inver," The Journal of Biological Chemistry, 263(15):6978-6955, (1988).
Rehm et al., "Heterologous expression of the acyl-acyl carrier protein thioesterase gene from the plant *Umbellularia californica* mediates polyhydroxyalkanoate biosynthesis in recombinant *Escherichia coli*," Appl Microbiol Biotechnol, 55:205-209, (2001).
Riesmeier et al., "Potato Sucrose Transporter Expression in Minor Veins Indicates a Role in Phloem Loading," The Plant Cell, 5:1591-1598, (1993).
Rismani-Yazdi et al., "Transcriptome sequencing and annotation of the microalgae *Dunaliella tertiolecta*: Pathway description and gene discovery for production of next-generation biofuels," BMC Genomics, 12:148, 17 pages; doi:10.1186/1471-2164-12-148, (2011).
Ritsema et al., "Engineering fructan metabolism in plants," J. Plant Physiol., 160:811-820, (2003).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Roig et al., "Candida albicans UBI3 and 11814 promoter regions confer differential regulation of invertase production to *Saccharomyces cerevisiae* cells in response to stress," Int Microbiol, 5:33-36, (2002).
Roitsch et al., "Expression of yeast invertase in oocytes from Xenopus laevis," Eur. J. Biochem, 181:733-739, (1989).
Roitsch et al., "Extracellular invertase: key metabolic enzyme and PR protein," Journal of Experimental Botany, Regulation of Carbon Metabolism Special Issue, 54(382):513-524, (2003).
Roitsch et al., "Function and regulation of plant invertases: sweet sensations," Trends in Plant Science , .9(12):606-613 , (2004).
Roitsch et al., "Induction of Apoplastic Invertase of Chenopodium rubrum by ID-Glucose and a Glucose Analog and Tissue-Specific Expression Suggest a Role in Sink-Source Regulation," Plant Physiol., 108:285-294, (1995).
Rosenberg et al., "A Green Light for Engineered Algae: Redirecting Metabolism to Fuel a Biotechnology Revolution," Current Opinion in Biotechnology. Tissue, Cell and Pathway Engineering, E-Pub 19:430-436, (2008).
Roy et al., "Production of Intracellular Fat by the Yeast of *Lipomyces starkeyi*," Indian Journal of Experimental Biology, 16(4):511-512, (1978).
Ruiz et al., "Lipids accumulation in Chlorella protothecoides through mixotrophic and heterotrophic cultures for biodiesel production," New Biotechnology, 255:S266-S266, (2009).
Running et al., "Extracellular production of L-ascorbic acid by Chlorella protothecoides, Prototheca species, and mutants of P. moriformis during aerobic culturing at low pH," Journal of Industrial Microbiology & Biotechnology, 29:93-98, (2002).
Running et al., "The pathway of L-ascorbic acid biosynthesis in the colourless microalga *Prototheca moriformis*," Journal of Experimental Botany, 54(389):1841-1849, (2003).
Saha et al., "Transformation in Aspergillus ochraceus," Current Microbiology, 30(2):83-86, (1995).
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Scholnick et al., "Urethane Foams from Animal Fats. IV. Rigid Foams from Epoxidized Glycerides," Journal of the American Oil Chemists' Society, 45(2):76-77, (1968).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Schütt et al., "The role of acyl carrier protein isoforms from Cuphea lanceolata seeds in the de-novo biosynthesis of medium-chain fatty acids," Publication, Planta, 205:263-268, (1998).
Seffernick et al., "Melamine Deaminase and Atrazine Chlorohdrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).
Sergeeva et al., "Vacuolar invertase regulates elongation of *Arabidopsis thaliana* roots as revealed by QTL and mutant analysis," PNAS, 103(8):2994-2999, (2006).
Shao et al., "Cloning and exprssion of metalothionein mutant α-KKS-α in *Anabaena* sp. PCC 7120," Marine Pollution Bulletin, 45(1012):163-167, (2002).

(56) References Cited

OTHER PUBLICATIONS

Sherson et al., "Roles of cell-wall invertases and monosaccharide transporters in the growth and development of *Arabidopsis*," Journal of Experimental Botany, 54(382):525-531, (2003).
Shi et al., "High-Yield Production of Lutein by the Green Microalga *Chlorella protothecoides* in Heterotrophic Fed-Batch Culture," Biotechnol. Prog., 18(4):723-727 (2002).
Shi et al., "Production and rapid extraction of lutein and the other lipid-soluble pigments from Chlorella protothecoides grown under heterotrophic and mixotrophic conditions," Nahrung, 43:109-113, (1999).
Simpson et al., "Requirements for mini-exon inclusion in potato invertase mRNAs provides evidence for exon-scanning interactions in plants," RNA, 6:422-433, (2000).
Sinha et al., "Metabolizable and Non-Metabolizable Sugars Activate Different Signal Transduction Pathways in Tomato," Plant Physiology, 128:1480-1489, (2002).
Sitthiwong et al., "Changes in Carbohydrate Content and the Activities of Acid Invertase, Sucrose Synthase and Sucrose Phosphate Synthase in Vegetable Soybean During Fruit Development," Asian Journal of Plant Sciences, 4(6):684-690, (2005).
Skolnick et al., "From genes to protein structure and function: novel applications of computational approaches in the genomic era," TIBTECH, 18: 34-39, (2000).
Smallwood et al., "Different Substitutions at Conserved Amino Acids in Domains II and III in the Sendai L RNA Polymerase Protein Inactivate Viral RNA Synthesis," Virology, 304:135-145, (2002).
Smith et al., "Comparison of Biosequences," Adv Appl Math, 2(4):482-489, (1981).
Smith et al., "Production of hydroxy fatty acids in the seeds of *Arabidopsis thaliana*," Biochemical Society Transactions, 28(6):947-950, (2000).
Sonnewald et al., "Transgenic tobacco plants expressing yeast-derived invertase in either the cytosol, vacuole or apoplast: a powerful tool for studying sucrose metabolism and sink/source interactions," The Plant Journal, 1(1):95-106, (1991).
Sorger et al., "Triacylglycerol biosynthesis in yeast," AppL Microbiol Biotechnol, 61:289-299, (2003).
Spolaore et al., "Commercial Applications of Microalgae," J. Biosci. Bioeng. 101(2):87-96 (2006).
Stemmer et al., "Single-Step Assembly of a Gene and Entire Plasmid from Large Numbers of Oligodeoxyribonucleotides," Gene, 164:49-53, (1995).
Sud et al., "Lipid Composition and Sensitivity of Prototheca wickerhamii to Membrane-Active ntimicrobial Agents," Antimicrobial Agents and Chemotherapy, 16:486-490, (1979).
Suda, et al., "Evidence for a novel Chlorella virus-encoded alginate lyase," FEMS Microbiology Letters, 180(1):45-53, (1999).
Suh et al., "What limits production of unusual monoenoic fatty acids in transgenic plants?," Planta, 215:584-595, (2002).
Sun et al., "Characterization of two chitinase genes and on chitosanase gene encoded by Chlorella virus PBCV-1," Virology, 263(2):376-387, (1999).
Sung et al., "The research on the lipid content and composition of microalgae and their impact factors," Marine Science, 12(33)122-128, (2009). (English translation of first two pages).
Swern et al. "Fractionation of tallow fatty acids:Preparation of purified oleic acid and an inedible olive oil substitute," Oil & Soap, 22(11):302-304 (1945).
Szabo et al., "Safety evaluation of a high lipid Whole Algalin Flour (WAF) from Chlorella protothecoides," Regulatory Toxicology and Pharmacology, 63:155-165, (2012).
Szabo et al., "Saftvaluation of Whole Algalin Protein (WAP) from Chlorella protothecoides," Food and Chemical Toxicology, 59:34-45, (2013).
Takeno et al., "Establishment of an overall transformation system for an oil-producing filamentous fungus, *Mortierella alpina* 1S-4," Appl Microbiol Biotechnol, 65:419-425, (2004).
Talbot et al., "Formulation and Production of Confectionery Fats," OFI Middle East 2007 Conference and Exhibition, 378 pages, (2007).
Talebi et al., "Genetic manipulation, a feasible tool to enhance unique characteristic of Chlarella vulgaris as a feedstock for biodiesel production," Mol Biol Rep, 40:4421-4428, (2013).
Tan et al., "Establishment of a Micro-Particle Bombardment Transformation System for Dunaliella Salina," J Microbiol.;43(4):361-365, (2005).
Tan et al., "Fatty acid production by heterotrophic Chlorella saccharophila," Hydrobiologia, 215:13-19, (1991).
Tang et al., "Insertion mutagenesis of Chlamydomonas reinhardtii by electroporation and heterologous DNA," Biochem Mol Biol Int, 36(5):1025-1035, (1995).
Tomasinsig et al., "The Cathelicidins—Structure, Function and Evolution," Current Protein and Peptide Science, 6: 23-34, (2005).
Tornabene et al., "Lipid composition of the nitrogen starved green alga *Neochloris oleoabundans*," Enzyme Microb. Technol., 5:435-440, (1983).
Trimble et al., "Structure of Oligosaccharides on *Saccharomyces* SUC2 Invertse Secreted by the Methylotrophic Yeast *Pichia pastoris*," J. Biol. Chem., 266(34):22807-22817, (1991).
Trimble et al., "Structure of oligosaccharides on *Saccharomyces* SUC2 Invertase Secreted by the Methylotrophic Yeast *Pichia pastoris*," The Journal of Biological Chemistry, 266(34):22807-33928, (1991).
Tymowska-Lalanne et al., "Expression of the *Arabidopsis thaliana* invertase gene family," Planta, 207: 259-265, (1998).
U.S. Appl. No. 12/131,766, Advisory Action dated Oct. 13, 2011.
U.S. Appl. No. 12/131,766, Non-Final Office Action dated Aug. 1, 2011.
U.S. Appl. No. 12/131,766, Non-Final Office Action dated Nov. 23, 2010.
U.S. Appl. No. 12/131,766, Non-Final Office Action dated Dec. 10, 2009.
U.S. Appl. No. 12/131,766, Requirement for Restriction/Election dated Aug. 5, 2009.
U.S. Appl. No. 12/131,766, Requirement for Restriction/Election dated Aug. 17, 2010.
U.S. Appl. No. 12/131,773, Advisory Action dated Jan. 27, 2014.
U.S. Appl. No. 12/131,773, Final Office Action dated Mar. 21, 2011.
U.S. Appl. No. 12/131,773, Final Office Action dated Oct. 15, 2013.
U.S. Appl. No. 12/131,773, Non-Final Office Action dated Jun. 5, 2013.
U.S. Appl. No. 12/131,773, Non-Final Office Action dated Jun. 25, 2010.
U.S. Appl. No. 12/131,773, Non-Final Office Action dated Dec. 15, 2009.
U.S. Appl. No. 12/131,773, Notice of Allowance and Examiner Initiated Interview Summary dated Apr. 1, 2014.
U.S. Appl. No. 12/131,773, Requirement for Restriction/Election dated Aug. 6, 2009.
U.S. Appl. No. 12/131,783, Final Office Action dated Jan. 12, 2012.
U.S. Appl. No. 12/131,783, Final Office Action dated Dec. 13, 2013.
U.S. Appl. No. 12/131,783, Non-Final Office Action dated Jun. 6, 2011.
U.S. Appl. No. 12/131,783, Non-Final Office Action dated Jul. 18, 2013.
U.S. Appl. No. 12/131,783, Notice of Allowance and Examiner Initiated Interview Summary dated Mar. 24, 2014.
U.S. Appl. No. 12/131,783, Requirement for Restriction/Election dated Apr. 19, 2011.
U.S. Appl. No. 12/131,793, Final Office Action dated Mar. 30, 2010.
U.S. Appl. No. 12/131,793, Non-Final Office Action dated Jun. 21, 2012.
U.S. Appl. No. 12/131,793, Non-Final Office Action dated Sep. 16, 2009.
U.S. Appl. No. 12/131,793, Non-Final Office Action dated Nov. 13, 2012.
U.S. Appl. No. 12/131,793, Notice of Allowance dated Apr. 3, 2013.
U.S. Appl. No. 12/131,793, Requirement for Restriction/Election dated Aug. 6, 2009.
U.S. Appl. No. 12/131,804, Final Office Action dated Feb. 2, 2011.

(56) References Cited

OTHER PUBLICATIONS

U.S. Appl. No. 12/131,804, Non-Final Office Action dated Oct. 26, 2012.
U.S. Appl. No. 12/131,804, Non-Final Office Action dated Mar. 3, 2010.
U.S. Appl. No. 12/131,804, Non-Final Office Action dated Jun. 7, 2012.
U.S. Appl. No. 12/131,804, Requirement for Restriction/Election dated Sep. 17, 2009.
U.S. Appl. No. 12/131,804, Requirement for Restriction/Election dated Nov. 18, 2009.
U.S. Appl. No. 12/194,389, Final Office Action dated Jan. 5, 2011.
U.S. Appl. No. 12/194,389, Non-Final Office Action dated Feb. 4, 2010.
U.S. Appl. No. 12/194,389, Notice of Allowance dated Jan. 15, 2014.
U.S. Appl. No. 12/194,389, Requirement for Restriction/Election dated Oct. 5, 2010.
U.S. Appl. No. 12/194,389, Requirement for Restriction/Election dated Nov. 2, 2009.
U.S. Appl. No. 12/628,140, Final Office Action dated Mar. 15, 2013.
U.S. Appl. No. 12/628,140, Final Office Action dated May 22, 2014.
U.S. Appl. No. 12/628,140, Final Office Action dated Sep. 12, 2013.
U.S. Appl. No. 12/628,140, Final Office Action dated Oct. 8, 2014.
U.S. Appl. No. 12/628,140, Non-Final Office Action dated Jul. 17, 2015.
U.S. Appl. No. 12/628,140, Non-Final Office Action dated Oct. 30, 2012.
U.S. Appl. No. 12/628,144, Final Office Action dated Nov. 16, 2010.
U.S. Appl. No. 12/628,144, Final Office Action dated Dec. 5, 2011.
U.S. Appl. No. 12/628,144, Final Office Action dated Dec. 12, 2014.
U.S. Appl. No. 12/628,144, Non-Final Office Action dated May 16, 2014.
U.S. Appl. No. 12/628,144, Non-Final Office Action dated Jun. 7, 2011.
U.S. Appl. No. 12/628,144, Non-Final Office Action dated Jul. 8, 2010.
U.S. Appl. No. 12/628,144, Requirement for Restriction/Election and Examiner Initiated Interview Summary dated Oct. 7, 2014.
U.S. Appl. No. 12/628,147, Examiner Interview Summary Record dated Mar. 3, 2011.
U.S. Appl. No. 12/628,147, Final Office Action dated Jul. 12, 2012.
U.S. Appl. No. 12/628,147, Final Office Action dated Oct. 1, 2010.
U.S. Appl. No. 12/628,147, Non-Final Office Action dated May 25, 2010.
U.S. Appl. No. 12/628,147, Non-Final Office Action dated Oct. 25, 2011.
U.S. Appl. No. 12/628,147, Notice of Allowance and Examiner Initiated Interview Summary dated Aug. 7, 2012.
U.S. Appl. No. 12/628,149, Non-Final Office Action dated Jun. 25, 2010.
U.S. Appl. No. 12/628,149, Non-Final Office Action dated Sep. 16, 2010.
U.S. Appl. No. 12/628,149, Notice of Allowance dated Dec. 15, 2010.
U.S. Appl. No. 12/628,150, Non-Final Office Action dated Apr. 29, 2010.
U.S. Appl. No. 12/628,150, Non-Final Office Action dated Oct. 13, 2010.
U.S. Appl. No. 12/628,150, Notice of Allowance dated Mar. 21, 2011.
U.S. Appl. No. 12/642,487, Final Office Action dated Jan. 30, 2014.
U.S. Appl. No. 12/642,487, Non-Final Office Action dated Jan. 4, 2013.
U.S. Appl. No. 12/642,487, Requirement for Restriction/Election dated Jun. 18, 2012.
U.S. Appl. No. 12/642,487, Requirement for Restriction/Election dated Nov. 8, 2012.
U.S. Appl. No. 12/772,163, Non-Final Office Action dated May 25, 2012.
U.S. Appl. No. 12/772,163, Non-Final Office Action dated Dec. 12, 2012.
U.S. Appl. No. 12/772,163, Notice of Allowance dated May 28, 2013.
U.S. Appl. No. 12/772,163, Requirement for Restriction/Election dated Jun. 24, 2011.
U.S. Appl. No. 12/772,164, Final Office Action dated May 24, 2012.
U.S. Appl. No. 12/772,164, Non-Final Office Action dated Oct. 12, 2011.
U.S. Appl. No. 12/772,164, Requirement for Restriction/Election dated Jul. 20, 2011.
U.S. Appl. No. 12/772,170, Final Office Action dated Feb. 21, 2012.
U.S. Appl. No. 12/772,170, Non-Final Office Action dated Sep. 13, 2011.
U.S. Application No. 12/772,170, Non-Final Office Action dated Dec. 17, 2013.
U.S. Application No. 12/772,170, Notice of Allowance and Examiner-Initiated Interview Summary dated Jul. 11, 2014.
U.S. Appl. No. 12/772,170, Requirement for Restriction/Election dated Jul. 13, 2011.
U.S. Appl. No. 12/772,173, Final Office Action dated May 7, 2012.
U.S. Appl. No. 12/772,173, Non-Final Office Action dated Dec. 16, 2011.
U.S. Appl. No. 12/772,173, Notice of Allowance dated Mar. 29, 2013.
U.S. Appl. No. 12/772,173, Notice of Allowance dated Jul. 10, 2013.
U.S. Appl. No. 12/772,173, Requirement for Restriction/Election dated Oct. 26, 2011.
U.S. Appl. No. 12/772,174, Non-Final Office Action dated Nov. 29, 2011.
U.S. Appl. No. 12/772,174, Requirement for Restriction/Election dated Aug. 10, 2011.
U.S. Appl. No. 12/960,388, Notice of Allowance dated May 28, 2013.
U.S. Appl. No. 12/960,388, Requirement for Restriction/Election dated Apr. 1, 2013.
U.S. Appl. No. 12/981,409, Non-Final Office Action dated Jan. 6, 2012.
U.S. Appl. No. 12/981,409, Notice of Allowance dated May 29, 2012.
U.S. Appl. No. 12/981,409, Requirement for Restriction/Election dated Apr. 19, 2012.
U.S. Appl. No. 12/981,409, Requirement for Restriction/Election dated Oct. 28, 2011.
U.S. Appl. No. 13/029,061, Requirement for Restriction/Election dated Nov. 29, 2011.
U.S. Appl. No. 13/045,500, Non-Final Office Action dated Mar. 9, 2012.
U.S. Appl. No. 13/045,500, Non-Final Office Action dated Jun. 5, 2014.
U.S. Appl. No. 13/045.500, Final Office Action dated Sep. 26, 2012.
U.S. Appl. No. 13/073,757, Non-Final Office Action dated Aug. 15, 2011.
U.S. Appl. No. 13/073,757, Non-Final Office Action dated Dec. 29, 2011.
U.S. Appl. No. 13/073,757, Notice of Allowance dated Apr. 17, 2012.
U.S. Appl. No. 13/087,311, Final Office Action dated Dec. 16, 2013.
U.S. Appl. No. 13/087,311, Non-Final Office Action dated Apr. 23, 2013.
U.S. Appl. No. 13/087,311, Non-Final Office Action dated Jun. 24, 2014.
U.S. Appl. No. 13/118,365, Final Office Action dated Jul. 22, 2013.
U.S. Appl. No. 13/118,365, Non-Final Office Action dated Feb. 11, 2013.
U.S. Appl. No. 13/118,365, Requirement for Restriction/Election dated Oct. 11, 2012.
U.S. Appl. No. 13/273,179, Non-Final Office Action dated Jan. 28, 2014.
U.S. Appl. No. 13/273,179, Notice of Allowance dated Jul. 11, 2014.

(56) References Cited

OTHER PUBLICATIONS

U.S. Appl. No. 13/273,179, Requirement for Restriction/Election dated Nov. 14, 2013.
U.S. Appl. No. 13/288,815, Final Office Action dated Oct. 22, 2014.
U.S. Appl. No. 13/288,815, Non-Final Office Action dated Jun. 18, 2014.
U.S. Appl. No. 13/288,815, Notice of Allowance dated Feb. 26, 2015.
U.S. Appl. No. 13/288,815, Requirement for Restriction/Election dated Jan. 30, 2014.
U.S. Appl. No. 13/365,253, Requirement for Restriction/Election dated Dec. 16, 2014.
U.S. Appl. No. 13/406,417, Non-Final Office Action dated Nov. 5, 2012.
U.S. Appl. No. 13/406,417, Requirement for Restriction/Election dated Apr. 30, 2012.
U.S. Appl. No. 13/464,948, Final Office Action dated Feb. 13, 2014.
U.S. Appl. No. 13/464,948, Non-Final Office Action dated Oct. 9, 2013.
U.S. Appl. No. 13/464,948, Notice of Allowance dated May 25, 2014.
U.S. Appl. No. 13/464,948, Requirement for Restriction/Election dated Aug. 21, 2013.
U.S. Appl. No. 13/479,194, Non-Final Office Action dated Mar. 26, 2014.
U.S. Appl. No. 13/479,200, Non-Final Office Action dated Apr. 10, 2013.
U.S. Appl. No. 13/479,200, Non-Final Office Action dated Sep. 9, 2013.
U.S. Appl. No. 13/479,200, Notice of Allowance dated Nov. 25, 2013.
U.S. Appl. No. 13/479,200,Requirement for Restriction/Election dated Jan. 15, 2013.
U.S. Appl. No. 13/527,480, Final Office Action dated Jan. 16, 2014.
U.S. Appl. No. 13/527,480, Non-Final Office Action dated Jun. 26, 2013.
U.S. Appl. No. 13/527,480, Requirement for Restriction/Election dated May 3, 2013.
U.S. Appl. No. 13/543,666, Non-Final Office Action dated Sep. 5, 2013.
U.S. Appl. No. 13/543,666, Notice of Allowance dated Feb. 10, 2014.
U.S. Appl. No. 13/543,666, Requirement for Restriction/Election dated Jan. 3, 2013.
U.S. Appl. No. 13/547,457, Final Office Action dated Mar. 20, 2014.
U.S. Appl. No. 13/547,457, Non-Final Office Action dated Jul. 8, 2013.
U.S. Appl. No. 13/547,457, Notice of Allowance and Examiner-Initiated Interview Summary dated May 29, 2014.
U.S. Appl. No. 13/550,412, Non-Final Office Action dated Oct. 29, 2012.
U.S. Appl. No. 13/550,412, Notice of Allowance dated Feb. 21, 2013.
U.S. Appl. No. 13/555,009, Non-Final Office Action dated Sep. 16, 2014.
U.S. Appl. No. 13/555,009, Notice of Allowance dated Jan. 9, 2015.
U.S. Appl. No. 13/555,009, Requirement for Restriction/Election dated Jun. 16, 2014.
U.S. Appl. No. 13/558,252, Final Office Action dated Jul. 9, 2013.
U.S. Appl. No. 13/558,252, Non-Final Office Action dated Jan. 18, 2013.
U.S. Appl. No. 13/558,252, Notice of Allowance dated Oct. 23, 2013.
U.S. Appl. No. 13/601,928, Non-Final Office Action dated Jan. 31, 2013.
U.S. Appl. No. 13/601,928, Notice of Allowance dated Feb. 26, 2013.
U.S. Appl. No. 13/601,937, Final Office Action dated Nov. 22, 2013.
U.S. Appl. No. 13/601,937, Non-Final Office Action dated Jun. 10, 2013.
U.S. Appl. No. 13/601,937, Requirement for Restriction/Election dated Feb. 27, 2013.
U.S. Appl. No. 13/621,722, Requirement for Restriction/Election dated Jan. 31, 2013.
U.S. Appl. No. 13/621,722, Final Office Action dated Oct. 25, 2013.
U.S. Appl. No. 13/621,722, Non-Final Office Action dated May 9, 2013.
U.S. Appl. No. 13/621,722, Notice of Allowance and Examiner Initiated Interview Summary dated Jan. 10, 2014.
U.S. Appl. No. 13/628,039, Non-Final Office Action dated Jun. 4, 2013.
U.S. Appl. No. 13/628,039, Notice of Allowance and Examiner-Initiated Interview Summary dated Feb. 20, 2014.
U.S. Appl. No. 13/628,039, Requirement for Restriction/Election dated Mar. 7, 2013.
U.S. Appl. No. 13/630,757, Non-Final Office Action dated Apr. 23, 2015.
U.S. Appl. No. 13/630,757, Non-Final Office Action dated Oct. 27, 2014.
U.S. Appl. No. 13/630,757, Requirement for Restriction/Election dated Jun. 12, 2014.
U.S. Appl. No. 13/650,018, Non-Final Office Action dated Dec. 23, 2013.
U.S. Appl. No. 13/650,018, Notice of Allowance dated Apr. 1, 2015.
U.S. Appl. No. 13/650,018, Notice of Allowance dated Apr. 10, 2015.
U.S. Appl. No. 13/650,018, Notice of Allowance dated Aug. 14, 2014.
U.S. Appl. No. 13/650,018, Requirement for Restriction/Election dated Aug. 22, 2013.
U.S. Appl. No. 13/650,024, Non-Final Office Action dated Jul. 2, 2013.
U.S. Appl. No. 13/650,024, Notice of Allowance dated Oct. 17, 2013.
U.S. Appl. No. 13/804,185, Non-Final Office Action dated Jun. 1, 2015.
U.S. Appl. No. 13/804,185, Requirement for Restriction/Election dated Mar. 16, 2015.
U.S. Appl. No. 13/849,330, Requirement for Restriction/Election dated Jan. 21, 2015.
U.S. Appl. No. 13/852,116, Final Office Action dated Aug. 18, 2014.
U.S. Appl. No. 13/852,116, Non-Final Office Action dated Mar. 26, 2014.
U.S. Appl. No. 13/852,116, Notice of Allowance dated Nov. 7, 2014.
U.S. Appl. No. 13/865,974, Non-Final Office Action dated May 2, 2014.
U.S. Appl. No. 13/865,974, Notice of Allowance dated Oct. 22, 2014.
U.S. Appl. No. 13/865,974, Requirement for Restriction/Election dated Jan. 29, 2014.
U.S. Appl. No. 13/889,214, Non-Final Office Action dated Sep. 18, 2013.
U.S. Appl. No. 13/889,214, Notice of Allowance dated Apr. 28, 2014.
U.S. Appl. No. 13/889,221, Non-Final Office Action dated Sep. 6, 2013.
U.S. Appl. No. 13/889,221, Notice of Allowance dated Apr. 24, 2014.
U.S. Appl. No. 13/941,342, Notice of Allowance dated Jul. 24, 2015.
U.S. Appl. No. 13/941,342, Requirement for Restriction/Election dated Apr. 13, 2015.
U.S. Appl. No. 13/941,346, Final Office Action dated Jun. 26, 2014.
U.S. Appl. No. 13/941,346, Non-Final Office Action dated Jan. 21, 2014.
U.S. Appl. No. 13/941,346, Non-Final Office Action dated Nov. 3, 2014.
U.S. Appl. No. 13/941,346, Notice of Allowance dated Feb. 23, 2015.
U.S. Appl. No. 13/941,353, Requirement for Restriction/Election dated Jan. 16, 2014.
U.S. Appl. No. 13/941,357, Final Office Action dated Nov. 6, 2014.

(56) References Cited

OTHER PUBLICATIONS

U.S. Appl. No. 13/941,357, Non-Final Office Action dated Jun. 3, 2014.
U.S. Appl. No. 13/941,357, Notice of Allowance dated Mar. 30, 2015.
U.S. Appl. No. 13/941,357, Requirement for Restriction/Election dated Jan. 7, 2014.
U.S. Appl. No. 14/184,288, Requirement for Restriction/Election dated Jun. 9, 2015.
U.S. Appl. No. 14/262,070, Non-Final Office Action dated Jul. 10, 2015.
U.S. Appl. No. 14/276,943, Requirement for Restriction/Election dated Jun. 4, 2015.
U.S. Appl. No. 14/285,354, Requirement for Restriction/Election dated Jul. 20, 2015.
U.S. Appl. No. 14/474,244, Final Office Action dated Jul. 30, 2015.
U.S. Appl. No. 14/474,244, Non-Final Office Action dated Apr. 24, 2015.
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2):155-159, (2003).
Vazquez-Bermudez et al., "Uptake of 2-Oxoglutarate in Synechococcus Strains Transformed with the *Escherichia coli* kgtP Gene," Journal of Bacteriology, 182(1):211-215, (2000).
Velayutham et al., "The Physical and Mechanical Properties of Polyurethanes from. Oleic Acid Polyols," Journal of Applied Polymer Science, 112:3554-3559, (2009). [Published on the Internet on Mar. 11, 2009: <URL: http://www.interscience.wiley.com>].
Voegele et al., "Cloning and Characterization of a Novel Invertase from the Obligate Biotroph Uromyces fabae and Analysis of Expression Patterns of Host and Pathogen Invertases in the Course of Infection," Molecular Plant Microbe Interactions, 19:625-634, (2006).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from Cuphea lanceolata," Plant Physiol., 106:785-786, (1994).
Walker et al., "Characrization of the Dunaliella tertiolecta RbcS Genes and Their Promoter ctivity in Chlamydomonates reinhardtii," Plant Cell Rep, 23(10-11):727-735, (2005).
Wang et al., "Rapid isolation and functional analysis of promoter sequences of the nitrate reductase gene from Chlorella ellipsoidea," J. Appl. Phycol., 16:11-16, (2004).
Warner et"Analysis of Tocopherols and Phytosterols in Vegetable Oils by HPLC with Evaporative Light-Scattering Detection," JAOCS, 67(11):827-831 (1990).
Weber et al., "Invertases and life beyond sucrose cleavage," Trends in Plant Science, 5(2):47-48, (2000).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3):307-340, (2003).

Wiberg et al., "The distribution of caprylate, caprate and laurate in lipids from developing and mature seeds of transgenic *Brassica napus* L.," Planta, 212:33-40, (2000).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).
Witkowski et al., "Conversion of a β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia coli* to Nitrogen-Fixing Filamentous Cyanobacteria," Proc Natl Acad Sci U S A., 81(5):1561-1565, (1984).
Wong et al., "*Arabidopsis thaliana* small subunit leader and transit peptide enhance the expression of Bacillus thuringiensis proteins in transgenic plants," Plant Mol Biol, 20(1):81-93, (1992).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (1994).
Xiong et al., "High-density fermentation of microalga *Chlorella protothecoides* in bioreactor for microbio-diesel production," Appl. Microbiol. Biotechnol., 78:29-36, (2008).
Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Yanase et al., "Expression of the Extracellular Levansucrase and Invertase Genes from Zymomonas mobilis in *Escherichia coli* Cells," Biosci, Biotechnol. Biochem., 62(9):1802-1805, (1998).
Yu et al., "Modifications of the metabolic pathways of lipid and triacylglycerol production in microalgae," Microbial Cell Factories, 10:91, (2011). [Retrieved from the Internet Jul. 24, 2012: <URL: http://www.micorbialcellfactories.com/content/10/1/91>].
Yuan et al., "Modification of the substrate specificity of an acyl-acyl carrier protein thioesterase by protein engineering," Proc. NatL Acad. Sci. USA, Biochemistry, 92:10639-10643, (1995).
Zaidul et al., "Supercritical carbon dioxide (SC-0O2) extraction and fractionation of palm kernel oil from palm kernel as cocoa butter replacers blend," Journal of Food Engineering, 73:210-216, (2006).
Zárate et al., "Characterization of the heterologous invertase produced by Schizosaccharomyces pombe from the SUCZ gene of *Saccharomyces cerevisiae*," Journal of Applied Bacteriology, 80:45-52(1996)
Zarowska et al., "Production of Citric Acid on Sugar Beet Molasses by Single and Mixed Cultures of Yarrowia Lipolytica," Electronic Journal of Polish Agricultural Universities, 4(2):1-7, (2001). [Retrieved from the Internet Oct. 3, 2011: <URL: http://www.ejpau.media.pl/volume4/issue2/biotechnology/art-01.html>].
Zhang et al., "Malic enzyme: the controlling activity for lipid production? Overexpression of malic enzyme in Mucor circinelloides leads to a 2.5-fold increase in lipid accumulation," Microbiology, 153(7):2013-2025, (2007).
Zhang et al., "Cloning and Characterization of an Invertase Gene From the Garden Pea (*Pisum sativum* L)," Jiesheng Zhang, M.S. Plant Biology Thesis, 82 pages, (2003).
Zhao et al., "Medium optimization for lipid production through co-fermentation of glucose and xylose by the oleaginous yeast *Lipomyces starkeyi*," Eur. J. Lipid Sci. Technol., 110:405-412, (2008).
Zlatanic et al., "Structure and Properties of Triolein-Based Polyurethane Networks," Biomacromolecules, 3:1048-1056, (2002).
Zurawski et al., "Nucleotide sequence of the gene for the Mr 32,000 thylakoid membrane protein from Spinacia oleracea and Nicotiana

(56) References Cited

OTHER PUBLICATIONS debneyi predicts a totally conserved primary translation product of Mr 38,950," Proc Natl Acad Sci, 79(24):7699-7703, (1982).
Day et al., "An investigation of the heterotrophic culture of the green alga *Tetraselmis*," Journal of Applied Phycology, 8:73-77, (1996).
Elumalai et al., "Optimizatin of abiotic conditions suitable for the production of biodiesel from Chlorella vulgaris," Indian J. Sci. Technol., 4(2):91-97, (2011).
Huss et al., "Deoxyribonucleic acid reassociation in the taxonomy of the genus *Chlorella*," Arch Microbiol, 150:509-511, (1988).
Kerton et al., "Alternative Solvents for Green Chemistry," RSC Publishing, 238 pages, (2009).
EPO Supplementary European Search Report and European Search Opinion for application EP12741997.6 dated Aug. 31, 2015.
EPO Supplementary European Search Report and European Search Opinion for application EP13778920.2 (EP13778920) dated Jan. 25, 2016.
PCT Invitation to Pay Additional Fees for application PCT/US2015/039951 dated Nov. 20, 2015.
U.S. Appl. No. 14/474,238, Non-Final Office Action dated Feb. 2, 2016.
U.S. Appl.No. 12/628,140, Final Office Action dated Feb. 2, 2016.
U.S. Appl. No. 13/365,253, Notice of Allowance dated Sep. 24, 2015.
U.S. Appl. No. 13/630,757, Notice of Allowance dated Oct. 23, 2015.
U.S. Appl. No. 13/804,185, Final Office Action dated Dec. 11, 2015.
U.S. Appl. No. 14/184,288, Non-Final Office Action dated Sep. 11, 2015.
U.S. Appl. No. 14/262,070, Notice of Allowance dated Oct. 20, 2015.
U.S. Appl. No. 14/276,943, Notice of Allowance dated Sep. 22, 2015.
U.S. Appl. No. 14/285,354, Notice of Allowance dated Feb. 1, 2016.
U.S. Appl. No. 14/474,244, Notice of Allowance dated Sep. 18, 2015.
U.S. Appl. No. 14/671,894, Non-Final Office Action dated Oct. 19, 2015.
U.S. Appl. No. 14/742,238, Requirement for Restriction/Election dated Nov. 10, 2015.
Blatti, Jillian L. et al., (Sep. 2012) "Manipulating Fatty Acid Biosynthesis in Microalgae for Biofuel through Protein-Protein Interactions," *PLoS ONE*, 7(9):e42949, 12pp.
Blatti, Jillian L. et al., (Jun. 2013) "Engineering fatty acid biosynthesis in microalgae for sustainable biodiesel," *Current Opinion in Chemical Biology*, 17(3):496-505.
Gimpel et al., (Dec. 15, 2015) "In Metabolic Engineering of Eukaryotic Microalgae: Potential and Challenges Come with Great Diversity," *Metabolic Engineering of Eukaryotic Microalgae, Frontiers in Microbiology*, 6(Article 1376):14pp.
U.S. Appl. No. 15/179,253, Restriction for Requirement, dated Sep. 28, 2017.
U.S. Appl. No. 15/179,253, Non-Final Rejection, dated Feb. 14, 2018.
U.S. Appl. No. 15/179,253, Notice of Allowance, dated Aug. 10, 2018.
U.S. Appl. No. 14/184,288, Notice of Allowance dated Feb. 3, 2016.
U.S. Appl. No. 15/173,335, Requirement for Restriction/Election dated Jul. 5, 2017.
U.S. Appl. No. 15/173,335, Non-Final Office Action dated Oct. 12, 2017.
U.S. Appl. No. 15/173,335, Final Office Action dated Apr. 9, 2018.
U.S. Appl. No. 15/173,335, Notice of Allowance dated Jul. 26, 2018.
U.S. Appl. No. 12/628,140, Non-Final Office Action dated Nov. 21, 2016.
U.S. Appl. No. 12/628,144, Final Office Action dated Mar. 1, 2016.
U.S. Appl. No. 12/628,144, Notice of Allowance dated Jun. 13, 2016.
U.S. Appl. No. 14/626,505, Requirement for Restriction/Election dated Apr. 26, 2016.
U.S. Appl. No. 14/626,505, Non-Final Office Action dated Jul. 19, 2016.
U.S. Appl. No. 15/443,209, Requirement for Restriction/Election dated Jul. 3, 2018.
U.S. Appl. No. 13/118,365, Notice of Allowance dated Sep. 20, 2013.
U.S. Appl. No. 14/975,016, Notice of Allowance dated Jan. 10, 2017.
U.S. Appl. No. 14/975,016, Notice of Allowance dated Jan. 31, 2017.
U.S. Appl. No. 14/975,016, Notice of Allowance dated Feb. 24, 2017.
U.S. Appl. No. 13/118,369, Requirement for Restriction/Election dated Dec. 13, 2015.
U.S. Appl. No. 13/118,369, Non-Final Office Action dated Mar. 28, 2013.
U.S. Appl. No. 13/118,369, Final Office Action dated Mar. 28, 2014.
U.S. Appl. No. 13/630,757, Supplemental Notice of Allowance dated Dec. 3, 2015.
U.S. Appl. No. 13/630,757, Miscellaneous Communication dated Dec. 17, 2015.
U.S. Appl. No. 13/630,757, Notice of Allowance (Supplemental Notice of Allowability) dated Jan. 15, 2016.
U.S. Appl. No. 14/819,117, Requirement for Restriction/Election dated Apr. 11, 2016.
U.S. Appl. No. 14/819,117, Non-Final Office Action dated Nov. 2, 2016.
U.S. Appl. No. 14/819,117, Final Office Action dated Mar. 22, 2017.
U.S. Appl. No. 14/819,117, Notice of Allowance dated Sep. 7, 2017.
U.S. Appl. No. 14/819,117, Supplemental Notice of Allowance dated Nov. 13, 2017.
U.S. Appl. No. 14/819,117, Notice of Allowance dated Jan. 16, 2018.
U.S. Appl. No. 14/819,117, Notice of Allowance dated Feb. 9, 2018.
U.S. Appl. No. 13/288,815, Requirement for Restriction/Election dated Feb. 11, 2014.
U.S. Appl. No. 14/730,671, Notice of Allowance dated Mar. 21, 2016..
U.S. Appl. No. 13/365,253, Non-Final Office Action dated Mar. 25, 2015.
U.S. Appl. No. 13/365,253, Notice of Allowance (Notice of Allowability) dated Nov. 6, 2015.
U.S. Appl. No. 14/974,983, Requirement for Restriction/Election dated Jul. 28, 2016.
U.S. Appl. No. 14/974,983, Non-Final Office Action dated Dec. 5, 2016.
U.S. Appl. No. 14/974,983, Final Office Action dated Jul. 19, 2017.
U.S. Appl. No. 14/974,983, Non-Final Office Action dated Oct. 26, 2017.
U.S. Appl. No. 14/974,983, Notice of Allowance dated Jun. 8, 2018.
U.S. Appl. No. 14/974,983, Corrected Notice of Allowability dated Jun. 20, 2018.
U.S. Appl. No. 13/804,185, Non-Final Office Action dated Jul. 20, 2016.
U.S. Appl. No. 13/804,185, Notice of Allowance dated Jan. 27, 2017.
U.S. Appl. No. 13/941,353, Notice of Allowance dated May 21, 2014.
U.S. Appl. No. 14/975,137, Notice of Allowance dated Sep. 6, 2016.
U.S. Appl. No. 15/369,557, Non-Final Office Action dated Jun. 23, 2017.
U.S. Appl. No. 15/369,557, Notice of Allowance dated Oct. 17, 2017.
U.S. Appl. No. 15/875,984, Non-Final Office Action dated Aug. 27, 2018.
U.S. Appl. No. 14/506,491, Requirement for Restriction/Election dated Jan. 19, 2017.
U.S. Appl. No. 14/506,491, Non-Final Office Action dated Jun. 1, 2017.
U.S. Appl. No. 14/506,491, Final Office Action dated Dec. 5, 2017.
U.S. Appl. No. 14/506,491, Notice of Allowance dated Apr. 9, 2018.

(56) References Cited

OTHER PUBLICATIONS

U.S. Appl. No. 14/796,406, Requirement for Restriction/Election dated Oct. 5, 2016.
U.S. Appl. No. 14/796,406, Non-Final Office Action dated Jan. 25, 2017.
U.S. Appl. No. 14/796,406, Notice of Allowance dated Jun. 15, 2017.
U.S. Appl. No. 14/796,406, Notice of Allowance dated Oct. 3, 2017.
U.S. Appl. No. 14/796,406, Notice of Allowance dated Jan. 11, 2018.
U.S. Appl. No. 15/950,048, Non-Final Office Action dated Aug. 23, 2018.
U.S. Appl. No. 15/092,538, Requirement for Restriction/Election dated Oct. 6, 2017.
U.S. Appl. No. 15/092,538, Non-Final Office Action dated Jan. 8, 2018.
U.S. Appl. No. 15/092,538, Final Office Action dated Jul. 25, 2018.
U.S. Appl. No. 13/087,305, Non-Final Office Action dated Aug. 15, 2012.
U.S. Appl. No. 13/087,305, Final Office Action dated Mar. 18, 2013.
U.S. Appl. No. 15/092,538, Non-Final Office Action dated Jan. 10, 2019.
PCT International Preliminary Report on Patentability dated Dec. 7, 2009 issued in PCT/US08/65563.
Australian Patent Examination Report No. 1 dated Jan. 23, 2013 issued in Application No. AU 2008259834.
Australian Patent Examination Report No. 1 dated May 4, 2015 issued in Application No. AU 2013251198.
Canadian Examination Report dated Nov. 30, 2015 issued in Application No. CA 2,689,724.
Chinese First Office Action dated Apr. 23, 2012 issued in Application No. CN 200880100976.9.
Chinese Second Office Action dated Jan. 21, 2013 issued in Application No. CN 200880100976.9.
Chinese Third Office Action dated May 28, 2013 issued in Application No. CN 200880100976.9.
Chinese Fourth Office Action dated Sep. 11, 2013 issued in Application No. CN 200880100976.9.
Chinese Fifth Office Action dated Jan. 23, 2014 issued in Application No. CN 200880100976.9.
Chinese First Office Action dated May 18, 2016 issued in Application No. CN 201410321130.5.
Colombian Opposition dated Sep. 5, 2011 [Brief Communication dated Sep. 5, 2011 re Application No. EP 06 075 479.3, D50-Declaration of Dr. Matthias Staufenbiel; D51-Wo-A-2004/016282; D52-Sturchler-Pierrat et al. *Proc Natl. Acad. Sci.* USA, 94:13287-13292 (1997)].
Colombian Office Action dated Jan. 28, 2013 issued in Application No. CO 09149183.
Colombian Office Action dated Jun. 13, 2013 issued in Application No. CO 09149183.
Colombian Office Action dated Sep. 25, 2013 issued in Application No. CO 09149183.
European Office Action dated Mar. 9, 2012 issued in Application No. EP 08 769 988.0.
Indonesian First Office Action dated Apr. 13, 2016 issued in Application No. W00200903371.
Indonesian Second Office Action dated Aug. 4, 2016 issued in Application No. W00200903371.
Indian Examination Report dated Oct. 4, 2016 issued in Application No. IN 8573/DELNP/2009.
Japanese Notice of Reason for Denial [no translation] dated May 24, 2016 issued in Application No. JP 2016-095504.
Korean Office Action dated Aug. 25, 2014 issued in Application No. KR 10-2009-7027618.
Mexican Office Action dated Oct. 13, 2011 issued in Application No. MX/A/2009/012850.
Mexican First Office Action dated Sep. 30, 2013 issued in Application No. MX/a/2012/000844.
Mexican Second Office Action dated Jan. 22, 2014 issued in Application No. MX/a/2012/000844.
Mexican Third Office Action dated Oct. 13, 2014 issued in Application No. MX/a/2012/000844.
Mexican Fourth Office Action dated Apr. 1, 2015 issued in Application No. MX/a/2012/000844.
Mexican Office Action dated Feb. 23, 2017 issued in Application No. MX/a/2015/008626.
Malaysian Examination and Search Report dated Dec. 31, 2013 issued in Application No. PI20095102.
Malaysian Examination and Adverse Report dated Dec. 31, 2014 issued in Application No. PI20095102.
Malaysian Examination and Clear Report dated Jul. 15, 2015 issued in Application No. PI20095102.
Malaysian Examination and Search Report dated May 15, 2017 issued in Application No. PI2014000965.
New Zealand First Examination Report dated Oct. 19, 2010 issued in Application No. NZ 581700.
New Zealand Examination Report dated Sep. 22, 2011 issued in Application No. NZ 581700.
New Zealand Examination Report dated Sep. 8, 2011 issued in Application No. NZ 595029.
New Zealand Examination Report dated Dec. 19, 2012 issued in Application No. NZ 595029.
Philippines Examination Report dated Apr. 7, 2014 issued in Application No. PH 1-2009-502294.
Philippines Examination Report dated Nov. 18, 2014 issued in Application No. PH 1-2009-502294.
Singapore Written Opinion and Search Report dated Apr. 29, 2011 issued in Application No. SG 200907978-1.
Thailand Office Action dated Feb. 22, 2011 issued in Application No. TH 0901005340.
Thailand Office Action dated Jul. 26, 2017 issued in Application No. TH 0901005340.
PCT International Preliminary Report on Patentability (Chapter I) dated May 31, 2011 issued in PCT/US2009/066142.
Australian Patent Examination Report No. 1 dated Dec. 9, 2014 issued in Application No. AU 2009319722.
Australian Patent Examination Report No. 1 dated Jul. 20, 2017 issued in Application No. AU 2016250460.
Canadian Examination Report dated Aug. 18, 2015 issued in Application No. CA 2,745,129.
Canadian Examination Report dated Oct. 3, 2016 issued in Application No. CA 2,745,129.
Canadian Examination Report dated Nov. 16, 2017 issued in Application No. CA 2,745,129.
Chinese First Office Action dated Apr. 26, 2013 issued in Application No. CN 200980155465.1.
Chinese Second Office Action dated Jan. 16, 2014 issued in Application No. CN 200980155465.1.
Chinese Third Office Action dated Aug. 28, 2014 issued in Application No. CN 200980155465.1.
Chinese Rejection Decision dated Mar. 24, 2015 issued in Application No. CN 200980155465.1.
Chinese Reexamination notification dated Nov. 10, 2016 issued in Application No. CN 200980155465.1.
Chinese Reexamination Decision dated Apr. 27, 2017 issued in Application No. CN 200980155465.1.
Chinese Fourth Office Action dated Sep. 25, 2017 issued in Application No. CN 200980155465.1.
Colombian Office Action dated Feb. 13, 2013 issued in Application No. CO 11.080.882.
Colombian Office Action dated Jun. 18, 2013 issued in Application No. CO 11.080.882.
Colombian Office Action dated Nov. 24, 2014 issued in Application No. CO 11.080.882.
Colombian Office Action dated Mar. 16, 2015 issued in Application No. CO 11.080.882.
Colombian Office Action dated Mar. 1, 2016 issued in Application No. CO 11.080.882.
European Extended Search Report dated Sep. 12, 2014 issued in Application No. EP 09 829 851.6.

(56) References Cited

OTHER PUBLICATIONS

European Office Action dated Jun. 25, 2015 issued in Application No. EP 09 829 851.6.
European Partial Search Report dated Sep. 12, 2016 issued in Application No. EP 16 16 6059.2.
European Extended Search Report dated Dec. 14, 2016 issued in Application No. EP 16 16 6059.2.
Indonesia Substantive Examination Report Stage 1 dated Aug. 5, 2015 issued in Application No. ID W-00 2011 02343.
Israel Office Action dated Sep. 30, 2013 issued in Application No. IL 213157.
First Examination Report, dated Nov. 23, 2017, issued in Inidina Patent Aplication No. 4960-DELNP-2011.
Japanese Office Action dated May 27, 2014 issued in Application No. JP 2011-538719.
Japanese Final Office Action dated Feb. 24, 2015 issued in Application No. JP 2011-538719.
Japanese Pre-Appeal Examination Report dated Aug. 27, 2015 issued in Application No. JP 2011-538719.
Japanese Office Action dated Jul. 1, 2016 issued in Application No. JP 2011-538719.
Japanese Office Action dated Oct. 31, 2016 issued in Application No. JP 2011-538719.
Japanese Office Action [no translation] dated May 9, 2016 issued in Application No. JP 2015-126360.
Japanese Final Office Action [no translation] dated Nov. 24, 2016 issued in Application No. JP 2015-126360.
Japanese Office Action [no translation] dated Oct. 27, 2017 issued in Application No. JP 2017-015080.
Japanese Office Action [no translation] dated Jul. 4, 2018 issued in Application No. JP 2017-015080.
Korean Office Action dated Nov. 14, 2015 issued in Application No. KR 102011-7014923.
Korean Office Action dated Oct. 5, 2016 issued in Application No. KR 10-2011-7014923.
Korean Office Action dated Nov. 15, 2017 issued in Application No. KR 102017-7021034, with English translation.
Malaysian Examination Report dated Mar. 31, 2016 issued in Application No. MY PI2011002435.
Mexican Office Action dated Sep. 14, 2012 issued in Application No. MX/a/2010/011065.
PCT International Search Report dated Nov. 5, 2010 issued in PCT/US2009/066141.
PCT International Preliminary Report on Patentability and Written Opinion dated Oct. 26, 2012 issued in PCT/US2009/066141.
Australian Patent Examination Report No. 1 dated Feb. 25, 2014 issued in Application No. AU 2009319721.
Australian Patent Examination Report No. 2 dated Oct. 29, 2015 issued in Application No. AU 2009319721.
Canadian Office Action dated Dec. 1, 2015 issued in Application No. CA 2,745,040.
Chinese First Office Action dated Dec. 23, 2013 issued in Application No. CN 200980155463.2.
Chinese Second Office Action dated Oct. 20, 2014 issued in Application No. CN 200980155463.2.
Colombian Office Action dated Mar. 21, 2013 issued in Application No. CO 11.080.835.
European Office Action dated Mar. 21, 2016 issued in Application No. EP 09 829 850.8.
European Extended Search Report dated May 16, 2016 issued in Application No. EP 09 829 850.8.
Indonesian Examination Report dated Feb. 22, 2017 issued in Application No. W-00201102342.
Israel Office Action dated Apr. 8, 2014 issued in Application No. IL 213154.
Israel Office Action dated Jun. 30, 2015 issued in Application No. IL 213154.
Israel Office Action dated Sep. 14, 2016 issued in Application No. IL 213154.
Indian Examination Report dated Sep. 1, 2017 issued in Application No. IN 4959/DELNP/2011.
Japanese Office Action dated May 13, 2014 issued in Application No. JP 2011-538718.
Japanese Office Action dated Jun. 1, 2015 issued in Application No. JP 2011-538718.
Japanese Office Action [no translation] dated Oct. 16, 2016 issued in Application No. JP 2014-227718.
Japanese Final Office Action [no translation] dated Jul. 13, 2016 issued in Application No. JP 2014-227718.
Korean Office Action dated Jan. 4, 2016 issued in Application No. KR 10-2011-7014925.
Korean Office Action dated Jul. 18, 2016 issued in Application No. KR 10-2011-7014925.
Korean Office Action dated Feb. 23, 2017 issued in Application No. KR 10-2011-7014925.
Korean Office Action dated Jan. 4, 2018, issued in Application No. KR 10-2017-7026170.
Mexican Office Action [no translation] dated Dec. 6, 2012 issued in Application No. MX/a/2011/005630.
Mexican Office Action [no translation] dated May 14, 2013 issued in Application No. MX/a/2011/005630.
Mexican Office Action [no translation] dated Dec. 9, 2013 issued in Application No. MX/a/2011/005630.
Malaysian Examination Report dated Mar. 15, 2017 issued in Application No. MY PI2011002435.
Australian Patent Examination Report No. 1 dated Jul. 21, 2016 issued in Application No. AU 2011257982.
Canadian Examination Report dated Feb. 23, 2017 issued in Application No. CA 2,801,057.
Chinese First Office Action dated May 29, 2014 issued in Application No. CN 201180036870.9.
Chinese Second Office Action dated Apr. 15, 2015 issued in Application No. CN 201180036870.9.
Chinese Third Office Action dated Nov. 4, 2015 issued in Application No. CN 201180036870.9.
Chinese Rejection Decision dated Apr. 14, 2016 issued in Application No. CN 201180036870.9.
Chinese Notification of Reexamination dated Jan. 26, 2017 issued in Application No. CN 201180036870.9.
European Extended Search Report dated Jun. 9, 2016 issued in Application No. EP 11 787 551.8.
European Office Action dated Jan. 25, 2017 issued in Application No. EP 11 787 551.8.
European Consultation by telephone dated May 29, 2017 issued in Application No. EP 11 787 551.8.
European Office Action dated Aug. 23, 2017 issued in Application No. EP 11 787 551.8.
Indonesian Office Action dated Sep. 21, 2017 issued in Application No. W00201205280.
Japanese Office Action dated Jul. 7, 2015 issued in Application No. JP 2013-512064.
Japanese Office Action dated Dec. 16, 2016 issued in Application No. JP 2016-001030.
Japanese Office Action dated Dec. 19, 2017 issued in Application No. JP 2017-48186, in Japanese ONLY.
Korean Office Action dated Nov. 29, 2017 issued in Application No. KR 10-2012-7034232.
Korean Office Action dated May 24, 2018 issued in Application No. KR 10-2012-7034232, with English translation.
Mexican Office Action dated Aug. 11, 2015 issued in Application No. MX/a/2012/013777.
Mexican Office Action dated Jan. 15, 2016 issued in Application No. MX/a/2012/013777.
Malaysian Examination Report dated Sep. 15, 2015 issued in Application No. MY PI 2012005117.
PCT International Search Report dated Nov. 3, 2011 issued in PCT/US2011/038464.
PCT Written Opinion of the International Searching Authority dated Nov. 3, 2011 issued in PCT/US2011/038464.
PCT International Preliminary Report on Patentability dated Jun. 28, 2012 issued in PCT/US2011/038464.

(56) References Cited

OTHER PUBLICATIONS

Australian Patent Examination Report No. 1 dated Feb. 26, 2015 issued in Application No. AU 2011257983.
Australian Examination Report No. 1 dated Feb. 1, 2017 issued in Application No. AU 2016202905.
Australian Examination Report No. 2 dated Aug. 28, 2017 issued in Application No. AU 2016202905.
Canadian Examination Report dated May 17, 2017 issued in Application No. CA 2,801,024.
Chinese First Office Action dated Oct. 29, 2013 issued in Application No. CN 201180036696.8.
Chinese Second Office Action dated Jun. 5, 2014 issued in Application No. CN 201180036696.8.
Chinese Rejection Decision dated Jan. 14, 2015 issued in Application No. CN 201180036696.8.
Chinese Re-examination Decision dated May 26, 2015 issued in Application No. CN 201180036696.8.
Chinese Third Office Action dated Jul. 31, 2015 issued in Application No. CN 201180036696.8.
Chinese Fourth Office Action dated Dec. 30, 2015 issued in Application No. CN 201180036696.8.
European Extended Search Report dated Feb. 19, 2016 issued in Application No. EP 11 787 552.6.
European Office Action dated Oct. 11, 2016 issued in Application No. EP 11 787 552.6.
Japanese Office Action dated Jul. 7, 2015 issued in Application No. JP 2013-512065.
Japanese Final Office Action dated Feb. 29, 2016 issued in Application No. JP 2013-512065.
Japanese Office Action [no translation] dated Jul. 8, 2016 issued in Application No. JP 2013-512605.
Japanese Office Action [no translation] dated Sep. 6, 2016 issued in Application No. JP 2015-199078.
Korean Office action [no translation] dated Dec. 11, 2017 issued in Application No. KR 10-2012-7034225.
Mexican Office Action dated Sep. 12, 2017 issued in Application No. MX/a/2012/013756.
Malaysian Examination Report dated Sep. 15, 2015 issued in Application No. MY PI 2012005120.
Australian Patent Examination Report No. 1 dated May 20, 2015 issued in Application No. AU 2011323288.
Australian Patent Examination Report No. 2 dated Mar. 23, 2016 issued in Application No. AU 2011323288.
Australian Patent Examination Report No. 1 dated Aug. 21, 2017 issued in Application No. AU 2016202999.
Canadian Office Action dated Aug. 8, 2017 issued in Application No. CA 2,816,125.
Canadian Notice of Allowance dated Apr. 27, 2018, issued in Application No. CA 2,816,125.
Chinese First Office Action dated Apr. 15, 2014 issued in Application No. CN 201180053258.2.
Chinese Second Office Action dated Feb. 2, 2015 issued in Application No. CN 201180053258.2.
Chinese Third Office Action dated Jul. 3, 2015 issued in Application No. CN 201180053258.2.
Chinese Fourth Office Action dated Dec. 16, 2015 issued in Application No. CN 201180053258.2.
Chinese Fifth Office Action dated Jun. 6, 2016 issued in Application No. CN 201180053258.2.
Chinese Sixth Office Action (Rejection Decision) dated Nov. 2, 2016 issued in Application No. CN 201180053258.2.
Chinese Notification of Reexamination dated Aug. 31, 2017 issued in Application No. CN 201180053258.2.
Chinese Decision on the Reexamination dated Mar. 2, 2018 issued in Application No. CN 201180053258.2.
European Office Action dated Aug. 15, 2014 issued in Application No. EP 11 785 851.4.
European Office Action dated Apr. 11, 2017 issued in Application No. EP 11 785 851.4.

Japanese Office Action dated Oct. 21, 2015 issued in Application No. JP 2013-537836
Japanese Office Action dated Feb. 12, 2016 issued in Application No. JP 2013-537836.
Japanese Office Action dated Apr. 3, 2017 issued in Application No. JP 2016-009933.
Japanese Office Action dated Dec. 14, 2017 issued in Application No. JP 2016-009933.
Mexican First Office Action dated Jul. 19, 2016 issued in Application No. MX/a/2013/004631.
Mexican Second Office Action dated Jan. 16, 2017 issued in Application No. MX/a/2013/004631.
Mexican Third Office Action dated May 10, 2017 issued in Application No. MX/a/2013/004631.
Mexican Fourth Office Action dated Jul. 18, 2017 issued in Application No. MX/a/2013/004631.
Mexican Notice of Allowance dated Dec. 13, 2017 issued in Application No. MX/a/2013/004631.
Malaysian Examination Report dated May 31, 2016 issued in Application No. MY PI2013001587.
Australian Patent Examination Report No. 1 dated Jul. 22, 2015 issued in Application No. AU 2012212079.
Australian Patent Examination Report No. 1 dated Oct. 19, 2017, issued in Application No. AU 2016247159.
Australian Patent Examination Report No. 2 dated Jun. 1, 2018, issued in Application No. AU 2016247159.
Canadian Examination Report dated Nov. 22, 2017 issued in Application No. CA 2,825,691.
Chinese First Office Action dated Apr. 7, 2015 issued in Application No. CN 201280007593.3.
Chinese Second Office Action dated Nov. 17, 2015 issued in Application No. CN 201280007593.3.
Chinese Third Office Action dated Apr. 26, 2016 issued in Application No. CN 201280007593.3.
Chinese Fourth Office Action dated Oct. 17, 2016 issued in Application No. CN 201280007593.3.
Chinese Rejection Decision dated May 26, 2017 issued in Application No. CN 201280007593.3.
European Partial Supplementary Search Report dated May 8, 2015 issued in Application No. EP 12 741 997.6.
European Office Action dated Feb. 6, 2017 issued in Application No. EP 12 741 997.6.
European Examination Report dated Oct. 10, 2017 issued in Application No. EP 12 741 997.6.
Japanese Office Action dated Jan. 25, 2016 issued in Application No. JP 2013552645.
Japanese Office Action [no translation] dated Apr. 20, 2017 issued in Application No. JP 2016-145348.
Japanese Office Action [with English Translation] dated Dec. 1, 2017 issued in Application No. JP 2016-145348.
Korean Office action [with English translation] dated Jun. 18, 2018 issued in Application No. KR 10-2013-7023181.
Mexican First Office Action dated Nov. 6, 2015 issued in Application No. MX/a/2013/008651.
Mexican Second Office Action dated Mar. 23, 2016 issued in Application No. MX/a/2013/008651.
Mexican Third Office Action dated Jul. 15, 2016 issued in Application No. MX/a/2013/008651.
Mexican First Office Action dated Apr. 24, 2017 issued in Application No. MX/a/2016/015902.
Mexican First Office Action dated May 14, 2018 issued in Application No. MX/a/2017/072309, with English Translation.
Malaysia Office Action dated Sep. 30, 2016 issued in Application No. MY PI2013002880.
PCT International Preliminary Report on Patentability dated Oct. 30, 2014 issued in PCT/US2013/037261.
Australian Patent Examination Report No. 1 dated Apr. 20, 2016 issued in Application No. AU 2013249172.
Australian Examination Report No. 2 dated Jan. 25, 2017 issued in Application No. AU 2013249172.
Chinese First Office Action dated Jul. 7, 2016 issued in Application No. CN 201380031877.0.

(56) References Cited

OTHER PUBLICATIONS

Chinese Second Office Action dated Mar. 24, 2017 issued in Application No. CN 201380031877.0.
Chinese Rejection Decision dated Oct. 10, 2017 issued in Application No. CN 201380031877.0.
European Examination Report dated Mar. 6, 2017 issued in Application No. EP 13 778 920.2.
Japanese First Office Action dated Mar. 10, 2017 issued in Application No. JP 2015-507197.
Mexican First Office Action dated Jul. 27, 2017 issued in Application No. MX/a/2014/012552.
Singapore Search Report and Written Opinion dated Mar. 24, 2016 issued in Application No. SG 11201406711T.
PCT International Report on Patentability and Written Opinion of the International Searching Authority dated Apr. 5, 2016 issued in PCT/US2014/059161.
Singapore Search Report and Written Opinion dated Aug. 7, 2017 issued in Application No. SG 11201602638S.
PCT International Search Report and Written Opinion of the International Searching Authority dated Jan. 29, 2016 issued in Application No. PCT/US2015/039951.
PCT International Preliminary Report on Patentability and Written Opinion dated Jan. 10, 2017 issued in PCT/US2015/039951.
PCT International Search Report and Written Opinion of the International Searching Authority dated Jan. 3, 2017 issued in PCT/US2016/053979.
PCT International Search Report and Written Opinion of the International Searching Authority dated Jul. 18, 2016 issued in PCT/US2016/026265.
PCT International Preliminary Report on Patentability and Written Opinion of the International Searching Authority dated Oct. 19, 2017 issued in PCT/US2016/026265.
First Office Action, Substantice Examination Report—Stage I, for Indonesian Patent Application No. W00201302051, dated Apr. 5, 2018, with English translation.
Japanese Office Action dated Jun. 13, 2018, for Japanese Patent Application No. 2016-009933.
Second Office Action for Malaysian Patent Application No. PI 2013001587, dated Jun. 14, 2018.
Notice to File a Response for Korean Patent Application No. 10-2013-7013979, dated Jun. 18, 2018.
Second Office Action for EPO Application No. 11 785 851.4, dated Jun. 28, 2018.
First Office Action for Indian Patent Application No. 4315/DELNP/2013, dated Jul. 31, 2018.
First Communication from the examining division, dated Dec. 7, 2017 issued in European Patent Application No. 15747630.0.
Second Communication from the examining division, dated Jul. 27, 2018 issued in European Patent Application No. 15747630.0.
Australian Patent Examination Report No. 1 dated Apr. 24, 2018 issued in Application No. AU 2017206206.
European Supplementary Search Report dated Dec. 11, 2017, issued in Application No. EP 13 778 920.2.
Japanese Second Office Action dated Nov. 8, 2017 issued in Application No. JP 2015-507197, with English Translation.
Japanese First Office Action dated Mar. 20, 2018 issued in Application No. JP 2017-115071. No translation.
Japanese Final Office Action dated Oct. 10, 2018 issued in Application No. JP 2017-115071. No translation.
Thai Patent Application No. 1701006025, First Office Office Action, dated Jun. 1, 2018, and English translation of relevant portions thereof.
Intellectual Property Office of Singapore, Invitation to Respond to Written Opinion, dated Sep. 10, 2018 and Written Opinion dated Aug. 23, 2018, for SG Patent No. 11201708236Q.
European Supplementary Search Report dated Oct. 5, 2018 issued in Application No. Ep 16 717 062.0.
Japanese Final Office Action dated Aug. 1, 2018, issued in Application No. Jp 2015-507197, with English Translation.

Canadian Examination Report dated Oct. 31, 2018, issued in Application No. CA 2,825,691.
Indonesia Substantive Examination Report Stage II, dated Nov. 21, 2018, issued in Application No. ID W-00 2011 02343.
Japanese Final Office Action, dated Aug. 31, 2018 issued in Application No. JP 2016-145348, with English Translation.
PCT International Preliminary Report on Patentability dated Apr. 12, 2018 dated Jan. 3, 2017 issued in PCT/US2016/053979.
First Communication from the examining division, dated Jun. 6, 2018 issued in European Patent Application No. 16778977.5.
PCT Invitation to Pay Additional Fees from the International Searching Authority dated Mar. 8, 2018, issued in PCT/US2017/055392.
PCT International Search Report and Written Opinion of the International Searching Authority, dated May 11, 2018, issued in PCT/US2017/055392.
Japanese Final Office Action dated Aug. 22, 2018 issued in Japanese Application No. JP 2016-519765. No translation.
Japanese Office Action dated Jul. 31, 2018 issued in Japanese Application No. JP 2017-48186, in Japanese Only.
Canadian Examination Report dated Mar. 13, 2018 issued in Application No. CA 2,801,024.
Canadian Examination Report dated Mar. 22, 2018 issued in Application No. CA 2,801,057.
First Examination Report, dated Feb. 27, 2018, issued in Indian Patent Aplication No. 10998-DELNP-2012, with English translation.
Indonesian First Office Action dated Mar. 21, 2018 issued in Application No. W00201205194, English Translation Only.
Australian Patent Examination Report No. 2, dated Apr. 13, 2018, issued in Application No. AU 2016250460.
Korean Office Action dated Jul. 27, 2018, issued in Application No. KR 10-2017-7026170, with English translation.
European Office Action dated Aug. 7, 2018, issued in Application No. EP 11 787 552.6.
First Communication from the examining division, dated Aug. 21, 2018 issued in European Patent Application No. 11 158 642.6.
First Office Action, dated Dec. 4, 2018, issued in Japanese Patent Application No. JP2018-020280. No translation.
Second Office Action dated Dec. 5, 2018 issued in Japanese Application No. JP 2016-519765. No translation.
First Office Action, dated Nov. 26, 2018, issued in Chinese Patent Application No. CN 201480065275.1, with English Translation.
First Office Action, Substantice Examination Report—Stage I, dated Dec. 14, 2018, for Indonesian Patent Application No. P00201602983, with English Translation.
First Office Action, Substantice Examination Report—Stage I, dated Dec. 17, 2018, for Indonesian Patent Application No. P00201406246, with English Translation.
First Office Action, Jan. 8, 2019, for Japanese Patent Application No. JP2018-061680. No translation.
GenBank Accession No. AAC49269.1 "FatB2 [Cuphea hookeriana]", (Apr. 30, 1996), 2pp.
GenBank Accession No. ACQ42234.1 "Tbifunctional oleate 12-hydroxylase:desaturase [Physaria fendleri]", May 2009, Salywon et al.
GenBank Accession No. ALM22867.1 "lysophosphatidic acid acyltransferase 2 [Cuphea viscosissima]," Nov. 8, 2015, 2pp.
GenBank Accession No. ALM22871.8 "microsomal lysophosphatidic acid acyltransferase 2c [Cuphea avigera var. pulcherrima]," Nov. 8, 2015, 2pp.
GenBank Accession No. KT694311.1 "Cuphea avigera var. pulcherrima plastid lysophosphatidic acid acyltransferase 1 mRNA, complete cds; nuclear gene for plastid product," Nov. 8, 2015, 2pp.
GenBank Accession No. KT694310.1 "Cuphea viscosissima lysophosphatidic acid acyltransferase 2 mRNA, complete cds," Nov. 8, 2015, 2pp.
GenBank Accession No. KT694314.1 "Cuphea avigera var. pulcherrima microsomal lysophosphatidic acid acyltransferase 2c mRNA, complete cds," Nov. 8, 2015, 2pp.
GenBank: Accession No. L42851.1, "Prototheca wickerhamii large subunit ribosomal RNA (rrnL) gene, partial sequence; chloroplast

(56) References Cited

OTHER PUBLICATIONS gene for chloroplast product," Nov. 21, 2001. [retrieved from the Internet on Dec. 23, 2009 at http://www.ncbi.nlm.nih.gov/nuccore/17028073].
Geneseq: Database Accession No. AED66345, CN1618976, May 25, 2005, Zhang et al., 11pp.
GenBank Accession No. M94159.1 "California Bay Tree thioesterase mRNA, complete cds", (Apr. 27, 1993), 2pp.
GenBank: "Codon Usage Database file for Chlorella vulgaris," Jun. 2007. [Retrieved from the Internet Aug. 26, 2010: ,URL: http://www.kazusa.or.jp/coldo/cgi-bin/showcodon.cgi?species=3077] 2pp.
GenBank: U31813 "Cinnamomum camphora acyl-ACP thioesterase mRNA, complete cds," Jan. 31, 1996, 2pp.
Geneseq: Database Accession No. AXE01814, "Palmitic acid production-related gene, SEQ:20024," XP002750550, Oct. 14, 2010.
Geneseq: Database Accession No. ADJ49365, "Oil-associated gene related protein #865," XP002750551, Jun. 15, 2007.
UNIPROT Database publication; Borza et al., SubName: Plastid acyl-[acyl-carrier protein] desaturase. AC No. Q5IWZ3, Feb. 15, 2005, URL: http://www.genome.jp/dbget-bin/www_bget?uniprot:Q5IWZ3_PROWI, 1 page.
UNIPROT Accession No. P41758. Phosphoglycerate kinase, chloroplastic. Jul. 22, 2008. [Retrieved from the Internet Aug. 25, 2010: <http://http://www.uniprot.org/uniprot/P41758.txt?version=44>]: amino acids 1-60.
UNIPROT Accession No. P41758. Phosphoglycerate kinase, chloroplastic. Nov. 25, 2008. [Retrieved from the Internet Aug. 12, 2010: <http://www.uniprot.org/uniprot/P41758.txt?version=46>].
Geneseq: Database Accession No. AF060519.2, Dehesh, K. et al., "Cuphea Hookeriana 3-ketoacyl-ACP synthase (Kas4) mRNA, complete cds," May 22, 2003.
Geneseq: Database Accession No. AWK61076, "Nucleotide sequence SEQ ID 134280," retrieved from EBI accesion No. GSB:AWK61076, Oct. 29, 2009.
Geneseq: Database Accesion No. BAN54762, "Plasmid pSZ1491 DNA contrct, SEQ ID 232," retrieved from EBI accession No. GSB;BAN54762, Jun. 20, 2013.
Abate et al., (1987) "Production of ethanol by a flocculent Saccharomyces sp. In a continuous upflow reactor using sucrose, sugar-cane juice, and molasses as the carbon source," *MIRCEN Journal*, 3:401-409.
Abbadi et al., (2000) "Knockout of the regulatory site of 3-ketoacyl-ACP synthase III enhances short-and medium-chain acyl-ACP synthesis," *The Plant Journal*, 24(1): 1-9.
Alvarez et al., (2002) "Triacylglycerols in prokaryotic microorganisms," *Appl Microbiol Biotechnol*, 60(4): 367-376.
Angerbauer et al., (2008) "Conversion of sewage sludge into lipids by Lipomyces starkeyl for biodiesel production," Bioresource Technology, 99(8):3051-3056.
Anonymous, (Mar. 2010) "Hydroprocessing Oils," IP.com.2010, 10:118-117 [Electronic publication date: Mar. 24, 2010 (IPCOM000194448D)].
Beld et al., (Oct. 23, 2014) "Versatility of acyl-acyl carrier protein synthetases," *Chem. Biol.*, 21(10): 1293-1299.
Biello et al., (2008) "Biofuel of the Future: Oil from Algae," Scientific American, 4pp. [Retrieved from the Internet Mar. 9, 2015: <URL:http://www.scientificamerican.com/article/biofuel-of-the-future>].
Bognar, A. (1998) "Comparative study of frying to other cooking techniques influence on the nutritive value," *Grasas y Aceites*, 49(3-4);250-260.
Bohacenko et al., (2001) "Detection of Olive Oils Authenticity by Determination of their Sterol Content using LC/GC," *Czech J. Food Sci.*, 19(3):97-103.
Bouchard et al., (1989) "Characterization of Depolymerized Cellulosic Residues," *Wood Sci. Technol.*, 23:343-355.
Broun et al., (1998) "A bifunctional oleate 12-hydroxylase: desaturase from Lesquerella fendleri," *The Plant Journal*, 13(2):201-210.
Butzen et al., (2007) "High Oleic Soybean," *Crop Insights*, 17(17):3pp [Retrieved on Dec. 3, 2008 from www.McCormickcompany.net].

Cahoon et al., (1998) "A Determinant of Substrate Specificity Predicted from the Acyl-Acyl Carrier Protein Desaturase of Developing Cat's Claw Seed," *Plant Physiol.*, 117:593-598.
Campbell et al., (1990) "Codon Usage in Higher Plants, Green Algae, and Cyanobacteria," *Plant Physiol.*, 92:1-11.
Canakci et al., (2001) "Biodiesel production from oils and fats with high free fatty acids," *Transaction of the ASABE*, 44(6): 1429-1436.
Cantrill et al., (2008) "Phytosterols, Phytostanols and their esters (Chemical and Technical Assessment)," *Proceedings of 69th JEFCA*, pp. 1-13.
Chang et al., (2004) "Deletion of the Δ12-oleic acid desaturase gene of a nonaflatoxigenic Aspergillus parasiticus field isolate affects conidiation and sclerotial development," *Journal of Applied Microbiology*, 97:1178-1184.
Chen et al., (1996) "Heterotrophic Growth of Chlamydomonas reinhardtii on Acetate in Chemostat Culture," *Process Biochemistry*, 31(6):601-604.
Chen et al., (2011) "Structural classification and properties of ketoacyl synthases," *Protein Science*, 20(10):1659-1667.
Chisti et al., (2007) "Biodiesel from microalgae," *Biotechnology Advances*, 25(3):294-306.
Chi et al., (Apr. 2008) "Fatty Acid Biosynthesis in Eukaryotic Photosynthetic Microalgae: Identification of a Microsomal Delta 12 Desaturase in *Chlamydomonas reinhardtii*," *The Journal of Microbiology*, 46(2):189-201.
Cook et al., (1967) "Photo-Assimilation of Acetate by an Obligate Phototrophic Strain of Euglena gracilis," *Publication, J. Protozool.*, 14(3):382-384.
Covello et al., (1996) "Functional Expression of the Extraplastidial *Arabidopsis thaliana* Oleate Desaturase Gene (*FAD2*) in *Saccharomyces cerevisiae,*" *Plant Physiol.*, 111:223-226.
Croft et al., (2006) "MINIREVIEWS- Algae Need Their Vitamins," *Eukaryotic Cell*, 5(8):1175-1183 [Downloaded from http://ec.asm.org/on Sep. 27, 2017].
Croft et al., (2007) "Thiamine biosynthesis in algae is regulated by riboswitches," *Proceedings of the National Academy of Sciences of the United States of America*, 104(52):20770-20775.
Curtain, (2000) "Plant Biotechnology—The growth of Australia's algal b-carotene industry," *Australasian Biotech.*, 10(3):19-23. Retrieved from the Internet Apr. 5, 2010:, <http://www.bioline.org.br/request?au00032>1.
Dai et al., (2007) "Biodiesel generation from oleaginous yeast Rhodotorula glutinis with xylose assimilating capacity," *African Journal of Biotechnology*, 6(18):2130-2134.
Dehesh et al., (2001) "Overexpression of 3-Ketoacyl-Acyl-Carrier Protein Synthase IIIs in Plants Reduces the Rate of Lipid Synthesis," *Plant Physiology*, 125:1103-1114.
Demirbas et al., (2003) "Fuel Conversional Aspects of Palm Oil and Sunflower Oil," *Energy Sources*, 457-466.
Deng et al., (2001) "Ionic Liquid as a Green Catalytic Reaction Medium for Esterifications," *J. Mol. Catalysis A: Chemical*, 165:33-36.
Desmond, (2009) "Phylogenomics of Sterol Synthesis: Insights into the Origin, Evolution, and Diversity of a Key Eukaryotic Feature," *Genome Biol. Evol.*, 1:364-381.
Elumalai et al., (2011) "Optimizatin of abiotic conditions suitable for the production of biodiesel from Chlorella vulgaris," *Indian J. Sci. Technol.*, 4(2):91-97.
Erhan et al., (Mar. 2000) "Lubricant basestocks from vegetable oils," *Industrial Crops and Products*, 11(2-3):277-282.
Facciotti et al., (May 1998) "Molecular dissection of the plant acyl-acyl carrier protein thioesterases," *Fett/Lipid, LIPID-WEINHEIM*, 100(4-5), S.:167-172. [<URL:http://www.researchgate.net/publication/247961590>].
Florencio, et al., (1998) "A factorial approach for a sugarcane juice-based low cost culture medium: increasing the astaxanthin production by the red yeast *Phaffia rhodozyma*," Bioprocess and Biosystems Engineering, 19(3): 161-164.
Fukuda et al., (2001) "Biodiesel Fuel Production by Transesterification of Oils," *J. Biosci. Bioeng.*, 92(5):405-416.
Gabay et al., (2010) "Stigmasterol: a phytosterol with potential anti-osteoarthritic properties," *Osteoarthritis and Cartilage*, 18:106-116.

(56) References Cited

OTHER PUBLICATIONS

Garay et al., (2014) "Accumulation of High-Value lipids in Single-Cell Microorganisms: A Mechanistic Approach and Future Perspectives," *J. of Agric. and Food Chem.*, 62:2709-2727.
Garrote et al., (2001) "Manufacture of Xylose-Based Fermentation Media from Corncobs by Posthydrolysis of Autohydrolysis Liquors," *Appl Biochem Biotechnol*, 95(3):195-207.
Ghose et al., (1979) "Rapid Ethanol Fermentation of Cellulose Hydrolysate. I. Batch Versus Continuous Systems," *Biotechnology Bioengineer*, XXI:1387-1400.
Gouveia et al., (1996) "Microalgal biomass as a sustainable alternative raw material," *Argo Food Industry Hi-Tech, Teknoscience*, 7(3):29-34.
Guo et al., (2009) "Increase in nervonic acid content in transformed yeast and transgenic plants by introduction of a Lunaria annua L. 3-ketoacyl-CoA synthase (KCS) gene," *Plant Mol. Biol.*, 69:565-575.
Gusakov et al., (2007) "Design of Highly Efficient Cellulase Mixtures for Enzymatic Hydrolysis of Cellulose," *Biotechnol. and Bioengineering*, 97(5):1028-1038.
Ha et al., (2011) "Engineered *Saccharomyces* cerevisiae capable of simultaneous cellobiose and xylose fermentation," PNAS, 108(2):504-509.
Haas et al., (2007) "The General Applicability of in Situ Transesterification for the Production of Fatty Acid Esters from a Variety of Feedstocks," *J. Am Oil. Chem. Soc.*, 84:963-970.
Hahn-Hägerdal et al., (2007) "Towards industrial pentose-fermenting yeast strains," *Appl Microbiol Biotechnol*, 74:937-953.
Hase et al., (1964) "Nutritional Control of Cell Pigmentation in *Chlorella Protothecoides* With Special Reference to The Degeneration of Chloroplast Induced by Glucose," Plant and Cell Physiology, 5(2):227-240, Abstract, 2pp. [Retrieved on Jun. 3, 2010 from http://pcp.oxfordjounals.org/cgi/content/abstract/5/2/227].
Helmensteine, (2011) "Gasoline and Octane Ratings," About.com, Chemistry, 1 page. [Retrieved from the Internet Oct. 3, 2011: <URL: http://chemistry.about.com/cs/howthingswork/a/aa070401a.htm>].
Hitoshi Funahashi et al., (1999) "Effects of pH Shift and Agitation Speed on Chlorophyll Biosynthesis in Heterotrophic Culture of Chlorella," *Yamaguchi University, Department of Applied Chemistry and Chemical Engineering*, 25(2):214-219.
Hodge, (2006) "Chemistry and Emissions of NExBTL," *Neste Oil*. [Retrieved from the Internet Jan. 10, 2012: <http://bioenergy.ucdavis.edu/downloads/Neste_NExBTL_Enviro_Benefits_ofparaffins.pdf>], pp. 4.
Hortensteiner et al., (2000) "Chlorophyll breakdown in Chlorella protothecoides: characterization of degreening and cloning of degreening-related genes," Plant Molecular Biology, 42:439-450.
Hsieh et al., (1998) "A PII-like Protein in *Arabidopsis*: Putative Role in Nitrogen Sensing," *Proc Natl Acad Sci USA*, 95(23):13965-13970.
Hsieh et al., (2012) "Accumulation of Lipid Production in *Chlorella minutissima* by Triacylglycerol Biosynthesis-Related Genes Cloned from *Saccharomyces cerevisiae* and *Yarrowia lypolytica*," *The Journal of Microbiology*, 50(3):526-534.
Huang et al., (1979) "Sterols as ecological indicators," *Geochimica et Cosmochimica Acta*, 43:739-745.
Huber et al., (2005) "Production of Liquid Alkanes by Aqueous-Phase Processing of Biomass-Derived Carbohydrates," *Science*, 308:1446-1450.
Huber et al., (2006) "Synthesis of Transportation Fuels from Biomass: Chemistry, Catalysts, and Engineering," *Chem. Rev.*, 106:4044-4098.
Husic et al., (1986) "Effect of Osmotic Stress on Carbon Metabolism in *Chlamydomonas reinhardtii*," *Plant. Physiol.*, 82(2):594-596.
Itoh et al., (Apr. 1973) "Sterol Composition of 19 Vegetable Oils," *Journal of the American Oil Chemists' Society*, 5:122-125.
Iwasaki et al., (2000) "Enzymatic synthesis of structured lipids," *Journal of Molecular Catalysis B: Enzymatic*, 10:129-140.
Jeoh et al., (2007) "Cellulase Digestibility of Pretreated Biomass Is Limited by Cellulose Acessibility," *Biotechnol Bioeng.*, 98(1):112-122.
Kamurthy et al. (2013) "Antinocieptive Activity of Stigmosterol-3-Glyceryl-2-Linoleiate, Campesterol and Daucosterol Isolated From *Aerva Lanata* Linn. Aerial Parts," *Asian J Pharm Clin Res*, 6(1): 149-152.
Kessler et al., "Physiological and Biochemical Contributions to the Taxonomy of the Genus Prototheca III. Utilization of Organic Carbon and Nitrogen Compounds," *Arch Microbiol*, 132:103-106, (1982).
Kihlberg et al., (1972) "Nutritive Value, Effect," *The Microbe as a Source of Food, Department of Applied Microbiology*, Karolinska Institutet, Stockholm, Sweden, p. 440.
Klosty et al., (1952) "Sterols of Algae, The Occurrence of Ergosterol in Chiorelia pyrarwidosa," *J Am Chem. Soc., Notes*, 74(6): 1601-1601.
Knothe, (2006) "Analyzing Biodiesel: Standards and Other Methods," *JAOCS*, 83(10):823-833.
Khozin-Goldberg et al. (2011) "Unravelling algal lipid metabolism: Recent advances in gene identification," *BIOCHEMIE*, 93:91-100.
Kosa et al., (Feb. 2011) "Lipids from heterotrophic microbes: advances in metabolism research," *Trends in Biotechnology*, 29(2):53-61.
Kris-Etherton et al., (1999) "Monounsaturated Fatty Acids and Risk of Cardiovascular Disease," *Circulation*, 100:1253-1258.
Kuo et al., "Diversity of Oleic Acid, Ricinoleic Acid and Linoleic Acid Conversions Among Pseudomonas aeruginosa Strains," *Current Microbiology*, 49:261-266, (2004).
Lahaye, (1991) Marine Algae as Sources of Fibres: Determination of Soluble and Incoluble Dietary Fibre Contents in Some 'Sea Vegetables', *J. Sci. Food Agric.* 54:587-594.
La Scala et al., (2002) "The effect of fatty acid composition on the acrylation kinetics of epoxidized triacylglycerols," *Journal of the American Oil Chemists' Society*, 79(1):59-63.
Lalonde et al., (1999) "The Dual Function of Sugar Carriers: Transport and Sugar Sensing," *The Plant Cell*, 11:707-726.
Lammens et al., (2006) "Arabidopsis thaliana cell wall invertase in complex with ligands," *HASYLAB, Annual Report 2006, Part II, Scientific User Contributions Part II, Protein Crystallography at EMBL Beamlines*, pp. 61-62. [Retrieved from the Internet Aug. 21, 2012: <http://hasyweb.desy.de/science/annual_reports/2006_report/part2/contrib/72/17730.pdf>].
Lapidot et al., (2002) "Stable Chloroplast Transformation of the Unicellular Red Alga Porphyridium Species," *Plant Physiol*, 129:7-12.
Lara et al., (2004) "Extracellular Invertase Is an Essential Component of Cytokinin-Mediated Delay of Senescence," *The Plant Cell*, 16:1276-1287.
Leonard et al., (Mar. 1998) A *Cuphea* β-ketoacyl-ACP synthase shifts the synthesis of fatty acids toward shorter chains in *Arabidopsis* seeds expressing *Cuphea* FatB thioesterases, *The Plant Journal*, 13(5):621-628.
Li et al., (2002) "Isolation and Purification of Lutein from the Microalga *Chlorella vulgaris* by Extraction after Saponification," *J. Agric. Food Chem.*, 50(5):1070-1072.
Li et al., (2007) "Enzymatic synthesis of biodiesel oil into yeast," *The Chinese Journal of Process Engineering*, 7(1):137-140 [machine translation by Google translation (online)].
Li et al., (2007) "Large-scale biodiesel production from microalga Chlorella protothecoides through heterotrophic cultivation in bioreactors," *Biotechnology and Bioengineering*, 98(4):764-771.
Li et al., (2008) "Biofuels from Microalgae," Articles: Biocatalysts and Bioreactor Design, *Biotechnol. Prog*, 24(4):815-820.
Li et al., (2008) "Perspectives of microbial oils for biodiesel production," *Appl. Microbiol. Biotechnol.*, 80(5):749-756. [Abstract Only].
Liang et al., (2004) "Current microalgal health food R & D activities in China," *Hydrobiologia*, 512:45-48.
Liu et al., (2007) "Biodiesel production by direct methanolysis of oleaginous microbial biomass," *Journal of Chemical Technology and Biotechnology*, 82(8):775-780.

(56) References Cited

OTHER PUBLICATIONS

Liu et al., (2013) "Lipid metabolism in microalgae distinguishes itself," *Current Opinion in Biotechnology*, 24:300-309.
Lord, (2008) "Taurine is essential for cats," [retrieved from the Internet Apr. 6, 2010 at http://www.vetlord.org/taurine-is-essential-for-cats/], 9pp.
Lu et al., (2008) "Overproduction of free fatty acids in *E. coli*: Implications for biodiesel production," *Metabolic Engineering*, 10:333-339.
Lu et al., (2009) "Molecular cloning and stress-dependent expression of a gene encoding $\Delta^{12}$-fatty acid desaturase in the Antartic microalga *Chlorella vulgaris* NJ-7," *Extremophiles*, 13: 875-884.
Liu et al., (Sep. 2012) "High-oleic canola oils and their food applications," [Retrieved from www.aocs.org], 4 pages.
Lv, Hexin et al., (2013) "Transcriptome analysis of *Chlamydomonas reinhardtii* during the process of lipid accumulation," *Genomics*, 101:229-237.
Matsuka et al., (1966) *Plant and Cell Physiol.*, 7:149-162.
Meguro et al., (2001) "Original Communication Solubilization of phytosterols in diacylglycerol versus triacylglycerol improves the serum cholesterol-lowering effect," *European Journal of Clinical Nutrition*, 55:513-517.
Miao et al., (2006) "Biodiesel Production From Heterotrophic Microalgal Oil," *Biosource Technology*, 97(06): 841-846.
Mitsuda, (1973) "Protein Isolates From *Chlorella* Algae, *Torula* Yeasts, and Hydrocarbon-Assimilating Microorganisms," *Nutr. Sci. Vitaminol.*, 19:1-13.
Moon et al., (2013) "Mixotrophic growth with acetate or volatile fatty acids maximizes growth and lipid production in Chlamydomonas reinhardtii," *Algal Research*, 2:235-357.
Muller et al., (1997) "Nitrogen and hormonal responsiveness of the 22 kDa alpha-zein and b-32 genes in maize endosperm is displayed in the absence of the transcriptional regulator Opaque-2," *Plant J.*, 12(2):281-291. [Abstract only].
Neish et al., (1951) "Carbohydrate Nutrition of *Cholorella Vulgaris*," *Canadian Journal of Botany*, 29:68-78.
Nes et al., (1990) "Sterol phylogenesis and algal evolution," *Proc Natl Acad Sci USA*, 87(19):7565-7569.
Nes et al., (2011) "Biosynthesis of Cholesterol and Other Sterols," *Chem Rev.*, 111:6423-6451.
Norton et al., (1991) "Identification of Ergosta-6(7),8(14),25(27)-trien-3β-ol and Ergosta-5(6),7(8),25(27),-trien-3β-ol, Two New Steroidal Trienes Synthesized by Prototheca wicherhamii," *Lipids*, 26:247-249.
O'Grady et al., (2011) "Heterotrophic growth and lipid production of Chlorella protothecoides on glycerol," *Bioprocess Biosyst Eng*, 34:121-125.
Orthoefer, Frank T. (May 2005) "Performance of trans-free vegetable oils in shortenings and deep-fat frying," *Lipid Technology*, 17(5):101-106.
Otles et al., (2001) "Fatty Acid Composition of Chlorella and Spirulina Microalgae Species," *Journal of AOAC International*, 84(6): 1708-1714.
"Pamuyu/Pamu Kakuyu No Riyo, [translated as: Utilization of Palm Oil/Palm Kernel Oil]," Jul. 31, 1990, pp. 112-121. [no translation].
Papanikolaou et al., (2004) "The effect of raw glycerol concentration on the production of 1,3-propanediol by *Clostridium butyricum*," *J. Chem. Technol. Biotechnol.*, 79:1189-1196.
Patterson et al. (1967) "Sterols of Chlorella. II. The Occurrence of an Unusual Sterol Mixture in Chlorella vulgaris," *Plant Physiol.*, 42:1457-1459.
Patterson et al. (1969) "Sterols of Chlorella. III. Species Containing Ergosterol," *Comp. Biochem. Physiol.*, 31:391-394.
Pidkowich et al., (Mar. 13, 2007) "Modulating seed β-ketoacyl-acyl carrier protein synthase II level converts the composition of a temperate seed oil to that of a palm-like tropical oil," *PNAS*, 104(11):4742-4747.
Puglia et al., (2008) "In viva spectrophotometric evaluation of skin barrier recovery after topical application of soybean phytosterols," *J. Cosmet. Sci.*, 59:217-224.

Quinchia et al., (May 2012) "Low-temperature flow behaviour of vegetable oil-based lubricants," *Industrial Crops and Products*, 37(1):383-388.
Radakovits et al., (2011) "Genetic engineering of fatty acid chain length in *Phaeodactylum tricornutum*," *Metabolic Engineering*, 13:89-95.
Rastogi et al., (1997) "Footprinting of the spinach nitrite reductase gene promoter reveals the preservation of nitrate regulatory elements between fungi and higher plants," *Plant Mol. Biol.*, 34(3):465-476. [Abstract only].
Roscoe et al., (2001) "Mutations in the fatty acid elongation 1 gene are associated with a loss of beta-ketoacyl-CoA synthase activity in low erucic acid rapeseed," *FEBS Letters*, 492:107-111.
Sakai et al., (2007) "Effect of Lignocellulose-Derived Inhibitors on Growth of and Ethanol Production by Growth-Arrested *Corynebacterium glutamicum R*," *Applied and Environmental Microbiology*, 73(7):2349-2353.
Sakhno, (2010) "Fatty acid composition variability of rapeseed oil: Classical breeding and biotechnology (in Russian)", *Cytology and Genetics*, No. 6:70-80, [English Abstract on p. 77].
Salou et al., (1994) "Growth and Energetics of *Leuconostoc oenos* during Cometabolism of Glucose with Citrate or Fructose," *Applied and Environmental Microbiology*, 60(5):1459-1466.
Sansawa et al., (2004) "Production of Intracellular Phytochemicals in Chlorella under Heterotrophic Conditions," *Journal of Bioscience and Bioengineering*, 98(6):437-444.
Schechter et al., (1974) "Relations between Structure and Function in Cytoplasmic Membrane Vesicles Isolated from an *Escherichia coli* Fatty-Acid Auxotroph," *Eur. J. Biochem*, 49:61-76.
Schomburg et al., (eds.) (2013) "A12-fatty-acid desaturase," *Springer Handbook of Enzymes S8, Class 1 Oxidoreductases: EC 1*, 668-678.[DOI 10.1007/978-3-642-36265-1_97].
Schütt et al., (2002) "β-Ketoacyl-acyl carrier protein synthase IV: a key enzyme for regulation of medium-chain fatty acid synthesis in Cuphea lanceolata seeds," *Planta*, 215:847-854.
Sheehan et al., (1998) "A Look Back at the U.S. Department of Energy's Aquatic Species Program: Biodiesel from Algae," *NREL/TP-580-24190*.
Shen et al., (2010) "Heterotrophic Culture of *Chlorella protothecoides* in Various Nitrogen Sources for Lipid Production," *Appl Biochem Biotechnol*, 160:1674-1684.
Shetty et al., (1978) "Effect of Thiol Reagents on Extractability of Protein from Yeast," *Biotechnology and Bioengineering*, John Wiley & Sons, Inc. XX:755-756.
Shi et al., (2000) "Heterotrophic production of biomass and lutein by *Chlorella protothecoides* on various nitrogen sources," *Enzyme and Microbial Technology*, 27:312-318.
Shi et al., (2001) "High Yield Production of Lutein by Heterotrophic *Chlorella Protothecoides* in Fed-Batch Systems," *Algae and their Biotechnological Potential, Kluwer Academic Publishers*, pp. 107-119.
Shi et al., (1999) "Production of biomass and lutein by *Chlorella protothecoides* at various glucose concentrations in heterotrophic cultures," *Process Biochemistry*, 34:341-347.
Singh et al., (2015) "An Introduction to Microalgae: Diversity and Significance," Chapter 2, *Handbook of Marine Microalgae, Biotechnology Advances*, Editor: Kin, Se-Kwon, Publisher: *Elsevier Ltd., London, UK*, 15pp.
Snyder et al., (2009) "Acyltransferase action in the modification of seed oil biosynthesis," *New Biotechnology*, 26(1/2): 11-16.
Son et al., (1999) Induction and Cultures of Mountain Ginseng Adventitious Roots and AFLP Analysis for Identifying Mountain Ginseng,: *Biotechnol. Bioprocess Eng.*, 4:119-123.
St. Onge et al., (2002) "Physiological effects of medium-chain triglycerides: potential agents in the prevention of obesity," *Nutrition*, 132:329-332.
Sturchler-Pierrat et al., (Nov. 1997) "Two amyloid precursor protein transgenic mouse models with Alzheimer disease-like pathology," *Proc. Natl. Acad. Sci. USA*, 94:13287-13292.
Subramaniam et al., (2010) "Microbial lipids from renewable resources: production and characterization," *J Ind Microbiol Biotechnol*, 37:1271-1287.

(56) References Cited

OTHER PUBLICATIONS

Takaku et al., (2001) "Isolation of an Antitumor Compound from *Agaricus blazei* Murill and Its Mechanism of Action," *J. Nutr.*, 131:1409-1413. [Retrieved from the Internet May 14, 2013: ,URL: http://jn.nutrition.org.].
Takashima et al., (1964) "Further Notes on the Growth and Chlorophyll Formation of *Chlorella Protothecoides*," *Plant & Cell Physiol.*, 5:321-332.
Takeda, (1991) "Sugar Composition of the Cell Wall and the Taxonomy of *Chlorella (Chlorophyceae)*," *Journal of Psychology*, 27(2):224-232, Online Abstract, 2pp. [Retrieved on Jun. 4, 2010 at http://www3.interscience.wiley.conm/journal/119345932/abstract].
Takeno et al. (2005) "Improvement of the fatty acid composition of an oil-producing filamentous fungus, *Moritierella alpina* 1S-4 through RNA interference with Δ12-desaturase gene expression," *Appl. Environ. Microbiol.*, 71(9):5124-5128.
Tan et al., (1997) "Saponified Palm Kernel Oil and Its Major Free Fatty-Acids as Carbon Substrates for the Production of Polyhydroxyalkanoates in Pseudomonas-Putida Pga 1," *Applied Microbiology and Biotechnology*, 47(3):207-211.
Tasaki et al., (1977) "Digestibility of Yellow Chlorella in Suckling Goat Kids," *The Japanese Journal of Zootechnical Science*, 48(11):661-663.
Taylor et al., (1995) "Continuous Fermentation and Stripping of Ethanol," *Biotechnol. Prog.*, 11(6):693-698.
Thavarungkul et al., (1999) "Batch injection analysis for the determination of sucrose in sugar can juice using immobilized invertase and thermometric detection," *Biosensors & Biolectronics*, 14:19-25.
"The Artisan Rototherm®," (2011) Artisan Industries Inc., Bulletin 9904, 2 pp. [Retrieved from the Internet Dec. 14, 2011:<URL: http://artisanind.com/ps/docs/rototherm.pdf>].
Thiry et al., (2002) "Optimizing scale-up fermentation processes," *Trends in Biotechnology*, 20:103-105.
Van De Loo et al., (1995) "An oleate 12-hydroxylase from Ricinus communis L. is a fatty acyl desaturase homolog," *Proc. Natl. Acad. Sci. USA*, 92:6743-6747.
Van Gerpen, (2005) *Fuel Processing Technology*, 86:1097-1107.
Van Gerpen, "Commercial Biodiesel Production," Oilseed and Biodiesel Workshop, Billings, Montana, Jan. 9, 2008, downloaded from http://www.deq.state.mt.us/Energy/bioenergy/Biodiesel_Production_Educ_Presentations/10 Montana Production Jan. 2008 JVP.pdf on Mar. 10, 2010.
Volkman et al., (2003) "Sterols in microorganisms," *Appl Microbial Biotechnol*, 60:495-506.
Wang et al., (Jun. 1998) *Principle and Technology of Plant Genetic Engineering, Beijing: Science Press*, pp. 34-35 [19pp].
Wang et al., (2004) "Quantitative estimate of the effect of cellulase components during degradation of cotton fibers," *Carbohydr. Res.*, 339(4):819-824.
Weber et al., (2000) "Invertases and life beyond sucrose cleavage," *Trends in Plant Science*, 5(2):47-48.
Wei et al., (2008) "Enhanced production of lutein in heterotrophic *Chlorella protothecoides* by oxidative stress," Sci China Ser C-Life Sci, 51(12):1088-1093.
Whittle et al., (2001) "Engineering Δ9-16:0-Acyl Carrier Protein (ACP) Desaturase Specificity Based on Combinatorial Saturation Mutagenesis and Logical Redesign of the Castor Δ9-18:0-ACP Desaturase," The Journal of Biological Chemistry, 276(24):21500-21505.
Wyman et al., (2005) "Comparative Sugar Recovery Data From Laboratory Scale Application of Leading Pretreatment Technologies to Corn Stover," *Bioresour Technol.*, 96(18):2026-2032.
Xu et al., (2006) "High quality biodiesel production from a microalga *Chlorella protothecoides* by heterotrophic growth in fermenters," *Journal of Biotechnology*, 126:499-507.
Zhang et al., (1999) "A kinetic model for lutein production by the green microalga *Chlorella protothecoides* in heterotrophic culture," *Journal of Industrial Microbiology & Biotechnology*, 23:503-507.
Zhao et al., (2005) "Toward cheaper microbial oil for biodiesel oil," *China Biotechnology*, 25(2):8-11.
Branch, Andrea D., "A Good antisense molecule is hard to find", TIBS, (Feb. 1998), 23:45-50.
Kozak, Marilyn, "Initiation of Translation in Prokaryotes and Eukaryotes", Gene, (Jul. 8, 1999), 234:187-208.
Zhou et al., "Global analysis of Gene transcription regulation in prokaryotes", *Cell Mol Life Sci*, (Aug. 21, 2006), 63(19-20):2260-2290.
Sadowski, M.I. et al., "The Sequence-Structure relationship and protein function prediction", *Current Opinion in Structural Biology*, (May 4, 2009), 19:357-362.
Branden, Carl and John Tooze, *Introduction to Protein Structure*, (Jul. 1, 1991), Garland Publishing Inc., New York, p. 247.
Gunstone, Frank D., "Minor Specialty Oils," Chapter 5, *Nutraceutical and Specialty Lipids and their Co-Products*, ed. Shahidi Fereidoon, CRC Press, Published Mar. 14, 2006, p. 91-125.
Adubofuor, J. et al. "Nutrient composition of Allanblackia Paviflora seed kernels and oil compared with some plant fats and oils and application of the oil in soap preparation", *Journal of Cereals and Oil Seeds*, (Feb. 2013), vol. 4(1), pp. 1-9, Available online at http://www.academicjournals.org/JCO, DOI: 10.5897/JCO12.020.

MICROBIAL OILS WITH LOWERED POUR POINTS, DIELECTRIC FLUIDS PRODUCED THEREFROM, AND RELATED METHODS

CROSS-REFERENCE TO RELATED APPLICATIONS

This application is a divisional of U.S. application Ser. No. 15/179,253, filed Jun. 10, 2016, which is a continuation of U.S. application Ser. No. 14/730,671, filed Jun. 4, 2015 (now patented as U.S. Pat. No. 9,388,435, issued Jul. 12, 2016), which is a continuation of U.S. application Ser. No. 13/288,815, filed Nov. 3, 2011 (now patented as U.S. Pat. No. 9,066,527, issued May 17, 2012), which claims the benefit under 35 U.S.C. 119(e) of prior U.S. Provisional Application No. 61/546,932, filed Oct. 13, 2011; prior U.S. Provisional Application No. 61/522,231, filed Aug. 10, 2011; prior U.S. Provisional Application No. 61/438,966, filed Feb. 2, 2011; and prior U.S. Provisional Application No. 61/409,902, filed Nov. 3, 2010, which are all hereby incorporated by reference in their entireties.

REFERENCE TO A SEQUENCE LISTING

This application includes an electronic sequence listing in a file named "14730671-Sequence.txt", created on Jan. 16, 2019 and containing 229,296 bytes, which is hereby incorporated by reference in its entirety for all purposes.

FIELD OF THE INVENTION

The present invention relates to the production of oils from microorganisms and methods for processing those oils to improve their pour points, as well as products derived from them, including food oil and foods comprising such oil and industrial products such as lubricants and dielectric fluids. Embodiments of the invention therefore relate to the fields of chemistry, particularly oleochemistry, food oils and their production and use, lubricants and their production, dielectric fluids, feedstocks and their production, microbiology, and molecular biology.

BACKGROUND

Fossil fuel is a general term for buried combustible geologic deposits of organic materials, formed from decayed plants and animals that have been converted to crude oil, coal, natural gas, or heavy oils by exposure to heat and pressure in the earth's crust over hundreds of millions of years. Fossil fuels are a finite, non-renewable resource.

Many industries, including plastics and chemical manufacturers, rely heavily on the availability of hydrocarbons as a feedstock for their manufacturing processes.

PCT Pub. Nos. 2008/151149 describe methods and materials for cultivating microalgae for the production of oil, extraction of microbial oil, and production of food, food oil, fuels, and other oleochemicals from oil produced by oleaginous microbes.

One important oleochemical application is the production of industrial dielectric fluids, which are used for electrical insulation and cooling or heat dissipation in transformers and other electrical devices. These electrical devices include power and distribution transformers, circuit breakers, capacitors, switchgear, X-ray machines and insulating cables.

Bio-based oil, particularly high-oleic acid soybean oil, has been used as a dielectric fluid in sealed transformers since the 1990s (see Srivastava (2009) *Int'l J Computer Electrical Eng*, v. 1(2) pp. 212-216). Current bio-based dielectric fluids are purified, high-oleic triacylglycerols (TAGs) with incorporated additives (see U.S. Pat. No. 6,274,067 and US Patent App. Nos 20100243969 and 20080283803). For example, the primary benefits of high-oleic acid soybean oil dielectric fluid versus mineral oil-based dielectric fluid are (i) an increased fire point (2×), (ii) an increased transformer life (4-8×), and (iii) a lower cost of remediating spills due to bio-based oil's high biodegradability (>3×) and lower toxicity (see Schneider (2006) *J Sci Food Agric*, v. 86 pp: 1769-1780).

The primary disadvantages of bio-based oils over mineral-based oils are the oxidative instability of bio-based oils, the increased cost of procuring bio-based oils and transitioning equipment from mineral-based oils to bio-based oils see Schneider (2006), supra). Although bio-based dielectric fluids occupy a significant portion of the dielectric fluid market, mineral-oil based dielectric fluids currently dominate the market. Another significant disadvantage is the cost of production of these soy-based oils and their diversion of an important food source into non-food applications.

SUMMARY

In certain embodiments, the present invention provides microbial oils with improved pour point, methods for making such oils, and products derived from them. Pour point is a function of relative concentrations of saturated to unsaturated fatty acids of the triglyceride oil and the the chain length of the fatty acids. In embodiments of the methods of the invention, the initial pour point of microbial oil is reduced by reducing the relative proportion of the saturated fraction, including palmitic and stearic triglycerides known as the stearin fraction. In accordance with these methods, the oil is fractionated to reduce the saturated triglycerides concentration of the oil. This can be accomplished in accordance with embodiments of the invention by dry fractionation, an illustrative process for carrying out "winterization". In one embodiment of this method, microbial (e.g., algal) oil is optionally first refined, bleached, deodorized or degummed to produce "RBD oil," which is characterized by an initial pour point. The temperature of the RBD oil is then lowered in a controlled manner until crystal nuclei are formed and then held at that first crystallization temperature (i.e., for several hours) to produce crystals. The crystals are then removed by filtration to produce two fractions: a solid phase containing some or most of the stearin fraction, and a liquid phase containing mostly the olein fraction. This liquid phase is characterized by a second pour point that is lower than the initial pour point, e.g, the second pour point can be between about −10° C. and about −40° C., and the fatty acid composition of the can be at least 50% C18:1 and less than 10% C18:2. The liquid phase can be subjected to fractionation again to a second, lower crystallization temperature to effect a further removal of stearin. In illustrative embodiments, the first crystallization temperature is between above 15° C. to about 50° C., and the second crystallization temperature is between about −15° C. and about 15° C.

In any event, the resulting purified liquid fraction, is equivalent to or substantially similarly to a super olein oil as commonly known in the vegetable oil industry, has better thermal properties than the native algal oil. In some embodiments, the properties are further improved by the addition of a chemical pour point depressant that reduces the pour point even further, as may be desired for specific applications. The microbial oil provided by this method can be used not only in food applications, but also in industrial applications, such as the production of lubricants, hydraulic fluids, industrial oils and dielectric fluids. For industrial applications (e.g., dielectric fluids), one or more additives that can be added to the microbial oil (in addition to, or instead of, a pour point depressant) include: an antioxidant, metal ion deactivator, corrosion inhibitor, demulsifier, anti-wear additive or anti-hydrolysis compound.

In various embodiments, the microbial oil is derived from oleaginous microbes, such as microalgal cells, having distinct lipid profiles (i.e., distinct fatty acid profiles), including recombinant cells expressing exogenous genes encoding proteins such as one or more fatty acyl-ACP thioesterases. In illustrative embodiments, the microbial oil is derived from a genetically engineered microbe engineered to express one or more exogenous genes, and the method additionally includes cultivating the microbe until the microbe has at least 10% oil by dry weight, and separating the oil from the microbe to produce a microbial oil that can then be refined, bleached, deodorized and optionally degummed, as described above. Other oleaginous microbes, including yeast, fungi, and bacteria, with similar or distinct lipid profiles can also be employed. In certain embodiments, the present invention thus provides methods of making lipids and oil-based products, including dielectric fluids, from such microalgal and/or oleaginous microbes, including yeast, fungi and bacteria.

In certain embodiments, the invention provides a product including a microbial oil, wherein the microbial oil has a pour point of between about 10° C. and about −40° C., and wherein the fatty acid composition of the microbial oil is at least about 50% C18:1 and less than about 10% C18:2. In variations of such embodiments, the product has a pour point of between −10° C. and about −40° C. The microbial oil in the product can include, for example, include at least about 60%, at least about 70%, or at least about 80% C18:1. In some cases, the microbial oil can include less than about 5% C18:2 (e.g., is at least about 80% C18:1 and less than about 5% C18:2). In particular embodiments, the microbial oil in the product has an iodine value between about 25 and about 200. The microbial oil can, in certain embodiments, be produced by a genetically engineered microbe engineered to express one or more exogenous genes. Illustrative microbes for this purpose include species from the genus *Prototheca* or *Chlorella*. (e.g., *Prototheca moriformis*). Such microbes can be engineered to express, for example, one or more exogenous genes encoding sucrose invertase and/or fatty acyl-ACP thioesterase. In illustrative embodiments, a microbe is engineered to express exogenous genes encoding two or more fatty acyl-ACP thioesterases or sucrose invertase and one or more fatty acyl-ACP thioesterases.

In various embodiments, the product includes one or more additive(s), such as an antioxidant, a metal ion deactivator, a corrosion inhibitor, a demulsifier, an anti-wear additive, a pour point depressant, or an anti-hydrolysis compound. Illustrative products include a lubricant, a hydraulic fluid, an industrial oil, or a dielectric fluid. Dielectic fluids, in particular, can have one or more of the above-discussed additives.

In some cases, the microbial oil-based product is a dielectric fluid. In some embodiments, the microbial oil used in the dielectric fluid has one or more of the following attributes: (i) less than 0.4 micrograms/ml total carotenoids; (ii) less than 0.001 micrograms/ml lycopene; (iii) less than 0.02 micrograms/ml beta carotene; (iv) less than 0.02 milligrams of chlorophyll per kilogram of oil; (v) 0.40-0.60 milligrams of gamma tocopherol per 100 grams of oil; (vi) 3-9 mg campesterol per 100 grams of oil; or (vii) less than 0.5 milligrams of total tocotrienols per gram of oil. In some cases, the dielectric fluid has one or more of the following properties: viscosity at 40° C. of less than about 110 cSt, e.g., in the range of 20-30 cSt; (b) viscosity at 100° C. in the range of about 2 to about 15 cSt, e.g., 4-8 cSt; (c) a viscosity index (VI, a unitless number) at 40° C. of at least 35, including but not limited to a VI of 35 to 80, a VI of 80 to 110, a VIT of 110 to 125, a VI of 125 to 160, and, in some embodiments a VI of greater than 160; (d) a pour point (the lowest temperature at which the liquid will flow) of −8 to 10° C. or lower, including but not limited to a pour point of −20 to −25° C. or lower, and, in some embodiments, a pour point of −30° C., or −40° C. or lower; (e) lubricity equivalent to ASTM D2882; (f) low volatility; (g) a high flash point, including a flash point of 150° C. or higher, including a flash point of 300° C. or higher; (h) a fire point of 150° C. or higher (e.g., above 300° C.), including a flash point of 300° C. or higher; (i) low reactivity, including resistance to decomposition in the presence of acids and bases, good thermal stability, low susceptibility to reaction with oxygen, and a low neutralization number (0.06 or lower, for example 0.03 or lower); (j) good miscibility, including high demulsibility; (k) a power factor at 25° C. of 1% or lower, including but not limited to 0.5% or lower, 0.15% or lower, 0.1% or lower, and, in some embodiments 0.05% or lower, (l) a power factor at 100° C. of 1.5% or lower, including but not limited to 1% or lower, 0.3% or lower, and, in some embodiments 0.1% or lower; (m) a high dielectric strength; (n) a low dissipation factor; (o) a low electrical conductivity; (p) high specific heat, including but not limited to a specific heat of at least 0.39 cal/gm/° C., and, in some embodiments, a specific heat of at least 0.45 cal/gm/° C. or higher; and (q) is biodegradable, i.e., breaks down into carbon dioxide and water in the presence of microbes, such that at least 15% or more of the dielectric fluid degrades under standard test conditions biodegrades in 28 days, and in some embodiments, 30% or more, or 70% or more, or 100% biodegrades under these conditions.

The invention also provides an electrical component including the above-described dielectric fluid. In certain embodiments, the electrical component is a transformer.

The invention further provides a method of producing a product including a microbial oil. In certain embodiments, the product has a pour point of between about −10° C. and about −40° C., and wherein the fatty acid composition of the microbial oil is at least 50% C18:1 and less than 10% C18:2. In such embodiments, the method entails cultivating a genetically engineered microbe engineered to express one or more exogenous genes until the microbe has at least 10% oil by dry weight and then separating the oil from the microbe. The microbial oil is then subjected to refining, bleaching, deodorizing and, optionally, degumming to produce RBD oil. The method can, optionally, further entail adding an antioxidant, metal ion deactivator, corrosion inhibitor, demulsifier, anti-wear additive, pour point depressant, or anti-hydrolysis compound to the RBD oil. Illustrative engineered microbes for can include species from the genus *Prototheca* or *Chlorella*. (e.g., *Prototheca moriformis*). Such microbes can be engineered to express, for example, one or more exogenous genes encoding sucrose invertase and/or fatty acyl-ACP thioesterase. In illustrative embodiments, a microbe is engineered to express exogenous genes encoding two or more fatty acyl-ACP thioesterases or sucrose invertase and one or more fatty acyl-ACP thioesterases.

In one embodiment, the present invention provides a method of making a dielectric fluid, the method comprising the steps of: (a) cultivating an oleaginous microbe to provide an oleaginous microbe that is at least 10% lipid by dry weight, (b) separating the lipid from the oleaginous microbe, and (c) subjecting the lipid to at least one processing step selected from the group consisting of refining, bleaching, deodorizing, degumming, and fractionating by crystallizing or dry fractionation or by winterizing.

In some specific embodiments of the method, the oleaginous microbe is selected from the group consisting of microalgae, oleaginous yeast, oleaginous fungi and oleaginous bacteria. In some cases, the oleaginous microbe is an oleaginous bacteria that is *Rhodococcus opacus*. In some cases, the oleaginous microbe is an oleaginous fungi. In some cases, the oleaginous fungi is a species listed in Table 3. In some cases, the oleaginous microbe is an oleaginous yeast. In some cases, the oleaginous yeast is a species listed in Table 2. In some cases, the oleaginous microbe is a microalgae. In some cases, the microalgae is a species listed in Table 1. In some cases, the microalgae is of the genus *Prototheca*.

In some embodiments, the dielectric fluid produced by the method has one or more of the following attributes: (i) 0.05-0.244 mcg/g total carotenoids; (ii) less than 0.003 mcg/g lycopene; (iii) less than 0.003 mcg/g beta carotene; (iv) 0.045-0.268 mcg/g chlorophyll A; (v) 38.3-164 mcg/g gamma tocopherol; (vi) less than 0.25% brassicasterol, campesterol, stignasterol, or beta-sitosterol; (vii) 249.6-325.3 mcg/g total tocotrienols; (viii) 0.003-0.039 mcg/g lutein; and (ix) 60.8-261.7 mcg/g tocopherols. In some embodiments, the dielectric fluid produced by the method has a property selected from the group consisting of: (a) viscosity at 40° C. of less than about 110 cSt, e.g., in the range of 20-30 cSt; (b) viscosity at 100° C. in the range of about 2 to about 15 cSt, e.g., 4-8 cSt; (c) a viscosity index at 40° C. of at least 35; (d) a pour point of −8 to −10° C. or lower, including-15 to −25° C. or lower; (e) lubricity equivalent to ASTM D2882; (f) a flash point of 150° C. or higher; (g) a neutralization number of 0.06 or lower; (h) a power factor at 25° C. of 1% or lower; (i) a specific heat of at least 0.39 cal/gm/° C.; and (j) biodegradability such that at least 15% or more of the dielectric fluid degrades under standard test conditions in 28 days.

In some cases, the dielectric fluid is admixed with one or more of the following additives: (a) an antioxidant; (b) a deactivator of metal ions; (c) a corrosion inhibitor; (d) a demulsifier; (e) an anti-wear additive; (f) a malan styrene copolymer; (g) a pour point depressant, including but not limited to VISCOPLEX® 10-310 or 1-133 (Rohmax-Evonik Additives GmbH), or other poly(alkyl) acrylates and poly (methyl)acrylates such as INFINEUM® V-351 (Infineum UK limited), PMA-D110 and PMA D; or (h) a carbodiimide; or (i) synthetic esters or (j) poly alfa olefins (PAO) or (k) ester of estolides.

In another embodiment, the present invention provides a dielectric fluid comprising an oleaginous microbial oil, wherein said dielectric fluid comprises less than approximately 10% C18:2. In some cases, the dielectric fluid comprises less than approximately 5% C18:2. In some cases, the dielectric fluid comprises less than approximately 2% C18:2. In some cases, the dielectric fluid further comprises at least 65% C18:1. In some cases, the dielectric fluid further comprises less than 30% C16:0.

In some embodiments, the microbial oil is blended with another oil to produce the dielectric fluid in accordance with embodiments of the invention. In some cases, the other oil is not a microbial oil. In some cases, the other oil is selected from the group consisting of soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, *Cuphea*, flax, peanut, choice white grease, lard, Camellina sativa, mustard seed, cashew nut, oats, lupine, kenaf, calendula, help, coffee, linseed (flax), hazelnut, euphorbia, pumpkin seed, coriander, camellia, sesame, safflower, rice, tung tree, cocoa, copra, opium poppy, castor beans, pecan, jojoba, macadamia, Brazil nuts, avocado, oleaginous yeast, oleaginous bacteria, petroleum, or a distillate fraction of any of the preceding oils.

In some embodiments, the content of the other oil in the dielectric fluid is less than 30%. In some cases, the content of the other oil in the dielectric fluid is less than 20%. In some cases, the content of the other oil in the dielectric fluid is less than 10%. In some embodiments, the content of the microbial oil in the dielectric fluid is less than 50%. In some cases, the content of the microbial oil in the dielectric fluid is less than 25%. In some cases, the content of the microbial oil in the dielectric fluid is less than 10%.

In another embodiment, the present invention provides a dielectric fluid comprising one or more of the following additives: (a) an antioxidant, including but not limited to BHT and other phenols; (b) a deactivator of metal ions such as Cu, Zn, and the like, including but not limited to a benzotriazole; (c) corrosion inhibitors, including but not limited to ester sulfonates and succinic acid esters; (d) demulsifiers; (e) anti-wear additives, including but not limited to zinc dithiophosphate; (f) additives to depress the pour point, including but not limited to malan styrene copolymers and poly(alkyl)acrylates, including but not limited to polymethacrylates; and (g) compounds that protect against hydrolysis, including but not limited to carbodiimides.

These and other embodiments of the invention are described in the detailed description below, and are exemplified in the examples below. Any or all of the features discussed above and throughout this application can be combined in various embodiments of the present invention.

BRIEF DESCRIPTION OF THE DRAWINGS

The invention may be understood by reference to the following description taken in conjunction with the accompanying drawings that illustrate certain specific embodiments of the present invention.

DETAILED DESCRIPTION

Figure 1:
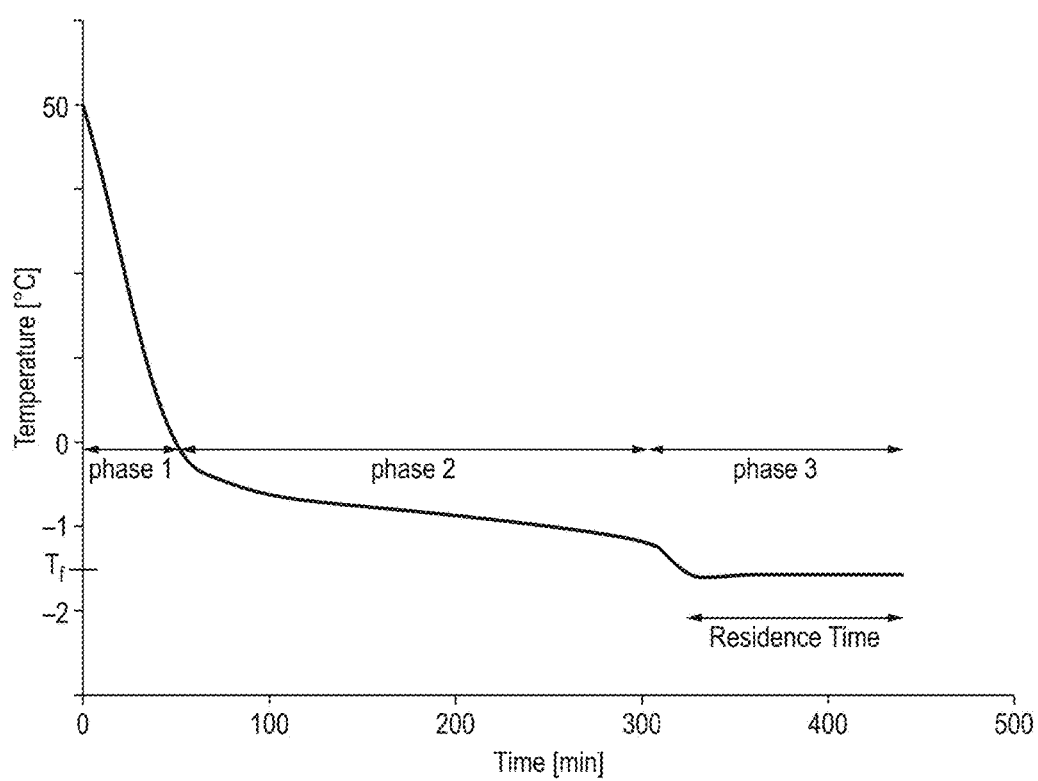
FIG. 1, Typical cooling profile for RBD oil fractionation (Tf=filtration temperature).

The present invention arises, in part, from the discovery that *Prototheca* and other oleaginous microorganisms have, in certain embodiments, unexpectedly advantageous properties for the production of dielectric fluids, among other applications, such as biodegradable lubricants, especially engine oils and hydraulic fluids, which were previously mainly based on mineral oils. Lubricants based on microbial oil can be used to replace of petroleum lubricants in chainsaw bar, drilling muds and oils, straight metalworking fluids, food industry lubricants, open gear oils, biodegradable grease, hydraulic fluids, marine oils and outboard engine lubricants, oils for water and underground pumps, rail flange lubricants, shock absorber lubricants, tractor oils, agricultural equipment lubricants, elevator oils, mould release oils, two stroke engine lubricants and other lubricants.

The present invention also arises, in part, from the discovery of processes for modifying microbial oils to reduce their pour point. Transesterification of lipids yields long-chain fatty acid esters. Other enzymatic and chemical processes can be tailored to yield fatty acids, aldehydes, alcohols, alkanes, and alkenes. In some applications, hydrocarbon compounds useful in dielectric fluids are produced.

This detailed description is divided into sections for the convenience of the reader. Section I provides definitions of terms used herein. Section II provides a description of culture conditions useful in embodiments of the methods of the invention. Section III provides a description of genetic engineering methods and materials. Section IV provides a description of genetic engineering of microbes to enable sucrose utilization, with specific reference to microalgae, as exemplified by *Prototheca*. Section V provides a description of genetic engineering of to modify lipid biosynthesis. Section VI describes methods for making microbial oils of embodiments of the invention and products derived therefrom, such as dielectric fluids. Section VII discloses examples that illustrate the various embodiments of the invention.

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

"Active in microalgae" refers to a nucleic acid that is functional in microalgae. For example, a promoter that has been used to drive an antibiotic resistance gene to impart antibiotic resistance to a transgenic microalgae is active in microalgae.

"Acyl carrier protein" or "ACP" is a protein that binds a growing acyl chain during fatty acid synthesis as a thiol ester at the distal thiol of the 4'-phosphopantetheine moiety and comprises a component of the fatty acid synthase complex.

"Acyl-CoA molecule" or "acyl-CoA" is a molecule comprising an acyl moiety covalently attached to coenzyme A through a thiol ester linkage at the distal thiol of the 4'-phosphopantetheine moiety of coenzyme A.

"Antioxidant" is a molecule that is capable of inhibiting the oxidation of other molecules. Antioxidants are frequently added to industrial products. A common use is as stabilizers in fuels and lubricants to prevent oxidation, and in gasolines to prevent the polymerization that leads to the formation of engine-fouling residues. They are also widely used to prevent the oxidative degradation of polymers such as rubbers, plastics and adhesives that causes a loss of strength and flexibility in these materials.

"Anti-hydrolysis compound" is a molecule that inhibits the decomposition of a chemical compound by reaction with water. Carbodiimides, for example, can be employed as anti-hydrolysis compounds. Anti-hydrolysis compounds are commercially available, e.g., from SpecialChem, among others.

"Anti-wear additive" is an additive to a fluid (e.g., a lubricating oil) that results in longer machine life due to higher wear and score resistance of the components. Anti-wear additives prevent direct metal-to-metal contact between the machine parts when the oil film is broken down. Typically, the additive reacts with the metal on the part surface and forms a film, which may slide over the friction surface. Anti-wear additives typically contain zinc and phosphorus compounds. Examples of anti-wear additives include zinc dithiophosphate (ZDP), zinc dialkyl dithio phosphate (ZDDP, also acts as a corrosion inhibitor and antioxidant), tricresyl phosphate (TCP, used for high-temperature operation), halocarbons (chlorinated paraffins, for extreme pressure operations), glycerol mono-oleate, stearic acid (which adheres to surfaces via reversible adsorption process under 150° C., useful for mild contact conditions.

"Area Percent" refers to the area of peaks observed using FAME GC/FID detection methods in which every fatty acid in the sample is converted into a fatty acid methyl ester (FAME) prior to detection. For example, a separate peak is observed for a fatty acid of 14 carbon atoms with no unsaturation (C14:0) compared to any other fatty acid such as C14:1. The peak area for each class of FAME is directly proportional to its percent composition in the mixture and is calculated based on the sum of all peaks present in the sample (i.e. [area under specific peak/total area of all measured peaks]×100). When referring to lipid (fatty acid) profiles of oils and cells described herein, "at least 4% C8-C14" means that at least 4% of the total fatty acids in the cell or in the extracted glycerolipid composition have a chain length that includes 8, 10, 12 or 14 carbon atoms.

"Axenic" refers to a culture of an organism free from contamination by other living organisms.

"Biodiesel" is a biologically produced fatty acid alkyl ester suitable for use as a fuel in a diesel engine.

"Biomass" is material produced by growth and/or propagation of cells. Biomass may contain cells and/or intracellular contents as well as extracellular material, includes, but is not limited to, compounds secreted by a cell.

"Bioreactor" is an enclosure or partial enclosure in which cells are cultured, optionally in suspension.

"Breakdown voltage" of of a dielectric fluid is the voltage at which the dielectric fluid loses its insulating properties.

"Catalyst" is an agent, such as a molecule or macromolecular complex, capable of facilitating or promoting a chemical reaction of a reactant to a product without becoming a part of the product. A catalyst increases the rate of a reaction, after which, the catalyst may act on another reactant to form the product. A catalyst generally lowers the overall activation energy required for the reaction such that it proceeds more quickly or at a lower temperature. Thus, a reaction equilibrium may be more quickly attained. Examples of catalysts include enzymes, which are biological catalysts; heat, which is a non-biological catalyst; and metals used in fossil oil refining processes.

"Cellulosic material" is the product of digestion of cellulose, including glucose and xylose, and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

"Co-culture", and variants thereof such as "co-cultivate" and "co-ferment", refer to the presence of two or more types of cells in the same bioreactor. The two or more types of cells may both be microorganisms, such as microalgae, or may be a microalgal cell cultured with a different cell type. The culture conditions may be those that foster growth and/or propagation of the two or more cell types or those that facilitate growth and/or proliferation of one, or a subset, of the two or more cells while maintaining cellular growth for the remainder.

"Cofactor" is any molecule, other than the substrate, required for an enzyme to carry out its enzymatic activity.

"Complementary DNA" or "cDNA" is a DNA copy of mRNA, usually obtained by reverse transcription of messenger RNA (mRNA) or amplification (e.g., via polymerase chain reaction ("PCR")).

"Corrosion inhibitor" is molecule that, when added to a fluid, decreases the corrosion rate of a metal or an alloy in contact with the fluid.

"Cultivated", and variants thereof such as "cultured" and "fermented", refer to the intentional fostering of growth (increases in cell size, cellular contents, and/or cellular activity) and/or propagation (increases in cell numbers via mitosis) of one or more cells by use of selected and/or controlled conditions. The combination of both growth and propagation may be termed proliferation. Examples of selected and/or controlled conditions include the use of a defined medium (with known characteristics such as pH, ionic strength, and carbon source), specified temperature, oxygen tension, carbon dioxide levels, and growth in a bioreactor. Cultivate does not refer to the growth or propagation of microorganisms in nature or otherwise without human intervention; for example, natural growth of an organism that ultimately becomes fossilized to produce geological crude oil is not cultivation.

"Cytolysis" is the lysis of cells in a hypotonic environment. Cytolysis is caused by excessive osmosis, or movement of water, towards the inside of a cell (hyperhydration). The cell cannot withstand the osmotic pressure of the water inside, and so it explodes.

"Delipidated meal" and "delipidated microbial biomass" is microbial biomass after oil (including lipids) has been extracted or isolated from it, either through the use of mechanical (i.e., exerted by an expeller press) or solvent extraction or both. Delipidated meal has a reduced amount of oil/lipids as compared to before the extraction or isolation of oil/lipids from the microbial biomass but does contain some residual oil/lipid.

"Demulsifier" is a molecule that either breaks emulsions (usually liquid-liquid emulsions) or prevents them from forming. Demulsifiers are typically based on the following chemistries: acid catalysed phenol-formaldehyde resins, base catalysed phenol-formaldehyde resins, polyamines, di-epoxides, polyols. These molecules are usually ethoxylated (and/or propoxylated) to provide the desired degree of water/oil solubility. The addition of ethylene oxide increases water solubility, whereas propylene oxide decreases it. Commercially available demulsifier formulations are typically a mixture of two to four different chemistries, in carrier solvent(s) such as xylene, Heavy Aromatic Naptha (HAN), isopropanol, methanol, 2-ethylhexanol or diesel.

"Dielectric" or a "dielectric fluid" is a fluid that does not conduct, or has a very low level of conductivity of, an electric current under normal circumstances (or under the circumstances of its intended use). Dielectric fluids are used for electrical insulation, cooling and lubrication, for example, in transformers and other electrical devices. Electrical devices that utilize dielectric fluids include power and distribution transformers, circuit breakers, capacitors, switchgear, X-ray machines, and insulating cables.

"Dielectric strength" of a material (e.g., insulator) is the maximum voltage required to produce a dielectric breakdown, i.e., failure of its insulating properties, expressed as volts per unit thickness. The dielectric strength of a material can be determined according the standard methods, for example ASTM test methods D1816, D877, D3300, D117, D2413, D6180, D6181, or D1310.

"Expression vector" or "expression construct" or "plasmid" or "recombinant DNA construct" refer to a nucleic acid that has been generated via human intervention, including by recombinant means or direct chemical synthesis, with a series of specified nucleic acid elements that permit transcription and/or translation of a particular nucleic acid in a host cell. The expression vector can be part of a plasmid, virus, or nucleic acid fragment. Typically, the expression vector includes a nucleic acid to be transcribed operably linked to a promoter.

"Exogenous gene" is a nucleic acid that codes for the expression of an RNA and/or protein that has been introduced ("transformed") into a cell, and is also referred to as a "transgene". A transformed cell may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plasmid) or as an episomal molecule.

"Exogenously provided" refers to a molecule provided to the culture media of a cell culture.

"Expeller pressing" is a mechanical method for extracting oil from raw materials such as soybeans and rapeseed. An expeller press is a screw type machine, which presses material through a caged barrel-like cavity. Raw materials enter one side of the press and spent cake exits the other side while oil seeps out between the bars in the cage and is collected. The machine uses friction and continuous pressure from the screw drives to move and compress the raw material. The oil seeps through small openings that do not allow solids to pass through. As the raw material is pressed, friction typically causes it to heat up.

"Fatty acid" is a carboxylic acid with a long aliphatic tail (chain). The aliphatic portion of the fatty acid can be fully saturated (no double bond(s)) or can be unsaturated at one or more various portions of the molecule. Most naturally occurring fatty acids have a chain of an even number of carbon atoms, from 4 to 28. Fatty acids can be components of triglycerides or other lipids, e.g., phospholipids, sphingolipids. Fatty acids can be characterized by "lipid numbers." Lipid numbers take the form C:D, where C is the number of carbon atoms in the fatty acid and D is the number of double bonds in the fatty acid. Accordingly, "C18:1" refers to a a fatty acid with 18 carbons and 1 double bond, whereas "C18:2" refers to a fatty acid with 18 carbons and 2 double bonds.

"Fatty acyl-ACP thioesterase" is an enzyme that catalyzes the cleavage of a fatty acid from an acyl carrier protein (ACP) during lipid synthesis.

"Fatty acyl-CoA/aldehyde reductase" is an enzyme that catalyzes the reduction of an acyl-CoA molecule to a primary alcohol.

"Fatty acyl-CoA reductase" is an enzyme that catalyzes the reduction of an acyl-CoA molecule to an aldehyde.

"Fatty aldehyde decarbonylase" is an enzyme that catalyzes the conversion of a fatty aldehyde to an alkane.

"Fatty aldehyde reductase" is an enzyme that catalyzes the reduction of an aldehyde to a primary alcohol.

Fire point of a material is the temperature at which it will continue to burn for at least 5 seconds after ignition by an open flame. The fire point can be determined according standard methods, for example ASTM test methods D92 or D1310.

"Flash point" is the lowest temperature at which a material can vaporize to form an ignitable mixture in air. At the flash point, the material may ignite, but the vapors produced upon the ignition may not be produced at a sufficient rate to sustain combustion. The flash point can be determined according standard methods, for example ASTM test methods D3278, D3828, D56, or D93.

"Fixed carbon source" is a molecule(s) containing carbon, typically an organic molecule, that is present at ambient temperature and pressure in solid or liquid form in a culture media that can be utilized by a microorganism cultured therein.

"Heterotrophic" as it pertains to culture conditions is culturing in the substantial absence of light while utilizing or metabolizing a fixed carbon source.

"Homogenate" is biomass that has been physically disrupted.

"Hydraulic fluid" is the fluid serving as the power transmission medium in a hydraulic system.

"Hydrocarbon" is a molecule containing only hydrogen and carbon atoms wherein the carbon atoms are covalently linked to form a linear, branched, cyclic, or partially cyclic backbone to which the hydrogen atoms are attached. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, and squalene.

"Hydrogen:carbon ratio" is the ratio of hydrogen atoms to carbon atoms in a molecule on an atom-to-atom basis. The ratio may be used to refer to the number of carbon and hydrogen atoms in a hydrocarbon molecule. For example, the hydrocarbon with the highest ratio is methane $CH_4$ (4:1).

"Hydrophobic fraction" is the portion, or fraction, of a material that is more soluble in a hydrophobic phase in comparison to an aqueous phase. A hydrophobic fraction is substantially insoluble in water and usually non-polar.

"Increase lipid yield" refers to an increase in the lipid productivity of a microbial culture by, for example, increasing dry weight of cells per liter of culture, increasing the percentage of cells that constitute lipid, or increasing the overall amount of lipid per liter of culture volume per unit time.

"Inducible promoter" is a promoter that mediates transcription of an operably linked gene in response to a particular stimulus.

"Industrial oil" is an oil that is useful in industry. Common industrial oils include chainsaw bar lubricant, metal working fluids, food grade lubricants, gear oils, marine oils, engine lubricants, tractor oils, agricultural equipment lubricants, elevator oils, mould release oils, and the like. "Chainsaw bar lubricant" is used for the external lubrication of the bar and chain of chainsaws. "Metal working fluids" are fluids used to cool and/or lubricate the process of shaping a piece of metal into a useful object. "Food grade lubricants" are lubricants that are acceptable for use in meat, poultry and other food processing equipment, applications and plants. "Gear oils" are oils that are useful for lubricating gears, e.g., in transmissions, transfer cases, and differentials in automobiles, trucks, and other machinery. "Marine oils" are oils that are useful for lubricating the moving parts of marine equipment. "Engine lubricants" are used for lubrication of various internal combustion engines. While the main function is to lubricate moving parts, engine lubricants can also clean, inhibit corrosion, improve sealing, and cool the engine by carrying heat away from moving parts. "Tractor oils" are oils that are useful for lubricating the moving parts on tractors. "Agricultural equipment lubricants" are lubricants that are useful for lubricating the moving parts of agricultural equipment. "Elevator oils" are oils used as hydraulic fluid in hydraulic elevators. "Mould release oils" are oils useful in the production of formed articles using a mould. Mould release oils facilitate release of the formed article from the mould and can have surface conditioning characteristics that provide a desired surface finish.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"In situ" means "in place" or "in its original position".

"Iodine value" (or "iodine number") is a measure of the degree of unsaturation of an oil. It is the mass of iodine that is consumed by the unsaturated bonds in an oil. For example, an oil with an iodine value of 50 is an oil in which 100 grams of oil would consume 50 grams of iodine. Iodine values are routinely determined in the art. Standard methods to determine iodine values include ASTM D5768-02 (2006) and DIN 53241.

"Limiting concentration of a nutrient" is a concentration of a compound in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

"Lipase" is a water-soluble enzyme that catalyzes the hydrolysis of ester bonds in water-insoluble, lipid substrates. Lipases catalyze the hydrolysis of lipids into glycerols and fatty acids.

"Lipid modification enzyme" refers to an enzyme that alters the covalent structure of a lipid. Examples of lipid modification enzymes include a lipase, a fatty acyl-ACP thioesterase, a desaturase, including a stearoyl acyl carrier protein desaturase (SAD) and a fatty acyl desaturase (FAD), and a fatty aldehyde decarbonylase.

"Lipid pathway enzyme" is any enzyme that plays a role in lipid metabolism, i.e., either lipid synthesis, modification, or degradation, and any proteins that chemically modify lipids, as well as carrier proteins.

"Lipid" or "lipids" are a class of molecules that are soluble in nonpolar solvents (such as ether and chloroform) and are relatively or completely insoluble in water. Lipid molecules have these properties, because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" are a subgroup of lipids called "triacylglycerides."

"Lubricant" is a substance capable of reducing friction, heat, and/or wear when introduced as a film between solid surfaces "Lysate" is a solution containing the contents of lysed cells.

"Lysing" or "lysis" is disrupting the cellular membrane and optionally the cell wall of a biological organism or cell sufficient to release at least some intracellular content.

"Metal ion deactivator," also known as "metal deactivator" or "metal deactivating agent (MDA)" is a fuel and/or oil additive used to stabilize fluids by deactivating (usually by sequestering) metal ions. The metal ions may be produced by the action of naturally occurring acids in the fuel and acids generated in lubricants by oxidative processes with the metallic parts of systems.

"Microalgae" is a eukarytotic microbial organism that contains a chloroplast or plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. "Microalgae" also refers to obligate heterotrophic microorganisms that have lost the ability to perform photosynthesis, such as certain dinoflagellate algae species and species of the genus *Prototheca*.

"Microorganism" and "microbe" are microscopic unicellular organisms.

"Naturally co-expressed" with reference to two proteins or genes means that the proteins or their genes are co-expressed naturally in a tissue or organism from which they are derived, e.g., because the genes encoding the two proteins are under the control of a common regulatory sequence or because they are expressed in response to the same stimulus.

"Oil" refers to any triacylglyceride oil, produced by organisms, including oleaginous yeast, plants, and/or animals. "Oil," as distinguished from "fat", refers, unless otherwise indicated, to lipids that are generally, but not always, liquid at ordinary room temperatures and pressures. For example, "oil" includes vegetable or seed oils derived from plants, including without limitation, an oil derived from avocado, Brazil nuts, calendula, camelina, camelina sativa, canola, cashew nut, castor beans, cocoa butter (also known as cacao, which is a triacylglyceride oil derived from the cacao bean that is solid at typical room temperatures and pressures), coconut, coffee, copra, coriander, corn, cotton seed, *cuphea*, euphorbia, hazelnut, hemp, jatropha, jojoba, kenaf, linseed, lupine, macadamia, mustard seed, oats, olive, opium poppy, palm, palm kernel, peanut, pecan, pumpkin seed, rapeseed, rice, safflower, sesame, soy, sunflower, and tung oil tree, as well as combinations thereof. "Microbial oil" refers to an oil derived from a microbe.

"Oleaginous yeast" means yeast that can naturally accumulate more than 20% of their dry cell weight as lipid and are of the Dikarya subkingdom of fungi. Oleaginous yeast include, but are not limited to, organisms such as *Yarrowia lipolytica, Rhodotorula glutinis, Cryptococcus curvatus*, and *Lipomyces starkeyi*.

"Osmotic shock" is the rupture of cells in a solution following a sudden reduction in osmotic pressure. Osmotic shock is sometimes induced to release cellular components of such cells into a solution.

"Polysaccharide-degrading enzyme" is any enzyme capable of catalyzing the hydrolysis, or saccharification, of any polysaccharide. For example, cellulases catalyze the hydrolysis of cellulose.

"Polysaccharides" or "glycans" are carbohydrates made up of monosaccharides joined together by glycosidic linkages. Cellulose is a polysaccharide that makes up certain plant cell walls. Cellulose can be depolymerized by enzymes to yield monosaccharides such as xylose and glucose, as well as larger disaccharides and oligosaccharides.

"Pour point" is the lowest temperature at which a liquid will pour or flow under a specific set of conditions. Exemplary pour point standards include ASTM D97-11, D5853-11, and D5949-10, but others known to, or developed by, those of skill in the art can be employed in making pour point determinations in connection with the methods described herein.

"Pour point depressants" or "PPDs" are polymers that control wax crystal formation in oils or lubricants, resulting in lower pour point and improved low temperature flow performance.

"Promoter" is a nucleic acid control sequence that directs transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Recombinant" refers to a cell, nucleic acid, protein or vector, that has been modified due to the introduction of an exogenous nucleic acid or the alteration of a native nucleic acid. Thus, e.g., recombinant cells express genes that are not found within the native (non-recombinant) form of the cell or express native genes differently than those genes are expressed by a non-recombinant cell. A "recombinant nucleic acid" is a nucleic acid originally formed in vitro, in general, by the manipulation of nucleic acid, e.g., using polymerases and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant. Similarly, a "recombinant protein" is a protein made using recombinant techniques, i.e., through the expression of a recombinant nucleic acid.

"RBD oil" is an oil that has been subjected to refining, bleaching, or deodorizing.

"Renewable diesel" is a mixture of alkanes (such as C10:0, C12:0, C14:0, C16:0 and C18:0) produced through hydrogenation and deoxygenation of lipids.

"Saccharification" is a process of converting biomass, usually cellulosic or lignocellulosic biomass, into monomeric sugars, such as glucose and xylose. "Saccharified" or "depolymerized" cellulosic material or biomass refers to cellulosic material or biomass that has been converted into monomeric sugars through saccharification.

"Sonication" is a process of disrupting biological materials, such as a cell, by use of sound wave energy.

"Species of furfural" is 2-furancarboxaldehyde or a derivative that retains the same basic structural characteristics.

"Stover" is the dried stalks and leaves of a crop remaining after a grain has been harvested.

"Sucrose utilization gene" is a gene that, when expressed, aids the ability of a cell to utilize sucrose as an energy source. Proteins encoded by a sucrose utilization gene are referred to herein as "sucrose utilization enzymes" and include sucrose transporters, sucrose invertases, and hexokinases such as glucokinases and fructokinases.

"Transformer" is a device that transfers electrical energy from one circuit to another through inductively coupled conductors, typically the transformer's coils.

The terms "winterizing" oil or "winterization of oil" refer to a process that includes removing the higher melting point components from an oil and/or adding one or more pour point depressant(s).

II. CULTIVATION AND CULTURE CONDITIONS

In certain embodiments, the present invention generally relates to cultivation of oleaginous microbes, such as wild-type and recombinant microalgae, including *Chlorella* and *Prototheca* species and strains, and yeast, fungi, and bacteria species and strains, for the production of microbial oil (lipids). For the convenience of the reader, this section is subdivided into subsections. Subsection 1 describes *Prototheca* species and strains and how to identify new *Prototheca* species and strains and related microalgae by genomic DNA comparison, as well as other microalgae, yeast, fungi, and bacteria useful in the methods described herein. Subsection 2 describes bioreactors useful for cultivation. Subsection 3 describes media for cultivation. Subsection 4 describes oil (lipid) production in accordance with illustrative cultivation methods described herein. Subsection 5 describes types of oleaginous yeast suitable for use in the methods described herein, culture conditions for generating yeast biomass, and the lipid profiles and chemical composition of the biomass prepared in accordance with illustrative methods described herein.

1. *Prototheca* Species and Strains and Other Oleaginous Microbes

*Prototheca* is a remarkable microorganism for use in the production of lipid, because it can produce high levels of lipid, particularly lipid suitable for dielectric fluid and other lubricant production. The lipid produced by *Prototheca* has a higher degree of saturation than that produced by other microalgae. Moreover, *Prototheca* lipid is generally free of pigment (low to undetectable levels of chlorophyll and certain carotenoids) and in any event contains much less pigment than lipid from other microalgae. Moreover, recombinant *Prototheca* cells provided for use in the methods described herein can be used to produce lipid in greater yield and efficiency, and with reduced cost, relative to the production of lipid from other microorganisms. Illustrative *Prototheca* species and strains for use in the methods described herein include *Prototheca wickerhamii*, *Prototheca stagnora* (including UTEX 327), *Prototheca portoricensis*, *Prototheca moriformis* (including UTEX strains 1441, 1435), and *Prototheca zopfii*. Species of the genus *Prototheca* are obligate heterotrophs.

Species of *Prototheca* for use in the methods described herein can be identified by amplification of certain target regions of the genome. For example, identification of a specific *Prototheca* species or strain can be achieved through amplification and sequencing of nuclear and/or chloroplast DNA using primers and methodology using any region of the genome, for example using the methods described in Wu et al., *Bot. Bull. Acad. Sin.* (2001) 42:115-121 Identification of *Chlorella* spp. isolates using ribosomal DNA sequences. Well established methods of phylogenetic analysis, such as amplification and sequencing of ribosomal internal transcribed spacer (ITS1 and ITS2 rDNA), 23S rRNA, 18S rRNA, and other conserved genomic regions can be used by those skilled in the art to identify species of not only *Prototheca*, but other hydrocarbon and lipid producing organisms with similar lipid profiles and production capability. For examples of methods of identification and classification of algae also see for example *Genetics*, 2005 August; 170(4):1601-10 and *RNA*, 2005 April; 11(4):361-4.

Thus, genomic DNA comparison can be used to identify suitable species of microalgae to be used in the methods described herein. Regions of conserved genomic DNA, such as but not limited to DNA encoding for 23 S rRNA, can be amplified from microalgal species and compared to consensus sequences in order to screen for microalgal species that are taxonomically related to the preferred microalgae used in the methods described herein. Examples of such DNA sequence comparison for species within the *Prototheca* genus are shown below. Genomic DNA comparison can also be useful to identify microalgal species that have been misidentified in a strain collection. Often a strain collection will identify species of microalgae based on phenotypic and morphological characteristics. The use of these characteristics may lead to miscategorization of the species or the genus of a microalgae. The use of genomic DNA comparison can be a better method of categorizing microalgae species based on their phylogenetic relationship.

Illustrative microalgae for use in the methods described herein typically have genomic DNA sequences encoding for 23 S rRNA that have at least 99%, least 95%, at least 90%, or at least 85% nucleotide identity to at least one of the sequences listed in SEQ ID NOs: 11-19.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of an algorithm suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (at the web address www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=-4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A wide variety of oleaginous microbes in addition to *Prototheca* can be used in the methods described herein. For example, *Chlorella*, including but not limited to strains of the *protothecoides* species of *Chlorella*, is an excellent microalgae for use in the methods described herein. Considerations affecting the selection of microorganisms for use in the methods described herein in addition to production of suitable lipids or hydrocarbons for production of oils, fuels, and oleochemicals, can include one or more of the following: (1) high lipid content as a percentage of cell weight; (2) ease of growth; (3) ease of genetic engineering; and (4) ease of biomass processing. In particular embodiments, the wild-type or genetically engineered microorganism yields cells that are at least 40%, at least 45%, at least 50%, at least 55%, at least 60%, at least 65%, or at least 70% or more microbial oil (i.e., lipids and fatty acids). Preferred organisms grow (and are grown) heterotrophically (on sugars in the substantial absence of light). Microalgae generally are excellent microbes for use in the methods described herein. Examples of microalgae that can be used to practice the methods include, but are not limited to the following algae listed in Table 1.

TABLE 1

Examples of oleaginous microalgae.

*Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora sp., Anabaena, Ankistrodesmus, Ankistrodesmus falcatus, Boekelovia hooglandii, Borodinella sp., Botryococcus braunii, Botryococcus sudeticus, Carteria, Chaetoceros gracilis, Chaetoceros muelleri, Chaetoceros muelleri subsalsum, Chaetoceros sp., Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca var. vacuolata, Chlorella glucotropha, Chlorella infusionum, Chlorella infusionum var. actophila, Chlorella infusionum var.auxenophila, Chlorella kessleri, Chlorella lobophora (strain SAG 37.88), Chlorella luteoviridis, Chlorella luteoviridis var.aureoviridis, Chlorella luteoviridis var.lutescens, Chlorella miniata, Chlorella minutissima, Chlorella mutabilis, Chlorella nocturna, Chlorella parva, Chlorella photophila, Chlorella pringsheimii, Chlorella protothecoides* (including any of UTEX strains 1806, 411, 264, 256, 255, 250, 249, 31, 29, 25, and CCAP strains 211/17 and 211/8d), *Chlorella protothecoides var.acidicola, Chlorella regularis, Chlorella regularis var.minima, Chlorella regularis var.umbricata, Chlorella reisiglii, Chlorella saccharophila, Chlorella saccharophila var.ellipsoidea, Chlorella salina, Chlorella simplex, Chlorella sorokiniana, Chlorella sp., Chlorella sphaerica, Chlorella stigmatophora, Chlorella vannielii, Chlorella vulgaris, Chlorella vulgaris, Chlorella vulgaris f. tertia, Chlorella vulgaris var. autotrophica, Chlorella vulgaris var.viridis, Chlorella vulgaris var. vulgaris, Chlorella vulgaris var.vulgaris f. tertia, Chlorella vulgaris var.vulgaris f. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena, Franceia sp., Fragilaria crotonensis, Fragilaria sp., Gleocapsa sp., Gloeothamnion sp., Hymenomonas sp., Isochrysis aff. galbana, Isochrysis galbana, Lepocinclis, Micractinium, Micractinium* (UTEX LB 2614), *Monoraphidium minutum Monoraphidium sp., Nannochloris sp., Nannochloropsis salina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia*

TABLE 1-continued

Examples of oleaginous microalgae.

sp., *Ochromonas* sp., *Oocystis parva, Oocystis pusilla, Oocystis* sp.,
*Oscillatoria limnetica, Oscillatoria* sp., *Oscillatoria subbrevis,
Pascheria acidophila, Pavlova* sp.*, Phagus, Phormidium, Platymonas* sp.,
*Pleurochrysis carterae, Pleurochrysis dentate, Pleurochrysis* sp.,
*Prototheca wickerhamii, Prototheca stagnora, Prototheca portoricensis,
Prototheca moriformis, Prototheca zopfii, Pyramimonas* sp.*, Pyrobotrys,
Sarcinoid chrysophyte, Scenedesmus armatus, Spirogyra, Spirulina
platensis, Stichococcus* sp.*, Synechococcus* sp.*, Tetraedron, Tetraselmis* sp.*,
Tetraselmis suecica, Thalassiosira weissflogii,* and *Viridiella fridericiana*

In addition to microalgae, oleaginous yeast can accumulate more than 20% of their dry cell weight as lipid and so are useful in the methods described herein. In one embodiment of the present invention, a microorganism producing a lipid or a microorganism from which oil can be extracted, recovered, or obtained, is an oleaginous yeast. Examples of oleaginous yeast that can be used in the methods described herein include, but are not limited to, the oleaginous yeast listed in Table 2. Illustrative methods for the cultivation of oleaginous yeast (*Yarrowia lipolytica* and *Rhodotorula graminis*) in order to achieve high oil content are provided in the examples below.

TABLE 2

Examples of oleaginous yeast.

*Candida apicola, Candida* sp., *Cryptococcus curvatus,
Cryptococcus terricolus, Debaromyces hansenii, Endomycopsis
vernalis, Geotrichum carabidarum, Geotrichum cucujoidarum,
Geotrichum histeridarum, Geotrichum silvicola, Geotrichum vulgare,
Hyphopichia burtonii, Lipomyces lipofer, Lypomyces orentalis,
Lipomyces starkeyi, Lipomyces tetrasporous, Pichia mexicana,
Rodosporidium sphaerocarpum, Rhodosporidium toruloides Rhodotorula
aurantiaca, Rhodotorula dairenensis, Rhodotorula diffluens, Rhodotorula
glutinus, Rhodotorula glutinis* var.*glutinis, Rhodotorula gracilis,
Rhodotorula graminis Rhodotorula minuta, Rhodotorula mucilaginosa,
Rhodotorula mucilaginosa* var.*mucilaginosa, Rhodotorula terpenoidalis,
Rhodotorula toruloides, Sporobolomyces alborubescens, Starmerella
bombicola, Torulaspora delbruekii, Torulaspora pretoriensis, Trichosporon
behrend, Trichosporon brassicae, Trichosporon domesticum, Trichosporon
laibachii, Trichosporon loubieri, Trichosporon loubieri* var.*loubieri,
Trichosporon montevideense, Trichosporon pullulans, Trichosporon* sp.,
*Wickerhamomyces Canadensis, Yarrowia lipolytica,*
and *Zygoascus meyerae.*

In one embodiment of the present invention, a microorganism producing a lipid or a microorganism from which a lipid can be extracted, recovered or obtained, is a fungus. Examples of fungi that can be used in the methods described herein include, but are not limited to, the fungi listed in Table 3.

TABLE 3

Examples of oleaginous fungi.

*Mortierella, Mortierrla vinacea, Mortierella
alpine, Pythium debaryanum, Mucor
circinelloides, Aspergillus ochraceus,
Aspergillus terreus, Pennicillium iilacinum,
Hensenulo, Chaetomium, Cladosporium,
Malbranchea, Rhizopus,* and *Pythium*

Thus, in one embodiment of the present invention, the microorganism used for the production of microbial biomass for use in the methods described herein is a fungus. Examples of suitable fungi (e.g., *Mortierella alpine, Mucor circinelloides,* and *Aspergillus ochraceus*) include those that have been shown to be amenable to genetic manipulation, as described in the literature (see, for example, *Microbiology,* July; 153(Pt.7): 2013-25 (2007); *Mol Genet Genomics,* June; 271(5): 595-602 (2004); *Curr Genet,* March; 21(3):215-23 (1992); *Current Microbiology,* 30(2):83-86 (1995); Sakuradani, NISR Research Grant, "Studies of Metabolic Engineering of Useful Lipid-producing Microorganisms" (2004); and PCT/JP2004/012021).

In other embodiments of the present invention, a microorganism producing a lipid or a microorganism from which oil can be extracted, recovered, or obtained is an oleaginous bacterium. Oleaginous bacteria are bacteria that can accumulate more than 20% of their dry cell weight as lipid. Species of oleaginous bacteria for use in the methods described herein, include species of the genus *Rhodococcus,* such as *Rhodococcus opacus* and *Rhodococcus* sp. Methods of cultivating oleaginous bacteria, such as *Rhodococcus opacus,* are known in the art (see Waltermann, et al., (2000) *Microbiology,* 146: 1143-1149). Illustrative methods for cultivating *Rhodococcus opacus* to achieve high oil content are provided in the examples below.

2. Bioreactor

Microrganisms are cultured both for purposes of conducting genetic manipulations and for production of microbial oil (e.g., hydrocarbons such as lipids, fatty acids, aldehydes, alcohols, and alkanes). The former type of culture is conducted on a small scale and initially, at least, under conditions in which the starting microorganism can grow. Culture for purposes of hydrocarbon production is usually conducted on a large scale (e.g., 10,000 L, 40,000 L, 100,000 L or larger bioreactors) in a bioreactor. Microalgae, including *Prototheca* species, as well as the other oleaginous microbes described herein, are typically cultured in the methods described herein in liquid media within a bioreactor. Typically, the bioreactor does not allow substantial amounts of light or any amount of light to enter. In some embodiments, the entire cultivation step(s) of the oleaginous microbe, including microalgae, is performed under substantial absence of light.

The bioreactor or fermentor is used to culture microalgal cells through the various phases of their physiological cycle. Bioreactors offer many advantages for use in heterotrophic growth and propagation methods. Microalgae and other oleaginous microbes described herein are typically fermented in large quantities in liquid, such as in suspension cultures as an example. Bioreactors such as steel fermentors can accommodate very large culture volumes (40,000 liter and greater capacity bioreactors are used in various embodiments of the invention). Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor.

Bioreactors can be configured to flow culture media though the bioreactor throughout the time period during which the microalgae reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the microalgal (or other microbial) 1 biomass is cultured in an aqueous medium for a period of time during which the microalgae reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject microalgal cultures to mixing. Mixing may be continuous or intermittent. For example, in some embodiments, a turbulent flow regime of gas entry and media entry is not maintained for reproduction of microalgae until a desired increase in number of said microalgae has been achieved.

Bioreactor ports can be used to introduce, or extract, gases, solids, semisolids, and liquids, into the bioreactor chamber containing the microalgae. While many bioreactors have more than one port (for example, one for media entry, and another for sampling), it is not necessary that only one substance enter or leave a port. For example, a port can be used to flow culture media into the bioreactor and later used for sampling, gas entry, gas exit, or other purposes. Preferably, a sampling port can be used repeatedly without altering compromising the axenic nature of the culture. A sampling port can be configured with a valve or other device that allows the flow of sample to be stopped and started or to provide a means of continuous sampling. Bioreactors typically have at least one port that allows inoculation of a culture, and such a port can also be used for other purposes such as media or gas entry.

Bioreactors ports allow the gas content of the culture of microalgae to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

3. Media

Microalgal as well as other microbial culture media typically contains components such as a fixed nitrogen source, a fixed carbon source, trace elements, optionally a buffer for pH maintenance, and phosphate (typically provided as a phosphate salt). Other components can include salts such as sodium chloride, particularly for seawater microalgae. Nitrogen sources include organic and inorganic nitrogen sources, including, for example, without limitation, molecular nitrogen, nitrate, nitrate salts, ammonia (pure or in salt form, such as, $(NH_4)_2SO_4$ and $NH_4OH$), protein, soybean meal, cornsteep liquor, and yeast extract. Examples of trace elements include zinc, boron, cobalt, copper, manganese, and molybdenum in, for example, the respective forms of $ZnCl_2$, $H_3BO_3$, $CoCl_2 \cdot 6H_2O$, $CuCl_2 \cdot 2H_2O$, $MnCl_2 \cdot 4H_2O$ and $(NH_4)_6Mo_7O_{24} \cdot 4H_2O$.

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can be difficult to predict. In some cases, certain strains of microorganisms may be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at www.utex.org/, a site maintained by the University of Texas at Austin, 1 University Station A6700, Austin, Tex., 78712-0183, for its culture collection of algae (UTEX). For example, various fresh water and salt water media include those described in PCT Pub. No. 2008/151149, incorporated herein by reference.

In a particular example, Proteose Medium is suitable for axenic cultures, and a 1 L volume of the medium (pH ~6.8) can be prepared by addition of 1 g of proteose peptone to 1 liter of Bristol Medium. Bristol medium comprises 2.94 mM $NaNO_3$, 0.17 mM $CaCl_2 \cdot 2H_2O$, 0.3 mM $MgSO_4 \cdot 7H_2O$, 0.43 mM, 1.29 mM $KH_2PO_4$, and 1.43 mM NaCl in an aqueous solution. For 1.5% agar medium, 15 g of agar can be added to 1 L of the solution. The solution is covered and autoclaved, and then stored at a refrigerated temperature prior to use. Another example is the *Prototheca* isolation medium (PIM), which comprises 10 g/L potassium hydrogen phthalate (KHP), 0.9 g/L sodium hydroxide, 0.1 g/L magnesium sulfate, 0.2 g/L potassium hydrogen phosphate, 0.3 g/L ammonium chloride, 10 g/L glucose 0.001 g/L thiamine hydrochloride, 20 g/L agar, 0.25 g/L 5-fluorocytosine, at a pH in the range of 5.0 to 5.2 (see Pore, 1973, App. Microbiology, 26: 648-649). Other suitable media for use with the methods described herein can be readily identified by consulting the URL identified above, or by consulting other organizations that maintain cultures of microorganisms, such as SAG, CCAP, or CCALA. SAG refers to the Culture Collection of Algae at the University of Göttingen (Göttingen, Germany), CCAP refers to the culture collection of algae and protozoa managed by the Scottish Association for Marine Science (Scotland, United Kingdom), and CCALA refers to the culture collection of algal laboratory at the Institute of Botany (Třeboň, Czech Republic). Additionally, U.S. Pat. No. 5,900,370 describes media formulations and conditions suitable for heterotrophic fermentation of *Prototheca* species.

For cost-efficient production, selection of a fixed carbon source is important, as the cost of the fixed carbon source must be sufficiently low to make oil production economical. Suitable carbon sources include, for example, acetate, floridoside, fructose, galactose, glucuronic acid, glucose, glycerol, lactose, mannose, N-acetylglucosamine, rhamnose, raffinose, stachyose, sucrose, and/or xylose. Suitable feedstocks useful in accordance with the methods described herein include, for example, black liquor, corn starch, depolymerized cellulosic material, milk whey, invert sugar (glucose/fructose), molasses, potato, sorghum, sucrose, sugar beet, sugar cane, thick cane juice, rice, and wheat. Carbon sources can also be provided as a mixture, such as a mixture of sucrose and depolymerized sugar beet pulp.

The one or more carbon source(s) can be supplied at a concentration of at least about 50 µM, at least about 100 µM, at least about 500 µM, at least about 5 mM, at least about 50 mM, and at least about 500 mM, of one or more exogenously provided fixed carbon source(s). Highly concentrated carbon sources as feedstock for fermentation are preferred, and in various embodiments, the carbon source is provided in a feedstock at a concentration approaching its maximum solubility (i.e., at a concentration exceeding 90% solubility, such as a concentration of 95% or higher, i.e., 99% solubility).

For example, in some embodiments glucose levels of at least 300 g/L, at least 400 g/L, at least 500 g/L, or at least 600 g/L or more are used in the feedstock in a fed batch cultivation, in which the highly concentrated fixed carbon source is fed to the cells over time as the cells grow and accumulate microbial oil (lipid). In other embodiments, sucrose levels of at least 500 g/L, at least 600 g/L, at least 700 g/L, at least 800 g/L or more are used in the feedstock in a fed batch cultivation. Non-limiting examples of highly concentrated sucrose carbon sources include thick cane juice, sugar cane juice, sugar beet juice and molasses. Carbon sources of particular interest for purposes of the methods described herein include cellulose (in a depolymerized form), glycerol, sucrose, and sorghum, each of which is discussed in more detail below.

In accordance with the methods described herein, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstocks have been found to be inhibitory to yeast growth, and yeast cannot use the 5-carbon sugars produced from cellulosic materials (e.g., xylose from hemi-cellulose). By contrast, microalgae can grow on processed cellulosic material. Cellulosic materials generally include about 40-60% cellulose; about 20-40% hemicellulose; and 10-30% lignin.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), soybean meal, wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

Cellulosic materials are treated to increase the efficiency with which the microbe can utilize the sugar(s) contained within the materials. The methods described herein can be practiced to take advantage of new methods for the treatment of cellulosic materials after acid explosion so that the materials are suitable for use in a heterotrophic culture of microbes (e.g., microalgae and oleaginous yeast). As discussed above, lignocellulosic biomass is comprised of various fractions, including cellulose, a crystalline polymer of beta 1,4 linked glucose (a six-carbon sugar), hemicellulose, a more loosely associated polymer predominantly comprised of xylose (a five-carbon sugar) and to a lesser extent mannose, galactose, arabinose, lignin, a complex aromatic polymer comprised of sinapyl alcohol and its derivatives, and pectins, which are linear chains of an alpha 1,4 linked polygalacturonic acid. Because of the polymeric structure of cellulose and hemicellulose, the sugars (e.g., monomeric glucose and xylose) in them are not in a form that can be efficiently used (metabolized) by many microbes. For such microbes, further processing of the cellulosic biomass to generate the monomeric sugars that make up the polymers can be very helpful to ensuring that the cellulosic materials are efficiently utilized as a feedstock (carbon source).

Celluose or cellulosic biomass is subjected to a process, termed "explosion", in which the biomass is treated with dilute sulfuric (or other) acid at elevated temperature and pressure. This process conditions the biomass such that it can be efficiently subjected to enzymatic hydrolysis of the cellulosic and hemicellulosic fractions into glucose and xylose monomers. The resulting monomeric sugars are termed cellulosic sugars. Cellulosic sugars can subsequently be utilized by microorganisms to produce a variety of metabolites (e.g., lipid). The acid explosion step results in a partial hydrolysis of the hemicellulose fraction to constitutent monosaccharides. These sugars can be completely liberated from the biomass with further treatment. In some embodiments, the further treatment is a hydrothermal treatment that includes washing the exploded material with hot water, which removes contaminants such as salts. This step is not necessary for cellulosic ethanol fermentations due to the more dilute sugar concentrations used in such processes. In other embodiments, the further treatment is additional acid treatment. In still other embodiments, the further treatment is enzymatic hydrolysis of the exploded material. These treatments can also be used in any combination. The type of treatment can affect the type of sugars liberated (e.g., five carbon sugars versus six carbon sugars) and the stage at which they are liberated in the process. As a consequence, different streams of sugars, whether they are predominantly five-carbon or six-carbon, can be created. These enriched five-carbon or six-carbon streams can thus be directed to specific microorganisms with different carbon utilization cabilities.

The methods described herein typically involve fermentation to higher cell densities than what is achieved in ethanol fermentation. Because of the higher densities of the cultures for heterotrophic lipid production, the fixed carbon source (e.g., the cellulosic derived sugar stream(s)) is preferably in a concentrated form. The glucose level of the depolymerized cellulosic material is preferably at least 300 g/liter, at least 400 g/liter, at least 500 g/liter or at least 600 g/liter prior to the cultivation step, which is optionally a fed batch cultivation in which the material is fed to the cells over time as the cells grow and accumulate lipid. Cellulosic sugar streams are not used at or near this concentration range in the production of cellulosic ethanol. Thus, in order to generate and sustain the very high cell densities during the production of lignocellulosic oil, the carbon feedstock(s) must be delivered into the heterotrophic cultures in a highly concentrated form. However, any component in the feedstream that is not a substrate for, and is not metabolized by, the oleaginous microorganism will accumulate in the bioreactor, which can lead to problems if the component is toxic or inhibitory to production of the desired end product. While lignin and lignin-derived by-products, carbohydrate-derived byproducts such as furfurals and hydroxymethyl furfurals, and salts derived from the generation of the cellulosic materials (both in the explosion process and the subsequent neutralization process), and even non-metabolized pentose/hexose sugars can present problems in ethanolic fermentations, these effects are amplified significantly in a process in which their concentration in the initial feedstock is high. To achieve sugar concentrations from cellulosic materials of 300 g/L, 400 g/L, 500 g/L, or higher for six-carbon sugars that may be used in large scale production applications of the present invention, the concentration of these toxic materials can be 20 times higher than the concentrations typically present in ethanolic fermentations of cellulosic biomass.

The explosion process treatment of the cellulosic material utilizes significant amounts of sulfuric acid, heat and pressure, thereby liberating by-products of carbohydrates, namely furfurals and hydroxymethyl furfurals. Furfurals and hydroxymethyl furfurals are produced during hydrolysis of hemicellulose through dehydration of xylose into furfural and water. In some embodiments of the present invention, these by-products (e.g., furfurals and hydroxymethyl furfurals) are removed from the saccharified lignocellulosic material prior to introduction into the bioreactor. In certain embodiments of the present invention, the process for removal of the by-products of carbohydrates is hydrothermal treatment of the exploded cellulosic materials. In addition, in particular embodiments, the present invention provides methods in which strains capable of tolerating compounds such as furfurals or hydroxymethyl furfurals are used for production. In another embodiment, the present invention also provides methods for using microorganisms that are not only capable of tolerating furfurals in the fermentation media, but are actually able to metabolize these by-products during fermentation.

The explosion process also generates significant levels of salts. For example, typical conditions for explosion can result in conductivites in excess of 5 mS/cm when the exploded cellulosic biomass is resuspended at a ratio of 10:1 water:solids (dry weight). In certain embodiments of the present invention, the diluted exploded biomass is subjected to enzymatic saccharification, and the resulting supernatant is concentrated up to 25 fold for use in the bioreactor. The salt level (as measured by conductivity) in the concentrated sugar stream(s) can be unacceptably high (up to 1.5 M $Na^+$ equivalents). Additional salts are generated upon neutralization of the exploded materials for the subsequent enzymatic saccharification process as well. In accordance with the methods described herein, these salts can be removed so that the resulting concentrated cellulosic sugar stream(s) can be used in heterotrophic processes for producing lipid. In some embodiments, the method of removing these salts is deionization with resins, such as, but not limited to, DOWEX Marathon MR3. In certain embodiments, the deionization with resin step occurs before sugar concentration or pH adjustment and hydrothermal treatment of biomass prior to saccharification, or any combination of the preceding; in other embodiments, the step is conducted after one or more of these processes. In other embodiments, the explosion process itself is changed so as to avoid the generation of salts at unacceptably high levels. For example, a suitable alternative to sulfuric acid (or other acid) explosion of the cellulosic biomass is mechanical pulping to render the cellulosic biomass receptive to enzymatic hydrolysis (saccharification). In still other embodiments, native strains of microorganisms resistant to high levels of salts or genetically engineered strains with resistance to high levels of salts are used.

A preferred embodiment for the process of preparing of exploded cellulosic biomass for use in heterotrophic microbial oil production using oleaginous microbes is conducted as follows. A first step comprises adjusting the pH of the resuspended exploded cellulosic biomass to the range of 5.0-5.3 followed by washing the cellulosic biomass three times. This washing step can be accomplished by a variety of means including the use of desalting and ion exchange resins, reverse osmosis, hydrothermal treatment (as described above), or just repeated re-suspension and centrifugation in deionized water. This wash step results in a cellulosic stream whose conductivity is between 100-300 µS/cm and the removal of significant amounts of furfurals and hydroxymethyl furfurals. Decants from this wash step can be saved to concentrate five-carbon sugars liberated from the hemicellulose fraction. A second step comprises enzymatic saccharification of the washed cellulosic biomass. In one embodiment, Accellerase (Genencor) is used. A third step comprises the recovery of sugars via centrifugation or decanting and rinsing of the saccharified biomass. The resulting biomass (solids) is an energy dense, lignin rich component that can be used as fuel or sent to waste. The recovered sugar stream in the centrifugation/decanting and rinse process is collected. A fourth step comprises microfiltration to remove contaminating solids with recovery of the permeate. A fifth step comprises a concentration step which can be accomplished using a vacuum evaporator. This step can optionally include the addition of antifoam agents such as P'2000 (Sigma/Fluka), which is sometimes necessary due to the protein content of the resulting sugar feedstock.

In another embodiment of the methods of the invention, the carbon source is glycerol, including acidulated and non-acidulated glycerol byproduct from biodiesel transesterification. In one embodiment, the carbon source includes glycerol and at least one other carbon source. In some cases, all of the glycerol and the at least one other fixed carbon source are provided to the microorganism at the beginning of the fermentation. In some cases, the glycerol and the at least one other fixed carbon source are provided to the microorganism simultaneously at a predetermined ratio. In some cases, the glycerol and the at least one other fixed carbon source are fed to the microbes at a predetermined rate over the course of fermentation.

Some microalgae undergo cell division faster in the presence of glycerol than in the presence of glucose (see PCT Pub. No. 2008/151149). In these instances, two-stage growth processes, in which cells are first fed glycerol to increase cell density rapidly, and are then fed glucose to accumulate microbial oil (lipids), can improve the efficiency with which the oil is produced. The use of the glycerol byproduct of the transesterification process provides significant economic advantages when put back into a production process for microbial oil. Other feeding methods are provided as well, such as those employing mixtures of glycerol and glucose as the fixed carbon source. Feeding such mixtures also captures similar economic benefits. In addition, in certain embodiments, the invention provides methods of feeding alternative sugars to microalgae such as sucrose in various combinations with glycerol.

In another embodiment of the methods of the invention, the carbon source is invert sugar. Invert sugar is produced by splitting the sucrose into its monosaccharide components, fructose and glucose. Production of invert sugar can be achieved through several methods that are known in the art. One such method is heating an aqueous solution of sucrose. Often, catalysts are employed to accelerate the conversion of sucrose into invert sugar. These catalysts can be biological; for example, enzymes such as invertases and sucrases can be added to the sucrose to accelerate the hydrolysis reaction to produce invert sugar. Acid is an example of a non-biological catalyst that, when paired with heat, can accelerate the hydrolysis reaction. Once the invert sugar is made, it is less prone to crystallization compared to sucrose and thus provides advantages for storage and fed batch fermentations, where, in the case of heterotrophic cultivation of microbes, including microalgae, there is a need for a concentrated carbon source. In one embodiment, the carbon source is invert sugar, preferably in a concentrated form (at least 90% of its maximum solubility in the conditions used, as described above), i.e., at least 800 g/liter, at least 900 g/liter, at least 1000 g/liter or at least 1100 g/liter. The invert sugar, preferably in a concentrated form, is fed to the cells over time as the cells grow and accumulate lipid.

In another embodiment of the methods of the invention, the carbon source is sucrose, including a complex feedstock containing sucrose, such as thick cane juice from sugar cane processing. As noted above, because of the higher densities of the cultures for heterotrophic oil production, the fixed carbon source (e.g., sucrose, glucose, etc.) is in a concentrated form, i.e., at least 500 g/liter, at least 600 g/liter, at least 700 g/liter or at least 800 g/liter of the fixed carbon source prior to the cultivation step, which is optionally a fed batch cultivation in which the material is fed to the cells over time as the cells grow and accumulate lipid. In some cases, the carbon source is sucrose in the form of thick cane juice, typically in a concentrated form, i.e., at least 60% solids or about 770 g/liter sugar, at least 70% solids or about 925 g/liter sugar, or at least 80% solids or about 1125 g/liter sugar prior to the cultivation step, which is optionally a fed batch cultivation. The concentrated thick cane juice is fed to the cells over time as the cells grow and accumulate lipid.

In one embodiment, the culture medium further includes at least one sucrose utilization enzyme. In some cases, the culture medium includes a sucrose invertase. In one embodiment, the sucrose invertase enzyme is a secretable sucrose invertase enzyme encoded by an exogenous sucrose invertase gene expressed by the population of microorganisms. Thus, in some cases, as described in more detail in Section IV, below, the microbe used in the methods described herein has been genetically engineered to express a sucrose utilization enzyme, such as a sucrose transporter, a sucrose invertase, a hexokinase, a glucokinase, or a fructokinase.

Complex feedstocks containing sucrose include waste molasses from sugar cane processing; the use of this low-value waste product of sugar cane processing can provide significant cost savings in the production of hydrocarbons and other oils. Another complex feedstock containing sucrose that is useful in the methods described herein is sorghum, including sorghum syrup and pure sorghum. Sorghum syrup is produced from the juice of sweet sorghum cane. Its sugar profile consists of mainly glucose (dextrose), fructose and sucrose.

4. Oil Production

For the production of oil (lipid) in accordance with the methods described herein, it is preferable to culture cells in the dark, as is the case, for example, when using extremely large (40,000 liter and higher) fermentors that do not allow light to strike the culture. For example, *Prototheca* and other microalgae species can be grown and propagated for the production of oil in a medium containing a fixed carbon source and in the absence of light; such growth is known as heterotrophic growth.

As an example, an inoculum of lipid-producing microalgal cells is introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after the end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of fatty acids in the oil produced, and/or production of a specific fatty acid and corresponding lipid(s).

Preferably, microorganisms grown using conditions described herein and others known in the art comprise at least about 20% by weight of lipid, preferably at least about 40% by weight, more preferably at least about 50% by weight, and most preferably at least about 60% by weight. Process conditions can be adjusted to increase the yield of lipids suitable for a particular use and/or to reduce production cost. For example, in certain embodiments, a microalgae or other oleaginous microbe is cultured in the presence of a limiting concentration of one or more nutrients, such as, for example, nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular embodiments, the increase in lipid yield is at least about: 10%, 50%, 100%, 200%, or 500%. The microbe can be cultured in the presence of a limiting amount of a nutrient for a portion of the total culture period or for the entire period. In particular embodiments, the nutrient concentration is cycled between a limiting concentration and a non-limiting concentration at least twice during the total culture period. Lipid content of cells can be increased by continuing the culture for increased periods of time while providing an excess of carbon, but limiting or no nitrogen.

In another embodiment, lipid yield is increased by culturing a lipid-producing microbe (e.g., microalgae) in the presence of one or more cofactor(s) for a lipid pathway enzyme (e.g., a fatty acid synthetic enzyme). Generally, the concentration of the cofactor(s) is sufficient to increase microbial oil (e.g., lipids and fatty acids) yield over microbial oil yield in the absence of the cofactor(s). In a particular embodiment, the cofactor(s) are provided to the culture by including in the culture a microbe (e.g., microalgae) containing an exogenous gene encoding the cofactor(s). Alternatively, cofactor(s) may be provided to a culture by including a microbe (e.g., microalgae) containing an exogenous gene that encodes a protein that participates in the synthesis of the cofactor. In certain embodiments, suitable cofactors include a vitamin required by a lipid pathway enzyme, such as, for example: biotin and pantothenate. Genes encoding cofactors suitable for use in the methods described herein or that participate in the synthesis of such cofactors are well known and can be introduced into microbes (e.g., microalgae or other oleaginous microbe described herein), using contructs and techniques such as those described above.

The specific examples of bioreactors, culture conditions, and heterotrophic growth and propagation methods described herein can be combined in any suitable manner to improve efficiencies of microbial growth and lipid and/or protein production.

Microalgal biomass with a high percentage of oil/lipid accumulation by dry weight has been generated (see PCT Pub. No. 2008/151149). Microalgal biomass generated by the culture methods described herein and useful in accordance with the methods described herein comprises at least 10% microalgal oil by dry weight. In some embodiments, the microalgal biomass comprises at least 25%, at least 50%, at least 55%, or at least 60% microalgal oil by dry weight. In some embodiments, the microalgal biomass contains from 10-90% microalgal oil, from 25-75% microalgal oil, from 40-75% microalgal oil, or from 50-70% microalgal oil by dry weight.

The microalgal oil of the biomass described herein, or extracted from the biomass for use in the methods and compositions described herein can comprise glycerolipids with one or more distinct fatty acid ester side chains. Glycerolipids are comprised of a glycerol molecule esterified to one, two or three fatty acid molecules, which can be of varying lengths and have varying degrees of saturation. The length and saturation characteristics of the fatty acid molecules (and the microalgal oils containing them) can be manipulated to modify the properties or proportions of the fatty acid molecules in the microalgal oils described herein via culture conditions or via lipid pathway engineering, as described in more detail in Section V, below. Thus, specific blends of algal (or other microbial) oil can be prepared either within a single species of algae or by mixing together the biomass or algal oil from two or more species of microalgae, or by blending algal oil described herein with oils from other sources such as soy, rapeseed, canola, palm, palm kernel, coconut, corn, waste vegetable, Chinese tallow, olive, sunflower, cottonseed, chicken fat, beef tallow, porcine tallow, microalgae, macroalgae, microbes, *Cuphea*, flax, peanut, choice white grease, lard, Camellina sativa, mustard seed, cashew nut, oats, lupine, kenaf, calendula, help, coffee, linseed (flax), hazelnut, euphorbia, pumpkin seed, coriander, camellia, sesame, safflower, rice, tung tree, cocoa, copra, opium poppy, castor beans, pecan, jojoba, macadamia, Brazil nuts, avocado, petroleum, or a distillate fraction of any of the preceding oils.

As noted above, the oil composition, i.e., the properties and proportions of the fatty acid constituents of the glycerolipids, can also be manipulated by combining biomass or oil from at least two distinct species of microalgae. In some embodiments, at least two of the distinct species of microalgae have different glycerolipid profiles. The distinct species of microalgae can be cultured together or separately as described herein, preferably under heterotrophic conditions, to generate the respective oils. Different species of microalgae can contain different percentages of distinct fatty acid constituents in the cell's glycerolipids.

Generally, *Prototheca* strains have lipid profiles with C16 and C18 fatty acids as the predominant species. Such longer chain length fatty acids, especially the monosaturated C16 and C18 fatty acids (i.e., C16:1 and C18:1) are generally preferred for production of dielectric fluids (see, for example, U.S. Pat. No. 6,274,067). For example, *Prototheca moriformis* (UTEX 1435), *Prototheca stagnora* (UTEX 327), and *Prototheca moriformis* (UTEX 1441) contain between 12% and 30% C16 fatty acids and between 50% and 58% C18:1 fatty acids. *Chlorella* protothecoides (UTEX 250) contains about 73% C18:1 fatty acids, and other *Chlorella* protothecoides strains, including, but not limited to, UTEX 25, UTEX 249, UTEX 256, UTEX 264, UTEX 411, CCAP 211/17, CCAP 221/8D and SAG 221 10d, can contain between 7% and 18% C 16 fatty acids and between 55% and 75% C18:1 fatty acids. In various embodiments, microbial oil (lipid) useful in products described herein (such as dielectric fluids) is at least about 50% C18:1, e.g., at least about 55%, at least about 60%, at least about 65%, at least about 70%, at least about 75%, at least about 80%, at least about 85%, and at least about 90% C18:1. In these or other embodiments, the microbial oil (lipid) is less than about 10% C18:2, e.g., less than about 7.5%, less than about 5%, less than about 2.5%, and less than about 1% C18:2. The microbial oil can have any combination of percentages of C18:1 and C18:2 that adds up to 100% or less. For example the microbial oil can have at least 50% C18:1 and less than 10% C18:2 or at least 80% C18:1 and less than 5% C18:2.

Microalgal (or other microbial) oil (lipid) can also include other constituents produced by the microalgae, or incorporated into the microalgal oil from the culture medium. These other constituents can be present in varying amount depending on the culture conditions, the species, the extraction method used to recover oil from the biomass and other factors that may affect oil composition. Non-limiting examples of such constituents include carotenoids, present at less than 0.4 micrograms/ml; lycopene, present at less than 0.001 micrograms/ml; beta carotene, present at less than 0.02 micrograms/ml; chlorophyll, present at less than 0.02 milligrams per kilogram of oil; gamma tocopherol, present from 0.40 to 0.60 milligrams per 100 grams of oil; campesterol, present from 3 to 9 milligrams per 100 grams of oil; and tocotrienols, present at less than 0.5 milligrams per gram of oil.

The other constituents can include, without limitation, phospholipids, tocopherols, tocotrienols, carotenoids (e.g., alpha-carotene, beta-carotene, lycopene, etc.), xanthophylls (e.g., lutein, zeaxanthin, alpha-cryptoxanthin and beta-crytoxanthin), and various organic or inorganic compounds. In some cases, the oil extracted from *Prototheca* species comprises between 0.003 to 0.039 micrograms lutein/gram of oil, less than 0.003 micrograms lycopene/gram of oil; and less than 0.003 micrograms beta carotene/gram of oil.

5. Oleaginous Yeast Strains and Culture Conditions

The present invention provides methods for producing oils/lipids from oleaginous yeast biomass. The invention arose, in part, from discoveries that yeast biomass can be prepared with a high oil content and the extracted oil can be converted into a variety of useful products, including dielectric fluids and other lubricants. Yeast oil, which can comprise a mixture of saturated and mid to longer chain fatty acids (e.g., C16 and C18 fatty acids), provides excellent starting material for the preparation of chemicals including dielectric fluids.

A variety of species of yeast that produce suitable oils and/or lipids can be used in accordance with the methods described herein, although yeast that naturally produces high levels of suitable oils or lipids are preferred.

In particular embodiments, the oleaginous yeast comprise cells that are at least 20% or more triglyceride oil by dry weight. In other embodiments, the oleaginous yeast contains at least 25-35% or more triglyceride oil by dry weight. Generally, in these embodiments, the more oil contained in the oleaginous yeast, the more oil that can be extracted from the biomass, so the oleaginous yeast can be cultured to contain at least 40%, at least 50%, or at least 60% or more triglyceride oil by dry weight are typically preferred. Not all types of lipids are desirable for use in chemicals, such as dielectric fluids, as they may have an undesirable chain length, saturation levels, or associated with undesireable contaminants. These considerations also influence the selection of oleaginous yeast (or any other microbe) for use in the methods described herein.

Suitable species of oleaginous yeast for use in the methods described herein include, but are not limited to *Candida apicola, Candida* sp., *Cryptococcus curvatus, Cryptococcus terricolus, Debaromyces hansenii, Endomycopsis vernalis, Geotrichum carabidarum, Geotrichum cucujoidarum, Geotrichum histeridarum, Geotrichum silvicola, Geotri-*

*chum vulgare, Hyphopichia burtonii, Lipomyces lipofer, Lypomyces orentalis, Lipomyces starkeyi, Lipomyces tetrasporous, Pichia mexicana, Rodosporidium sphaerocarpum, Rhodosporidium toruloides Rhodotorula aurantiaca, Rhodotorula dairenensis, Rhodotorula diffluens, Rhodotorula glutinus, Rhodotorula glutinis* var. *glutinis, Rhodotorula gracilis, Rhodotorula graminis Rhodotorula minuta, Rhodotorula mucilaginosa, Rhodotorula mucilaginosa* var. *mucilaginosa, Rhodotorula terpenoidalis, Rhodotorula toruloides, Sporobolomyces alborubescens, Starmerella bombicola, Torulaspora delbruekii, Torulaspora pretoriensis, Trichosporon behrend, Trichosporon brassicae, Trichosporon domesticum, Trichosporon laibachii, Trichosporon loubieri, Trichosporon loubieri* var. *loubieri, Trichosporon montevideense, Trichosporon pullulans, Trichosporon* sp., *Wickerhamomyces Canadensis, Yarrowia lipolytica,* and *Zygoascus meyerae.*

Species of oleaginous yeast for use in the methods described herein can be identified by comparison of certain target regions of their genome with those same regions of species identified herein; preferred species are those that exhibit identity or at least a very high level of homology with the species identified herein and produce similar amounts, and similar types of, lipid as the strains specifically described herein. For examples, identification of a specific oleaginous yeast species or strain can be achieved through amplification and sequencing of genomic DNA using primers and methodology using appropriate regions of the genome, for example using the methods described in Kurtzman and Robnett, *Antonie van Leeuwenhoek* 73(4): 331-371 (1998), Identification and phylogeny of ascomycetous yeasts from analysis of nuclear large subunit (26S) ribosomal DNA partial sequences. Well established methods of phylogenetic analysis, such as amplification and sequencing of nuclear 18S and 26S and internal transcribed spacer (ITS) regions of ribosomal RNA genes and other conserved regions can be used by those skilled in the art to identify species of oleaginous yeasts suitable for use in the methods disclosed herein.

Thus, genomic DNA comparison can be used to identify suitable species of oleaginous yeast to be used in the methods described herein. Regions of conserved genomic DNA, such as, but not limited to conserved genomic sequences between 3' regions of fungal 18S and 5' regions of fungal 26S rRNA genes can be amplified from yeast species that may be, for example, taxonomically related to the preferred oleaginous yeasts used in the methods described herein and compared to the corresponding regions of those preferred species. Species that exhibit a high level of similarity are then selected for use in the methods described herein. Example 6 describes genomic sequencing of conserved 3' regions of fungal 18S and 5' regions of fungal 26S rRNA for 48 strains of oleaginous yeast strains. Sequence comparison to determine percent nucleotide or amino acid identity can be performed using the same methods disclosed above for microalgae/microorganisms.

Oleaginous yeast are cultured in liquid media to propagate biomass in accordance with the methods described herein. In the methods described herein, oleaginous yeast species are grown in a medium containing a fixed carbon source and/or fixed nitrogen source in the absence of light (heterotrophic growth). Heterotrophic growth of oleaginous yeast usually occurs in an aerobic environment. For example, heterotrophic growth for extended periods of time such as 10 to 15 or more days under limited nitrogen conditions can result in accumulation of light lipid/oil content in cells.

Oleaginous yeast culture media typically contains components such as a fixed carbon source (discussed below), a fixed nitrogen source (such as protein, soybean meal, yeast extract, cornsteep liquor, ammonia (pure or in salt form), nitrate, or nitrate salt), trace elements, optionally a buffer for pH maintenance, and phosphate (a source of phosphorous; other phosphate salts can be used).

In a particular example, a medium suitable for culturing oleaginous yeast strains is YPD medium. This medium is suitable for axenic cultures, and a 1 L volume of the medium (pH~6.8) can be prepared by addition of 10 g bacto-yeast, 20 g bacto-peptone and 40 g glucose into distilled water. For 1.5% agar medium, 15 g of agar can be added to 1 L of the solution. The solution is covered and autoclaved, and then stored at a refrigerated temperature prior to use. Other methods for the growth and propagation of oleaginous yeast strains to generate high lipid levels as a percentage of dry weight have been described (see for example Li et al., *Enzyme and Microbial Technology* (2007) 41:312-317 (demonstrating the culturing *Rhodosporidium toruloides* to 67.5% w/w lipid using fed batch fermentation)). High lipid/oil content in oleaginous yeast can typically be generated by increasing the length of fermentation while providing an excess of carbon source under nitrogen limitation.

Solid and liquid growth media are generally available from a wide variety of sources, and instructions for the preparation of particular media that is suitable for a wide variety of strains of oleaginous yeast can be found, for example, online at www.dsmz.de/microorganisms/medium/pdf/DSMZ_Medium 186.pdf Other suitable media for use with the methods described herein can be readily identified by consulting the URL identified above, or by consulting other organizations that maintain cultures of oleaginous yeast such as Fungal Culture Collections of The World Austrian Center of Biological Resources and Applied Mycology (www.biotec.boku.ac.at/acbr.html); The Biomedical Fungi and Yeasts Collection (bccm.belspo.be/about/ihem.php); Czech Collection of Microorganisms (sci.muni.cz/ccm/index.html); Institut Pasteur (www.pasteur.fr/ip/easysite/go/03b-000011-08h/); German Collection of Microorganisms and Cell Cultures (www.dsmz.de/); Mychoteca Univesitatis Taurinenesis (web086.unito.it/cgi-bin/bioveg/documenti.pl/Show?_id=b522); Riken Bioresource Center Japan Collection of Microorganisms (www.jcm.riken.jp/JCM/announce.shtml); The National Collection of Yeast Cultures (www.ncyc.co.uk/); ATCC (www.atcc.org/); Phaff Yeast Culture Collection (www.phaffcollection.org/).

Oleaginous yeast useful in accordance with the methods described herein are found in various locations and environments throughout the world. As a consequence of their isolation from other species and their resulting evolutionary divergence, the particular growth medium for optimal growth and generation of oil and/or lipid and/or protein from any particular species of microbe can be difficult or impossible to predict, but those of skill in the art can readily find appropriate media by routine testing in view of the disclosure herein. In some cases, certain strains of microorganisms may be unable to grow on a particular growth medium because of the presence of some inhibitory component or the absence of some essential nutritional requirement required by the particular strain of microorganism. The examples below provide exemplary methods of culturing various species of oleaginous yeast to accumulate high levels of lipid as a percentage of dry cell weight.

The fixed carbon source is a key component of the medium. Suitable fixed carbon sources for purposes of the methods described herein, include for example, glucose, fructose, sucrose, lactose, galactose, xylose, mannose, rhamnose, arabinose, N-acetylglucosamine, glycerol, glucuronic acid, raffinose, stachyose, and/or acetate. Subsection 3 (Media) above contains a more detailed discussion regarding suitable carbon sources.

Process conditions can be adjusted to increase the percentage weight of cells that is lipid (oil). For example, in certain embodiments, oleaginous yeast is cultured in the presence of a limiting concentration of one or more nutrients, such as, for example, nitrogen, phosphate, and certain metallic ions, while providing an excess of a fixed carbon source, such as glucose. Nitrogen limitation tends to increase microbial lipid yield over microbial lipid yield in a culture in which nitrogen is provided in excess. In particular embodiments, the increase in lipid yield is at least about 10%, 50%, 100%, 200%, or 500%. The microbe can be cultured in the presence of a limiting amount of a nutrient for a portion of the total culture period or for the entire period. In some embodiments, the nutrient concentration is cycled between a limiting concentration and a non-limiting concentration at least twice during the total culture period.

In a steady growth state, the cells accumulate oil (lipid) but do not undergo cell division. In one embodiment of the invention, the growth state is maintained by continuing to provide all components of the original growth media to the cells with the exception of a fixed nitrogen source. Cultivating oleaginous yeast by feeding all nutrients originally provided to the cells except a fixed nitrogen source, such as through feeding the cells for an extended period of time, results in a higher percentage of lipid by dry cell weight.

In other embodiments, high lipid biomass is generated by feeding a fixed carbon source to the cells after all fixed nitrogen has been consumed for extended periods of time, such as at least one or two weeks. In some embodiments, cells are allowed to accumulate oil in the presence of a fixed carbon source and in the absence of a fixed nitrogen source for over 10, over 15, or over 20 days. Oleaginous yeast grown using conditions described herein or otherwise known in the art can comprise at least about 20% lipid by dry weight, and often comprise 35%, 45%, 55%, 65%, and even 75% or more lipid by dry weight. Percentage of dry cell weight as lipid in microbial lipid production can therefore be improved by holding cells in a growth state in which they consume carbon and accumulate oil but do not undergo cell division.

Conditions in which nitrogen is in excess tends to increase microbial protein yield over microbial oil yield in a culture in which nitrogen is not provided in excess. Suitable nitrogen sources for oleaginous yeast may come from organic nitrogen sources and/or inorganic nitrogen sources.

Non-limiting examples of organic nitrogen sources are yeast extract, peptone, corn steep liquor, and corn steep powder. Non-limiting examples of preferred inorganic nitrogen sources include, for example, and without limitation, $(NH_4)_2SO_4$ and $NH_4OH$. In one embodiment, the culture media for carrying out the invention contains only inorganic nitrogen sources. In another embodiment, the culture media for carrying out the invention contains only organic nitrogen sources. In yet another embodiment, the culture media for carrying out the invention contains a mixture of organic and inorganic nitrogen sources.

An example of a medium formulation used to grow oleaginous yeast includes: 7 g/L $KH_2PO_4$; 2 g/L $Na_2HPO_4$; 1.5 g/L $MgSO_4.7H_2O$; 1.5 g/L yeast extract; 0.2 g/L $CaCl_2.6H_2O$; 0.1 g/L $FeCl_3.6H_2O$; 0.001 g/L biotin and 0.001 g/L $ZnSO_4.7H_2O$ with a pH level adjusted to 5.5 with HCL and with 12 g/L glucose and 30 g/L $NH_4Cl$ as a nitrogen source. Another medium that is used to grow oleaginous yeast includes: 20 g/L glucose; 0.5 g/L yeast extract; 5 g/L $(NH_4)_2SO_4$; and 1 g/L $KH_2PO_4$; 0.5 g/L $MgSO_4.7H_2O$. One medium formulation for the growth of oleaginous yeast in a fermentor consists of: 30 g/L glucose; 20 g/L xylose; 2 g/L $(NH_4)_2SO_4$; 1 g/L $KH_2PO_4$; and 0.5 g/L $MgSO_4.7H_2O$.

In the methods described herein, a bioreactor or fermentor is used to culture oleaginous yeast cells through the various phases of their physiological cycle. As an example, an inoculum of lipid-producing oleaginous yeast cells is introduced into the medium; there is a lag period (lag phase) before the cells begin to propagate. Following the lag period, the propagation rate increases steadily and enters the log, or exponential, phase. The exponential phase is in turn followed by a slowing of propagation due to decreases in nutrients such as nitrogen, increases in toxic substances, and quorum sensing mechanisms. After this slowing, propagation stops, and the cells enter a stationary phase or steady growth state, depending on the particular environment provided to the cells. For obtaining lipid rich biomass, the culture is typically harvested well after the end of the exponential phase, which may be terminated early by allowing nitrogen or another key nutrient (other than carbon) to become depleted, forcing the cells to convert the carbon sources, present in excess, to lipid. Culture condition parameters can be manipulated to optimize total oil production, the combination of fatty acid species produced, and/or production of a specific oil.

To produce high lipid oleaginous yeast, cells are preferably fermented in large quantities in liquid, such as in suspension cultures as an example. Bioreactors such as steel fermentors (5000 liter, 10,000 liter, 80,000 liter, and larger volumes are used in various embodiments of the invention) can accommodate very large culture volumes. Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture.

Bioreactors can be configured to flow culture media though the bioreactor throughout the time period during which the oleaginous yeast reproduce and increase in number. In some embodiments, for example, media can be infused into the bioreactor after inoculation but before the cells reach a desired density. In other instances, a bioreactor is filled with culture media at the beginning of a culture, and no more culture media is infused after the culture is inoculated. In other words, the oleaginous yeast biomass is cultured in an aqueous medium for a period of time during which the yeast reproduce and increase in number; however, quantities of aqueous culture medium are not flowed through the bioreactor throughout the time period. Thus in some embodiments, aqueous culture medium is not flowed through the bioreactor after inoculation.

Bioreactors equipped with devices such as spinning blades and impellers, rocking mechanisms, stir bars, means for pressurized gas infusion can be used to subject oleaginous yeast cultures to mixing. Mixing may be continuous or intermittent. As briefly mentioned above, bioreactors are often equipped with various ports that, for example, allow the gas content of the culture to be manipulated. To illustrate, part of the volume of a bioreactor can be gas rather than liquid, and the gas inlets of the bioreactor to allow pumping of gases into the bioreactor. Gases that can be beneficially pumped into a bioreactor include air, air/$CO_2$ mixtures, noble gases, such as argon, and other gases. Bioreactors are typically equipped to enable the user to control the rate of entry of a gas into the bioreactor. As noted above, increasing gas flow into a bioreactor can be used to increase mixing of the culture.

Increased gas flow affects the turbidity of the culture as well. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor.

The specific examples of bioreactors, culture conditions, and heterotrophic growth and propagation methods described herein can be combined in any suitable manner to improve efficiencies of microbial growth and lipid and/or protein production.

Oleaginous yeast cultures generated according to the methods described above yield oleaginous yeast biomass in fermentation media. To prepare this biomass, as well as to prepare microalgal or other microbial biomass, for extraction of oil, the biomass is typically concentrated, or harvested, from the fermentation medium. At the point of harvesting the oleaginous yeast biomass from the fermentation medium, the biomass comprises predominantly intact cells suspended in an aqueous culture medium. To concentrate the biomass, a dewatering step can be performed. Dewatering or concentrating refers to the separation of the biomass from fermentation broth or other liquid medium and so is solid-liquid separation. Thus, during dewatering, the culture medium is removed from the biomass (for example, by draining the fermentation broth through a filter that retains the biomass), or the biomass is otherwise removed from the culture medium. Common processes for dewatering include centrifugation, filtration, and the use of mechanical pressure. These processes can be used individually or in any combination.

Centrifugation involves the use of centrifugal force to separate mixtures. During centrifugation, the more dense components of the mixture migrate away from the axis of the centrifuge, while the less dense components of the mixture migrate towards the axis. By increasing the effective gravitational force (i.e., by increasing the centrifugation speed), more dense material, such as solids, separate from the less dense material, such as liquids, and so separate out according to density. Centrifugation of biomass and broth or other aqueous solution forms a concentrated paste comprising the oleaginous yeast cells. Centrifugation does not remove significant amounts of intracellular water. In fact, after centrifugation, there may still be a substantial amount of surface or free moisture in the biomass (e.g., upwards of 70%), so centrifugation is not considered to be a drying step.

Filtration can also be used for dewatering. One example of filtration that is suitable for the methods described herein is tangential flow filtration (TFF), also known as cross-flow filtration. Tangential flow filtration is a separation technique that uses membrane systems and flow force to separate solids from liquids. For an illustrative suitable filtration method, see Geresh, Carb. Polym. 50; 183-189 (2002), which describes the use of a MaxCell A/G Technologies 0.45 uM hollow fiber filter. Also see, for example, Millipore Pellicon® devices, used with 100 kD, 300 kD, 1000 kD (catalog number P2C01MC01), 0.1 uM (catalog number P2VVPPV01), 0.22 uM (catalog number P2GVPPV01), and 0.45 uM membranes (catalog number P2HVMPV01). The retentate preferably does not pass through the filter at a significant level, and the product in the retentate preferably does not adhere to the filter material. TFF can also be performed using hollow fiber filtration systems. Filters with a pore size of at least about 0.1 micrometer, for example about 0.12, 0.14, 0.16, 0.18, 0.2, 0.22, 0.45, or at least about 0.65 micrometers, are suitable. Preferred pore sizes of TFF allow solutes and debris in the fermentation broth to flow through, but not microbial cells.

Dewatering can also be effected with mechanical pressure directly applied to the biomass to separate the liquid fermentation broth from the microbial biomass sufficient to dewater the biomass but not to cause predominant lysis of cells. Mechanical pressure to dewater microbial biomass can be applied using, for example, a belt filter press. A belt filter press is a dewatering device that applies mechanical pressure to a slurry (e.g., microbial biomass taken directly from the fermentor or bioreactor) that is passed between the two tensioned belts through a serpentine of decreasing diameter rolls. The belt filter press can actually be divided into three zones: the gravity zone, where free draining water/liquid is drained by gravity through a porous belt; a wedge zone, where the solids are prepared for pressure application; and a pressure zone, where adjustable pressure is applied to the gravity drained solids.

After concentration, oleaginous yeast biomass is processed, as described hereinbelow, to prepare it for oil extraction.

Oleaginous yeast biomass with a high percentage of oil/lipid accumulation by dry weight has been generated using different methods of culture, including methods known in the art. Oleaginous yeasts with a higher percentage of accumulated oil/lipid are useful in the methods described herein. *Candida* 107 was shown to be able to accumulate up to 40% lipid wt/wt under nitrogen limiting conditions (Gill et al., *Appl and Environ Microbiology* (1977) pp. 231-239). Li et al. demonstrated the production of *Rhodosporidium toruloids* 44 in fed-batch cultures to a lipid content of 48% w/w (Li et al., *Enzyme and Microbial Technology* (2007) 41:312-317. *Yarrowia lipolytica* has been shown to be able to produce between 0.44-0.54 g of lipid per gram of biomass when using animal fat (stearin) as a carbon source (Panpanikolaou et al., *Appl Microbiol Biotechnol* (2002) 58:308-312.

Biomass generated by the culture methods described herein and useful in accordance with the methods described herein comprises at least 10% oil by dry weight. In some embodiments, the biomass comprises at least 25%, at least 50%, at least 55%, or at least 60% oil by dry weight. In some embodiments, the biomass contains from 10-90% oil, from 25-75% oil, from 40-75% oil, or from 50-70% oil by dry weight.

The oil of the biomass described herein, or extracted from the biomass for use in the methods and compositions described herein can comprise glycerolipids with one or more distinct fatty acid ester side chains. Glycerolipids are comprised of a glycerol molecule esterified to one, two or three fatty acid molecules, which can be of varying lengths and have varying degrees of saturation. The oil composition, i.e., the properties and proportions of the fatty acid consitutents of the glycerolipids, can be manipulated by combining biomass or oil from at least two distinct species of oleaginous yeast (or a strain of oleaginous yeast and another oil producing microbe). In some embodiments, at least two of the distinct species of microbe have different glycerolipid profiles. The distinct species of microbe can be cultured together or separately as described herein, preferably under heterotrophic conditions, to generate the respective oils. Different species of microbe can contain different percentages of distinct fatty acid constituents in the cell's glycerolipids.

*Yarrowia lipolytica* has been genetically engineered. An embodiment of the invention uses engineered strains of *Yarrowia lipolytica* containing lipid modification enzymes to make oils suitable for use as lubricants and dielectric fluids. Examples of engineering *Yarrowia* are described in U.S. Pat. Nos. 7,465,565 and 7,273,746 and U.S. patent application Ser. Nos. 10/840,579, 11/613,420, 11/714,377 and 11/264,737.

III. GENETIC ENGINEERING METHODS AND MATERIALS

The methods described herein can be practiced using recombinant microalgae or other recombinant oleaginous microbes. This section describes methods and materials for genetically modifying oleaginous microbes, such as microalgae, specifically exemplifying *Prototheca* cells, to make recombinant host cells useful in the methods described herein, including but not limited to recombinant *Prototheca moriformis, Prototheca zopfii, Prototheca krugani*, and *Prototheca stagnora* host cells. The description of these methods and materials is divided into subsections for the convenience of the reader. In subsection 1, transformation methods are described. In subsection 2, genetic engineering methods using homologous recombination are described. In subsection 3, expression vectors and components are described.

1. Engineering Methods—Transformation

Cells can be transformed by any suitable technique including, e.g., biolistics, electroporation (see Maruyama et al. (2004), *Biotechnology Techniques* 8:821-826), glass bead transformation and silicon carbide whisker transformation. Another method that can be used involves forming protoplasts and using $CaCl_2$ and polyethylene glycol (PEG) to introduce recombinant DNA into microalgal or other microbial cells (see Kim et al. (2002), *Mar. Biotechnol.* 4:63-73, which reports the use of this method for the transformation of *Chorella ellipsoidea*). Co-transformation of microalgae can be used to introduce two distinct vector molecules into a cell simultaneously (see for example Protist 2004 December; 155(4):381-93).

Biolistic methods (see, for example, Sanford, Trends In Biotech. (1988) 6:299 302, U.S. Pat. No. 4,945,050); electroporation (Fromm et al., Proc. Nat'l. Acad. Sci. (USA) (1985) 82:5824 5828), use of a laser beam, microinjection or any other method capable of introducing DNA into a microalgae can also be used for transformation of oleaginous microbes, such as a *Prototheca* cell.

2. Engineering Methods—Homologous Recombination

Homologous recombination relates to the ability of complementary DNA sequences to align and exchange regions of homology. In the homologous recombination process, transgenic DNA ("donor") containing sequences homologous to the genomic sequences being targeted ("template") is introduced into the organism and then undergoes recombination into the genome at the site of the corresponding genomic homologous sequences. The mechanistic steps of this process, in most cases, include: (1) pairing of homologous DNA segments; (2) introduction of double-stranded breaks into the donor DNA molecule; (3) invasion of the template DNA molecule by the free donor DNA ends followed by DNA synthesis; and (4) resolution of double-strand break repair events that result in final recombination products.

The ability to carry out homologous recombination in a host organism has many practical implications for what can be done at the molecular genetic level and is useful in the generation of an oleaginous microbe that can produced tailored oils (lipids). By its very nature, homologous recombination is a precise gene targeting event; hence, most transgenic lines generated with the same targeting sequence will be essentially identical in terms of phenotype, necessitating the screening of far fewer transformation events. Homologous recombination also targets gene insertion events into the host chromosome, resulting in excellent genetic stability, even in the absence of genetic selection. Because different chromosomal loci can impact gene expression, even from heterologous promoters/UTRs, homologous recombination can be a method of querying loci in an unfamiliar genome environment and to assess the impact of a particular genome environment on gene expression.

Particularly useful genetic engineering applications using homologous recombination co-opt specific host regulatory elements such as promoters/UTRs to drive heterologous gene expression in a highly specific fashion. For example, ablation or knockout of desaturase genes/gene families with a heterologous gene encoding a selective marker can be used to increase overall percentage of saturated fatty acids produced in the host cell. Example 4 describes the homologous recombination targeting constructs and a working example of such desaturase gene ablations (knockouts) generated in *Prototheca moriformis*. Another approach to decreasing expression of an endogenous gene is to use an RNA-induced method of downregulation or silencing of gene expression including, but not limited to, an RNAi or antisense approach, as well as a dsRNA approach. Antisense, RNAi, dsRNA, and hairpin RNA approaches are well known in the art and include the introduction of an expression construct that, when expressed as mRNA, leads to the formation of a hairpin RNA or an expression construct containing a portion of the target gene that is transcribed in the antisense orientation. All of these approaches result in the decreased expression of the target gene. Example 4 also describes expression constructs and a working example of the downregulation of an endogenous *Prototheca moriformis* delta 12 desaturase gene (FADc) by a hairpin RNA approach.

Because homologous recombination is a precise gene targeting event, it can be used to modify any nucleotide(s) within a gene or region of interest precisely, so long as sufficient flanking regions have been identified. Therefore, homologous recombination can be used as a means to modify regulatory sequences impacting gene expression of RNA and/or proteins. It can also be used to modify protein coding regions to modify enzyme activities such as substrate specificity, affinity, and Km, thus effecting the desired change in metabolism of the host cell. Homologous recombination provides a powerful means to manipulate the host genome resulting in gene targeting, gene conversion, gene deletion, gene duplication, and gene inversion, and in the exchange of gene expression regulatory elements such as promoters, enhancers and 3'UTRs.

Homologous recombination can be achieved using targeting constructs containing pieces of endogenous sequences to "target" the gene or region of interest within the endogenous host cell genome. Such targeting sequences can either be located 5' of the gene or region of interest, 3' of the gene/region of interest, or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

For purposes of non-limiting illustration, regions of donor DNA sequences that are useful for homologous recombination include the KE858 region of DNA in *Prototheca moriformis*. KE858 is a 1.3 kb genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. This region and examples of using this region for homologous recombination targeting has been described in PCT Application No. PCT/US2009/66142. Another useful region of donor DNA is the 6S genomic sequence.

3. Vectors and Vector Components

Vectors for transformation of microorganisms can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell. To aid the reader, this subsection is divided into subsections. Subsection A describes control sequences that can be contained on vectors. Subsection B describes genes typically contained in vectors as well as codon optimization methods and genes prepared using them.

A. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microalgae or other oleaginous microbe contains a coding sequence for a desired gene product (for example, a selectable marker, a lipid pathway modification enzyme, or a sucrose utilization enzyme) in operable linkage with a promoter active in the microalgae or other oleaginous microbe. Alternatively, if the vector does not contain a promoter in operable linkage with the coding sequence of interest, the coding sequence can be transformed into the cells such that it becomes operably linked to an endogenous promoter at the point of vector integration. The promoterless method of transformation has been proven to work in microalgae (see for example Plant Journal 14:4, (1998), pp. 441-447) and other microbes.

Many promoters are active in microalgae, including promoters that are endogenous to the algae being transformed, as well as promoters that are not endogenous to the algae being transformed (i.e., promoters from other algae, promoters from higher plants, and promoters from plant viruses or algae viruses). Illustrative exogenous and/or endogenous promoters that are active in microalgae (as well as antibiotic resistance genes functional in microalgae) are described in PCT Pub. No. 2008/151149 and references cited therein.

The promoter used to express an exogenous gene can be the promoter naturally linked to that gene or can be a heterologous gene promoter. Some promoters are active in more than one species of microalgae. Other promoters are species-specific. Illustrative promoters include promoters such as β-tubulin from *Chlamydomonas reinhardtii*, used in the Examples below, and viral promoters, such as promoters derived from cauliflower mosaic virus (CMV) and *chlorella* virus, which have been shown to be active in multiple species of microalgae (see for example Plant Cell Rep. 2005 March; 23(10-11):727-35; J Microbiol. 2005 August; 43(4): 361-5; Mar Biotechnol (NY). 2002 January; 4(1):63-73). Another promoter that is suitable for use for expression of exogenous genes in *Prototheca* is the *Chlorella sorokiniana* glutamate dehydrogenase promoter/5'UTR. Typically, at least 10, 20, 30, 40, 50, or 60 nucleotides or more of these sequences containing a promoter are used. Illustrative promoters useful for expression of exogenous genes in *Prototheca* are listed in the sequence listing of this application, such as the promoter of the *Chlorella* HUP1 gene (SEQ ID NO:1) and the *Chlorella ellipsoidea* nitrate reductase promoter (SEQ ID NO:2). *Chlorella* virus promoters can also be used to express genes in *Prototheca*, such as SEQ ID NOs: 1-7 of U.S. Pat. No. 6,395,965. Additional promoters active in *Prototheca* can be found, for example, in Biochem Biophys Res Commun. 1994 Oct. 14; 204(1):187-94; Plant Mol Biol. 1994 October; 26(1):85-93; Virology. 2004 Aug. 15; 326(1):150-9; and Virology. 2004 Jan. 5; 318(1):214-23.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods described herein. Inducible promoters useful in the methods described herein include those that mediate transcription of an operably linked gene in response to a stimulus, such as an exogenously provided small molecule (e.g, glucose, as in SEQ ID NO: 1), temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as termination regions are relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

The methods described herein may also make use of vectors containing control sequences and recombinant genes that provide for the compartmentalized expression of a gene of interest. Organelles for targeting are chloroplasts, plastids, mitochondria, and endoplasmic reticulum. In addition, the methods described herein may also make use of control sequences and recombinant genes and vectors containing them described herein that provide for the secretion of a protein outside the cell.

Proteins expressed in the nuclear genome of *Prototheca* can be targeted to the plastid using plastid targeting signals. Plastid targeting sequences endogenous to *Chlorella* are known, such as genes in the *Chlorella* nuclear genome that encode proteins that are targeted to the plastid; see for example GenBank Accession numbers AY646197 and AF499684, and in one embodiment, vectors containing such control sequences are used in the methods described herein to target expression of a protein to a *Prototheca* plastid.

The Examples below describe the use of algal plastid targeting sequences to target heterologous proteins to the correct compartment in the host cell. cDNA libraries were made using *Prototheca moriformis* and *Chlorella protothecodies* cells and are described in PCT Application No. PCT/US2009/066142.

In another embodiment, the expression of a polypeptide in *Prototheca* or another oleaginous microbe is targeted to the endoplasmic reticulum. The inclusion of an appropriate retention or sorting signal in an expression vector ensures that proteins are retained in the endoplasmic reticulum (ER) and do not go downstream into Golgi. For example, the IMPACTVECTOR1.3 vector, from Wageningen UR—Plant Research International, includes the well known KDEL retention or sorting signal. With this vector, ER retention has a practical advantage in that it has been reported to improve expression levels 5-fold or more. The main reason for this appears to be that the ER contains lower concentrations and/or different proteases responsible for post-translational degradation of expressed proteins than are present in the cytoplasm. ER retention signals functional in green microalgae are known. For example, see Proc Natl Acad Sci USA. 2005 Apr. 26; 102(17):6225-30.

In another embodiment of the present invention, a polypeptide is targeted for secretion outside the cell into the culture media. See Hawkins et al., Current Microbiology Vol. 38 (1999), pp. 335-341 for examples of secretion signals active in *Chlorella* that can be used in other microalgae, such as *Prototheca*, as well.

B. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated, in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, or its corresponding gene product, is called a selectable marker. Any of a wide variety of selectable markers can be employed in a transgene construct useful for transforming *Prototheca* or any other oleaginous microbe useful in the methods described herein. Examples of suitable selectable markers include the G418 resistance gene, the nitrate reductase gene (see Dawson et al. (1997), Current Microbiology 35:356-362), the hygromycin phosphotransferase gene (HPT; see Kim et al. (2002), Mar. Biotechnol. 4:63-73), the neomycin phosphotransferase gene, and the ble gene, which confers resistance to phleomycin (Huang et al. (2007), Appl. Microbiol. Biotechnol. 72:197-205). Methods of determining sensitivity of microalgae and other oleaginous microbes to antibiotics are well known. For example, see Mol Gen Genet. 1996 Oct. 16; 252(5):572-9.

Other selectable markers that are not antibiotic-based can also be employed in a transgene construct useful for transforming microalgae in general, including *Prototheca* species. Genes that confers the ability to utilize certain carbon sources that were previously unable to be utilized by the microalgae can also be used as a selectable marker. By way of illustration, *Prototheca moriformis* strains typically grow poorly, if at all, on sucrose. Using a construct containing a sucrose invertase gene can confer the ability of positive transformants to grow on sucrose as a carbon substrate.

For purposes of certain embodiments of the methods described herein, the expression vector used to prepare a recombinant host cell will include at least two, and often three, genes, if one of the genes is a selectable marker. For example, a genetically engineered *Prototheca* can be made by transformation with vectors that comprise, in addition to a selectable marker, one or more exogenous genes, such as, for example, a sucrose invertase gene or an acyl ACP-thioesterase gene. One or both genes can be expressed using an inducible promoter, which allows the relative timing of expression of these genes to be controlled to enhance the lipid yield and conversion to fatty acid esters. Expression of the two or more exogenous genes may be under control of the same inducible promoter or under control of different inducible (or constitutive) promoters. In the latter situation, expression of a first exogenous gene can be induced for a first period of time (during which expression of a second exogenous gene may or may not be induced), and expression of a second exogenous gene can be induced for a second period of time (during which expression of a first exogenous gene may or may not be induced).

In other embodiments, the two or more exogenous genes (in addition to any selectable marker) are: a fatty acyl-ACP thioesterase and a fatty acyl-CoA/aldehyde reductase, the combined action of which yields an alcohol product. Further provided are other combinations of exogenous genes, including without limitation, a fatty acyl-ACP thioesterase and a fatty acyl-CoA reductase to generate aldehydes. In one embodiment, the vector provides for the combination of a fatty acyl-ACP thioesterase, a fatty acyl-CoA reductase, and a fatty aldehyde decarbonylase to generate alkanes. In each of these embodiments, one or more of the exogenous genes can be expressed using an inducible promoter.

Other illustrative vectors that express two or more exogenous genes include those encoding both a sucrose transporter and a sucrose invertase enzyme and those encoding both a selectable marker and a secreted sucrose invertase. The recombinant *Prototheca* or other microalgal or microbial cell transformed with either type of vector produces lipids at lower manufacturing cost due to the engineered ability to use sugar cane (and sugar cane-derived sugars) as a carbon source. Insertion of the two exogenous genes described above can be combined with the disruption of polysaccharide biosynthesis through directed and/or random mutagenesis, which steers even greater carbon flux into lipid production. Individually and in combination, trophic conversion, engineering to alter lipid production, and treatment with exogenous enzymes alter the lipid composition produced by a microorganism. The alteration can be a change in the amount of lipids produced, the amount of one or more lipid (fatty acid) species produced relative to other lipid species, and/or the types of lipid species produced in the microorganism. For example, microalgae can be engineered to produce a higher amount and/or percentage of TAGs.

For optimal expression of a recombinant protein, it is beneficial to employ coding sequences that produce mRNA with codons preferentially used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

Codon-optimized nucleic acids useful for the successful expression of recombinant proteins in *Prototheca* are described herein. Codon usage in *Prototheca* species was analyzed by studying cDNA sequences isolated from *Prototheca moriformis*. This analysis represents the interrogation over 24,000 codons and resulted in Table 4 below.

TABLE 4

Preferred codon usage in Prototheca strains.

| Ala | GCG | 345 (0.36) | Asn | AAT | 8 (0.04) |
|---|---|---|---|---|---|
|  | GCA | 66 (0.07) |  | AAC | 201 (0.96) |
|  | GCT | 101 (0.11) | Pro | CCG | 161 (0.29) |
|  | GCC | 442 (0.46) |  | CCA | 49 (0.09) |
| Cys | TGT | 12 (0.10) |  | CCT | 71 (0.13) |
|  | TGC | 105 (0.90) |  | CCC | 267 (0.49) |
| Asp | GAT | 43 (0.12) | Gln | CAG | 226 (0.82) |
|  | GAC | 316 (0.88) |  | CAA | 48 (0.18) |
| Glu | GAG | 377 (0.96) | Arg | AGG | 33 (0.06) |
|  | GAA | 14 (0.04) |  | AGA | 14 (0.02) |
| Phe | TTT | 89 (0.29) |  | CGG | 102 (0.18) |
|  | TTC | 216 (0.71) |  | CGA | 49 (0.08) |
| Gly | GGG | 92 (0.12) |  | CGT | 51 (0.09) |
|  | GGA | 56 (0.07) |  | CGC | 331 (0.57) |
|  | GGT | 76 (0.10) | Ser | AGT | 16 (0.03) |
|  | GGC | 559 (0.71) |  | AGC | 123 (0.22) |
| His | CAT | 42 (0.21) |  | TCG | 152 (0.28) |
|  | CAC | 154 (0.79) |  | TCA | 31 (0.06) |
| Ile | ATA | 4 (0.01) |  | TCT | 55 (0.10) |
|  | ATT | 30 (0.08) |  | TCC | 173 (0.31) |
|  | ATC | 338 (0.91) | Thr | ACG | 184 (0.38) |
| Lys | AAG | 284 (0.98) |  | ACA | 24 (0.05) |
|  | AAA | 7 (0.02) |  | ACT | 21 (0.05) |
| Leu | TTG | 26 (0.04) |  | ACC | 249 (0.52) |
|  | TTA | 3 (0.00) | Val | GTG | 308 (0.50) |
|  | CTG | 447 (0.61) |  | GTA | 9 (0.01) |
|  | CTA | 20 (0.03) |  | GTT | 35 (0.06) |
|  | CTT | 45 (0.06) |  | GTC | 262 (0.43) |
|  | CTC | 190 (0.26) | Trp | TGG | 107 (1.00) |
| Met | ATG | 191 (1.00) | Tyr | TAT | 10 (0.05) |
|  |  |  |  | TAC | 180 (0.95) |
|  |  |  | Stop | TGA/TAG/TAA |  |

In other embodiments, the gene in the recombinant vector has been codon-optimized with reference to a microalgal strain other than a *Prototheca* strain or another microbial strain. For example, methods of recoding genes for expression in microalgae are described in U.S. Pat. No. 7,135,290. Additional information for codon optimization is available, e.g., at the codon usage database of GenBank.

While the methods and materials described herein allow for the introduction of any exogenous gene into *Prototheca* or other microalgae or other oleaginous microbes, genes relating to sucrose utilization and lipid pathway modification are of particular interest for microbes unable to utilize it naturally or for microbes that utilize it inefficiently, as discussed in the following sections.

IV. SUCROSE UTILIZATION

In embodiment, the recombinant *Prototheca* or other microalgal or other microbial cell contains one or more exogenous sucrose utilization genes. In various embodiments, the one or more genes encode one or more proteins selected from the group consisting of a fructokinase, a glucokinase, a hexokinase, a sucrose invertase, a sucrose transporter. For example, expression of a sucrose transporter and a sucrose invertase allows *Prototheca* or any other microalgal or other microbial cell to transport sucrose into the cell from the culture media and hydrolyze sucrose to yield glucose and fructose. Optionally, a fructokinase can be expressed as well in instances where endogenous hexokinase activity is insufficient for maximum phosphorylation of fructose. Examples of suitable sucrose transporters are GenBank accession numbers CAD91334, CAB92307, and CAA53390. Examples of suitable fructokinases are GenBank accession numbers P26984, P26420 and CAA43322.

In one embodiment, the methods described herein are practiced with a *Prototheca* host cell that secretes a sucrose invertase. Secretion of a sucrose invertase obviates the need for expression of a transporter that can transport sucrose into the cell. This is because a secreted invertase catalyzes the conversion of a molecule of sucrose into a molecule of glucose and a molecule of fructose, both of which can be transported and utilized by microbes useful in the methods described herein. For example, expression of a sucrose invertase (such as SEQ ID NO:3) with a secretion signal (such as that of SEQ ID NO:4 (from yeast), SEQ ID NO:5 (from higher plants), SEQ ID NO:6 (eukaryotic consensus secretion signal), and SEQ ID NO:7 (combination of signal sequence from higher plants and eukaryotic consensus) generates invertase activity outside the cell. Expression of such a protein, as enabled by the genetic engineering methodology disclosed herein, allows cells already capable of utilizing extracellular glucose as an energy source to utilize sucrose as an extracellular energy source.

*Prototheca* species expressing an invertase that is secreted into a media containing sucrose are a preferred microalgal species for the production of microbial oil for use as a dielectric fluid or other lubricant (for production of food oils, some consumers may prefer oil produced using non-recombinant microbes). The expression and extracellular targeting of this fully active protein allows the resulting host cells to grow on sucrose, whereas their non-transformed counterparts cannot. Thus, the practice of the methods described herein may utilize *Prototheca* recombinant cells with a codon-optimized invertase gene, including but not limited to the yeast invertase gene, integrated into their genome such that the invertase gene is expressed as assessed by invertase activity and sucrose hydrolysis. Invertase genes are useful as selectable markers in *Prototheca* and other microalgal recombinant cells, as such cells are able to grow on sucrose, while their non-transformed counterparts cannot; and methods for selecting recombinant host cells using an invertase is a powerful, selectable marker for algal molecular genetics.

The successful expression of a sucrose invertase in *Prototheca* also demonstrates that heterologous (recombinant) proteins can be expressed in an algal cell and successfully transit outside of the cell and into the culture medium in a fully active and functional form. Thus, methods and reagents for expressing a wide and diverse array of heterologous proteins in microalgae and secreting them outside of the host cell are available. Such proteins include, for example, industrial enzymes such as, for example, lipases, proteases, cellulases, pectinases, amylases, esterases, oxidoreductases, transferases, lactases, isomerases, and invertases.

Examples of suitable sucrose invertases include those identified by Genbank accession numbers CAB95010, NP_012104 and CAA06839. Non-limiting examples of suitable invertases are listed below in Table 5. Amino acid sequences for each listed invertase are included in the Sequence Listing below. In some cases, the exogenous sucrose utilization gene suitable for use in the methods and vectors described herein encodes a sucrose invertase that has at least 40, 50, 60, 75, or 90% or higher amino acid identity with a sucrose invertase selected from Table 5.

of lipids produced are useful in the methods described herein. The pathway can further, or alternatively, be modified to alter the properties and/or proportions of various lipid molecules produced through enzymatic processing of lipids and intermediates in the fatty acid pathway. In various embodiments, the recombinant cells have, relative to their untransformed counterparts, an increased or optimized lipid yield per unit volume and/or per unit time, carbon chain length (e.g., for industrial chemicals, including but not limited to dielectric fluids, and other applications requiring lipid feedstock), reduced number of double or triple bonds, optionally to zero, and increasing the hydrogen:carbon ratio of a particular species of lipid (fatty acid) or of a population of distinct lipid.

In particular embodiments, one or more key enzymes that control branch points in metabolism to fatty acid synthesis have been up-regulated or down-regulated to improve lipid

TABLE 5

Sucrose invertases.

| Description | Organism | GenBank Accession No. | SEQ ID NO: |
|---|---|---|---|
| Invertase | *Chicorium intybus* | Y11124 | SEQ ID NO: 20 |
| Invertase | *Schizosaccharomyces pombe* | AB011433 | SEQ ID NO: 21 |
| beta-fructofuranosidase (invertase) | *Pichia anomala* | X80640 | SEQ ID NO: 22 |
| Invertase | *Debaryomyces occidentalis* | X17604 | SEQ ID NO: 23 |
| Invertase | *Oryza sativa* | AF019113 | SEQ ID NO: 24 |
| Invertase | *Allium cepa* | AJ006067 | SEQ ID NO: 25 |
| Invertase | *Beta vulgaris* subsp. *Vulgaris* | AJ278531 | SEQ ID NO: 26 |
| beta-fructofuranosidase (invertase) | *Bifidobacterium breve* UCC2003 | AAT28190 | SEQ ED NO: 27 |
| Invertase | *Saccharomyces cerevisiae* | NP_012104 | SEQ ID NO: 8 (nucleotide) SEQ ID NO: 28 (amino acid) |
| Invertase A | *Zymomonas mobilis* | AA038865 | SEQ ID NO: 29 |

The secretion of an invertase to the culture medium by *Prototheca* enables the cells to grow as well on waste molasses from sugar cane processing as they do on pure reagent-grade glucose; the use of this low-value waste product of sugar cane processing can provide significant cost savings in the production of lipids and other oils. Thus, methods described herein may involve the use of a microbial culture containing a population of *Prototheca* or other microalgal microorganisms, and a culture medium comprising (i) sucrose and (ii) a sucrose invertase enzyme. In various embodiments the sucrose in the culture comes from sorghum, sugar beet, sugar cane, molasses, or depolymerized cellulosic material (which may optionally contain lignin). While the microbes exemplified here are altered such that they can utilize sucrose, the methods and reagents described herein can be applied so that feedstocks such as cellulosics are utilizable by an engineered host microbe with the ability to secrete cellulases, pectinases, isomerases, or the like, such that the breakdown products of the enzymatic reactions are no longer just simply tolerated but rather utilized as a carbon source by the host.

V. LIPID PATHWAY ENGINEERING

In addition to altering the ability of *Prototheca* (or other microalgal or other microbial cells) to utilize feedstocks such as sucrose-containing feedstocks, recombinant *Prototheca* (or other microalgal or other microbial cells) that have been modified to alter the properties and/or proportions production. Up-regulation can be achieved, for example, by transforming cells with expression constructs in which a gene encoding the enzyme of interest is expressed, e.g., using a strong promoter and/or enhancer elements that increase transcription. Such constructs can include a selectable marker such that the transformants can be subjected to selection, which can also be used for amplification of the construct and a concomitant increase in the expression level of the encoded enzyme. Examples of enzymes suitable for up-regulation according to the methods described herein include pyruvate dehydrogenase, which plays a role in converting pyruvate to acetyl-CoA (examples, some from microalgae, include Genbank accession numbers NP_415392; AAA53047; Q1XDM1; and CAF05587). Up-regulation of pyruvate dehydrogenase can increase production of acetyl-CoA, and thereby increase fatty acid synthesis. Acetyl-CoA carboxylase catalyzes the initial step in fatty acid synthesis. Accordingly, this enzyme can be up-regulated to increase production of fatty acids (examples, some from microalgae, include Genbank accession numbers BAA94752; AAA75528; AAA81471; YP_537052; YP_536879; NP_045833; and BAA57908). Fatty acid production can also be increased by up-regulation of acyl carrier protein (ACP), which carries the growing acyl chains during fatty acid synthesis (examples, some from microalgae, include Genbank accession numbers A0T0F8; P51280; NP_849041; YP_874433). Glycerol-3-phosphate acyltransferase catalyzes the rate-limiting step of fatty acid synthesis. Up-regulation of this enzyme can increase fatty acid production (examples, some from microalgae, include Genbank accession numbers AAA74319; AAA33122; AAA37647; P44857; and ABO94442).

Up- and/or down-regulation of genes can be applied to global regulators controlling the expression of the genes of the fatty acid biosynthetic pathways. Accordingly, one or more global regulators of fatty acid synthesis can be up- or down-regulated, as appropriate, to inhibit or enhance, respectively, the expression of a plurality of fatty acid synthetic genes and, ultimately, to increase lipid production. Examples include sterol regulatory element binding proteins (SREBPs), such as SREBP-1a and SREBP-1c (for examples, see Genbank accession numbers NP_035610 and Q9WTN3).

The methods described herein can also be practiced with recombinant *Prototheca* (or other microalgal or other microbial) cells that have been modified to contain one or more exogenous genes encoding lipid modification enzymes such as, for example, fatty acyl-ACP thioesterases (see Table 6), fatty acyl-CoA/aldehyde reductases (see Table 8), fatty acyl-CoA reductases, fatty aldehyde decarbonylase, fatty aldehyde reductases, desaturases (such as stearoyl-ACP desaturases and fatty acyl desaturases) and squalene synthases (see GenBank Accession number AF205791). In some embodiments, genes encoding a fatty acyl-ACP thioesterase and a naturally co-expressed acyl carrier protein are transformed into a *Prototheca* (or other microalgal or other microbial) cell, optionally with one or more genes encoding other lipid modification enzymes. In other embodiments, the ACP and the fatty acyl-ACP thioesterase may have an affinity for one another that imparts an advantage when the two are used together in the microbes and methods described herein, irrespective of whether they are or are not naturally co-expressed in a particular tissue or organism. Thus, in certain embodiments, the present invention contemplates both naturally co-expressed pairs of these enzymes as well as those that share an affinity for interacting with one another to facilitate cleavage of a length-specific carbon chain from the ACP.

In still other embodiments, an exogenous gene encoding a desaturase is transformed into the *Prototheca* (or other microalgal or other microbial) cell in conjunction with one or more genes encoding other lipid modification enzymes to provide modifications with respect to lipid saturation. In another embodiment, an endogenous desaturase gene is overexpressed (e.g., through the introduction of additional copies of the gene) in a *Prototheca* (or other microalgal or other microbial) cell. Stearoyl-ACP desaturase (see, e.g., GenBank Accession numbers AAF15308; ABM45911; and AAY86086), for example, catalyzes the conversion of stearoyl-ACP to oleoyl-ACP. Up-regulation of this gene can increase the proportion of monounsaturated fatty acids produced by a cell; whereas down-regulation can reduce the proportion of monounsaturates. For illustrative purposes, stearoyl-ACP desaturases (SAD) are responsible for for the synthesis of C18:1 fatty acids from C18:0 precursors. Another family of desaturases are the fatty acyl desaturases (FAD), including delta 12 fatty acid desaturases. These desaturases also provide modifications with respect to lipid saturation. For illustrative purposes, delta 12 fatty acid desaturases are responsible for the synthesis of C18:2 fatty acids from C18:1 precursors. Similarly, the expression of one or more glycerolipid desaturases can be controlled to alter the ratio of unsaturated to saturated fatty acids such as ω-6 fatty acid desaturase, ω-3 fatty acid desaturase, or ω-6-oleate desaturase. In some embodiments, the desaturase can be selected with reference to a desired carbon chain length, such that the desaturase is capable of making location specific modifications within a specified carbon-length substrate, or substrates having a carbon-length within a specified range. In another embodiment, if the desired fatty acid profile is an increase in monounsaturates (such as C16:1 and/or C18:1) overexpression of a SAD or expression of a heterologous SAD can be coupled with the silencing or inactivation (e.g., through mutation, RNAi, hairpin RNAs, knockout of an endogenous desaturase gene, etc.) of a fatty acyl desaturase (FAD). Example 4 below describes the targeted ablation or knockout of stearoyl-ACP desaturases and delta 12 fatty acid desaturases and also describes the use of hairpin RNA antisense constructs to decrease the expression of an endogenous desaturase gene.

Thus, in particular embodiments, microbes of the present invention are genetically engineered to express one or more exogenous genes selected from an acyl-ACP thioesterase, an acyl-CoA/aldehyde reductase, a fatty acyl-CoA reductase, a fatty aldehyde reductase, a desaturase, a fatty aldehyde decarbonylase, or a naturally co-expressed acyl carrier protein. Suitable expression methods are described above for expression of a lipase gene, including, among other methods, inducible expression and compartmentalized expression. A fatty acyl-ACP thioesterase cleaves a fatty acid from an acyl carrier protein (ACP) during lipid synthesis. Through further enzymatic processing, the cleaved fatty acid is then combined with a coenzyme to yield an acyl-CoA molecule. This acyl-CoA is the substrate for the enzymatic activity of a fatty acyl-CoA reductase to yield an aldehyde, as well as for a fatty acyl-CoA/aldehyde reductase to yield an alcohol. The aldehyde produced by the action of the fatty acyl-CoA reductase identified above is the substrate for further enzymatic activity by either a fatty aldehyde reductase to yield an alcohol, or a fatty aldehyde decarbonylase to yield an alkane or alkene.

In some embodiments, fatty acids, glycerolipids, or the corresponding primary alcohols, aldehydes, alkanes, or alkenes, generated by the methods described herein, contain 16 or 18 carbon atoms. Preferred fatty acids for the production of dielectric fluids or the corresponding alcohols, aldehydes, alkanes and alkenes contain 16-18 carbon atoms. In certain embodiments, the above fatty acids are saturated (with no carbon-carbon double or triple bonds; mono-unsaturated (single double bond); poly-unsaturated (two or more double bonds; and can be either linear (not cyclic) or branched or a mixture of the two types. For dielectric fluids, mono-unsaturated fatty acids are preferred, especially oleic acid (C18:1). To increase production of lipids having the desired chain length and/or degree of saturation, one can engineer the microalgal cell to over-express a thioesterase with the desired chain-length specificity, to knockout production of thioesterases with shorter chain length specificity or to reduce the expression of such genes, and/or to knock-out desaturase genes responsible for the degree of saturation in the desired lipids.

Various enzymes described above typically have a preferential specificity for hydrolysis of a substrate containing a specific number of carbon atoms. For example, a fatty acyl-ACP thioesterase may have a preference for cleaving a fatty acid having 12 carbon atoms from the ACP. In some embodiments, the ACP and the length-specific thioesterase may have an affinity for one another that makes them particularly useful as a combination (e.g., the exogenous ACP and thioesterase genes may be naturally co-expressed in a particular tissue or organism from which they are derived). Therefore, in various embodiments, the recombinant *Prototheca* (or other microalgal or other microbial) cell of the invention can contain an exogenous gene that encodes a protein with specificity for catalyzing an enzymatic activity (e.g., cleavage of a fatty acid from an ACP, reduction of an acyl-CoA to an aldehyde or an alcohol, or conversion of an aldehyde to an alkane) with regard to the number of carbon atoms contained in the substrate. The enzymatic specificity can, in various embodiments, be for a substrate having from 8 to 34 carbon atoms and preferably from 16 to 18 carbon atoms.

Other fatty acyl-ACP thioesterases suitable for use with the microbes and methods described herein include, without limitation, those listed in Table 6.

TABLE 6

Fatty acyl-ACP thioesterases and GenBank accession numbers.

*Umbellularia californica* fatty acyl-ACP thioesterase (GenBank #AAC49001)
*Cinnamomum camphora* fatty acyl-ACP thioesterase (GenBank #Q39473)
*Umbellularia californica* fatty acyl-ACP thioesterase (GenBank #Q41635)
*Myristica fragrans* fatty acyl-ACP thioesterase (GenBank #AAB71729)
*Myristica fragrans* fatty acyl-ACP thioesterase (GenBank #AAB71730)
*Elaeis guineensis* fatty acyl-ACP thioesterase (GenBank #ABD83939)
*Elaeis guineensis* fatty acyl-ACP thioesterase (GenBank #AAD42220)
*Populus tomentosa* fatty acyl-ACP thioesterase (GenBank #ABC47311)
*Arabidopsis thaliana* fatty acyl-ACP thioesterase (GenBank #NP 172327)
*Arabidopsis thaliana* fatty acyl-ACP thioesterase (GenBank #CAA85387)
*Arabidopsis thaliana* fatty acyl-ACP thioesterase (GenBank #CAA85388)
*Gossypium hirsutum* fatty acyl-ACP thioesterase (GenBank #Q9SQI3)
*Cuphea lanceolata* fatty acyl-ACP thioesterase (GenBank #CAA54060)
*Cuphea hookeriana* fatty acyl-ACP thioesterase (GenBank #AAC72882)
*Cuphea calophylla* subsp.*mesostemon* fatty acyl-ACP thioesterase (GenBank #ABB71581)
*Cuphea lanceolata* fatty acyl-ACP thioesterase (GenBank #CAC19933)
*Elaeis guineensis* fatty acyl-ACP thioesterase (GenBank #AAL15645)

TABLE 6-continued

Fatty acyl-ACP thioesterases and GenBank accession numbers.

*Cuphea hookeriana* fatty acyl-ACP thioesterase (GenBank #Q39513)
*Gossypium hirsutum* fatty acyl-ACP thioesterase (GenBank #AAD01982)
*Vitis vinifera* fatty acyl-ACP thioesterase (GenBank #CAN81819)
*Garcinia mangostana* fatty acyl-ACP thioesterase (GenBank #AAB51525)
*Brassica juncea* fatty acyl-ACP thioesterase (GenBank #ABI18986)
*Madhuca longifolia* fatty acyl-ACP thioesterase (GenBank #AAX51637)
*Brassica napus* fatty acyl-ACP thioesterase (GenBank #ABH11710)
*Oryza sativa* (indica cultivar-group) fatty acyl-ACP thioesterase (GenBank#EAY86877)
*Oryza sativa* (japonica cultivar-group) fatty acyl-ACP thioesterase (GenBank #NP_001068400)
*Oryza sativa* (indica cultivar-group) fatty acyl-ACP thioesterase (GenBank #EAY99617)
*Cuphea hookeriana* fatty acyl-ACP thioesterase (GenBank #AAC49269)
*Ulmus Americana* fatty acyl-ACP thioesterase (GenBank #AAB71731)
*Cuphea lanceolata* fatty acyl-ACP thioesterase (GenBank #CAB60830)
*Cuphea palustris* fatty acyl-ACP thioesterase (GenBank #AAC49180)
*Iris germanica* fatty acyl-ACP thioesterase (GenBank #AAG43858)
*Iris germanica* fatty acyl-ACP thioesterase (GenBank #AAG43858.1)
*Cuphea palustris* fatty acyl-ACP thioesterase (GenBank AAC49179)
*Myristica fragrans* fatty acyl-ACP thioesterase (GenBank #AAB71729)
*Myristica fragrans* fatty acyl-ACP thioesterase (GenBank #AAB717291.1)
*Cuphea hookeriana* fatty acyl-ACP thioesterase (GenBank #U39834)
*Umbelluaria californica* fatty acyl-ACP thioesterase (GenBank #M94159)
*Cinnamomum camphora* fatty acyl-ACP thioesterase (GenBank #U31813)
*Ricinus communis* fatty-acyl ACP thioesterase (GenBank #ABS30422.1)

Bio-oil based chemicals such as dielectric fluids have fatty acid compositions of high oleic acid (C18:1) originating from natural esters (i.e., seed oils) such as from sunflower oil and canola oil. Table 7 shows the fatty acid profiles of common commercial seed oils. All commercial seed oil data below were compiled from the US Pharmacopeias Food and Chemicals Codes, 7$^{th}$ Ed. 2010-2011.

TABLE 7

Lipid profiles of commercial seed oils.

|  | C8:0 | C10:0 | C12:0 | C14:0 | C16:0 | C18:0 | C18:1 | C18:0-diOH | C18:1-OH | C18:2 | C18:3 α |
|---|---|---|---|---|---|---|---|---|---|---|---|
| *R. communis* (Castor oil) | 0 | 0 | 0 | 0 | 0.9-1.6 | 1.0-1.8 | 3.7-6.7 | 0.4-1.3 | 83.6-89.0 | 0 | 0.2-0.6 |
| *C. nucifera* (Coconut oil) | 5.0-9.0 | 4.0-8.0 | 44-52 | 15-21 | 8.0-11.0 | 1.0-4.0 | 5.0-8.0 | 0 | 0 | 0-2.5 | 0 |
| *Z. mays* (Corn oil) | 0 | 0 | 0 | <1.0 | 8.0-19.0 | 0.5-4.0 | 19-50 | 0 | 0 | 38-65 | <2.0 |
| *G. barbadense* (Cottonseed oil) | 0 | 0 | <0.1 | 0.5-2.0 | 17-29 | 1.0-4.0 | 13-44 | 0 | 0 | 40-63 | 0.1-2.1 |
| *B. rapa, B napus, B. juncea* (Canola) | 0 | 0 | <0.1 | <0.2 | <6.0 | <2.5 | >50 | 0 | 0 | <40 | <14 |
| *O. europea* (Olive) | 0 | 0 | 0 | <0.1 | 6.5-20.0 | 0.5-5.0 | 56-85 | 0 | 0 | 3.5-20.0 | <1.2 |
| *A. hypogaea* (Peanut) | 0 | 0 | <0.1 | <0.2 | 7.0-16.0 | 1.3-6.5 | 35-72 | 0 | 0 | 13.0-43 | <0.6 |
| *E. guineensis* (Palm kernel) | 3.0-5.0 | 2.5-6.0 | 40-52 | 14.0-18.0 | 7.0-10.0 | 1.0-3.0 | 11.0-19.0 | 0 | 0 | 0.5-4.0 | 0 |
| *E. guineensis* (Palm) | 0 | 0 | 0 | 0.5-5.9 | 32.0-47.0 | 2.0-8.0 | 34-44 | 0 | 0 | 7.2-12.0 | 0 |
| *C. tinctorus* (Safflower) | 0 | 0 | <0.1 | <0.1 | 2.0-10.0 | 1.0-10.0 | 7.0-16.0 | 0 | 0 | 72-81 | <1.5 |
| *H. annus* (Sunflower) | 0 | 0 | <0.1 | <0.5 | 3.0-10.0 | 1.0-10.0 | 14-65 | 0 | 0 | 20-75 | <0.5 |
| *G. max* (Soybean) | 0 | 0 | <0.1 | <0.5 | 7.0-12.0 | 2.0-5.5 | 19-30 | 0 | 0 | 48-65 | 5.0-10.0 |
| *L. usitatissimum* (Solin-Flax) | 0 | 0 | <0.1 | <0.5 | 2.0-9.0 | 2.0-5.0 | 8.0-60 | 0 | 0 | 40-80 | <5.0 |
| *B. parkii* (Sheanut) | 0 | 0 | 0 | 0 | 3.8-4.1 | 41.2-56.8 | 34.0-46.9 | 0 | 0 | 3.7-6.5 | 0 |

Fatty acyl-CoA/aldehyde reductases suitable for use with the microbes and methods described herein include, without limitation, those listed in Table 8.

TABLE 8

Fatty acyl-CoA/aldehyde reductases listed by GenBank accession numbers.

AAC45217, YP_047869, BAB85476, YP_001086217, YP_580344, YP_001280274, YP_264583, YP_436109, YP_959769, ZP_01736962, ZP_01900335, ZP_01892096, ZP_01103974, ZP_01915077, YP_924106, YP_130411, ZP_01222731, YP_550815, YP_983712, YP_001019688, YP_524762, YP_856798, ZP_01115500, YP_001141848, NP_336047, NP_216059, YP_882409, YP_706156, YP_001136150, YP_952365, ZP_01221833, YP_130076, NP_567936, AAR88762, ABK28586, NP_197634, CAD30694, NP_001063962, BAD46254, NP_001030809, EAZ10132, EAZ43639, EAZ07989, NP_001062488, CAB88537, NP_001052541, CAH66597, CAE02214, CAH66590, CAB88538, EAZ39844, AAZ06658, CAA68190, CAA52019, and BAC84377

Acyl-ACP thioesterases are the terminators of higher plant (and some microalgal species) fatty acid biosynthesis, and in most plant species, this is carried out by members of the FatA gene family, whose role is to terminate elongation at the C16:0 to C18:0 stage. In species that synthesize shorter chain fatty acids (such as *Cuphea, Elaeis, Myristica*, or *Umbellularia*), a different group of acyl-ACP thioesterases encoded by FatB genes carry out this termination step.

Other suitable enzymes for use in the methods described herein include those that have at least 70% amino acid identity with one of the proteins listed in Tables 6 and 8, and that exhibit the corresponding desired enzymatic activity (e.g., cleavage of a fatty acid from an acyl carrier protein, reduction of an acyl-CoA to an aldehyde or an alcohol, or conversion of an aldehyde to an alkane). In additional embodiments, the enzymatic activity is present in a sequence that has at least about 75%, at least about 80%, at least about 85%, at least about 90%, at least about 95%, or at least about 99% identity with one of the above described sequences, all of which are hereby incorporated by reference.

By selecting the desired combination of exogenous genes to be expressed (or endogenous genes to be inactivated or both), one can tailor the oil generated by the microbe, which may then be extracted from the aqueous biomass. For example, the microbe can contain: (i) an exogenous gene encoding a fatty acyl-ACP thioesterase; (ii) optionally, a naturally co-expressed acyl carrier protein or an acyl carrier protein having affinity for the fatty acid acyl-ACP thioesterase; (iii) a mutated endogenous desaturase gene, wherein the mutation renders the desaturase gene or desaturase protein inactive, such as a desaturase knockout; (iv) overexpression of an endogenous stearoyl acyl carrier protein desaturase or the expression of a heterologous SAD; and (v) any combination of the foregoing.

Genes encoding such enzymes, such as fatty acyl ACP thioesterases, can be obtained from cells already known to exhibit significant lipid production such as *Chlorella* protothecoides. Genes already known to have a role in lipid production, e.g., a gene encoding an enzyme that saturates double bonds, can be transformed individually into recipient cells. Methods for identifying genes that can alter (improve) lipid production in microalgae are described in PCT Pub. No. 2008/151149, incorporated herein by reference.

Thus, in certain embodiments, the practice of the present invention may utilize a *Prototheca* or other microalgal or other microbial cell that has been genetically engineered to express a lipid pathway enzyme at an altered level compared to a wild-type cell of the same species. In some cases, the cell produces more lipid compared to the wild-type cell when both cells are grown under the same conditions. In some cases, the cell has been genetically engineered and/or selected to express a lipid pathway enzyme at a higher level than the wild-type cell. In some cases, the lipid pathway enzyme is selected from the group consisting of pyruvate dehydrogenase, acetyl-CoA carboxylase, acyl carrier protein, and glycerol-3 phosphate acyltransferase. In some cases, the cell has been genetically engineered and/or selected to express a lipid pathway enzyme at a lower level than the wild-type cell. In one embodiment in which the cell expresses the lipid pathway enzyme at a lower level, the lipid pathway enzyme comprises citrate synthase.

In some embodiments, the cell has been genetically engineered and/or selected to express a global regulator of fatty acid synthesis at an altered level compared to the wild-type cell, whereby the expression levels of a plurality of fatty acid synthetic genes are altered compared to the wild-type cell. In some cases, the lipid pathway enzyme comprises an enzyme that modifies a fatty acid. In some cases, the lipid pathway enzyme is selected from a stearoyl-ACP desaturase and a glycerolipid desaturase. In some cases, the cell has been genetically engineered and/or selected to express a lower level of a lipid pathway enzyme, or not to express a specific lipid pathway enzyme at all (i.e., wherein a lipid pathway enzyme has been knocked out or replaced with an exogenous gene).

In other embodiments, practice of the present invention utilizes an oil-producing microbe containing one or more exogenous genes and/or one or more inactivated, endogenous genes, wherein the exogenous or endogenous genes encode protein(s) selected from the group consisting of a fatty acyl-ACP thioesterase, a fatty acyl-CoA reductase, a fatty aldehyde reductase, a fatty acyl-CoA/aldehyde reductase, a fatty aldehyde decarbonylase, a desaturase, and an acyl carrier protein. In another embodiment, an endogenous desaturase gene is overexpressed in a microbe containing one or more of the above exogenous genes. In one embodiment, the exogenous gene is in operable linkage with a promoter, which is inducible or repressible in response to a stimulus. In some cases, the stimulus is selected from the group consisting of an exogenously provided small molecule, heat, cold, and limited or no nitrogen in the culture media. In some cases, the exogenous gene is expressed in or otherwise targeted to a cellular compartment. In some embodiments, the cellular compartment is selected from the group consisting of a chloroplast, a plastid and a mitochondrion. In some embodiments the microbe is *Prototheca moriformis, Prototheca krugani, Prototheca stagnora* or *Prototheca zopfii*.

In one embodiment, the exogenous gene or inactivated endogenous gene encodes a fatty acid acyl-ACP thioesterase. In some cases, the thioesterase encoded by the exogenous or inactivated endogenous gene catalyzes the cleavage of an 8 to 18-carbon fatty acid from an acyl carrier protein (ACP). In some cases, the thioesterase encoded by the exogenous gene or inactivated endogenous gene catalyzes the cleavage of a 10 to 14-carbon fatty acid from an ACP. In one embodiment, the thioesterase encoded by the exogenous gene or inactivated endogenous gene catalyzes the cleavage of a 12-carbon fatty acid from an ACP. In some embodiments, the thioesterase encoded by the exogenous gene catalyzes the cleavage of a 16-18 carbon fatty acid from an ACP.

In one embodiment, the exogenous gene encodes a fatty acyl-CoA/aldehyde reductase. In some cases, the reductase encoded by the exogenous gene catalyzes the reduction of an 8 to 18-carbon fatty acyl-CoA to a corresponding primary alcohol. In some cases, the reductase encoded by the exogenous gene or inactivated endogenous gene catalyzes the reduction of a 10 to 14-carbon fatty acyl-CoA to a corresponding primary alcohol. In one embodiment, the reductase encoded by the exogenous gene or inactivated endogenous gene catalyzes the reduction of a 12-carbon fatty acyl-CoA to dodecanol.

Practice of the methods described herein may utilize a recombinant Prototheca (or other microalgal or microbial) cell containing two exogenous genes (or two inactivated endogenous genes), wherein a first exogenous gene or inactivated endogenous gene encodes a fatty acyl-ACP thioesterase and a second exogenous gene or inactivated endogenous gene encodes a protein selected from the group consisting of a fatty acyl-CoA reductase, a fatty acyl-CoA/aldehyde reductase, and an acyl carrier protein. In some cases, the two exogenous genes are each in operable linkage with a promoter, which is inducible in response to a stimulus. In some cases, each promoter is inducible in response to an identical stimulus, such as limited or no nitrogen in the culture media. Limitation or complete lack of nitrogen in the culture media stimulates oil production in some microorganisms such as Prototheca and other microalgal and other microbial species, and can be used as a trigger to induce oil (lipid) production to high levels. When used in combination with the genetic engineering methods disclosed herein, the lipid as a percentage of dry cell weight can be pushed to high levels such as at least 30%, at least 40%, at least 50%, at least 60%, at least 70% and at least 75%.

The novel oils (lipids) and dielectric fluids derived from them disclosed herein are distinct from other naturally occurring oils that are high in C16 and C18 fatty acids, such as sunflower and canola oil.

In one embodiment, the thioesterase encoded by the first exogenous gene catalyzes the cleavage of an 8 to 18-carbon fatty acid from an ACP. Additionally, in those embodiments where oils of longer chain length are desired, expression of one or more shorter chain length (i.e., below C14, such as C12, C10, and/or C8) TE and/or corresponding ACP genes is reduced (via altering its expression) or eliminated (via a knockout, for example).

In the various embodiments described above, the Prototheca (or other microalgal or other microbial) cell can contain at least one exogenous or at least one inactivated (or engineered to reduce expression) endogenous gene encoding a lipid pathway enzyme. In some cases, the lipid pathway enzyme is selected from the group consisting of a stearoyl-ACP desaturase, a fatty acid desaturase, a glycerolipid desaturase, a pyruvate dehydrogenase, an acetyl-CoA carboxylase, an acyl carrier protein, and a glycerol-3 phosphate acyltransferase. In other cases, the Prototheca or other cell contains a lipid modification enzyme selected from the group consisting of a fatty acyl-ACP thioesterase, a fatty acyl-CoA/aldehyde reductase, a fatty acyl-CoA reductase, a fatty aldehyde reductase, a fatty aldehyde decarbonylase, and/or an acyl carrier protein.

VI. PRODUCTION OF MICROBIAL OIL AND PRODUCTS DERIVED THEREFROM

1. Production of Microbial Oil

For the production of microbial oil in accordance with the methods described herein, the raw, unprocessed oil (lipids) produced by microbial cells is harvested, or otherwise collected, by any convenient means. The oil can be isolated by whole cell extraction, for example. In this method, the cells are first disrupted, and then intracellular and cell membrane/cell wall-associated lipids and fatty acids as well as extracellular hydrocarbons can be separated from the cell mass, such as by use of centrifugation as described above. Intracellular lipids produced in microorganisms are, in many embodiments, extracted after or during the process of lysing the microbial cells.

More specifically, after completion of culturing, the microorganisms are typically separated from the fermentation broth. Often, the separation is effected by centrifugation to generate a concentrated paste of microbial biomass. The biomass can then optionally be washed with a washing solution (e.g., DI water) to get rid of the fermentation broth and debris. Optionally, the washed microbial biomass may also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially. The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular embodiments, the microorganism is lysed after growth, for example to increase the exposure of microbial oil for extraction or further processing. If an exogenous lipase gene is being utilized, the timing of lipase expression (e.g., via an inducible promoter) or cell lysis can be adjusted to optimize the yield of lipids and/or hydrocarbons. A number of lysis techniques are described below. These techniques can be used individually or in combination.

In one embodiment of the present invention, the step of lysing a microorganism comprises heating of a cellular suspension containing the microorganism. In this embodiment, the fermentation broth containing the microorganisms (or a suspension of microorganisms isolated from the fermentation broth) is heated until the microorganisms, i.e., the cell walls and membranes of microorganisms, degrade or breakdown. Typically, temperatures applied are at least 50° C. Higher temperatures, such as at least 30° C., at least 60° C., at least 70° C., at least 80° C., at least 90° C., at least 100° C., at least 110° C., at least 120° C., or at least 130° C. or higher, are used for more efficient cell lysis. Lysing cells by heat treatment can be performed by boiling the microorganism. Alternatively, heat treatment (without boiling) can be performed in an autoclave. The heat treated lysate may be cooled for further treatment. Cell disruption can also be performed by steam treatment, i.e., through addition of pressurized steam. Steam treatment of microalgae for cell disruption is described, for example, in U.S. Pat. No. 6,750, 048. In some embodiments, steam treatment may be achieved by sparging steam into the fermentor and maintaining the broth at a desired temperature for less than about 90 minutes, preferably less than about 60 minutes, and more preferably less than about 30 minutes.

In another embodiment of the present invention, the step of lysing a microorganism comprises adding a base to a cellular suspension containing the microorganism. The base should be strong enough to hydrolyze at least a portion of the proteinaceous compounds of the microorganisms used. Bases which are useful for solubilizing proteins are known in the art of chemistry. Exemplary bases which are useful in embodiments of the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

In another embodiment of the present invention, the step of lysing a microorganism comprises adding an acid to a cellular suspension containing the microorganism. Acid lysis can be effected using an acid at a concentration of 10-500 mN or preferably 40-160 nM. Acid lysis is preferably performed at above room temperature (e.g., at 40-160°, i.e., a temperature of 50-1300). For moderate temperatures (e.g., room temperature to 100° C. and particularly room temperature to 650), acid treatment can usefully be combined with sonication or other cell disruption methods.

In another embodiment of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515).

In other embodiments of the present invention, lysis is accomplished using an enzyme such as, for example, a cellulase such as a polysaccharide-degrading enzyme, optionally from *Chlorella* or a *Chlorella* virus, and/or a protease, such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), Alcalase 2.4 FG (Novozymes), and Flavourzyme 100 L (Novozymes). Any combination of a protease and a polysaccharide-degrading enzyme can also be used, including any combination of the preceding proteases and polysaccharide-degrading enzymes.

In another embodiment, lysis can be performed using an expeller press. In this process, biomass is forced through a screw-type device at high pressure, lysing the cells and causing the intracellular lipid to be released and separated from the protein and fiber (and other components) in the cell.

In another embodiment of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

In another embodiment of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules. Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

In another embodiment of the present invention, the step of lysing a microorganism is performed by applying an osmotic shock (i.e., suspending the microorganism cells in a hypotonic solution).

In another embodiment of the present invention, the step of lysing a microorganism comprises infection of the microorganism with a lytic virus. A wide variety of viruses are known to lyse microorganisms suitable for use in the methods described herein, and the selection and use of a particular lytic virus for a particular microorganism is within the level of skill in the art. For example, *paramecium bursaria chlorella* virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable *chlorella* virus. Methods of infecting species of *Chlorella* with a *chlorella* virus are known. See for example *Adv. Virus Res.* 2006; 66:293-336; *Virology,* 1999 Apr. 25; 257(1):15-23; *Virology,* 2004 Jan. 5; 318(1):214-23; *Nucleic Acids Symp. Ser.* 2000; (44):161-2; *J. Virol.* 2006 March; 80(5):2437-44; and *Annu. Rev. Microbiol.* 1999; 53:447-94.

In another embodiment of the present invention, the step of lysing a microorganism comprises autolysis. In this embodiment, a microorganism is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one embodiment, the lytic gene encodes a polysaccharide-degrading enzyme. In certain other embodiments, the lytic gene is a gene from a lytic virus. Thus, for example, a lytic gene from a *Chlorella* virus can be expressed in an algal cell; see *Virology* 260, 308-315 (1999); *FEMS Microbiology Letters* 180 (1999) 45-53; *Virology* 263, 376-387 (1999); and *Virology* 230, 361-368 (1997). Expression of lytic genes is preferably done using an inducible promoter, such as a promoter active in microalgae that is induced by a stimulus such as the presence of a small molecule, light, heat, and other stimuli.

Various methods are available for separating lipids from cellular lysates produced by the above methods. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334). Miao and Wu describe a protocol of the recovery of microalgal lipid from a culture of *Chlorella prototheocoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Thus, lipids, lipid derivatives and hydrocarbons generated by the microorganisms described herein can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Other methods for extracting lipids from microorganisms are described in PCT application No. U.S. Ser. No. 10/031,108, incorporated herein by reference.

Lipids and lipid derivatives such as fatty aldehydes, fatty alcohols, and hydrocarbons such as alkanes produced by cells as described herein can be modified by the use of one or more enzymes, including a lipase. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

2. Further Processing of Microbial Oil

Thus, lipids and hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Once lipids are extracted, the lipids can be, in accordance with the methods described herein, put through one or more processing steps. These processing steps are distinct from refining steps performed on crude oil (e.g., petroleum and other sources) when producing fuels. These processing steps are in some aspects comparable to those performed on seed oils during production for human consumption. In some embodiments, the extracted lipids are degummed to extract lecithin and other phospholipids. In other embodiments, the extracted lipids are refined using a base or alkaline metal. In still other embodiments, the extracted lipids are passed through a bleaching clay, usually an acidic clay. In other embodiments, the extracted lipids are deodorized to eliminate or reduce volatile impurities such as aldehydes and ketones. In still other embodiments, the extracted lipids are winterized to eliminate or reduce waxes or saturated fats. The foregoing processing steps can be performed in any and all combinations on the extracted lipids, depending on the characteristics of the desired product. Extracted lipids that have been refined (e.g., with a base or alkaline metal), bleached (e.g., with a bleaching clay) and/or deodorized is usually referred to as RBD oil. RBD oil produced from extracted lipids from microalgae and/or oleaginous yeast described herein are useful in a variety of industrial applications, including the production of dielectric fluids.

In some embodiments, degumming is performed to remove contaminants such as phospholipids from the oil. In some embodiments of the invention, degumming of the extracted oil is part of the refining, bleaching and deodorizing (or RBD). The RBD process eliminates or reduces the odor, color and/or taste of the extracted oil. In some embodiments, the refining process usually consists of two steps, degumming and a neutralization step that removes the free fatty acids (FFA) in the oil through caustic stripping with sodium hydroxide. The bleaching step may involve mixing the oil with various bleaching clays to absorb color, trace metals and sulfur compounds. The deodorizing step may be a distillation process that occurs at low pressure and high temperature. In an illustrative distillation process, the oil is put under a vacuum and heated with steam to remove any leftover taste or odors and FFAs. Deodorizing can also be achieved by treatment with activated charcoal.

The above-recited steps can serve to reduce the pour point. In various embodiments, the pour point of the microbial oil (lipid) can be reduced to about −10 degrees C., about −15 degrees C., about −20 degrees C., about −25 degrees C., about 30 degrees C., about −35 degrees C., or about −40 degrees C. In addition, the pour point of the microbial oil can fall within any range bounded by any of these values, e.g., about −10 degrees C. to −40 degrees C. or about −15 degrees C. to about −35 degrees C., etc. The reduction in pour point may occur because these steps reduce the relative proportion of the saturated fraction, which consists primarily of palmitic and stearic triglycerides, known as the stearin fraction. Fractionating the oil reduces the saturated triglycerides concentration of the oil. Fractionation may be accomplished by dry fractionation, as in the winterizing process known in the vegetable oil industry. In this process, the microbial (e.g., algal) oil is first refined, bleached and deodorized by methods similar to those used in the vegetable oil industry. This results in oil with a pour point in the range of −5 to −10 degrees C., for example −8 degrees C.

The temperature of the RBD oil may then lowered in a controlled manner until crystal nuclei are formed. The oil may then be then held at that crystallization temperature for several hours to facilitate growth of the crystals. The crystals are then removed by filtration to result in two fractions: a solid phase containing some or most of the stearin fraction, and a liquid phase containing mostly the olein fraction. This results in oil with a pour point in the range of −8 to −15 degrees C., for example −11 degrees C. The liquid phase can be subjected to fractionation again to a lower crystallization temperature to effect a further removal of stearin. The resulting purified liquid fraction, equivalent to a super olein, as commonly known in the vegetable oil industry, has better thermal properties than the native microbial oil. For example, a second fractionation can result in oil with a pour point in the range of −15 degrees to −25 degrees C., for example −20 degrees C. The resulting oil is exceptionally useful in a variety of applications, including, importantly food applications, in which the microbial oil can be used as a cheaper, and often healthier, replacement, in whole or in part, of animal and vegetable oils.

3. Products Derived from Microbial Oils

Microbial oils described herein can also be used to produce products, such as lubricants, hydraulic fluids, industrial oils, or dielectric fluids. Common industrial oils include chainsaw bar lubricants, metal working fluids, food grade lubricants, gear oils, marine oils, engine lubricants, tractor oils, agricultural equipment lubricants, elevator oils, mould release oils, and the like. Dielectic fluids are typically used to cool and/or electrically insulate electrical components (especially in high voltage electrical power distribution equipment), such as, for example, autoreclosers, capacitors, circuit breakers, high voltage fluid-filled transmission cables, power distribution components, switching gear (e.g., a high-voltage loadbreak switch, such as those described in U.S. Pat. No. 6,797,909), transformers, transmission components, and voltage regulators.

Traditional dielectric fluids include the mineral oil-based lubricants. These include the Group 1, II, and II+ base oils, which are petroleum base oils that have been conventionally refined or mildly hydrotreated and have a viscosity index (VI) of less than 120. These also include the Group III base oils (including "synthetic motor oil" in the US) that are highly refined conventional oil products. The Group III base oils can be made by hydroprocessing (hydrocracking and/or hydroisomerizing) Group 1 or Group II/II+ base oils and contain less saturates, sulfur, and nitrogen than the Group I, II, or II+ base oils and have a VI greater than 120. The American Society of Testing and Materials (ASTM) establishes specifications for dielectric fluids and other hydrocarbon compositions (such as diesel fuel (ASTM D975), jet fuel (ASTM D1655), and biodiesel (ASTM D6751)) according to any of a number of factors, such as the boiling point, cetane number, cloud point, flash point, viscosity, aniline point, sulfur content, water content, ash content, copper strip corrosion, and carbon residue.

Bio-based dielectric fluids can be prepared by a variety of processes. For example, one process, starting with crude vegetable oil involves the steps of degumming, alkali refining, bleaching, deodorizing, hydrogenating, winterizing (to yield RBD vegetable oil), treating with clay to remove trace polar compounds and acidic materials (see U.S. Pat. No. 6,274,067), and combining with additives to produce bio-based dielectric fluids.

Key properties of dielectric fluids include viscosity, flammability, reactivity, miscibility, electrical insulating capability, biodegradability, and cost of manufacture. While these and other properties are reviewed below, the reader can better appreciate some of the advantages of certain embodiments of the present invention by understanding some of the advantages and disadvantages of traditional bio-based dielectric fluids over mineral oil-based dielectric fluids. For viscosity, bio-based dielectric fluids generally have a higher viscosity and pour point, and thus poorer low temperature properties relative to mineral oil-based dielectric fluids. However, the viscosity of the latter may vary from lot to lot due to the inconsistency between and complexity of the compounds in various sources of mineral oil. Bio-based dielectric fluids generally have higher flash and fire points (by at least two fold) relative to mineral-oil based dielectric fluids. Bio-based dielectric fluids generally have inferior hydrolytic, thermal, and oxidative stability, and a higher acid number (by about two fold) relative to mineral-oil based dielectric fluids. Bio-based dielectric fluids generally are more biodegradable and have lower toxicity relative to mineral-oil based dielectric fluids and are made from a renewable, as opposed to non-renewable, resource. Bio-based dielectric fluids generally cost more to produce and require more additives relative to mineral-oil based dielectric fluids.

The methods of the present invention provide new dielectric fluids that, in certain embodiments, have all of the advantages of traditional bio-based dielectric fluids with fewer, and in some embodiments, none of, the disadvantages. These and other advantages of the present methods can be better appreciated after consideration of the following discussion of the general properties of dielectric fluids.

Ideally, the viscosity of a dielectric fluid should vary as little as possible with temperature. Viscosity is a measure of the resistance of a fluid to flow or shear ("thickness") and is measured in kinematic (kv) and absolute (dynamic) (cSt or $mm^2/s$ @ 40 and 100° C.). (ASTM D2270-04; ASTM D445; ASTM D88). Generally, the least viscous lubricant which adequately forces two moving surfaces apart is desired. Viscosity is sometimes considered the most important characteristic of a hydraulic fluid. If the viscosity is too high, then friction, pressure drop, power consumption, and heat generation increase. If the viscosity is too low, then increased internal leakage may result under higher operating temperatures. The oil film may be insufficient to prevent excessive wear or possible seizure of moving parts. Illustrative viscosities (in cSt units) of dielectric fluid derived from various sources are: mineral oil-derived: 20 at 40° C. and 4 at 100° C.; soybean oil-derived: 30 at 40° C. and 7.6 at 100° C.; sunflower oil-derived: 40 at 40° C. and 8.7 at 100° C.; and rapeseed (canola) oil-derived: 33 at 40° C. (Siniawski et al.; *J. Synthetic Lubrication;* 24, 101-110 (2007); Schneider; *J. Sci. Food Agric.,* 86, 1769-1780 (2006)). The methods of the present invention can, in particular embodiments, provide dielectric fluids having viscosities similar to those of dielectric fluids derived from the foregoing sources. In illustrative embodiments, the dielectric fluid has a viscosity at 40° C. of less than about 110 cSt, e.g., in the range of 20-30 cSt and/or a viscosity at 100° C. in the range of about 2 to about 15 cSt, e.g., 4-8 cSt.

The viscosity index (VI, a unitless number) is a measurement of the variation in viscosity with variation of temperature. For VI, one compares the kv of oil at 40° C. to two reference oils (with VI's of 0 and 100), where all oils have the same kv at 100° C. (ASTM D2270). The VI value generally should be as high as possible. High VI values indicate the viscosity of the oil changes little with temperature. In general: a low VI is below 35; a medium VI is 35 to 80; a high VI is 80 to 110; a very high VI is 110 to 125; a super VI is 125 to 160; and a super high VI is equal to or greater than 160. VIs of dielectric fluids derived from various starting materials include: mineral oil-derived: 103; soybean oil-derived: 246; and sunflower oil-derived: 206. (Siniawski et al.; *J. Synthetic Lubrication;* 24, 101-110

(2007)). The methods of the present invention can, in particular embodiments, provide dielectric fluids having VIs similar to those of dielectric fluids derived from the foregoing sources.

The pour point is the lowest temperature at which a liquid will pour or flow (° C.) (ASTM D97). The pour point should be at least 10° C. lower than the lowest anticipated ambient temperature at which the dielectric fluid is to be used. The pour points of dielectric fluids derived from various starting materials include: mineral oil-derived: −50° C.; soybean oil-derived: −9° C.; sunflower oil-derived: −12° C.; and rapeseed (canola) oil-derived: −21° C. (Siniawski et al.; *J. Synthetic Lubrication;* 24, 101-110 (2007)). The methods of the present invention can, in particular embodiments, provide dielectric fluids having pour points similar to those of dielectric fluids derived from the foregoing sources. In various embodiments, the pour point of a microbial oil-based dielectric fluid can be about −10 degrees C., about −15 degrees C., about −20 degrees C., about −25 degrees C., about 30 degrees C., about −35 degrees C., or about −40 degrees C. In addition, the pour point of the microbial oil-based dielectric fluid can fall within any range bounded by any of these values, e.g., about −10 degrees C. to −40 degrees C. or about −15 degrees C. to about −35 degrees C., etc.

For example, and as described above, RBD oil produced in accordance with the methods described herein can readily be produced with pour points of approximately −8° C. or lower. This pour point can be further lowered by admixing the RBD oil with a pour point depressant to achieve oils with pour points in the range of −15 to −20° C. or lower based on the amount of pour point depressant added to the oil. The olein fraction from a single fractionation readily produces oil with a pour point of about −11° C., which can be lowered by admixing the olein fraction with a pour point depressant to achieve oils with pour points in the range of −16 to −20° C. or lower based on the amount of pour point depressant added to the oil. The olein fraction from a second fractionation ("super olein") readily produces oil with a pour point of approximately −20° C., which can be lowered by admixing the super olein fraction with a pour point depressant to achieve oils with pour points below −20° C., i.e., −26° C. or lower based on the amount of pour point depressant added to the oil. A wide variety of pour point depressants are available commercially from Chevron, Oronite, Infineum, General Electric, RohmMax Evonik, and others. Illustrative pour point depressants for use with the microbial oils (lipids) described herein include VISCOPLEX® 10-310 or 1-133 (Rohmax-Evonik Additives GmbH), or other poly(alkyl) acrylates and poly(methyl)acrylates such as INFINEUM® V-351 (Infineum UK limitied), PMA-D110 and PMA D.

The lubricity (anti-wear properties) of a dielectric fluid is important, as premature wear occurs when the fluid viscosity is insufficient and the fluid film does not prevent surface contact (ASTM D2882). In some embodiments, the methods of the present invention provide dielectric fluids having good lubricity (equivalent or better than ASTM D2882).

The volatility, or the tendency for an oil to vaporize (atm vapor vs. ° C.), is also important for a dielectric fluid. Generally, lower volatility is preferred. In some embodiments, the methods of the present invention can provide dielectric fluids having volatility as low as and even lower than mineral oil-based and traditional bio-based dielectric fluids.

The flammability of the dielectric fluid is important. Generally, lower flammability is preferred (see "Bio-Based Lubricants: A Market Opportunity Study Update" United Soybean Board, November 2008, Omni Tech International, Ltd., www.soynewuses.org/downloads/reports/BioBased-LubricantsMarketStudy.pdf). The methods of the present invention can, in particular embodiments, provide dielectric fluids having flammability as low and even lower than mineral oil-based and traditional bio-based dielectric fluids.

The flash point is the lowest temperature (° C.) at which an oil vaporizes to form an ignitable mixture in air. ASTM D3278, D3828, D56, and D93 describe flash point specifications suitable for dielectric fluids. To prevent ignition of the oil, the flash point should generally be as high as possible. Flash points of dielectric fluids derived from various sources include: mineral oil-derived: 147° C.; and TAGs-derived (typical): 324° C. (New Safety Dielectric Coolants for Distribution and Power Transformers, www-.cooperpower.com/Library/pdf/00048.pdf) In some embodiments, the methods of the present invention can provide dielectric fluids having flash points similar to those of dielectric fluids derived from the foregoing sources and equal to or higher than ASTM D1310 and ASTM D92 specifications.

The fire point is lowest temperature (° C.) at which an oil will continue to burn for at least 5 seconds after ignition by an open flame. ASTM D1310 and ASTM D92 describe fire point specifications suitable for dielectric fluids. To prevent ignition of the oil, the fire point should be as high as possible. Fire points of dielectric fluids derived from various sources include: mineral oil-derived: 165° C.; and TAGs-derived (typical): 360° C. (New Safety Dielectric Coolants for Distribution and Power Transformers, www.cooperpower.com/Library/pdf/00048.pdf) In some embodiments, the methods of the present invention can provide dielectric fluids having fire points similar to those of dielectric fluids derived from the foregoing sources and equal to or higher than ASTM D1310 and ASTM D92 specifications. In some embodiments, that fire point is above 300° C., e.g., 300° C. to 450° C.

The reactivity of a dielectric fluid is important; the dielectric fluid should not react (or should have a low reactivity) with acids/bases, heat, and air.

Hydrolytic reactivity refers to the susceptibility of fluid to decomposition in the presence of acids or bases. ASTM D2619 and ASTM D943 describe hydrolytic reactivity suitable for dielectric fluids. In TAGs, the susceptible functional groups are the esters and acid/base susceptible functional groups. The methods of the present invention can, in particular embodiments, provide dielectric fluids having low hydrolytic reactivity (equivalent or better than ASTM D2619 and/or ASTM D943).

Thermal stability refers to the susceptibility of a dielectric fluid to thermal decomposition. In bio-oil-derived dielectric fluids, thermal instability is typically due to the β-hydrogens on glycerol, ultimately resulting in elimination products. The methods of the present invention can, in particular embodiments, provide dielectric fluids having high thermal stability (equal to or greater than that of traditional bio-oil-derived dielectric fluids).

Oxidative susceptibility refers to the susceptibility of a dielectric fluid to reaction with oxygen to form oxidation products. ASTM D943 and ASTM D2272 describe oxidative stability suitable for dielectric fluids. Low susceptibility to oxidation is desired; higher values indicate more oxidative lubricants. In certain embodiments, the methods of the present invention can, in particular embodiments, provide dielectric fluids having low oxidative susceptibility (e.g., ASTM D943 or ASTM D2272).

The neutralization number (acid value/acid number) is a measure of the amount of acid in an oil or dielectric fluid. Acids are formed as oils (or dielectric fluids) oxidize with age and service. Acids arise in bio-based lubricants from oxidation, ester thermolysis, or acid/base hydrolysis. ASTM D947, ASTM D3487, and ASTM D6871 describe neutralization numbers suitable for dielectric fluids. Generally, the acid value should be as low as possible. The acid number for standard mineral oil is 0.03 and for bio-based oil is 0.06. (Ester Transformer Fluids, IEEE/PES Transformer Committee Meeting, Oct. 7, 2003, www.transformerscommittee.org/info/F03/F03-EsterFluids.pdf). The methods of the present invention can, in particular embodiments, provide dielectric fluids having low acid numbers (e.g., ASTM D947, ASTM D3487, or ASTM D6871).

Miscibility refers to the ability of a fluid to mix with other fluids. Ideally, a dielectric fluid should mix well with other lubricants, fluids, and additives but not with water. Demulsibility refers to how well a hydraulic fluid resists mixing with water. Demulsibility is optimal in a dielectric fluid. Miscibility with desired lubricants and additives is optimal in a dielectric fluid. In certain embodiments, the methods of the present invention can, in particular embodiments, provide dielectric fluids with good miscibility and demulsibility.

Dielectric fluids should have good electrical insulation properties, i.e., they should prevent dissipation of electrical current. Insulation power factor tests are conducted on transformers to measure dielectric losses (measured in %). This value reports on the condition of the transformer—wetness, dryness, deterioration of insulation, condition of the windings, barriers, tap changers, bushings and oil. The power factor values associated with a dielectric fluid should be as low as possible, typically 0.5% or less. For example, the power factor of new oil shipped from a refinery should be no more than 0.05% at 25° C. and no more than 0.3% at 100° C. (IEEE Guideline C57, 106-1991 as cited in www.nttworldwide.com/tech2209.htm). For new oil in new equipment operating at or below 69 kV, the power factor should be no more than 0.15% at 25° C. and no more than 1.5% at 100° C.; operating at 69 kV to at or below 288 kV, the power factor should be no more than 0.10% at 25° C. and no more than 1.0% at 100° C.; operating at 345 kV or higher, the power factor should be no more than 0.05% at 25° C. and no more than 0.3% at 100° C. New oil for circuit breakers should have a power factor of no more than 0.05% at 25° C. and no more than 0.3% at 100° C. Oil used in circuit breakers should not have a power factor above 1.0% at 25° C. Certain embodiments of the methods of the present invention provide dielectric fluids with favorable power factor requirements.

The dielectric strength refers to the maximum electric field strength the dielectric fluid (electrical insulator) can resist before breaking down. The dielectric strength is measured in units of MV/m, (relative permittivity), and ASTM D877 provides specifications suitable for dielectric fluids. For use as an electrical insulator, the dielectric strength of the lubricant should be as high as possible. The methods of the present invention can, in particular embodiments, provide dielectric fluids with dielectric strengths equal or superior to those specified by ASTM D877.

The dissipation factor is a measure of electrical loss due to the dielectric fluid when used as an electrical insulator and is measured in % units at 25° C. ASTM D924 provides specifications suitable for dielectric fluids. As an electrical insulator, the dissipation factor value should be as low as possible. In certain embodiments, the methods of the present invention provide dielectric fluids with dissipation factors equal or superior to those specified by ASTM D924.

The electrical conductivity is a measure of a dielectric fluid's ability, when used as an electrical insulator, to conduct an electrical current and is measured in units of $S \cdot m^{-1}$. ASTM D2624 provides specifications suitable for dielectric fluids. As an insulator, the electrical conductivity value of the dielectric fluid should be as low as possible. The embodiments of the methods of the present invention provide dielectric fluids with favorable electrical conductivity compared to those specified by ASTM D2624.

For use in electrical transformers and other applications, the thermal properties of the dielectric fluid should be such that heat is efficiently transferred. Specific heat refers to the thermal capacity of a substance and is measured in units of cal/gm/° C. ASTM D-2766 provides specifications suitable for dielectric fluids. Higher specific heat values enable more efficient heat transfer and cooling. Specific heat values for mineral oil-derived dielectric fluids are generally about 0.39 and for TAGs-derived dielectric fluids about 0.45. (Safety Dielectric Coolants for Distribution and Power Transformers, www.cooperpower.com/Library/pdf/00048.pdf). Methods in accordance with embodiments of the present invention may provide dielectric fluids with specific heat values equal or higher to 0.39 and/or that meet ASTM D2624 specifications.

The environmental properties of a dielectric fluid are important. Generally, one should employ dielectric fluids selected so as to mitigate the environmental effects of a spill or other accident. Biodegradability refers to the property of a dielectric fluid to decompose into carbon dioxide and water in the environment and is generally measured in units of % per 28 days. OECD 301B and ASTM D-6046 provide biodegradability specifications suitable for dielectric fluids. Readily biodegradable biodegradability values are generally ~100%; inherently biodegradable biodegradability values are generally 20-70%; and non-biodegradable biodegradability values are generally negligible to 0%. Mineral oil-derived dielectric fluids generally have biodegradability values in the range of 15-35%, and bio-oil-derived dielectric fluids generally have biodegradability values in the range of 70-100%. Certain embodiments of the methods of the present invention may provide dielectric fluids with biodegradability values in the range of 70-100% (see *Renewable Lubricants Manual: Biobased Oils, Fluids, & Greases* www.renewablelubricants.com/RenewableLubricants-Manual_Biodegradable.html# Introduction).

The iodine value (or iodine number) is a measure of the degree of unsaturation on an oil. More specifically, the iodine value is the mass of iodine that is consumed by the unsaturated bonds in an oil. Drying oils have relatively high iodine values of about 175 or higher. Soybean oils are about 130, and olive oils have iodine values of about 80. Iodine values are routinely determined in the art. Standard methods to determine iodine values include ASTM D5768-02 (2006) and DIN 53241. In various embodiments, a microbial oil in a microbial oil-based product, e.g., a dielectric fluid, can have an iodine value of between about 25 and about 200, e.g., about 50, about 75, about 100, about 125, about 150, or about 175. Furthermore, the iodine value can be within any range bounded by any of these values, e.g., about 25 to about 175, about 50 to about 200, about 50 to about 175, etc.

Fatty acid unsaturation can also be altered. Increasing unsaturation decreases freezing/pour points. Monounsaturation, such as that seen in high oleic acid bio-lubricants, is currently optimal and represents a balance between pour point and oxidative reactivity. Monounsaturated oils react with air, but much more slowly than poly-unsaturated FAs or PUFAs. Examples of PUFAs include arachidonic acid (ARA), eicosapentaenoic acid (EPA), and docosahexaenoic acid (DHA). Di- and poly-unsaturated FAs are highly susceptible to oxidation and unsuitable for electrical applications. One problem with dielectric fluids derived from vegetable oils is the presence of polyunsaturated FAs (e.g., linoleic acid and linolenic acid). One advantage of the dielectric fluids of some embodiments of the present invention is that the microbial oil they comprise (or are derived from) contains less, and in some embodiments, no, di- and poly-unsaturated FAs than do dielectric fluids derived from other bio-oils.

The lipid profile of the dielectric fluid is usually highly similar to the lipid profile of the feedstock oil. High amounts of longer chain (C16-C18) mono-unsaturated fatty acids are preferable for use as dielectric fluids. Polyunsaturated fatty acids (such as C18:2, C18:3, ARA, EPA and DHA) are not preferred due to oxidation and the production of oxidation products. Saturated fatty acids tend to be solid or a liquid with a high freezing point, thereby making saturated fatty acids undesirable in large quantities in dielectric fluids. In various embodiments, microbial oil (lipid) useful in dielectric fluids is at least about 50% C18:1, e.g., at least about 55%, at least about 60%, at least about 65%, at least about 70%, at least about 75%, at least about 80%, at least about 85%, and at least about 90% C18:1. In these or other embodiments, the microbial oil (lipid) is less than about 10% C18:2, e.g., less than about 7.5%, less than about 5%, less than about 2.5%, and less than about 1% C18:2. The microbial oil can have any combination of percentages of C18:1 and C18:2 that adds up to 100% or less. For example the microbial oil can have at least 50% C18:1 and less than 10% C18:2 or at least 80% C18:1 and less than 5% C18:2.

For illustrative purposes, provided herein are TAG oils from oleaginous microbes that contain less than 2% C18:2 (see Example 4), compared to 20-75% in sunflower oil and 48-65% in soybean oil. Also provided are TAG oils with less than 0.5% C18:3, compared to 5-10% in soybean oil.

These and other properties of a dielectric fluid can be achieved, manipulated, and/or varied in accordance with the methods described herein so as to provide a product, such as a lubricant, a hydraulic fluid, a industrial oil, or dielectric fluid, suitable for any application. For example, genetic manipulation of oleaginous microbes can be performed, as described above, to alter chain length, saturation, and/or composition of the various fatty acids in the lipid. In certain embodiments, a microbial oil useful as described herein is produced by a genetically engineered microbe that has been engineered to exposes one or more exogenous genes. For example, the genetically engineered microbe can be *Prototheca* (e.g, *Prototheca moriformis*) or *Chlorella*. Illustrative exogenous genes include those encoding sucrose invertase and/or fatty acyl-ACP thioesterase.

In addition, lipid extracted from a microalgae or oleaginous yeast can be subjected to various chemical modifications to achieve a desired property in a dielectric fluid. Typical alterations include altering fatty acid (FA) chain length. Shorter-chain FAs have decreased pour points. Chemical modifications can also be used in accordance with embodiments of the methods of the invention to reduce unsaturation and include alkylation, radical addition, acylation, ene-reactions, hydroformylation, selective hydrogenation, oligomerization, hydroaminomethylation, acyloxylation, and epoxidation. In addition, or as an alternative, an additive, such as pour point depressant, can be admixed with the processed microbial oil to achieve a desired property, e.g., pour point. Illustrative additive are discussed in greated detail below.

As discussed above, in particular embodiments, the raw microbial oil extracted from an oleaginous microbe is typically "enriched" prior to incorporation into a product of the invention. For example, there can be contaminants in microbial lipids that can crystallize and/or precipitate and fall out of solution as sediment. Sediment formation is particularly a problem when a dielectric fluid is used at lower temperatures. The sediment or precipitates may cause problems such as decreasing flow, clogging, etc. Processes are well-known in the art that specifically deal with the removal of these contaminants and sediments to produce a higher quality product. Examples for such processes include, but are not limited to, pretreatment of the oil to remove contaminants such as phospholipids and free fatty acids (e.g., degumming, caustic refining and silica adsorbant filtration).

Winterization can be used in accordance with embodiments of the methods of the invention to enrich the microbial oil. There are several approaches to winterizing a dielectric fluid in accordance with embodiments of the present invention. One approach is to blend the fluid with other dielectric fluids. Another approach is to use additives that can lower the freeze point. Dry fractionation can also be used to reduce the relative proportion of the saturated fraction (the stearin fraction). By cooling the oil, one can crystallize the saturates and then filter out the crystals. Fractionation selectively separates a fluid into individual components or fractions, allowing for the removal or inclusion of specific fractions. Other fractionation methods include urea fractionation, solvent fractionation and thermal distillation.

Diatomaceous earth or other filtering material such as bleaching clay may then added to the cooled liquid to form a slurry, which may then filtered through a pressure leaf or other type of filter to remove the particulates. The filtered liquid may then be run through a polish filter to remove any remaining sediments and diatomaceous earth, so as to produce a final product. Alternatively, or in addition, this product, or the microbial oil produced at the end of any of the foregoing process steps, can be admixed with a pour point depressant to produce a product of the invention, such as a dielectric fluid.

In one embodiment of the present invention, a method for producing a lubricant oil or a dielectric fluid is provided that comprises the steps of (a) cultivating a lipid-containing microorganism using methods disclosed herein, (b) lysing a lipid-containing microorganism to produce a lysate, (c) isolating the lipid composition from the lysed microorganism, and (d) enriching the isolated lipid composition, whereby a lubricant oil or dielectric fluid is produced. Typically, step (d) will include one or more refining, bleaching, and/or deodorizing steps and one or more fractionation steps to reduce the relative proportion of the saturated fraction by removing palmitic and/or stearic triglycerides. In a further embodiment, the lubricant oil or dielectric fluid resulting from step (d) is admixed with a pour point depressant.

Optionally, other additives for increasing the oxidative stability of the isolated lipids can be admixed with the microbial oil, lubricant, or dielectric fluid produced by these methods. Examples of such additives include antioxidants such as tocopherols (vitamin E, e.g., alpha-, beta- and/or delta-tocopherol), ascorbic acid (vitamin C). Suitable antioxidants are commercially available. The BASF company markets a line of suitable phenol based and amine based antioxidants under the brand name IRGANOX®.

IRGANOX L109, IRGANOX L64, IRGANOX L57, other IRGANOX antioxidants, and other phenol based and amine based compounds are suitable as antioxidant additives to the oils and products including dielectric fluids. Other nonlimiting examples of antioxidants include butylated hydroxy anisole (BHA), butylated hydroxy toluene (BHT), mono-tertiary butyl hydro quinone (TBHQ), butylated hydroanisole, tetrahydrobutrophenone, ascorbyl palmitate, and propyl gallate. In certain embodiments, a microbial oil-based product, e.g., a dielectric fluid, additionally includes an antioxidant at 0.1% to 5% by weight, and preferably at 0.5% to 2%.

Other additives that can be optionally added to the isolated lipids for use as products such as dielectric fluids are deactivators for metal ions, corrosion inhibitors, anti-wear additives, and/or hydrolysis protectants. Some widely used additives in dielectric fluids are described in Schneider, 2006, *J Science Food and Agriculture;* 86: 1769-1780.). Metal ion deactivators have two main functions. They suppress chemical attack on the surface of the metal and they also passivate the metal surface to suppress any residues that may act as catalysts for radical (unpaired electron) formation. Metal deactivators are commercially available. For example, the BASF company provides a line of metal deactivators, including the IRGAMET® line of metal deactivators. The RTVANDERBILT company sells the CUVAN® line of metal deactivators. Other examples of metal deactivators include derivatized triazoles including 1-(di-isooctylaminomethyl)-1,2,4-triazole, 1-(2-methoxy-prop-2-yl)tolyltriazole, 1-(1-cyclohexyloxypropyl)tolyltriazole, 1-(1-cyclohexyloxyheptyl)tolyltriazole, 1-(1-cyclohexyloxybutyl)tolyltriazole, 1-[bis(2-ethylhexyl) aminomethyl-4-methylbenzotriazole, derivatized borons including triethyl borate, tripropyl borate, triisopropyl borate, tributyl borate, tripentyl borate, trihexyl borate, tricyclohexyl borate, trioctyl borate, triisooctyl borate, and other derivatized hydrazine metal deactivator, e.g., 2',3-bis[[3-[3,5-di-tert-butyl-4-hydroxyphenyl]propionyl]]proponiohydrazine, and the like.). In certain embodiments, a microbial oil-based product, e.g., a dielectric fluid, additionally includes one or more metal deactivators at 0.1% to 5% by weight, and preferably at 0.5% to 2%.

Thus, dielectric fluids prepared in accordance with the methods described herein may contain a number of additives, including but not limited to one or more of the following additives: (a) an antioxidant, including but not limited to BHT and other phenols; (b) a deactivator of metal ions such as Cu, Zn, and the like, including but not limited to a benzotriazole; (c) corrosion inhibitors, including but not limited to ester sulfonates and succinic acid esters; (d) demulsifiers; (e) anti-wear additives, including but not limited to zinc dithiophosphate; (f) additives to depress the pour point, including but not limited to malan styrene copolymers, poly(alkyl)acrylates, including but not limited to polymethacrylates; and (g) compounds that protect against hydrolysis, including but not limited to carbodiimides.

In certain embodiments, a method of the invention produces a product including a microbial oil that has a pour point of between about −10° C. and about −40° C., and wherein the fatty acid composition of the microbial oil is at least 50% C18:1 and less than 10% C18:2. The method entails cultivating a genetically engineered microbe engineered to express one or more exogenous genes until the microbe has at least 10% oil by dry weight. Illustrative genetically engineered microbes include *Prototheca* (e.g., *Prototheca moriformis*) or *Chlorella*. Illustrative exogenous genes include those encoding sucrose invertase and/or fatty acyl-ACP thioesterase. In some embodiments, the genetically engineered microbe expresses at least two exogenous genes, e.g., encoding sucrose invertase and fatty acyl-ACP thioesterase, encoding two different fatty acyl-ACP thioesterase, or encoding sucrose invertase and two different fatty acyl-ACP thioesterases. Once the microbe has at least 10% oil by dry weight, the oil is separated from the microbe and subjected to refining, bleaching, deodorizing or degumming to produce RBD oil. Optionally, an antioxidant, metal ion deactivator, corrosion inhibitor, demulsifier, anti-wear additive, pour point depressant, and/or anti-hydrolysis compound can be added to the RBD oil to produce a desired product.

In particular embodiments, a fractionation method of the invention produces a microbial oil suitable for incorporation into products (e.g., a dielectic fluid) that has a pour point of between about −10° C. and about −40° C., and wherein the fatty acid composition of the microbial oil is at least 50% C18:1 and less than 10% C18:2. The method entails subjecting a starting (i.e., "first") microbial oil to refining, bleaching, deodorizing or degumming to produce RBD oil, wherein the RBD oil is characterized by an initial pour point and a first temperature, lowering the temperature of the RBD oil to a second temperature, and filtering the RBD oil at the second temperature to provide a second microbial oil characterized by a second pour point that is lower than the initial pour point, wherein the second pour point is between about −10° C. and about −40° C., and wherein the fatty acid composition of the second microbial oil is at least 50% C18:1 and less than 10% C18:2. An illustrative first temperature is between above 15° C. to about 50° C., and an illustrative second temperature is between about −15° C. and about 15° C. Optionally, an antioxidant, metal ion deactivator, corrosion inhibitor, demulsifier, anti-wear additive, pour point depressant, and/or anti-hydrolysis compound can be added to the second microbial oil to produce a desired product. In variations of these embodiments, the first microbial oil is produced by cultivating a genetically engineered microbe engineered to express one or more exogenous genes until the microbe has at least 10% oil by dry weight and then separating the oil from the microbe to produce the first microbial oil. This method can be employed to produce, e.g., a lubricant, a hydraulic fluid, an industrial oil, or a dielectric fluid. In certain embodiments, where the product is a dielectic fluid, the fluid includes one or more of an antioxidant, a metal ion deactivator, a corrosion inhibitor, a demulsifier, an anti-wear additive, a pour point depressant, or an anti-hydrolysis compound.

In one embodiment of the invention, a dielectric fluid is produced by blending oils and/or dielectric fluids derived from oleaginous microbes with existing oils or dielectric fluids. The existing oils and dielectric fluids can be of plant or animal (or both, i.e., petroleum) in origin.

Thus, the present invention includes a variety of methods in which lipid from oleaginous microbes is undertaken to yield dielectric fluids and other products useful in a variety of industrial and other applications. Examples of processes for modifying oil produced by the methods disclosed herein include, but are not limited to, hydrolysis of the oil, hydroprocessing of the oil, and esterification of the oil. Other chemical modification of microalgal lipid include, without limitation, epoxidation, oxidation, hydrolysis, sulfations, sulfonation, ethoxylation, propoxylation, amidation, and saponification. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein.

In certain embodiments, a dielectric fluid described herein is employed in a an electrical system, such as a transformer, including a tank housing a transformer core/coil assembly, wherein the dielectric fluid surrounds the core/coil assembly. In variations of such embodiments, the tank also includes an oxygen absorbing material that is in contact with gases in the tank, but isolated from contact with the dielectric insulating fluid. Suitable oxygen absorbing materials are those that are capable of reducing the concentration of free oxygen in the atmosphere surrounding the dielectric fluid inside the tank and that in turn reduce the presence of dissolved oxygen in the fluid itself. Such compounds can be referred to as oxygen scavenging compounds. Useful oxygen scavenging compounds include those commonly employed in the food packaging industry. Representative of the oxygen scavenging compounds useful in the practice of the invention include the following: sodium sulfite; copper sulfate pentahydrate; a combination of carbon and activated iron powder; mixtures of hydrosulfite, calcium hydroxide, sodium bicarbonate and activated carbon; a metal halide powder coated on the surface of a metal powder; and combinations of alkali compounds, such as calcium hydroxide, with sodium carbonate or sodium bicarbonate. Mixtures and combinations of one or more of the above compositions are also considered useful. Also useful as oxygen scavenging compounds are those compositions provided according to U.S. Pat. No. 2,825,651, which is incorporated by reference, including an oxygen remover composition comprising an intermixing of a sulfite salt and an accelerator such as hydrated copper sulfate, stannous chloride, or cobaltous oxide. Another useful class of oxygen scavenging compounds includes those compositions comprising a salt of manganese, iron, cobalt or nickel, an alkali compound, and a sulfite or deliquescent compound, such as disclosed by U.S. Pat. No. 4,384,972, which also is incorporated by reference. Preferred oxygen scavenging compounds include (or include as their base component) at least one basic iron oxide, such as a ferrous iron oxide, or are made of mixtures of iron oxide materials. Useful iron oxide-containing compositions are available commercially, for example, under the "Ageless" trade name from the Mitsubishi Gas Chemical Company of Duncan, S.C. and under the "Freshmax" trade name from Multisorb Technologies, Inc. of Buffalo, N.Y. Also useful are oxygen absorbing agents comprising a mixture of ferrous salts and an oxidation modifier and/or a metallic sulfite or sulfate compound.

The invention, having been described in detail above, is exemplified in the following examples, which are offered to illustrate, but not to limit, the claimed invention.

VII. EXAMPLES

Example 1: Methods for Culturing Prototheca

Prototheca strains were cultivated to achieve a high percentage of oil by dry cell weight. Cryopreserved cells were thawed at room temperature and 500 ul of cells were added to 4.5 ml of medium (4.2 g/L $K_2HPO_4$, 3.1 g/L $NaH_2PO_4$, 0.24 g/L $MgSO_4$-$7H_2O$, 0.25 g/L Citric Acid monohydrate, 0.025 g/L $CaCl_2$ $2H_2O$, 2 g/L yeast extract) plus 2% glucose and grown for 7 days at 28° C. with agitation (200 rpm) in a 6-well plate. Dry cell weights were determined by centrifuging 1 ml of culture at 14,000 rpm for 5 min in a pre-weighed Eppendorf tube. The culture supernatant was discarded and the resulting cell pellet washed with 1 ml of deionized water. The culture was again centrifuged, the supernatant discarded, and the cell pellets placed at −80° C. until frozen. Samples were then lyophilized for 24 hrs and dry cell weights calculated. For determination of total lipid in cultures, 3 ml of culture was removed and subjected to analysis using an Ankom system (Ankom Inc., Macedon, N.Y.) according to the manufacturer's protocol. Samples were subjected to solvent extraction with an Amkom XT10 extractor according to the manufacturer's protocol. Total lipid was determined as the difference in mass between acid hydrolyzed dried samples and solvent extracted, dried samples. Percent oil dry cell weight measurements are shown in Table 9.

TABLE 9

| Percent oil by dry cell weight | | |
|---|---|---|
| Species | Strain | % Oil |
| Prototheca stagnora | UTEX 327 | 13.14 |
| Prototheca moriformis | UTEX 1441 | 18.02 |
| Prototheca moriformis | UTEX 1435 | 27.17 |

Microalgae samples from multiple strains from the genus Prototheca were genotyped. Genomic DNA was isolated from algal biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2× iProof HF master mix (BIO-RAD) was added to 0.4 µl primer SZ02613

(5'-TGTTGAAGAATGAGCCGGCGAC-3' (SEQ ID NO:9) at 10 mM stock concentration). This primer sequence runs from position 567-588 in Gen Bank accession no. L43357 and is highly conserved in higher plants and algal plastid genomes. This was followed by the addition of 0.4 µl primer SZ02615 (5'-CAGTGAGCTATTACGCACTC-3' (SEQ ID NO:10) at 10 mM stock concentration). This primer sequence is complementary to position 1112-1093 in Gen Bank accession no. L43357 and is highly conserved in higher plants and algal plastid genomes. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. Purified PCR products were subsequently TOPO cloned into PCR8/GW/TOPO and positive clones selected for on LB/Spec plates. Purified plasmid DNA was sequenced in both directions using M13 forward and reverse primers. In total, twelve *Prototheca* strains were selected to have their 23 S rRNA DNA sequenced and the sequences are listed in the Sequence Listing. A summary of the strains and Sequence Listing Numbers is included below. The sequences were analyzed for overall divergence from the UTEX 1435 (SEQ ID NO:15) sequence. Two pairs emerged (UTEX 329/UTEX 1533 and UTEX 329/UTEX 1440) as the most divergent. In both cases, pairwise alignment resulted in 75.0% pairwise sequence identity. The percent sequence identity to UTEX 1435 is also included below:

| Species | Strain | % nt identity | SEQ ID NO. |
|---|---|---|---|
| *Prototheca kruegani* | UTEX 329 | 75.2 | SEQ ID NO:11 |
| *Prototheca wickerhamii* | UTEX 1440 | 99 | SEQ ID NO:12 |
| *Prototheca stagnora* | UTEX 1442 | 75.7 | SEQ ID NO:13 |
| *Prototheca moriformis* | UTEX 288 | 75.4 | SEQ ID NO:14 |
| *Prototheca moriformis* | UTEX 1439; 1441; 1435; 1437 | 100 | SEQ ID NO:15 |
| *Prototheca wikerhamii* | UTEX 1533 | 99.8 | SEQ ID NO:16 |
| *Prototheca moriformis* | UTEX 1434 | 75.9 | SEQ ID NO:17 |
| *Prototheca zopfii* | UTEX 1438 | 75.7 | SEQ ID NO:18 |
| *Prototheca moriformis* | UTEX 1436 | 88.9 | SEQ ID NO:19 |

Lipid samples from a subset of the above-listed strains were analyzed for lipid profile using HPLC. Results are shown below in Table 10.

TABLE 10

| Diversity of lipid chains in *Prototheca* species | | | | | | | | | |
|---|---|---|---|---|---|---|---|---|---|
| Strain | C14:0 | C16:0 | C16:1 | C18:0 | C18:1 | C18:2 | C18:3 | C20:0 | C20:1 |
| UTEX 327 | 0 | 12.01 | 0 | 0 | 50.33 | 17.14 | 0 | 0 | 0 |
| UTEX 1441 | 1.41 | 29.44 | 0.70 | 3.05 | 57.72 | 12.37 | 0.97 | 0.33 | 0 |
| UTEX 1435 | 1.09 | 25.77 | 0 | 2.75 | 54.01 | 11.90 | 2.44 | 0 | 0 |

Oil extracted from *Prototheca moriformis* UTEX 1435 (via solvent extraction or using an expeller press was analyzed for carotenoids, chlorophyll, tocopherols, other sterols and tocotrienols. The results are summarized below in Table 11.

TABLE 11

Carotenoid, chlorophyll, tocopherol/sterols and tocotrienol analysis in oil extracted from *Prototheca moriformis* (UTEX 1435).

|  | Pressed oil (mcg/ml) | Solvent extracted oil (mcg/ml) |
|---|---|---|
| cis-Lutein | 0.041 | 0.042 |
| trans-Lutein | 0.140 | 0.112 |
| trans-Zeaxanthin | 0.045 | 0.039 |
| cis-Zeaxanthin | 0.007 | 0.013 |
| t-alpha-Crytoxanthin | 0.007 | 0.010 |
| t-beta-Crytoxanthin | 0.009 | 0.010 |
| t-alpha-Carotene | 0.003 | 0.001 |
| c-alpha-Carotene | none detected | none detected |
| t-beta-Carotene | 0.010 | 0.009 |
| 9-cis-beta-Carotene | 0.004 | 0.002 |
| Lycopene | none detected | none detected |
| Total Carotenoids | 0.267 | 0.238 |
| Chlorophyll | <0.01 mg/kg | <0.01 mg/kg |
| Tocopherols and Sterols | | |
| gamma Tocopherol | 0.49 | 0.49 |
| Campesterol | 6.09 | 6.05 |
| Stigmasterol | 47.6 | 47.8 |
| Beta-sitosterol | 11.6 | 11.5 |
| Other sterols | 445 | 446 |
| Tocotrienols | | |
| alpha Tocotrienol | 0.26 | 0.26 |
| beta Tocotrienol | <0.01 | <0.01 |
| gamma Tocotrienol | 0.10 | 0.10 |
| detal Tocotrienol | <0.01 | <0.01 |
| Total Tocotrienols | 0.36 | 0.36 |

Oil extracted from *Prototheca moriformis*, from four separate lots, was refined and bleached using standard vegetable oil processing methods. Briefly, crude oil extracted from *Prototheca moriformis* was clarified in a horizontal decanter, where the solids were separated from the oil. The clarified oil was then transferred to a tank with citric acid and water and left to settle for approximately 24 hours. After 24 hours, the mixture in the tank formed 2 separate layers. The bottom layer was composed of water and gums that were then removed by decantation prior to transferring the degummed oil into a bleaching tank. The oil was then heated along with another dose of citric acid. Bleaching clay was then added to the bleaching tank and the mixture was further heated under vacuum in order to evaporate off any water that was present. The mixture was then pumped through a leaf filter to remove the bleaching clay. The filtered oil was then passed through a final 5 μm polishing filter and then collected for storage until use. The refined and bleached (RB) oil was then analyzed for carotenoids, chlorophyll, sterols, tocotrienols and tocopherols. The results of these analyses are summarized in Table 12 below. "Nd" denotes none detected and the sensitivity of detection is listed below:

---

Sensitivity of Detection

Carotenoids (mcg/g) nd = <0.003 mcg/g

Chlorophyll (mcg/g) nd = <0.03 mcg/g

Sterols (%) nd = 0.25%

Tocopherols (mcg/g); nd = 3 mcg/g

---

TABLE 12

Carotenoid, chlorophyll, sterols, tocotrienols and tocopherol analysis from refined and bleached *Prototheca moriformis* oil.

| | Lot A | Lot B | Lot C | Lot D |
|---|---|---|---|---|
| Carotenoids (mcg/g) | | | | |
| Lutein | 0.025 | 0.003 | nd | 0.039 |
| Zeaxanthin | nd | nd | nd | nd |
| cis-Lutein/Zeaxanthin | nd | nd | nd | nd |
| trans-alpha-Cryptoxanthin | nd | nd | nd | nd |
| trans-beta-Cryptoxanthin | nd | nd | nd | nd |
| trans-alpha-Carotene | nd | nd | nd | nd |
| cis-alpha-Carotene | nd | nd | nd | nd |
| trans-beta-Carotene | nd | nd | nd | nd |
| cis-beta-Carotene | nd | nd | nd | nd |
| Lycopene | nd | nd | nd | nd |
| Unidentified | 0.219 | 0.066 | 0.050 | 0.026 |
| Total Carotenoids | 0.244 | 0.069 | 0.050 | 0.065 |
| Chlorophyll (mcg/g) | | | | |
| Chlorophyll A | 0.268 | 0.136 | 0.045 | 0.166 |
| Chlorophyll B | nd | nd | nd | nd |
| Total Chlorophyll | 0.268 | 0.136 | 0.045 | 0.166 |
| Sterols (%) | | | | |
| Brassicasterol | nd | nd | nd | nd |
| Campesterol | nd | nd | nd | nd |
| Stigmasterol | nd | nd | nd | nd |
| beta-Sitosterol | nd | nd | nd | nd |
| Total Sterols | nd | nd | nd | nd |
| Tocopherols (mcg/g) | | | | |
| alpha-Tocopherol | 23.9 | 22.8 | 12.5 | 8.2 |
| beta-Tocopherol | 3.72 | nd | nd | nd |
| gamma-Tocopherol | 164 | 85.3 | 43.1 | 38.3 |
| delta-Tocopherol | 70.1 | 31.1 | 18.1 | 14.3 |
| Total Tocopherols | 262 | 139.2 | 73.7 | 60.8 |
| Tocotrienols (mcg/g) | | | | |
| alpha-Tocotrienol | 190 | 225 | 253 | 239 |
| beta-Tocotrienol | nd | nd | nd | nd |
| gamma-Tocotrienol | 47.3 | 60.4 | 54.8 | 60.9 |
| delta-Tocotrienol | 12.3 | 16.1 | 17.5 | 15.2 |
| Total Tocotrienols | 250 | 302 | 325 | 315 |

The same four lots of *Prototheca moriformis* oil was also analyzed for trace elements and the results are summarized below in Table 13.

TABLE 13

Elemental analysis of refined and bleached *Prototheca moriformis* oil.

| | Lot A | Lot B | Lot C | Lot D |
|---|---|---|---|---|
| Elemental Analysis (ppm) | | | | |
| Calcium | 0.08 | 0.07 | <0.04 | 0.07 |
| Phosphorous | <0.2 | 0.38 | <0.2 | 0.33 |
| Sodium | <0.5 | 0.55 | <0.5 | <0.5 |
| Potassium | 1.02 | 1.68 | <0.5 | 0.94 |
| Magnesium | <0.04 | <0.04 | <0.04 | 0.07 |
| Manganese | <0.05 | <0.05 | <0.05 | <0.05 |
| Iron | <0.02 | <0.02 | <0.02 | <0.02 |
| Zinc | <0.02 | <0.02 | <0.02 | <0.02 |
| Copper | <0.05 | <0.05 | <0.05 | <0.05 |
| Sulfur | 2.55 | 4.45 | 2.36 | 4.55 |
| Lead | <0.2 | <0.2 | <0.2 | <0.2 |
| Silicon | 0.37 | 0.41 | 0.26 | 0.26 |
| Nickel | <0.2 | <0.2 | <0.2 | <0.2 |
| Organic chloride | <1.0 | <1.0 | <1.0 | 2.2 |
| Inorganic chloride | <1.0 | <1.0 | <1.0 | <1.0 |
| Nitrogen | 4.4 | 7.8 | 4.2 | 6.9 |
| Lithium | <0.02 | <0.02 | <0.02 | <0.02 |
| Boron | 0.07 | 0.36 | 0.09 | 0.38 |
| Aluminum | -- | <0.2 | <0.2 | <0.2 |
| Vanadium | <0.05 | <0.05 | <0.05 | <0.05 |
| Lovibond Color (° L) | | | | |
| Red | 5.0 | 4.3 | 3.2 | 5.0 |
| Yellow | 70.0 | 70.0 | 50.0 | 70.0 |
| Mono & Diglycerides by HPLC (%) | | | | |
| Diglycerides | 1.68 | 2.23 | 1.25 | 1.61 |
| Monoglycerides | 0.03 | 0.04 | 0.02 | 0.03 |
| Free fatty acids (FFA) | 1.02 | 1.72 | 0.86 | 0.83 |
| Soaps | 0 | 0 | 0 | |
| Oxidized and Polymerized Triglycerides | | | | |
| Oxidized Triglycerides (%) | 3.41 | 2.41 | 4.11 | 1.00 |
| Polymerized Triglycerides (%) | 1.19 | 0.45 | 0.66 | 0.31 |
| Peroxide Value (meq/kg) | 0.75 | 0.80 | 0.60 | 1.20 |
| p-Anisidine value (dimensionless) | 5.03 | 9.03 | 5.44 | 20.1 |
| Water and Other Impurities (%) | | | | |
| Karl Fisher Moisture | 0.8 | 0.12 | 0.07 | 0.18 |
| Total polar compounds | 5.02 | 6.28 | 4.54 | 5.23 |
| Unsaponifiable matter | 0.92 | 1.07 | 0.72 | 1.04 |
| Insoluble impurities | <0.01 | <0.01 | 0.01 | <0.01 |
| Total oil (%) | | | | |
| Neutral oil | 98.8 | 98.2 | 99.0 | 98.9 |

Example 2: General Methods for Biolistic Transforming *Prototheca*

Seashell Gold Microcarriers 550 nanometers were prepared according to the protocol from manufacturer. Plasmid (20 μg) was mixed with 50 μl of binding buffer and 60 μl (30 mg) of S550d gold carriers and incubated in ice for 1 min. Precipitation buffer (100 μl) was added, and the mixture was incubated in ice for another 1 min. After vortexing, DNA-coated particles were pelleted by spinning at 10,000 rpm in an Eppendorf 5415C microfuge for 10 seconds. The gold pellet was washed once with 500 μl of cold 100% ethanol, pelleted by brief spinning in the microfuge, and resuspended with 50 μl of ice-cold ethanol. After a brief (1-2 sec) sonication, 10 μl of DNA-coated particles were immediately transferred to the carrier membrane.

*Prototheca* strains were grown in proteose medium (2 g/L yeast extract, 2.94 mM NaNO3, 0.17 mM CaCl2.2H2O, 0.3 mM MgSO4.7H2O, 0.4 mM K2HPO4, 1.28 mM KH2PO4, 0.43 mM NaCl) with 2% glucose on a gyratory shaker until it reached a cell density of 2×10⁶ cells/ml. The cells were harvested, washed once with sterile distilled water, and resuspended in 50 μl of medium. 1×10⁷ cells were spread in the center third of a non-selective proteose media plate. The cells were bombarded with the PDS-1000/He Biolistic Particle Delivery system (Bio-Rad). Rupture disks (1350 psi) were used, and the plates were placed 6 cm below the screen/macrocarrier assembly. The cells were allowed to recover at 25° C. for 12-24 h. Upon recovery, the cells were scraped from the plates with a rubber spatula, mixed with 100 μl of medium and spread on plates containing the appropriate antibiotic selection. After 7-10 days of incubation at 25° C., colonies representing transformed cells were visible on the plates. Colonies were picked and spotted on selective (either antibiotic or carbon source) agar plates for a second round of selection.

Example 3: Expression of Heterologous Fatty Acyl Acp Thioesterase Genes in Microalgal Cells Methods for and the results of expressing heterologous thioesterase gene in microalgal cells, including *Prototheca* species, have been previously described in PCT Application No. PCT/US2009/66412, hereby incorporated by reference. This example describes results using other thioesterase gene/gene products from higher plant species.

A fatty acyl-ACP thioesterase from *Ricinus communis* was introduced into a *Prototheca moriformis* UTEX 1435 genetic background, and the codon-optimized cDNA sequence (SEQ ID NO:87) and amino acid sequences (from GenBank Accession No. ABS30422.1)(SEQ ID NO:88) are listed in the Sequence Listing. The expression construct contained 5' (SEQ ID NO:100) and 3' (SEQ ID NO:101) homologous recombination targeting sequences (flanking the construct) to the 6S genomic region for integration into the nuclear genome and a *S. cerevisiae* suc2 sucrose invertase coding region under the control of *C. reinhardtii* β-tubulin promoter/5'UTR and *Chlorella vulgaris* nitrate reductase 3' UTR. This *S. cerevisiae* suc2 expression cassette is listed as SEQ ID NO:78 and served as a selection marker. The *R. communis* coding region was under the control of the *Prototheca moriformis* Amt03 promoter/5'UTR (SEQ ID NO:84) and *C. vulgaris* nitrate reductase 3'UTR (SEQ ID NO:85). The *Ricinus communis* native transit peptide was also replaced with the transit peptide from *C. protothecoides* stearoyl desaturase (SEQ ID NO:86) and the cDNA sequence of the thioesterase with the replaced transit peptide is listed as SEQ ID NO:87. The entire *Ricinus communis* expression cassette was termed pSZ1375 and transformed into a *Prototheca moriformis* genetic background. Positive clones were screened on plates with sucrose as the sole carbon source. A subset of the positive clones were selected and grown under lipid production conditions and lipid (fatty acid) profiles were determined using direct transesterification methods as described above. The fatty acid profiles of the selected clones are summarized in Table 14 below.

TABLE 14

Fatty acid profiles of *Ricinus communis* ACP-thioesterase transgenic *Prototheca* cells.

| Strain | C10:0 | C12:0 | C14:0 | C16:0 | C18:0 | C18:1 | C18:2 |
|---|---|---|---|---|---|---|---|
| wildtype | 0.01 | 0.03 | 0.98 | 24.65 | 3.68 | 62.48 | 6.26 |
| pSZ1375 clone A | 0.01 | 0.03 | 0.91 | 18.34 | 2.55 | 67.93 | 8.35 |
| pSZ1375 clone B | 0.01 | 0.03 | 0.97 | 18.51 | 2.47 | 67.83 | 8.25 |
| pSZ1375 clone C | 0.01 | 0.03 | 0.93 | 18.65 | 2.84 | 67.58 | 7.90 |
| pSZ1375 clone D | 0.01 | 0.03 | 0.92 | 18.90 | 2.30 | 67.48 | 8.37 |

The results show that transformants with the *Ricinus communis* thioesterase transgene have altered levels of C16:0 fatty acids and, to a lesser extent, C18:0 fatty acids, relative to the wild-type strain. Also, there was a concomitant increase in the C18:1 fatty acid level when compared to the wild-type level.

Example 4: Altering the Levels of Saturated Fatty Acids in the Microalgae *Prototheca moriformis*

A. Decreasing Stearoyl ACP Desaturase and Delta 12 Fatty Acid Desaturase Expression by Gene Knock-Out Approach As part of a genomics screen using a bioinformatics based approach based on cDNAs, Illumia transcriptome and Roche 454 sequencing of genomic DNA from *Prototheca moriformis* (UTEX 1435), two specific groups of genes involved in fatty acid desaturation were identified: stearoyl ACP desaturases (SAD) and delta 12 fatty acid desaturases (Δ12 FAD). Stearoyl ACP desaturase enzymes are part of the lipid synthesis pathway and they function to introduce double bonds into the fatty acyl chains, for example, the synthesis of C18:1 fatty acids from C18:0 fatty acids. Delta 12 fatty acid desaturases are also part of the lipid synthesis pathway and they function to introduce double bonds into already unsaturated fatty acids, for example, the synthesis of C18:2 fatty acids from C18:1 fatty acids. Southern blot analysis using probes based on the two classes of fatty acid desaturase genes identified during the bioinformatics efforts indicated that each class of desaturase genes was likely comprised of multiple family members. Additionally the genes encoding stearoyl ACP desaturases fell into two distinct families. Based on these results, three gene disruption constructs were designed to disrupt multiple gene family members by targeting more highly conserved coding regions within each family of desaturase enzymes.

Three homologous recombination targeting constructs were designed using: (1) highly conserved portions of the coding sequence of delta 12 fatty acid desaturase (d12FAD) family members and (2) two constructs targeting each of the two distinct families of SAD, each with conserved regions of the coding sequences from each family. This strategy is designed to embed a selectable marker gene (the suc2 sucrose invertase cassette from *S. cerevisiae* conferring the ability to hydrolyze sucrose) into these highly conserved coding regions (targeting multiple family members) rather than a classic gene replacement strategy where the homologous recombination would target flanking regions of the targeted gene.

All constructs were introduced into the cells by biolistic transformation using the methods described above and constructs were linearized before being shot into the cells. Transformants were selected on sucrose containing plates/media and changes in fatty acid profile were assayed using the above-described method. Relevant sequences from each of the three targeting constructs are listed below.

| Description | SEQ ID NO: |
|---|---|
| 5' sequence of d12FAD targeting construct | SEQ ID NO: 30 |
| 3' sequence of d12FAD targeting construct | SEQ ID NO: 31 |
| d12FAD targeting construct cDNA sequence | SEQ ID NO: 32 |
| 5' sequence of SAD2A targeting construct | SEQ ID NO: 33 |
| 3' sequence of SAD2A targeting construct | SEQ ID NO: 34 |
| SAD2A targeting construct cDNA sequence | SEQ ID NO: 35 |
| 5' sequence of SAD2B targeting construct | SEQ ID NO: 36 |
| 3' sequence of SAD2B targeting construct | SEQ ID NO: 37 |
| SAD2B targeting construct cDNA sequence | SEQ ID NO: 38 |

Representative positive clones from transformations with each of the constructs were picked and the fatty acid profiles for these clones were determined (expressed in Area %) and summarized in Table 15 below.

TABLE 15

Fatty acid profiles for desaturase knockouts.

| Fatty Acid | d12FAD KO | SAD2A KO | SAD2B KO | wt UTEX 1435 |
|---|---|---|---|---|
| C8:0 | 0 | 0 | 0 | 0 |
| C10:0 | 0.01 | 0.01 | 0.01 | 0.01 |
| C12:0 | 0.03 | 0.03 | 0.03 | 0.03 |
| C14:0 | 1.08 | 0.985 | 0.795 | 1.46 |
| C16:0 | 24.42 | 25.335 | 23.66 | 29.87 |
| C18:0 | 6.85 | 12.89 | 19.555 | 3.345 |
| C18:1 | 58.35 | 47.865 | 43.115 | 54.09 |
| C18:2 | 7.33 | 10.27 | 9.83 | 9.1 |
| C18:3 alpha | 0.83 | 0.86 | 1 | 0.89 |
| C20:0 | 0.48 | 0.86 | 1.175 | 0.325 |

Each of the constructs had a measurable impact on the desired class of fatty acid, and in all three cases C18:0 levels increased markedly, particularly with the two SAD knockouts. Further comparison of multiple clones from the SAD knockouts indicated that the SAD2B knockout lines had significantly greater reductions in C18:1 fatty acids than the C18:1 fatty acid levels observed with the SAD2A knockout lines.

Additional Δ12 fatty acid desaturase (FAD) knockouts were generated in a *Prototheca moriformis* (UTEX 1435) background using the methods described above. To identify potential homologous of Δ12FADs, the following primers were used to amplify a genomic region encoding a putative FAD:

SEQ ID NO: 74
Primer 1 5'-TCACTTCATGCCGGCGGTCC-3'

SEQ ID NO: 75
Primer 2 5'- GCGCTCCTGCTTGGCTCGAA-3'

The sequences resulting from the genomic amplification of *Prototheca moriformis* genomic DNA using the above primers were highly similar, but indicated that multiple genes or alleles of Δ12FADs exist in *Prototheca moriformis*.

Based on this result, two gene disruption constructs were designed to ablate one or more Δ12FAD genes. The strategy was to embed a sucrose invertase (suc2 from *S. cerevisiae*) cassette, thus conferring the ability to hydrolyze sucrose as a selectable marker, into highly conserved coding regions rather than use a classic gene replacement strategy. The first construct, termed pSZ1124, contained 5' and 3' genomic targeting sequences flanking a *C. reinhardtii* β-tubulin promoter driving the expression of the *S. cerevisiae* suc2 gene and a *Chlorella vulgaris* nitrate reductase 3'UTR (*S. cerevisiae* suc2 cassette). The second construct, termed pSZ1125, contained 5' and 3' genomic targeting sequences flanking a *C. reinhardtii* β-tubulin promoter driving the expression of the *S. cerevisiae* suc2 gene and a *Chlorella vulgaris* nitrate reductase 3'UTR. The relevant sequences of the constructs are listed in the Sequence Listing:

SEQ ID NO: 76
pSZ1124 (FAD2B) 5' genomic targeting sequence

SEQ ID NO: 77
pSZ1124 (FAD2B) 3' genomic targeting sequence

SEQ ID NO: 78
S. cerevisiae suc2 cassette

SEQ ID NO: 79
pSZ1125 (FAD2C) 5' genomic targeting sequence

SEQ ID NO: 80
pSZ1125 (FAD2C) 3' genomic targeting sequence pSZ1124 and pSZ1125 were each introduced into a *Prototheca moriformis* background and positive clones were selected based on the ability to hydrolyze sucrose. Table 16 summarizes the fatty acid profiles (in Area %, generated using methods described above) obtained in two transgenic lines in which pSZ1124 and pSZ1125 targeting vectors were utilized.

TABLE 16

Fatty acid profiles of Δ12 FAD knockouts.

| | C10:0 | C12:0 | C14:0 | C16:0 | C16:1 | C18:0 | C18:1 | C18:2 | C18:3α |
|---|---|---|---|---|---|---|---|---|---|
| parent | 0.01 | 0.03 | 1.15 | 26.13 | 1.32 | 4.39 | 57.20 | 8.13 | 0.61 |
| FAD2B | 0.02 | 0.03 | 0.80 | 12.84 | 1.92 | 0.86 | 74.74 | 7.08 | 0.33 |
| FAD2C | 0.02 | 0.04 | 1.42 | 25.85 | 1.65 | 2.44 | 66.11 | 1.39 | 0.22 |

The transgenic containing the FAD2B (pSZ1124) construct gave a very interesting and unexpected result in lipid profile, in that the C18:2 levels, which would be expected to decrease, only decreased by about one Area %. However, the C18:1 fatty acid levels increased significantly, almost exclusively at the expense of the C16:0 levels, which decreased significantly. The transgenic containing the FAD2C (pSZ1125) construct also gave a change in fatty acid profile: the levels of C18:2 are reduced significantly along with a corresponding increase in C18:1 levels.

B. RNA Hairpin Approach to Down-Regulation of Delta 12 Desaturase (FADc) in *Prototheca* Cells Vectors down-regulating FADc (delta 12 desaturase gene) gene expression by hairpin RNAs were introduced into a *Prototheca moriformis* UTEX 1435 genetic background. The *Saccharomyces cerevisiae* suc2 sucrose invertase gene was utilized as a selectable marker, conferring the ability to grow on sucrose as a sole-carbon source to positive clones, and two types of constructs were used. The first type of construct utilized a portion of the first exon of the FADc coding region linked in cis to its first intron followed by a repeat unit of the first exon in reverse orientation. This type of construct was designed to form a hairpin when expressed as mRNA. Two constructs of this first type were created, one driven by the *Prototheca moriformis* Amt03 promoter (SEQ ID NO:84), termed pSZ1468, and a second driven by the *Chlamydomomas reinhardtii* β-tubulin promoter (SEQ ID NO:89), termed pSZ1469. The second type of construct utilized the large FADc exon 2 in the antisense orientation driven by either the *Prototheca moriformis* Amt03 promoter (SEQ ID NO:84), termed pSZ1470, or driven by the *Chlamydomomas reinhardtii* β-tubulin promoter (SEQ ID NO:89), termed pSZ1471. All four constructs had a *S. cerevisiae* suc2 sucrose invertase cassette (SEQ ID NO:78) and a 5' (SEQ ID NO:100) and 3' (SEQ ID NO:101) homologous recombination targeting sequences (flanking the construct) to the 6S genomic region for integration into the nuclear genome. Sequences of the FADc portions of each hairpin RNA construct along with the relevant portions of each construct are listed in the Sequence Listing as:

| Description | SEQ ID NO: |
| --- | --- |
| pSZ1468 FADc hairpin RNA cassette | SEQ ID NO: 90 |
| Relevant portions of the pSZ1468 construct | SEQ ID NO: 91 |
| pSZ1469 FADc hairpin RNA cassette | SEQ ID NO: 92 |
| Relevant portions of the pSZ1469 construct | SEQ ID NO: 93 |
| pSZ1470 FADc exon 2 of a hairpin RNA cassette | SEQ ID NO: 94 |
| Relevant portions of the pSZ1470 construct | SEQ ID NO: 95 |
| pSZ1471 FADc exon 2 of a hairpin RNA cassette | SEQ ID NO: 96 |
| Relevant portions of the pSZ1471 construct | SEQ ID NO: 97 |

Each of the four constructs was transformed into a *Prototheca moriformis* background and positive clones were screened using plates with sucrose as the sole carbon source. Positive clones were picked from each transformation and a subset were selected to determine the impact of the hairpin and antisense cassettes contained in pSZ1468, pSZ1469, pSZ1470 and pSZ1471 on fatty acid profiles. The selected clones from each transformation were grown under lipid producing conditions and the fatty acid profiles were determined using direct transesterification methods as described above. Representative fatty acid profiles from each of the transformations are summarized below in Table 17. Wildtype 1 and 2 cells were untransformed *Prototheca moriformis* cells that were run with each of the transformants as a negative control.

TABLE 17

Fatty acid profiles of *Prototheca moriformis* cells containing hairpin RNA constructs to down-regulate the expression of delta 12 desaturase gene (FADc).

| Strain | C10:0 | C12:0 | C14:0 | C16:0 | C18:0 | C18:1 | C18:2 |
| --- | --- | --- | --- | --- | --- | --- | --- |
| wildtype 1 | 0.01 | 0.03 | 1.20 | 27.08 | 4.01 | 57.58 | 7.81 |
| pSZ1468 clone A | 0.01 | 0.04 | 1.33 | 25.95 | 3.68 | 65.60 | 1.25 |
| pSZ1468 clone B | 0.01 | 0.03 | 1.18 | 23.43 | 2.84 | 65.32 | 4.91 |
| pSZ1468 clone C | 0.01 | 0.04 | 1.34 | 23.18 | 4.27 | 63.65 | 5.17 |
| pSZ1468 clone D | 0.01 | 0.03 | 1.24 | 23.00 | 3.85 | 61.92 | 7.62 |
| pSZ1470 clone A | 0.01 | 0.03 | 1.23 | 24.79 | 4.33 | 58.43 | 8.92 |
| pSZ1470 clone B | 0.01 | 0.03 | 1.26 | 24.91 | 4.14 | 57.59 | 9.64 |
| pSZ1470 clone C | 0.01 | 0.03 | 1.21 | 23.35 | 4.75 | 58.52 | 9.70 |
| wildtype 2 | 0.01 | 0.03 | 0.98 | 24.65 | 3.68 | 62.48 | 6.26 |
| pSZ1469 clone A | 0.01 | 0.03 | 1.05 | 21.74 | 2.71 | 71.33 | 1.22 |
| pSZ1469 clone B | 0.01 | 0.03 | 1.01 | 22.60 | 2.98 | 70.19 | 1.27 |
| pSZ1469 clone C | 0.01 | 0.03 | 1.03 | 19.82 | 2.38 | 72.95 | 1.82 |
| pSZ1469 clone D | 0.01 | 0.03 | 1.03 | 20.54 | 2.66 | 70.96 | 2.71 |
| pSZ1471 clone A | 0.01 | 0.03 | 1.03 | 18.42 | 2.63 | 66.94 | 8.55 |
| pSZ1471 clone B | 0.01 | 0.03 | 0.94 | 18.61 | 2.58 | 67.13 | 8.66 |
| pSZ1471 clone C | 0.01 | 0.03 | 1.00 | 18.31 | 2.46 | 67.41 | 8.71 |
| pSZ1471 clone D | 0.01 | 0.03 | 0.93 | 18.82 | 2.54 | 66.84 | 8.77 |

The above results show that the hairpin constructs pSZ1468 and pSZ1469 showed expected phenotypes: a reduction in C18:2 fatty acid levels and an increase in C18:1 fatty acid levels as compared to wildtype 1 and wildtype 2, respectively. The antisense constructs, pSZ1470 and pSZ1471 did not result in a decrease in C18:2 fatty acid levels but instead showed a slight increase when compared to wildtype 1 and wildtype 2, respectively and a slight decrease in C16:0 fatty acid levels.

C. Expression of an Exogenous Stearoyl-ACP Desaturase

The *Olea europaea* stearoyl-ACP desaturase (GenBank Accession No. AAB67840.1) was introduced into a *Prototheca moriformis* UTEX1435 genetic background. The expression construct contained a 5' (SEQ ID NO:100) and 3' (SEQ ID NO:101) homologous recombination targeting sequences (flanking the construct) to the 6S genomic region for integration into the nuclear genome and a *S. cerevisiae* suc2 sucrose invertase coding region under the control of *C. reinhardtii* β-tubulin promoter/5'UTR and *Chlorella vulgaris* nitrate reductase 3' UTR. This *S. cerevisiae* suc2 expression cassette is listed as SEQ ID NO:78 and served as a selection marker. The *Olea europaea* stearoyl-ACP desaturase coding region was under the control of the *Prototheca moriformis* Amt03 promoter/5'UTR (SEQ ID NO:84) and *C. vulgaris* nitrate reductase 3'UTR, and the native transit peptide was replaced with the *Chlorella* protothecoides stearoyl-ACP desaturase transit peptide (SEQ ID NO:86). The codon-optimized cDNA sequences and amino acid sequences (with the replaced transit peptide) are listed in the Sequence Listing as SEQ ID NO:98 and SEQ ID NO:99, respectively. The entire *O. europaea* SAD expression cassette was termed pSZ1377 and transformed into a *Prototheca moriformis* genetic background. Positive clones were screened on plates with sucrose as the sole carbon source. A subset of the positive clones were selected and grown under lipid production conditions and fatty acid profiles were determined using direct transesterification methods as described above. The fatty acid profiles of the selected clones are summarized in Table 18 below.

TABLE 18

Fatty acid profile of *Olea europaea* stearoyl-ACP desaturase transgenic *Prototheca moriformis* cells.

| Strain | C14:0 | C16:0 | C18:0 | C18:1 | C18:2 |
|---|---|---|---|---|---|
| wildtype | 0.88 | 22.82 | 3.78 | 64.43 | 6.54 |
| pSZ1377 clone A | 0.94 | 18.60 | 1.50 | 69.45 | 7.67 |
| pSZ1377 clone B | 0.93 | 18.98 | 1.35 | 69.12 | 7.67 |
| pSZ1377 clone C | 0.93 | 19.01 | 2.31 | 68.56 | 7.43 |

The above results demonstrate that the introduction of a heterologous desaturase, in this case a stearoyl-ACP desaturase from *Olea europaea*, can result in higher levels of C18:1 fatty acid and a concomitant decrease in C18:0 and C16:0 fatty acid levels.

Example 5: Cultivation of Oleaginous Yeast

Oleaginous yeast strains used in this and subsequent Examples were obtained from either the Deutsche Sammlung von Mikroorganismen un Zellkulturen GmbH (DSMZ), located at Inhoffenstrabe 7B, 38124 Braunschweig, Germany, or Centraalbureau voor Schimmelscultures (CBS) Fungal Biodiversity Centre located at P.O. Box 85167, 3508 Utrecht, the Netherlands. One hundred eighty five oleaginous yeast strains were screened for growth rate and lipid production.

All strains were rendered axenic via streaking to single colonies on YPD agar (YPD medium as described below with 2% agar added) plates. Single colonies from the YPD plates of each strain were picked and grown to late log phase in YPD medium (10 g bacto-yeast extract, 20 g bacto-peptone and 20 g glucose/1 L final volume in distilled water) on a rotary shaker at 200 rpm at 30° C.

For lipid productivity assessment, 2 mL of YPD medium was added to a 50 mL tared Bioreactor tube (MidSci, Inc.) and inoculated from a frozen stock of each strain. The tubes were then placed in a 30° C. incubator and grown for 24 hours, shaking at 200 rpm to generate a seed culture. After 24 hours, 8 mL of Y1 medium (Yeast nitrogen base without amino acids, Difco) containing 0.1M phthalate buffer, pH 5.0 was added and mixed well by pipetting gently. The resulting culture was divided equally into a second, tared bioreactor tube. The resulting duplicate cultures of 5 mL each were then placed in a 30° C. incubator with 200 rpm agitation for 5 days. The cells were then harvested for lipid productivity and lipid profile. 3 mL of the culture was used for determination of dry cell weight and total lipid content (lipid productivity) and 1 mL was used for fatty acid profile determination. In either case, the cultures were placed into tubes and centrifuged at 3500 rpm for 10 minutes in order to pellet the cells. After decanting the supernatant, 2 mL of deionized water was added to each tube and used to wash the resulting cell pellet. The tubes were spun again at 3500 rpm for 10 minutes to pellet the washed cells, the supernatant was then decanted and the cell pellets were placed in a −70° C. freezer for 30 minutes. The tubes were then transferred into a lyophilizer overnight to dry. The following day, the weight of the conical tube plus the dried biomass resulting from the 3 mL culture was recorded and the resulting cell pellet was subjected to total lipid extraction using an Ankom Acid Hydrolysis system (according to the manufacturer's instructions) to determine total lipid content.

Of the 185 strains screened, 30 strains were chosen based on the growth rate and lipid productivity. The lipid productivity (expressed as percent lipid of dry cell weight) of these 30 strains is summarized below in Table 19.

TABLE 19

Lipid productivity of oleaginous yeast strains.

| Species | Collection No. | % Lipid (DCW) |
|---|---|---|
| *Rhodotorula terpenoidalis* | CBS 8445 | 27 |
| *Rhodotorula glutinus* | DSMZ 70398 | 53.18 |
| *Lipomyces tetrasporous* | CBS 1810 | 51 |
| *Lipomyces tetrasporous* | CBS 7656 | 17.63 |
| *Lipomyces tetrasporous* | CBS 8724 | 18 |
| *Cryptococcus curvatus* | CBS 5324 | 53 |
| *Cryptococcus curvatus* | CBS 2755 | 48 |
| *Rhodosporidium sphaerocarpum* | CBS 2371 | 43 |
| *Rhodotorula glutinus* | CBS 4476 | 30.97 |
| *Lipomyces tetrasporous* | CBS 1808 | 29 |
| *Trichosporon domesticum* | CBS 8111 | 35.16 |
| *Trichosporon* sp. | CBS 7617 | 40.09 |
| *Lipomyces tetrasporous* | CBS 5911 | 27.63 |
| *Lipomyces tetrasporous* | CBS 5607 | 12.81 |
| *Cryptococcus curvatus* | CBS 570 | 38.64 |
| *Cryptococcus curvatus* | CBS 2176 | 40.57 |
| *Cryptococcus curvatus* | CBS 5163 | 35.26 |
| *Torulaspora delbruekii* | CBS 2924 | 40.00 |
| *Rhodotorula toruloides* | CBS 8761 | 36.52 |
| *Geotrichum histeridarum* | CBS 9892 | 33.77 |
| *Yarrowia lipolytica* | CBS 6012 | 29.21 |
| *Geotrichum vulgare* | CBS 10073 | 28.04 |
| *Trichosporon montevideense* | CBS 8261 | 25.60 |
| *Lipomyces starkeyi* | CBS 7786 | 25.43 |
| *Trichosporon behrend* | CBS 5581 | 23.93 |
| *Trichosporon loubieri* var. *loubieri* | CBS 8265 | 22.39 |
| *Rhodosporidium toruloides* | CBS 14 | 21.03 |
| *Trichosporon brassicae* | CBS 6382 | 20.34 |
| *Rhodotorula aurantiaca* | CBS 317 | 17.51 |
| *Sporobolomyces alborubescens* | CBS 482 | 10.09 |

Cell pellets resulting from 1 mL culture were subjected to direct transesterification and analysis by GC for fatty acid profile determination. A summary of the fatty acid profiles for 17 of the above yeast strains are summarized below in Table 20.

TABLE 20

Fatty acid profiles of oleaginous yeast strains.

| Species | Collection No. | C12:0 | C14:0 | C15:0 | C16:0 | C16:1 | C17:0 | C17:1 | C18:0 | C18:1 | C18:2 | >C20 |
|---|---|---|---|---|---|---|---|---|---|---|---|---|
| *Rhodotorula terpenoidalis* | CBS 8445 | 0.06 | 0.8 | 0.02 | 27.44 | 0.67 | 0.03 | 0.03 | 5.6 | 59.44 | 3.37 | 2.13 |
| *Rhodotorula glutinus* | DSMZ 70398 | 0.05 | 1.55 | 0.09 | 27.34 | 0.34 | 0.23 | 0.08 | 10.47 | 44.68 | 11.65 | 2.23 |
| *Lipomyces tetrasporous* | CBS 1810 | nd | 0.26 | 0.08 | 24.22 | 2.13 | 0.28 | 0.30 | 9.93 | 55.04 | 4.48 | 3.01 |

TABLE 20-continued

Fatty acid profiles of oleaginous yeast strains.

| Species | Collection No. | C12:0 | C14:0 | C15:0 | C16:0 | C16:1 | C17:0 | C17:1 | C18:0 | C18:1 | C18:2 | >C20 |
|---|---|---|---|---|---|---|---|---|---|---|---|---|
| *Lipomyces tetrasporous* | CBS 76556 | nd | 0.293 | 0.212 | 28.14 | 4.24 | 0.37 | 0.66 | 6.61 | 48.48 | 8.33 | 1.178 |
| *Lipomyces tetrasporous* | CBS 8724 | nd | 0.27 | 0.08 | 30.69 | 2.12 | 0.27 | 0.24 | 11.8 | 46.71 | 4.36 | 2.89 |
| *Cryptococcus curvatus* | CBS 5324 | nd | 0.27 | 0.22 | 23.31 | 0.49 | 0.12 | 0.09 | 11.55 | 50.78 | 10.80 | 1.61 |
| *Cryptococcus curvatus* | CBS 27556 | nd | 0.62 | 0.03 | 25.07 | 0.31 | 0.05 | 0.03 | 17.07 | 45.74 | 14.60 | 2.01 |
| *Rhodosporidium sphaerocarpum* | CBS 2371 | 0.03 | 0.68 | 0.03 | 17.86 | 0.13 | 0.54 | 0.17 | 10.4 | 51.01 | 14.60 | 1.82 |
| *Rhodotorula glutinus* | CBS 4476 | 0.021 | 0.47 | 0.02 | 24.64 | 0.16 | 0.064 | 0.27 | 13.73 | 42.46 | 16.29 | 1.642 |
| *Lipomyces tetrasporous* | CBS 1808 | 0.01 | 0.40 | 0.12 | 26.64 | 3.11 | 0.25 | 0.39 | 7.39 | 54.15 | 3.96 | 2.34 |
| *Trichosporon domesticum* | CBS 8111 | 0.066 | 0.486 | 0.10 | 23.19 | 0.11 | 0.37 | 0.033 | 30.65 | 29.75 | 11.66 | 3.414 |
| *Trichosporon sp.* | CBS 7617 | 0.046 | 0.527 | 0.063 | 24.26 | 0.187 | 0.171 | 0.026 | 19.61 | 41.95 | 9.97 | 2.61 |
| *Lipomyces tetrasporous* | CBS 5911 | 0.017 | 0.45 | 0.16 | 30.79 | 3.56 | 0.29 | 0.48 | 7.77 | 49.99 | 4.40 | 1.433 |
| *Lipomyces tetrasporous* | CBS 5607 | nd | 0.35 | 0.17 | 37.56 | 3.0 | 0.328 | 0.40 | 9.31 | 42.36 | 4.28 | 1.376 |
| *Cryptococcus curvatus* | CBS 570 | 0.017 | 0.21 | 0.09 | 12.78 | 0.13 | 0.147 | 0.09 | 19.6 | 53.17 | 8.42 | 4.01 |
| *Cryptococcus curvatus* | CBS 2176 | 0.02 | 0.31 | 0.09 | 19.0 | 0.87 | 0.08 | 0.10 | 7.24 | 60.51 | 9.26 | 2.154 |
| *Cryptococcus curvatus* | CBS 5163 | 0.019 | 0.34 | 0.06 | 22.7 | 0.70 | 0.13 | 0.10 | 10.65 | 51.36 | 10.34 | 2.24 | nd denotes none detected.

Fatty acid profile analysis was performed on additional strains of oleaginous yeast and several strains were found to produce a high percentage of C16:1 fatty acid including, *Torulaspora delbruekii* CBS 2924. This oleaginous yeast strain had a lipid productivity of approximately 40% lipid as a percentage of DCW and a fatty acid profile of: C12:0 (0.36%); C14:0 (1.36%); C15:0 (0.16%); C16:0 (10.82%); C 16:1 (42.9%); C17:0 (0.11%); C18:0 (2.1%); C18:1 (35.81%); C18:2 (4.62%). This strain was found to have a particularly high percentage of C16:1 (palmitoleic acid) as part of its fatty acid profile. Four additional strains were identified as producing a high percentage 16:1: *Yarrowia lipolytica* CBS 6012 (10.10%); *Yarrowia lipolytica* CBS 6331 (14.80%), *Yarrowia lipolytica* CBS 10144 (12.90%) and *Yarrowia lipolytica* CBS 5589 (14.20%).

Example 6: Genotyping Oleaginous Yeast Strains

Genotyping of 48 different strains of oleaginous yeast was performed. Genomic DNA was isolated from each of the 48 different strains of oleaginous yeast biomass as follows. Cells (approximately 200 mg) were centrifuged from liquid cultures 5 minutes at 14,000×g. Cells were then resuspended in sterile distilled water, centrifuged 5 minutes at 14,000×g and the supernatant discarded. A single glass bead ~2 mm in diameter was added to the biomass and tubes were placed at −80° C. for at least 15 minutes. Samples were removed and 150 µl of grinding buffer (1% Sarkosyl, 0.25 M Sucrose, 50 mM NaCl, 20 mM EDTA, 100 mM Tris-HCl, pH 8.0, RNase A 0.5 ug/ul) was added. Pellets were resuspended by vortexing briefly, followed by the addition of 40 ul of 5M NaCl. Samples were vortexed briefly, followed by the addition of 66 µl of 5% CTAB (Cetyl trimethylammonium bromide) and a final brief vortex. Samples were next incubated at 65° C. for 10 minutes after which they were centrifuged at 14,000×g for 10 minutes. The supernatant was transferred to a fresh tube and extracted once with 300 µl of Phenol:Chloroform:Isoamyl alcohol 12:12:1, followed by centrifugation for 5 minutes at 14,000×g. The resulting aqueous phase was transferred to a fresh tube containing 0.7 vol of isopropanol (~190 µl), mixed by inversion and incubated at room temperature for 30 minutes or overnight at 4° C. DNA was recovered via centrifugation at 14,000×g for 10 minutes. The resulting pellet was then washed twice with 70% ethanol, followed by a final wash with 100% ethanol. Pellets were air dried for 20-30 minutes at room temperature followed by resuspension in 50 µl of 10 mM TrisCl, 1 mM EDTA (pH 8.0).

Five µl of total algal DNA, prepared as described above, was diluted 1:50 in 10 mM Tris, pH 8.0. PCR reactions, final volume 20 µl, were set up as follows. Ten µl of 2× iProof HF master mix (BIO-RAD) was added to 0.4 µl primer SZ5434 forward primer (5' GTCCCTGCCCTTTGTACACAC-3' (SEQ ID NO:39) at 10 mM stock concentration) and 0.4 µl primer SZ5435 reverse primer (5'-TTGATATGCTTAAGT-TCAGCGGG-3' (SEQ ID NO:40) at 10 mM stock concentration). The primers were selected based on sequence conservation between three prime regions of 18S and five prime regions of fungal 26S rRNA genes. The forward primer is identical to nucleotides 1632-1652 of Genbank Ascension #AY550243 and the reverse primer is identical to nucleotides 464271-464293 of Genbank Ascension # NC_001144. Next, 5 µl of diluted total DNA and 3.2 µl dH$_2$O were added. PCR reactions were run as follows: 98° C., 45"; 98° C., 8"; 53° C., 12"; 72° C., 20" for 35 cycles followed by 72° C. for 1 min and holding at 25° C. For purification of PCR products, 20 µl of 10 mM Tris, pH 8.0, was added to each reaction, followed by extraction with 40 µl of Phenol:Chloroform:isoamyl alcohol 12:12:1, vortexing and centrifuging at 14,000×g for 5 minutes. PCR reactions were applied to S-400 columns (GE Healthcare) and centrifuged for 2 minutes at 3,000×g. The resulting purified PCR products were cloned and transformed into *E. coli* using ZeroBlunt PCR4Blunt-TOPO vector kit (Invitrogen) according to manufacturer's instructions. Sequencing reactions were carried out directly on ampicillin resistant colonies. Purified plasmid DNA was sequenced in both directions using M13 forward and reverse primers. Purified PCR products were subsequently TOPO cloned into PCR8/GW/TOPO and positive clones selected for on LB/Spec plates. Purified plasmid DNA was sequenced in both directions using M13 forward and reverse primers.

A list of the 48 strains of oleaginous yeast that were genotyped is in Table 21 along with the corresponding SEQ ID NOs.

TABLE 21

Genotyped oleaginous yeast strains.

| Strain Name | Strain Number | SEQ ID NO |
|---|---|---|
| *Rhodotorula glutinis* | DSMZ-DSM 7098 | SEQ ID NO: 41 |
| *Lipomyces tetrasporus* | CBS 5911 | SEQ ID NO: 41 |
| *Rhodotorula glutinis* var. *glutinis* | CBS 3044 | SEQ ID NO: 42 |
| *Lipomyces tetrasporus* | CBS 8664 | SEQ ID NO: 42 |
| *Lipomyces tetrasporus* | CBS 1808 | SEQ ID NO: 43 |
| *Lipomyces tetrasporus* | CBS 1810 | SEQ ID NO: 43 |
| *Lipomyces starkeyi* | CBS 1809 | SEQ ID NO: 44 |
| *Trichosporon montevideense* | CBS 8261 | SEQ ID NO: 44 |
| *Yarrowia lipolytica* | CBS 6331 | SEQ ID NO: 45 |
| *Cryptococcus curvatus* | CBS 5324 | SEQ ID NO: 46 |
| *Rhodotorula mucilaginosa* var. *mucilaginosa* | CBS 316 | SEQ ID NO: 46 |
| *Cryptococcus curvatus* | CBS 570 | SEQ ID NO: 46 |
| *Cryptococcus curvatus* | CBS 2176 | SEQ ID NO: 46 |
| *Cryptococcus curvatus* | CBS 2744 | SEQ ID NO: 46 |
| *Cryptococcus curvatus* | CBS 2754 | SEQ ID NO: 46 |
| *Cryptococcus curvatus* | CBS 2829 | SEQ ID NO: 46 |
| *Cryptococcus curvatus* | CBS 5163 | SEQ ID NO: 46 |
| *Cryptococcus curvatus* | CBS 5358 | SEQ ID NO: 46 |
| *Trichosporon* sp. | CBS 7617 | SEQ ID NO: 47 |
| *Spororbolomyces alborubescens* | CBS 482 | SEQ ID NO: 48 |
| *Rhodotorula glutinis* var. *glutinis* | CBS 324 | SEQ ID NO: 49 |
| *Rhodotorula glutinis* var. *glutinis* | CBS 4476 | SEQ ID NO: 50 |
| *Trichosporon behrend* | CBS 5581 | SEQ ID NO: 51 |
| *Geotrichum histeridarum* | CBS 9892 | SEQ ID NO: 52 |
| *Rhodotorula aurantiaca* | CBS 8411 | SEQ ID NO: 53 |
| *Cryptococcus curvatus* | CBS 8126 | SEQ ID NO: 53 |
| *Trichosporon domesticum* | CBS 8111 | SEQ ID NO: 54 |
| *Rhodotorula toruloides* | CBS 8761 | SEQ ID NO: 55 |
| *Rhodotorula terpendoidalis* | CBS 8445 | SEQ ID NO: 56 |
| *Yarrowia lipolytica* | CBS 10144 | SEQ ID NO: 57 |
| *Rhodotorula glutinis* var. *glutinis* | CBS 5805 | SEQ ID NO: 58 |
| *Yarrowia lipolytica* | CBS 10143 | SEQ ID NO: 59 |
| *Lipomyces tetrasporus* | CBS 5607 | SEQ ID NO: 60 |
| *Yarrowia lipolytica* | CBS 5589 | SEQ ID NO: 61 |
| *Lipomyces tetrasporus* | CBS 8724 | SEQ ID NO: 62 |
| *Rhodosporidium sphaerocarpum* | CBS 2371 | SEQ ID NO: 63 |
| *Trichosporon brassicae* | CBS 6382 | SEQ ID NO: 64 |
| *Cryptococcus curvatus* | CBS 2755 | SEQ ID NO: 65 |
| *Lipomyces tetrasporus* | CBS 7656 | SEQ ID NO: 65 |
| *Lipomyces starkeyi* | CBS 7786 | SEQ ID NO: 66 |
| *Yarrowia lipolytica* | CBS 6012 | SEQ ID NO: 67 |
| *Trichosporon loubieri* var. *loubieri* | CBS 8265 | SEQ ID NO: 68 |
| *Geotrichum vulgare* | CBS 10073 | SEQ ID NO: 69 |
| *Rhodosporidium toruloides* | CBS 14 | SEQ ID NO: 70 |
| *Rhodotorula glutinis* var. *glutinis* | CBS 6020 | SEQ ID NO: 71 |
| *Lipomyces orientalis* | CBS 10300 | SEQ ID NO: 71 |
| *Rhodotorula aurantiaca* | CBS 317 | SEQ ID NO: 72 |
| *Torulaspora delbrueckii* | CBS 2924 | SEQ ID NO: 73 |

Example 7: Cultivation of *Rhodococcus opacus* to Achieve High Oil Content

A seed culture of *Rhodococcus opacus* PD630 (DSM 44193, Deutsche Sammlung von Mikroorganismen und Zellkuttwen GmbH) was generated using 2 ml of a cryopreserved stock inoculated into 50 ml of MSM media with 4% sucrose (see Schlegel, et al., (1961) *Arch Mikrobiol* 38, 209-22) in a 250 ml baffle flask. The seed culture was grown at 30° C. with 200 rpm agitation until it reached an optical density of 1.16 at 600 nm. 10 ml of the seed flask culture was used to inoculate cultures for lipid production under two different nitrogen conditions: 10 mM $NH_4Cl$ and 18.7 mM $NH_4Cl$ (each in duplicate). The growth cultures were grown at 30° C. with 200 rpm agitation for 6 days. Cells grown in the 10 mM $NH_4Cl$ condition reached a maximal 57.2% (average) lipid by DCW after 6 days of culture. Cells grown in the 18.7 mM $NH_4Cl$ condition reached a maximal 51.8% (average) lipid by DCW after 5 days in culture.

A sample of *Rhodococcus opacus* biomass was subjected to direct transesterification and analyzed via GC/FID for a fatty acid profile. The results were: C14:0 (2.33); C15:0 (9.08); C16:0 (24.56); C16:1 (11.07); C17:0 (10.50); 2 double bond equivalent (2DBE) C17 species (19.90); C18:0 (2.49); C18:1 (17.41); C18:2 (0.05); C19:0 (0.75) and 2DBE C19 species (1.87).

Example 8: Extraction of Oil from Microorganisms

A. Extraction of Oil from Microalgae Using an Expeller Press and a Press Aid

Microalgal biomass containing 38% oil by DCW was dried using a drum dryer resulting in resulting moisture content of 5-5.5%. The biomass was fed into a French L250 press. 30.4 kg (67 lbs.) of biomass was fed through the press and no oil was recovered. The same dried microbial biomass combined with varying percentage of switchgrass as a press aid was fed through the press. The combination of dried microbial biomass and 20% w/w switchgrass yielded the best overall percentage oil recovery. The pressed cakes were then subjected to hexane extraction and the final yield for the 20% switchgrass condition was 61.6% of the total available oil (calculated by weight). Biomass with above 50% oil dry cell weight did not require the use of a pressing aid such as switchgrass in to extract oil. Other methods of extraction of oil from microalgae using an expeller press are described in PCT Application No. PCT/US2010/31108, incorporated herein by reference.

B. Extraction of Oil from Oleaginous Yeast Using an Expeller Press

Yeast strain *Rhodotorula glutinis* (DSMZ-DSM 70398) was obtained from the Deutsche Sammlung von Mikroorganismen und Zellkulturen GmbH (German Collection of Microorganism and Cell Culture, Inhoffenstraße 7B, 38124 Braunschweig, Germany. Cryopreserved cells were thawed and added to 50 mL YPD media (described above) with 1×DAS vitamin solution (1000×: 9 g/L tricine; 0.67 g/L thiamine-HCl; 0.01 g/L d-biotin; 0.008 cyannocobalamin; 0.02 calcium pantothenate; and 0.04 g/L p-Aminobenzoic acid) and grown at 30° C. with 200 rpm agitation for 18-24 hours until an OD reading was over 5 OD (A600). The culture was then transferred to 7-L fermentors and switched to YP1 medium (8.5 g/L Difco Yeast Nitrogen Base without Amino Acids and Ammonium Sulfate, 3 g/L Ammonium Sulfate, 4 g/L yeast extract) with 1×DAS vitamin solution. The cultures were sampled twice per day and assayed for OD (A600), dry cell weight (DCW) and lipid concentration. When the cultures reached over 50 g/L DCW, the cultures were harvested. Based on dry cell weight, the yeast biomass contained approximately 50% oil. Two samples of yeast biomass were subjected to direct transesterification and analyzed via GC/FID for a fatty acid profile. The results are expressed in Area Percent, and shown in Table 22, below.

TABLE 22

Fatty acid profile of transesterified yeast biomass samples.

| | C10:0 | C12:0 | C14:0 | C15:0 | C16:0 | C16:1 | C17:0 | C18:0 | C18:1 | C18:2 | C18:3α | ≥C:20 |
|---|---|---|---|---|---|---|---|---|---|---|---|---|
| Sample 1 | 0.03 | 0.21 | 3.36 | 0.25 | 33.26 | 0.76 | 0.20 | 6.88 | 42.68 | 9.28 | 1.33 | 1.1 |
| Sample 2 | 0.02 | 0.10 | 2.18 | 0.12 | 29.94 | 0.49 | 0.16 | 8.17 | 48.12 | 7.88 | 0.84 | 1.45 |

The harvested yeast broth was dried using three different methods for comparison: (1) tray dried in a forced air oven at 75° C. overnight; (2) dried on a drum dryer without concentration; and (3) the yeast broth was concentrated to 22% solids and the slurry was then dried on a drum dryer. Material from each of the three different drying conditions was heat conditioned and fed through a screw press for oil extraction. The press temperature was at 150° F. and the conditioned dried yeast biomass was held at about 190° F. until it was ready to be fed into the press.

The moisture content of the tray dried yeast was 1.45% and the dried yeast was then conditioned in an oven at 90° C. for 10 minutes. The moisture content after conditioning was 0.9%. The conditioned tray dried material was then fed into a bench-top Taby screw press (Taby Pressen Type 70 oil press with a 2.2 Hp motor and 70 mm screw diameter) for oil extraction. This material did not yield any significant amount of oil and heavy footing was observed with the press.

The moisture content of the drum dried yeast broth without concentration was 5.4% and the drum dried yeast was then conditioned in an oven at 90° C. for 20 minutes. The moisture content after conditioning was 1.4%. The conditioned drum dried yeast was then fed into a bench-top Taby screw press for oil extraction. This material oiled well, with minimal footing.

The moisture content of the drum dried concentrated yeast broth was 2.1% and the drum dried concentrated yeast was then conditioned in an oven at 90° C. for 20 minutes. The moisture content after conditioning was 1.0%. The conditioned drum dried concentrated yeast was then fed into a bench-top Taby screw press for oil extraction. This material oiled well, with minimal footing.

C. Drying and Oil Extraction from Oleaginous Bacteria

Oleaginous bacteria strain *Rhodococcus opacus* PD630 (DSMZ-DSM 44193) was cultured according to the methods provided herein to produce oleaginous bacteria biomass with approximately 32% lipid by DCW.

The harvested *Rhodococcus opacus* broth was concentrated using centrifugation and then washed with deionized water and resuspended in 1.8 L of deionized water. 50 grams of purified cellulose (PB20-Pre-co-Floc, EP Minerals, Nevada) was added to the resuspended biomass, and the total solids was adjusted with deionized water to 20%. The *Rhodococcus* biomass was then dried on a drum drier and the moisture content of the *Rhodococcus* after drum drying was approximately 3%.

The drum-dried material was then heat conditioned in a oven at 130° C. for 30 minutes with a resulting moisture content of approximately 1.2%. The heat conditioned biomass was then fed through a bench top Taby press (screw press) for oil extraction. The press temperature was at 209° F. and the conditioned dried yeast biomass was held at about 240° F. until it was ready to be fed into the press. Oil recovery was accompanied by heavy footing.

Example 9: Processing of Extracted Oil; Lowering of Pour Point

Summary

Microbial oil prepared in accordance with the foregoing examples can be processed in accordance with the methods described herein to improve its properties for use in foods and lubricants. In addition to the microbes described in the above examples, the microalgae *Chlorella protothecoides* is an excellent producer of microbial oil. For methods of culturing *Chlorella* species and strains to obtain high oil and to extract oil therefrom, see PCT Pub. Nos. 2008/151149, 2010/120939, and 2010/138,620, incorporated herein by reference.

Pour point was reduced in oil obtained from *Chlorella protothecoides* by reducing the relative proportion of the saturated fraction, which consists primarily of palmitic and stearic triglycerides known in the trade as the stearin fraction. This was accomplished by fractionating the oil to reduce the saturated triglycerides concentration of the oil. This was done by crystallizing or dry fractionation, similar to the winterizing process known in the vegetable oil industry. The algal oil was first refined, bleached and deodorized by methods described above (methods similar to those used in the vegetable oil industry could also be employed) to produce "RBD oil".

The temperature of the RBD oil was lowered in a controlled manner until crystal nuclei were formed. The oil was then held at that crystallization temperature for several hours to facilitate growth of the crystals. The crystals were then removed by filtration to result in two fractions: a solid phase containing some or most of the stearin fraction, and a liquid phase containing mostly the olein fraction. The liquid phase was subjected to fractionation again to a lower crystallization temperature to effect a further removal of stearin. The resulting purified liquid fraction, equivalent to a super olein as commonly known in the vegetable oil industry, has better thermal properties than the native algal oil.

Materials and Methods

Materials

Algal oil (refined, bleached, and deodorized) was produced by Solazyme, Inc (South San Francisco, Calif.). Table 23 summarizes the properties of the oil used in the study.

TABLE 23

Properties of algal oil used in the study

| Analysis | Value |
|---|---|
| Moisture [%] | 0.01 |
| Free fatty acid [% as oleic] | 0.03 |
| Iodine value | 83.5 |

TABLE 23-continued

Properties of algal oil used in the study

| Analysis | Value |
| --- | --- |
| Fatty Acid Profile | |
| 8:0 | 0.00 |
| 10:0 | 0.00 |
| 12:0 | 0.03 |
| 14:0 | 1.12 |
| 16:0 | 14.02 |
| 18:0 | 3.24 |
| 18:1 | 67.73 |
| 18:2 | 11.18 |
| 18:3 | 0.62 |
| 20:0 | 0.32 |
| 20:1 | 0.20 |

Poly alkyl methacrylate copolymer-based Pour Point Depressant (PPD) VISCOPLEX® 10-310 containing ~50% (w/w) of rapeseed oil carrier and VISCOPLEX® 1-133 containing refined mineral oil carrier were supplied by RohmMax Evonik (Horsham, Pa.).

Methods

A. Dry Fractionation: Crystallization

Around 2.5 kg of algal oil was placed in a 3-1 jacketed vessel connected to a temperature-controlled circulating water bath, which served to heat and cool the product (Crystallization & Degumming, Charleroi, Belgium). The reactor was fitted with a variable-speed agitator. Cooling was controlled by monitoring the temperatures of the oil and the water circulating between the double walls of the reactor. A droplet of crystal suspension was sampled from the reactor with a stick and deposited on a coverslip to monitor crystal formation at the end of cooling. The sample was analyzed immediately under a microscope before the crystals had a chance to melt.

The overall cooling pattern is shown in FIG. 1. Agitator speed was 30 rpm during the first phase and 15 rpm up to the end of the cooling program.

B. Dry Fractionation: Filtration

At the end of crystallization, the crystal suspension was filtered using a 1-L membrane press filter (Choquenet SA, Chauny, France). Filtration was carried out in a chamber that was kept at the final cooling temperature. The filtration time was 20 min and the filter supply pressure was 4 barg.

Figure 2:
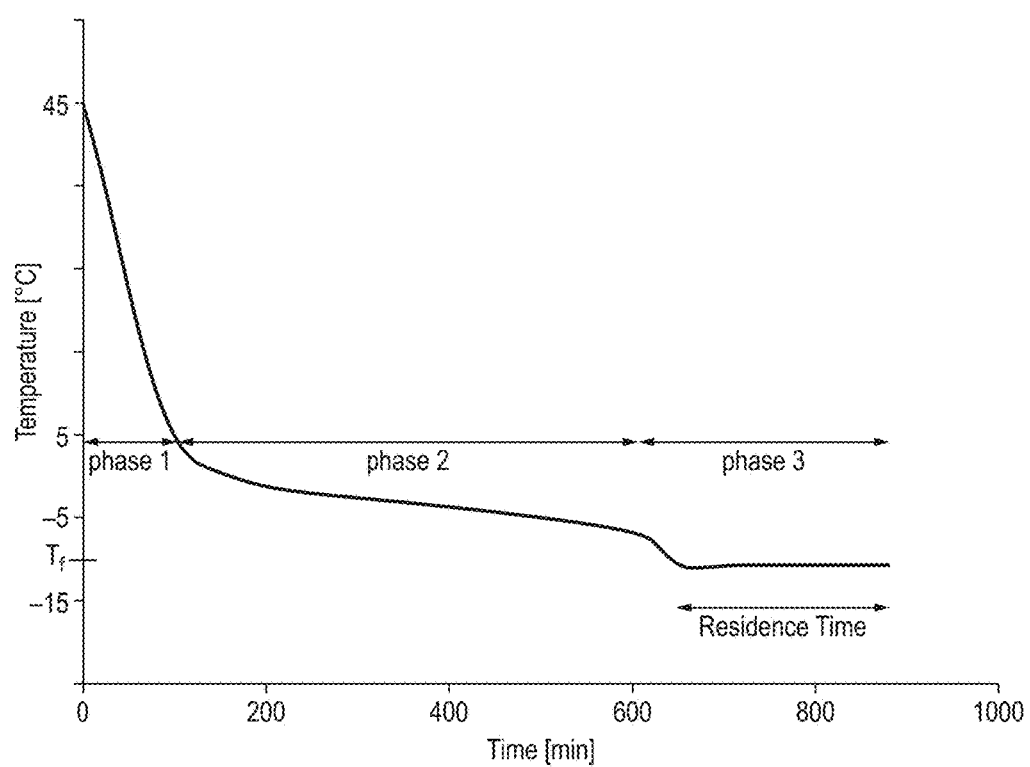
FIG. 2. Typical cooling profile for algal olein fractionation (Tf=filtration temperature).

At the end of the separation step, the stearin and olein fractions were weighed, the fraction yields calculated, and a sample of each fraction was set aside for further analysis. Algal super olein #1 was produced by processing the olein from the first fractionation and repeating the crystallization and filtration process described above following the cooling program shown in FIG. 2. Algal super olein #2 and #3 were produced by first fractionating deodorized oil and repeating the crystallization and filtration process using a cooling program similar to that shown in FIG. 2.

C. Pour Point (PP)

Pour Point Depressants (0.5 and 1.0 grams) were weighed into flasks. Algal oil, olein and superolein fractions (100 grams) were added to each flask. The mixtures were mixed thoroughly. Each sample was tested according to the D 97 ASTM (The American Society for Testing and Materials) standard method. The sample was poured into a test tube and heated without stirring in a water bath where the temperature was set at 48.0° C. The sample was heated until it reached 46.0° C. After heating, the sample was cooled to 25.0° C. (in a water bath). The sample was then placed in a metal cylinder in a methanol bath. The temperature of the methanol bath was set at −1.0° C. to −2.0° C. until the temperature of the sample reached 10.0° C. Then, the temperature of the methanol bath was reduced to −17.0° C. until the temperature of the sample reached −7.0° C. When the temperature of the sample was about 11.0° C. above the expected pour point, the sample was taken out of the methanol bath at every reduction by 3.0° C., to check the pour ability. The pour point of the sample was determined as the temperature when the sample in the test tube stopped pouring when taken out of the methanol bath. To the temperature recorded, 3.0° C. was added, to give the actual pour point value of the sample.

Figure 3:
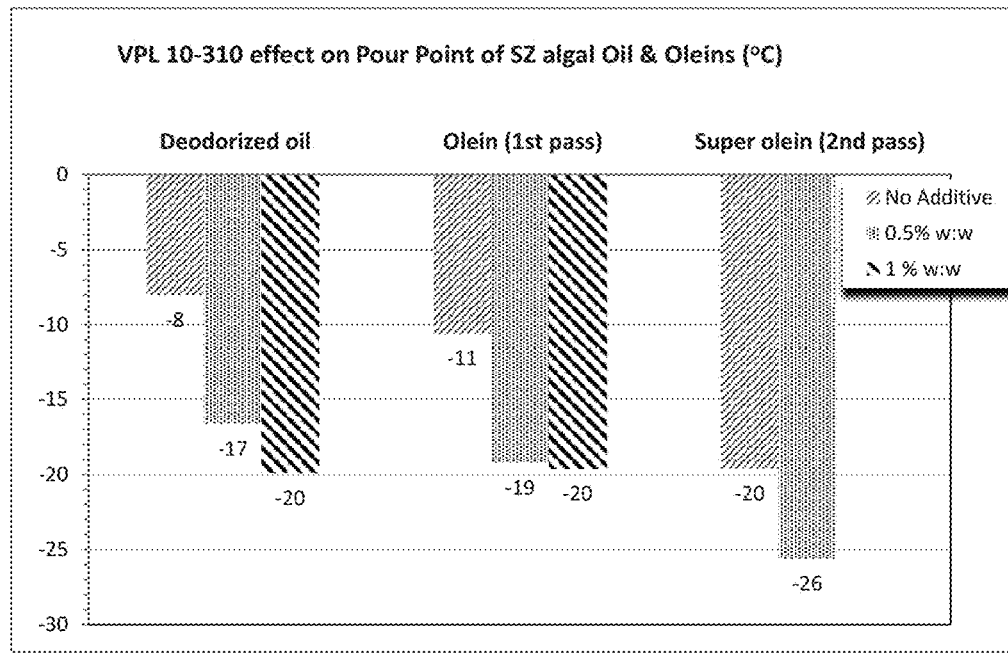
FIG. 3. VPL 10-310 effect on pour point of algal oil and fractionated oils. "Deodorized oil" is RBD oil; "olein" is olein #1; "super olein" is super olein #1."

The properties of the oil produced at each step could be further improved in accordance with the methods described herein by the addition of a chemical pour point depressant that reduced the pour point even further. The pour point depressants used for this example were VISCOPLEX® 10-310 and 1-133, both produced by Evonik, but similar results could be obtained using any standard pour point depressant. The results are shown in Table 24, below, and in FIG. 3.

TABLE 24

Effect of Fractionation and Pour Point[1] Depressants on Algal Oil (° C.)

| SAMPLE | No additive | VISCO-PLEX® 10-310[2] (% w:w) | | VISCO-PLEX® 1-133[3] (% w:w) | |
| --- | --- | --- | --- | --- | --- |
| | 0 | 0.5 | 1 | 0.5 | 1 |
| Refined, Bleached, Deodorized oil | −8 | −17 | −20 | −14 | −16 |
| Olein #1 (liquid from 1st fractionation) | −11 | −19 | −20 | −16 | −17 |
| Super Olein #1 (liquid from olein fractionation = 2nd pass) | −20 | −26 | NT | NT | NT |
| Super Olein #2 (liquid from olein fractionation = 2nd pass) | −14 | −20 | −23 | NT | NT |
| Super Olein #3 (liquid from olein fractionation = 2nd pass) | −20 | −23 | −29 | NT | NT |

[1]Pour point ASTM D97
[2]50:50 mix of poly(alkyl) acrylate and rapeseed oil. Rated biodegradable
[3]Mix of poly(alkyl) acrylate and refined mineral oil.
NT = Not Tested.

(1) Pour point ASTM D97
(2) 50:50 mix of poly(alkyl) acrylate and rapeseed oil. Rated biodegradable
(3) Mix of poly(alkyl) acrylate and refined mineral oil.
NT=Not Tested.

Example 10: Pour Points of Oil Produced from Engineered Microalgae

*Protheca moriformis* (UTEX 1435) was transformed with one of the following plasmid constructs in Table 25 using the methods of Example 2.

TABLE 25

Plasmid constructs used to transform *Protheca moriformis* (UTEX 1435).

| Plasmid Construct | Sequence Elements |
| --- | --- |
| 1 | 6SA-CrbTub_yInv_nr::CrbTub_hpFADc_nr-6SB |
| 2 | 65A-bTub-yInv-nr-6SB |
| 3 | FADc5'_btub-yInv-nr::amt03-S106SAD-CtOTE-nr-FADc3' |

TABLE 25-continued

Plasmid constructs used to transform Protheca moriformis (UTEX 1435).

| Plasmid Construct | Sequence Elements |
|---|---|
| 4 | SAD2B5'-CrbTub_yInv_ef1::amt03_CWTE2_nr-SAD2B3' |

Each of the constructs contained a region for integration into the nuclear genome and a *S. cerevisiae* suc2 sucrose invertase coding region under the control of *C. reinhardtii* β-tubulin promoter/5'UTR and *Chlorella vulgaris* nitrate reductase 3' UTR. This *S. cerevisiae* suc2 expression cassette is listed as SEQ ID NO:78 and served as a selection marker. Relevant sequences for the targeting regions used for nuclear genome integration are shown below.

| Description | SEQ ID NO: |
|---|---|
| 5' sequence for the 6S genomic targeting sequence | SEQ ID NO: 100 |
| 3' sequence for the 6S genomic targeting sequence | SEQ ID NO: 101 |
| 5' sequence for genomic integration at the FADc locus | SEQ ID NO: 102 |
| 3' sequence for genomic integration at the FADc locus | SEQ ID NO: 103 |
| 5' sequence for genomic integration at the SAD2B locus | SEQ ID NO: 36 |
| 3' sequence for genomic integration at the SAD2B locus | SEQ ID NO: 37 |

In addition to the sucrose selectable marker, three of the four constructs also contained different, additional sequences for the expression of either proteins or RNA. Table 26 lists important enzymes or hairpin RNA cassettes that are encoded by the DNA sequence in the indicated construct. All protein coding regions were codon optimized to reflect the codon bias inherent in *Protothecamoriformis* UTEX 1435 (see Table 2) nuclear genes. Both amino acid sequences and the cDNA sequences for the construct used are listed in the sequence listing.

TABLE 26

Plasmid constructs for thioesterases or hairpin RNA expression used to transform *Protheca moriformis* (UTEX 1435).

| Plasmid construct | Protein or hairpin RNA | Seq ID NO: |
|---|---|---|
| 1 | FADc hairpin | SEQ ID NO: 92 |
| 3 | *Carthamus tinctorius* ACP thioesterase (GenBank Accession No: AAA33019.1) | SEQ ID NO: 104 |
| 4 | *Cuphea wrightii* FatB2 thioesterase (GenBank Accession No. U56104) | SEQ ID NO: 105 |

Both the *Carthamus tinctorius* ACP thioesterase (CtOTE in Construct 3) and the *Cuphea wrightii* FatB2 thioesterase (CwTE2 in Construct 4) coding regions were under the control of the *Prototheca moriformis* Amt03 promoter/5'UTR (SEQ ID NO:84) and *C. vulgaris* nitrate reductase 3'UTR (SEQ ID NO:85). The native transit peptide of the *C. tinctorius* ACP thioesterase was replaced with the *Chlorella protothecoides* stearoyl-ACP desaturase transit peptide (SEQ ID NO:86). The codon-optimized cDNA sequences and amino acid sequences (with the replaced transit peptide) of the *C. tinctorius* ACP thioesterase are listed in the Sequence Listing as SEQ ID NO:106 and SEQ ID NO:104, respectively. The codon-optimized cDNA sequences and amino acid sequences of the *Cuphea wrightii* FatB2 thioesterase are listed in the Sequence Listing as SEQ ID NO: 107 and SEQ ID NO: 105, respectively. Construct 1 containing the FADc hairpin RNA is described in Example 4.

Each construct was transformed into a *Prototheca moriformis* genetic background. Positive clones were screened on plates with sucrose as the sole carbon source. A subset of the positive clones were selected and grown under lipid production conditions. Wild type UTEX 1435 was grown using glucose while all other transgenic lines were cultivated in sucrose. For each construct, transformants were grown and oil was isolated. The isolated oils were analyzed for fatty acid profiles and the pour points were determined as described herein. Pour points were determined using the ASTM D97 standard test method for pour point evaluation. The fatty acid profiles and the pour points of the oils for transgenic strains are shown in Table 27 below. Table 27 discloses the data for successful manipulation of the pour points of the oils produced by genetically engineered microalgae. The pour point of the oil transformed with Construct 3 was decreased from −10.5° C. to −19.5° C.

TABLE 27

Fatty acid profiles and pour point temperatures of *Prototheca moriformis* cells containing different constructs.

|  | Wild Type | Construct 1 | Construct 2 | Construct 3 | Construct 4 |
|---|---|---|---|---|---|
| C6:0 | 0 | 0 | 0 | 0 | 0 |
| C8:0 | 0 | 0 | 0 | 0 | 0 |
| C10:0 | 0 | 0 | 0.01 | 0.03 | 0.01 |
| C12:0 | 0.03 | 0.02 | 0.03 | 0.11 | 0.03 |
| C14:0 | 1.12 | 0.68 | 0.75 | 0.90 | 1.08 |
| C16:0 | 14.02 | 15.55 | 13.26 | 7.75 | 26.09 |
| C18:0 | 3.24 | 3.79 | 5.26 | 1.78 | 12.37 |
| C18:1 | 67.76 | 76.84 | 71.75 | 86.40 | 53.42 |
| C18:2 | 11.49 | 0.91 | 6.44 | 0.12 | 4.38 |
| C18:3α | 0.62 | 0.09 | 0.07 | 0.02 | 0.2 |
| Pour Point | −10.5° C. | −7.6° C. | −7.6° C. | −19.5° C. | 10.4° C. |

Example 11: Engineered Microalgae with Altered Fatty Acid Profiles

As described above, integration of heterologous genes to knockout or knockdown specific endogenous lipid pathway enzymes in *Prototheca* species can alter fatty acid profiles. As endogenous fatty acyl-ACP thioesterases catalyze the cleavage of a fatty acid from an acyl carrier protein during lipid synthesis, they are important lipid pathway enzymes in establishing the lipid profile of the host organism. Plasmid constructs were created to assess whether the lipid profile of a host cell can be affected as a result of a knockout or knockdown of an endogenous fatty acyl-ACP thioesterase gene, FATA1.

A. Altering Fatty Acid Profiles by Knockout of an Endogenous *Prototheca moriformis* Thioesterase Gene A classically mutagenized derivative of *Protheca moriformis* UTEX 1435, S1920, was transformed with one of the following plasmid constructs in Table 28 using the methods of Example 2. Each construct contained a region for integration into the nuclear genome to interrupt the endogenous FATA1 gene and a *S. cerevisiae* suc2 sucrose invertase coding region under the control of *C. reinhardtii* β-tubulin promoter/5'UTR and *Chlorella vulgaris* nitrate reductase 3' UTR. This *S. cerevisiae* suc2 expression cassette is listed as SEQ ID NO:78 and served as a selection marker. All protein coding regions were codon optimized to reflect the codon bias inherent in *Prototheca moriformis* UTEX 1435 (see Table 2) nuclear genes. Relevant sequences for the targeting regions for the FATA1 gene used for nuclear genome integration are shown below.

| Description | SEQ ID NO: |
| --- | --- |
| 5' sequence for integration into FATA1 locus | SEQ ID NO: 108 |
| 3' sequence for integration into FATA1 locus | SEQ ID NO: 109 |

TABLE 28

Plasmid constructs used to transform *Protheca moriformis* (UTEX 1435) S1920.

| Plasmid Construct | Sequence Elements |
| --- | --- |
| pSZ1883 | FATA1-CrbTub_yInv_nr-FATA1 |
| pSZ1925 | FATA1-CrbTub_yInv_nr::amt03_CwTE2_nr-FATA1 |

Relevant restriction sites in the construct FATA1-CrbTub_yInv_nr-FATA1 are indicated in lowercase in the sequence below, bold and underlining and are 5'-3' BspQ 1, Kpn I, Asc I, Mfe I, Sac I, BspQ I, respectively. BspQI sites delimit the 5' and 3' ends of the transforming DNA. Bold, lowercase sequences represent genomic DNA from S1920 that permit targeted integration at FATA1 locus via homologous recombination. Proceeding in the 5' to 3' direction, the *C. reinhardtii* β-tubulin promoter driving the expression of the yeast sucrose invertase gene (conferring the ability of S1920 to metabolize sucrose) is indicated by boxed text. The initiator ATG and terminator TGA for invertase are indicated by uppercase, bold italics while the coding region is indicated in lowercase italics. The *Chlorella* vulgar/s nitrate reductase 3' UTR is indicated by lowercase underlined text followed by the S190 FATA1 genomic region indicated by bold, lowercase text.

(SEQ ID NO: 111)

gctcttcggagtcactgtgccactgagttcgactggtagctgaatggagtcgctgctccactaaacgaattgtcagcaccgcca gccggccgaggacccgagtcatagcgagggtagtagcgcgccatggcaccgaccagcctgcttgccagtactggcgtctcttc cgcttctctgtggtcctctgcgcgctccagcgcgtgcgcttttccggtggatcatgcggtccgtggcgcaccgcagcggccgctg cccatgcagcgccgctgcttccgaacagtggcggtcagggccgcacccgcggtagccgtcctccggaacccgcccaagagt tttgggagcagcttgagccctgcaagatggcggaggacaagcgcatcttcctggaggagcaccggtgcgtggaggtccgggg ctgaccggccgtcgcattcaacgtaatcaatcgcatgatgatcagaggacacgaagtcttggtggcggtggccagaaacact gtccattgcaagggcatagggatgcgttccttcacctctcatttctcatttctgaatccctccctgctcactctttctcctcctccttc ccgttcacgcagcattcggggtaccctttcttgcgctatgacacttccagcaaaaggtagggcgggctgcgagacggcttcccggc gctgcatgcaacaccgatgatgcttcgacccccgaagctccttcggggctgcatgggcgctccgatgccgctccagggcgagcgc tgtttaaatagccaggccccgattgcaaagacattatagcgagctaccaaagccatattcaaacacctagatcactaccacttctacac aggccactcgagcttgtgatcgcactccgctaagggggcgcctcttcctcttcgtttcagtcacaacccgcaaacggcgcgccATG

*ctgctgcaggccttcctgttcctgctggccggcttcgccgccaagatcagcgcctccatgacgaagagacgtccgaccgccccct*

*ggtgcacttcaccccaacaagggctggatgaacgaccccaacggcctgtggtacgacgagaaggacgccaagtggcacctgt*

*acttccagtacaacccgaacgacaccgtctggggacgccttgttctggggccacgccacgtccgacgacctgaccaactggg*

*aggaccagcccatcgccatcgccccgaagcgcaacgactccggcgcctttctccggctccatggtggtggactacaacaacacct*

*ccggcttcttcaacgacaccatcgacccgcgccagcgctgcgtggccatctggacctacaacacccccggagtccgaggagcagt*

*acatctcctacagcctggacggcggctacacccttcaccgagtaccagaagaacccccgtgctggccgccaactccacccagttcc*

*gcgacccgaaggtcttctggtacgagccctcccagaagtggatcatgaccgcggccaagtcccaggactacaagatcgagatct*

*actcctccgacgacctgaagtcctggaagctggagtccgcgttcgccaacgagggcttcctcggctaccagtacgagtgccccgg*

*cctgatcgaggtccccaccgagcaggacccccagcaagtcctactgggtgatgttcatctccatcaacccggcgcccggccgg*

*cggctccttcaaccagtacttcgtcggcagcttcaacggcacccacttcgaggccttcgacaaccagtcccgcgtggtggacttcg*

-continued

*gcaaggactactacgccctgcagaccttcttcaacaccgacccgacctacgggagcgccctgggcatcgcgtgggcctccaact*

*gggagtactccgccttcgtgcccaccaacccctggcgctcctccatgtccctcgtgcgcaagttctccctcaacaccgagtaccag*

*gccaacccggagacggagctgatcaacctgaaggccgagccgatcctgaacatcagcaacgccggcccctggagccggttcg*

*ccaccaacaccacgttgacgaaggccaacagctacaacgtcgacctgtccaacagcaccggcaccctggagttcgagctggtg*

*tacgccgtcaacaccacccagacgatctccaagtccgtgttcgcggacctctccctctggttcaagggcctggaggaccccgagg*

*agtacctccgcatgggcttcgaggtgtccgcgtcctccttcttcctggaccgcgggaacagcaaggtgaagttcgtgaaggagaa*

*cccctacttcaccaaccgcatgagcgtgaacaaccagcccttcaagagcgagaacgacctgtcctactacaaggtgtacggcttg*

*ctggaccagaacatcctggagctgtacttcaacgacggcgacgtcgtgtccaccaacacctacttcatgaccaccgggaacgcc*

*ctgggctccgtgaacatgacgacgggggtggacaacctgttctacatcgacaagttccaggtgcgcgaggtcaag**TGA*caatt ggcagcagcagctcggatagtatcgacacactctggacgctggtcgtgtgatggactgttgccgccacacttgctgccttgacctgtga atatccctgccgcttttatcaaacagcctcagtgtgtttgatcttgtgtgtacgcgcttttgcgagttgctagctgcttgtgctatttgcgaata ccacccccagcatccccttccctcgtttcatatcgcttgcatcccaaccgcaacttatctacgctgtcctgctatccctcagcgctgctcct gctcctgctcactgcccctcgcacagccttggtttgggctccgcctgtattctcctggtactgcaacctgtaaaccagcactgcaatgctg atgcacgggaagtagtgggatgggaacacaaatggaggatcgtagagctcactagtatcgatttcgaagacagggtggttggctgg atggggaaacgctggtcgcgggattcgatcctgctgcttatatcctccctggaagcacacccacgactctgaagaagaaaacg tgcacacacacaacccaaccggccgaatatttgcttccttatcccgggtccaagagagactgcgatgccccctcaatcagcat cctcctccctgccgcttcaatcttccctgcttgcctgcgcccgcggtgcgccgtctgcccgcccagtcagtcactcctgcacaggc cccttgtgcgcagtgctcctgtaccctttaccgctccttccattctgcgaggcccccctattgaatgtattcgttgcctgtgtggcca agcgggctgctgggcgcgccgccgtcgggcagtgctcggcgactttggcggaagccgattgttcttctgtaagccacgcgcttg ctgctttgggaagagaaggggggggtactgaatggatgaggaggagaaggaggggtattggtattatctgagttgggtgaa gagc

To introduce the *Cuphea wrightii* ACP-thioesterase 2 (CwFatB2) gene (Accession No: U56104) into S1920 at the FATA1 locus, a construct was generated to express the protein coding region of the CwFatB2 gene under the control of the *Prototheca moriformis* Amt03 promoter/5'UTR (SEQ ID NO:84) and *C. vulgaris* nitrate reductase 3'UTR (SEQ ID NO:85). The construct that has been expressed in S1920 can be written as FATA1-CrbTub_yInv_nr::amt03_CwTE2_nr-FATA1.

Relevant restriction sites in the construct FATA1-CrbTub_yInv_nr::amt03_CwTE2_nr-FATA1 are indicated in lowercase, bold and underlining in the sequence below and are 5'-3' BspQ 1, Kpn I, Asc I, Mfe I, BamH I, EcoR I, Spe I, Asc I, Pac I, Sac I, BspQ I, respectively. BspQI sites delimit the 5' and 3' ends of the transforming DNA. Bold, lowercase sequences represent genomic DNA from S1920 that permit targeted integration at FATA1 locus via homologous recombination. Proceeding in the 5' to 3' direction, the *C. reinhardtii* β-tubulin promoter driving the expression of the yeast sucrose invertase gene (conferring the ability of S1920 to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *Prototheca moriformis*, indicated by boxed italics text. The Initiator ATG and terminator TGA codons of the *C. wrightii* ACP-thioesterase are indicated by uppercase, bold italics, while the remainder of the ACP-thioesterase coding region is indicated by bold italics. The *C. vulgaris* nitrate reductase 3' UTR is again indicated by lowercase underlined text followed by the S1920 FATA1 genomic region indicated by bold, lowercase text. The codon-optimized cDNA sequences and amino acid sequences of the *Cuphea wrightii* FatB2 thioesterase are listed in the Sequence Listing as SEQ ID NO: 107 and SEQ ID NO: 105, respectively.

(SEQ ID NO: 112)

gctcttcggagtcactgtgccactgagttcgactggtagctgaatggagtcgctgctccactaaacgaattgtcagcaccgcca gccggccgaggacccgagtcatagcgagggtagtagcgcgccatggcaccgaccagcctgcttgccagtactggcgtctcttc cgcttctctgtggtcctctgcgcgctccagcgcgtgcgcttttccggtggatcatgcggtccgtggcgcaccgcagcggccgctg cccatgcagcgccgctgcttccgaacagtggcggtcagggccgcacccgcggtagccgtcctccggaacccgcccaagagt tttgggagcagcttgagccctgcaagatggcggaggacaagcgcatcttcctggaggagcaccggtgcgtggaggtccgggg ctgaccggccgtcgcattcaacgtaatcaatcgcatgatgatcagaggacacgaagtcttggtggcggtggccagaaacact gtccattgcaagggcatagggatgcgttcctcacctctcatttctcatttctgaatccctccctgctcactctttctcctcctccttc ccgttcacgcagcattcgggg gtacc ctttcttgcgctatgacacttccagcaaaaggtagggcgggctgcgagacggcttcccggc gctgcatgcaacaccgatgatgcttcgaccccccgaagctccttcggggctgcatgggcgctccgatgccgctccagggcgagcgc tgtttaaatagccaggcccccgattgcaaagacattatagcgagctaccaaagccatattcaaacacctagatcactaccacttctacac aggccactcgagcttgtgatcgcactccgctaagggggcgcctcttcctcttcgtttcagtcacaacccgcaaac ggcgcgcc ATG

*ctgctgcaggccttcctgttcctgctggccggcttcgccgccaagatcagcgcctccatgacgaagagacgtccgaccgccccct*

*ggtgcacttcacccccaacaagggctggatgaacgaccccaacggcctgtggtacgacgagaaggacgccaagtggcacctgt*

*acttccagtacaacccgaacgacaccgtctggggacgcccttgttctggggccacgccacgtccgacgacctgaccaactggg*

*aggaccagccatcgccatcgccccgaagcgcaacgactccggcgccttctccggctccatggtggtggactacaacaacacct*

*ccggcttcttcaacgacaccatcgacccgcgccagcgctgcgtggccatctggacctacaacaccccggagtccgaggagcagt*

*acatctcctacagcctggacggcggctacaccttcaccgagtaccagaagaacccgtgctggccgccaactccacccagttcc*

*gcgacccgaaggtcttctggtacgagccctcccagaagtggatcatgaccgcggccaagtcccaggactacaagatcgagatct*

*actcctccgacgacctgaagtcctggaagctggagtccgcgttcgccaacgagggcttcctcggctaccagtacgagtgccccgg*

*cctgatcgaggtccccaccgagcaggaccccagcaagtcctactgggtgatgttcatctccatcaaccccggcgcccccggccgg*

*cggctccttcaaccagtacttcgtcggcagcttcaacggcacccacttcgaggccttcgacaaccagtcccgcgtggtggacttcg*

*gcaaggactactacgccctgcagaccttcttcaacaccgacccgacctacgggagcgccctgggcatcgcgtgggcctccaact*

*gggagtactccgccttcgtgcccaccaaccctggcgctcctccatgtcccctcgtgcgcaagttctccctcaacaccgagtaccag*

*gccaacccggagacggagctgatcaacctgaaggccgagccgatcctgaacatcagcaacgccggcccctggagccggttcg*

*ccaccaacaccacgttgacgaaggccaacagctacaacgtcgacctgtccaacagcaccggcaccctggagttcgagctggtg*

*tacgccgtcaacaccacccagacgatctccaagtccgtgttcgcggaccctctccctctggttcaagggcctggaggaccccgagg*

*agtacctccgcatgggcttcgaggtgtccgcgtcctccttcttcctggaccgcgggaacagcaaggtgaagttcgtgaaggagaa*

*ccctacttcaccaaccgcatgagcgtgaacaaccagcccttcaagagcgagaacgacctgtcctactacaaggtgtacggcttg*

*ctggaccagaacatcctggagctgtacttcaacgacggcgacgtcgtgtccaccaacacctacttcatgaccacgggaacgcc*

*ctgggctccgtgaacatgacgacggggtggacaacctgttctacatcgacaagttccaggtgcgcgaggtcaag*TGAcaatt ggcagcagcagctcggatagtatcgacacactctggacgctggtcgtgtgatggactgttgccgccacacttgctgccttgacctgtga atatccctgccgcttttatcaaacagcctcagtgtgtttgatcttgtgtgtacgcgcttttgcgagttgctagctgcttgtgctatttgcgaata ccacccccagcatcccttccctcgtttcatatcgcttgcatcccaaccgcaacttatctacgctgtcctgctatccctcagcgctgctcct -continued gctcctgctcactgcccctcgcacagccttggtttgggctccgcctgtattctcctggtactgcaacctgtaaaccagcactgcaatgctg atgcacgggaagtagtgggatgggaacacaaatggaggatcccgcgtctcgaacagagcgcgcagaggaacgctgaaggtctcg cctctgtcgcacctcagcgcggcatacaccacaataaccacctgacgaatgcgcttggttcttcgtccattagcgaagcgtccggttca cacacgtgccacgttggcgaggtggcaggtgacaatgatcggtggagctgatggtcgaaacgttcacagcctagggatatcgaatc ggccgacaggacgcgcgtcaaaggtgctggtcgtgtatgccctggccggcaggtcgttgctgctgctggttagtgattccgcaacc ctgattttggcgtcttattttggcgtggcaaacgctggcgcccgcgagccgggccggcggcgatgcggtgccccacggctgccgg aatccaagggaggcaagagcgcccgggtcagttgaagggcttacgcgcaaggtacagccgctcctgcaaggctgcgtggtgg aattggacgtgcaggtcctgctgaagttcctccaccgcctcaccagcggacaaagcacggtgtatcaggtccgtgtcatccactc taaagagctcgactacgacctactgatggccctagattcttcatcaaaaacgcctgagacacttgcccaggattgaaactccctga agggaccaccaggggccctgagttgttccttccccccgtggcgagctgccagccaggctgtacctgtgatcgaggctggcggga aaataggcttcgtgtgctcaggtcatgggaggtgcaggacagctcatgaaacgccaacaatcgcacaattcatgtcaagctaatc agctatttcctcttcacgagctgtaattgtcccaaaattctggtctaccgggggtgatccttcgtgtacgggccttccctcaaccctag gtatgcgcgcatgcggtcgccgcgcaactcgcgcgagggccgagggtttgggacgggccgtcccgaaatgcagttgcacccgg atgcgtggcaccttttttgcgataatttatgcaatggactgctctgcaaaattctggctctgtcgccaaccctaggatcagcggcgtag gatttcgtaatcattcgtcctgatggggagctaccgactaccctaatatcagcccgactgcctgacgccagcgtccacttttgtgcac acattccattcgtgcccaagacatttcattgtggtgcgaagcgtccccagttacgctcacctgtttcccgacctccttactgttctgtcg acagagcgggcccacaggccggtcgcagccactagtatggtggtggccgccgccgcagcagcgccttcttcccgtgcccgc ccccgccccaccccaagcccggcaagttcggcaactggcccagcagcctgagccagcccttcaagcccaagagcaacccc aacggccgcttccaggtgaaggccaacgtgagcccccacgggcgcgcccccaaggccaacggcagcgccgtgagcctgaag tccggcagcctgaacaccctggaggacccccccagcagcccccccccgcaccttcctgaaccagctgcccgactggagccg cctgcgcaccgccatcaccaccgtgttcgtggccgccgagaagcagttcacccgcctggaccgcaagagcaagcgccccgaca tgctggtggactggttcggcagcgagaccatcgtgcaggacggcctggtgttccgcgagcgcttcagcatccgcagctacgagat cggcgccgaccgcaccgccagcatcgagaccctgatgaaccacctgcaggacaccagcctgaaccactgcaagagcgtggg cctgctgaacgacggcttcggccgcaccccccgagatgtgcacccgcgacctgatctgggtgctgaccaagatgcagatcgtggtg aaccgctaccccacctggggcgacaccgtggagatcaacagctggttcagccagagcggcaagatcggcatgggccgcgagt ggctgatcagcgactgcaacaccggcgagatcctggtgcgcgccaccagcgcctgggccatgatgaaccagaagacccgccg cttcagcaagctgccctgcgaggtgcgccaggagatcgcccccacttcgtggacgccccccccgtgatcgaggacaacgacc gcaagctgcacaagttcgacgtgaagaccggcgacagcatctgcaagggcctgacccccggctggaacgacttcgacgtgaac cagcacgtgagcaacgtgaagtacatcggctggattctggagagcatgccaccgaggtgctggagacccaggagctgtgcag cctgaccctggagtaccgccgcgagtgcggccgcgagagcgtggtggagagcgtgaccagcatgaacccagcaaggtgggc gaccgcagccagtaccagcacctgctgcgcctggaggacggcgccgacatcatgaagggccgcaccgagtggcgcccccaag aacgccggcaccaaccaaccgcgccatcagcaccTGAttaattaactcgaggcagcagcagctcggatagtatcgacacactctgga cgctggtcgtgtgatggactgttgccgccacacttgctgccttgacctgtgaatatccctgccgcttttatcaaacagcctcagtgtgtttg -continued

```
atcttgtgtgtacgcgcttttgcgagttgctagctgcttgtgctatttgcgaataccaccccagcatcccttccctcgtttcatatcgcttg catcccaaccgcaacttatctacgctgtcctgctatccctcagcgctgctcctgctcctgctcactgcccctcgcacagccttggtttggg ctccgcctgtattctcctggtactgcaacctgtaaaccagcactgcaatgvtgatgcacgggaagtagtgggatgggaacacaaatgg aaagvttgagctcttgttttccagaaggagttgctccttgagcctttcattctcagcctcgataacctccaaagccgctctaattgtggagg gggttcgaagacagggtggttggctggatggggaaacgctggtcgcgggattcgatcctgctgcttatatcctcccggaagca cacccacgactctgaagaagaaaacgtgcacacacacaacccaaccggccgaatatttgcttccttatcccgggtccaagag agactgcgatgcccccctcaatcagcatcctcctccctgccgcttcaatcttccctgcttgcctgcgccgcggtgcgccgtctgc ccgcccagtcagtcactcctgcacaggcccctgtgcgcagtgctcctgtacccttacgctccttccattctgcgaggccccct attgaatgtattcgttgcctgtgtggccaagcgggctgctgggcgcgccgccgtcgggcagtgctcggcgactttggcggaagc cgattgttcttctgtaagccacgcgcttgctgctttgggaagagaagggggggggtactgaatggatgaggaggagaaggag gggtattggtattatctgagttgggtgaagagc
```

Upon transformation of FATA1-CrbTub_yInv_nr-FATA1 into S1920, primary transformants were clonally purified and grown under standard lipid production conditions at pH 5.0 similar to the conditions as disclosed in Example 1. Fatty acid profiles were analyzed using standard fatty acid methyl ester gas chromatography flame ionization (FAME GC/FID) detection methods. Table 29 below provides the fatty acid profiles of several transformants.

TABLE 29

Fatty acid profiles of *Prototheca moriformis* cells containing a selectable marker to disrupt an endogenous FATA1 allele.

| Transformation | % C14:0 | % C16:0 | % C18:0 | % C18:1 | % C18:2 |
|---|---|---|---|---|---|
| Wildtype | 1.23 | 25.68 | 2.83 | 60.54 | 7.52 |
| pSZ1883 Transformant 1 | 0.86 | 16.95 | 1.75 | 68.44 | 9.78 |
| pSZ1883 Transformant 2 | 0.85 | 17.33 | 1.71 | 68.57 | 9.31 |
| pSZ1883 Transformant 3 | 0.82 | 17.40 | 1.78 | 68.55 | 9.22 |
| pSZ1883 Transformant 4 | 0.84 | 17.43 | 1.78 | 68.25 | 9.53 |

TABLE 29-continued

Fatty acid profiles of *Prototheca moriformis* cells containing a selectable marker to disrupt an endogenous FATA1 allele.

| Transformation | % C14:0 | % C16:0 | % C18:0 | % C18:1 | % C18:2 |
|---|---|---|---|---|---|
| pSZ1883 Transformant 5 | 0.75 | 17.64 | 2.02 | 69.02 | 8.61 |

These results show that ablation of the host's endogenous FATA1 allele alters the lipid profile of the engineered microalgae. The impact of targeting a selectable marker to the endogenous FATA1 allele is a clear diminution of C16:0 fatty acid production with an increase in C18:1 fatty acid production.

Upon transformation of FATA1-CrbTub_yInv_nr::amt03_CwTE2_nr-FATA1 into S1920, primary transformants were clonally purified and grown under standard lipid production conditions at pH 7.0 with different carbon sources provided to a total concentration of 40 g/L. The sucrose concentration was 40 g/L. Where only glucose was used as the carbon source, glucose was provided at 40 g/L. Where glucose and fructose was used as the carbon source, glucose was provided at 20 g/L and fructose was provided at 20 g/L. Fatty acid profiles were assessed by GC-FID. The resulting fatty acid profiles are listed in Table 30.

TABLE 30

Fatty acid profiles of *Prototheca moriformis* cells containing a selectable marker and an exogenous thioesterase to disrupt an endogenous FATA1 allele.

| Transformant | Copy Number | Carbon source | % C10:0 | % C12:0 | % C14:0 | % C16:0 | % C18:0 | % C18:1 | % C18:2 |
|---|---|---|---|---|---|---|---|---|---|
| Wildtype | 0 | Glucose | 0.01 | 0.04 | 1.38 | 28.83 | 3.00 | 56.05 | 8.21 |
| Wildtype | 0 | Glucose | 0.01 | 0.04 | 1.50 | 29.38 | 3.00 | 55.29 | 8.23 |
| Wildtype | 0 | Glucose/Fructose | 0.01 | 0.05 | 1.48 | 28.58 | 3.20 | 57.14 | 7.27 |
| Wildtype | 0 | Glucose/Fructose | 0.01 | 0.04 | 1.54 | 29.05 | 3.23 | 56.47 | 7.32 |
| pSZ1925 Transformant 1 | >2 | Glucose/Fructose | 4.29 | 19.98 | 9.17 | 20.68 | 3.47 | 34.38 | 6.37 |
| pSZ1925 Transformant 2 | >2 | Glucose/Fructose | 3.11 | 16.17 | 9.91 | 15.97 | 1.57 | 45.72 | 5.81 |

TABLE 30-continued

Fatty acid profiles of *Prototheca moriformis* cells containing a selectable marker and an exogenous thioesterase to disrupt an endogenous FATA1 allele.

| Transformant | Copy Number | Carbon source | % C10:0 | % C12:0 | % C14:0 | % C16:0 | % C18:0 | % C18:1 | % C18:2 |
|---|---|---|---|---|---|---|---|---|---|
| pSZ1925 Transformant 3 | >2 | Sucrose | 4.84 | 24.22 | 11.56 | 19.48 | 2.67 | 29.56 | 6.02 |
| pSZ1925 Transformant 4 | >2 | Sucrose | 3.24 | 16.67 | 10.39 | 16.34 | 1.43 | 44.41 | 6.00 |
| pSZ1925 Transformant 5 | 1-2 | Glucose/Fructose | 0.18 | 1.64 | 1.85 | 14.43 | 2.12 | 70.30 | 7.63 |
| pSZ1925 Transformant 6 | 1-2 | Glucose/Fructose | 0.18 | 1.56 | 1.74 | 13.56 | 2.25 | 71.04 | 7.72 |
| pSZ1925 Transformant 7 | 1-2 | Sucrose | 0.19 | 1.69 | 1.89 | 13.79 | 3.15 | 69.97 | 7.68 |
| pSZ1925 Transformant 8 | 1-2 | Sucrose | 0.15 | 1.26 | 1.49 | 13.44 | 2.73 | 71.46 | 7.77 |

Concordant with targeting a selectable marker alone to the host's FATA1 allele, integration of a selectable marker concomitant with an exogenous thioesterase alters the lipid profile of the engineered microalgae. As above, targeting an exogenous gene to the FATA1 allele results in a clear diminution of C16:0 fatty acid production. The additional expression of the CwTE2 thioesterase at the FATA1 locus also impacts mid chain fatty acids and C18:1 fatty acid production to an extent that is dependent upon the level of exogenous thioesterase activity present in the transformants analyzed. Genes bordered by repeat units such as the *C. vulgaris* nitrate reductase 3' UTR in constructs such as FATA1-CrbTub_yInv_nr::amt03_CwTE2_nr-FATA1, can be amplified upon integration in the host genome. There is good concordance between copy number of the amplified transgene at the target integration site and thioesterase levels as revealed either by impacts on fatty acid profiles or recombinant protein accumulation as assessed by western blotting.

Transgenic lines in which the CwTE2 gene has undergone amplification show a marked increase in mid chain (C10:0-C14:0) fatty acids and a concurrent decrease in C18:1 fatty acids. In contrast, those transformants in which CwTE2 has undergone little or no amplification (likely 1-2 copies) are consistent with lower expression of the exogenous thioesterase, resulting in a slight increase in mid chain fatty acids and a far greater impact on the increase of C18:1 fatty acids.

Collectively, these data show that ablation of the host's endogenous FATA1 allele alters the lipid profile of the engineered microalgae.

B. Altering Lipid Profiles by Knockdown of an Endogenous *Prototheca moriformis* Thioesterase Gene A construct, pSZ1773, to down-regulate the *Prototheca moriformis* FATA1 gene expression by a hairpin RNA was introduced into a *Prototheca moriformis* UTEX 1435 S1920 genetic background. The *Saccharomyces cerevisiae* suc2 sucrose invertase gene was utilized as a selectable marker, conferring the ability to grow on sucrose as a sole-carbon source. The portion of the construct that encodes the hairpin RNA utilized the first exon of FatA1 coding region, followed by the endogenous intron, and a repeat unit of the first exon in the reverse orientation. 5' and 3' homologous recombination targeting sequences (flanking the construct) to the 6S genomic region, listed as SEQ ID NO: 100 and 101 respectively, were included for integration of the hairpin construct into the nuclear genome. This construct is designated 6S::β-Tub:suc2:nr::β-tub:hairpinFatA:nr::6S.

Relevant restriction sites in 6S::β-Tub:suc2:nr::β-tub:hairpin FatA:nr::6S are indicated in lowercase, bold and underlining in the sequence below and are 5'-3' BspQ 1, Kpn I, Mfe I, BamH I, EcoR I, Spe I, Xho I, Sac I, BspQ I, respectively. BspQI sites delimit the 5' and 3' ends of the transforming DNA. Bold, lowercase sequences represent genomic DNA from S1920 that permit targeted integration at 6s locus via homologous recombination. Proceeding in the 5' to 3' direction, the *C. reinhardtii* β-tubulin promoter driving the expression of the yeast sucrose invertase gene (conferring the ability of S1920 to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the second *C. reinhardtii* β-tubulin promoter driving the expression of the Hairpin FatA1, indicated by boxed italics text. The initiator ATG codon of the FatA1 is indicated by uppercase, bold italics, while the remainder of the first exon of FatA1 coding region is indicated by uppercase. The intron of the FatA gene is indicated as underlined uppercase, and a linker region shown in underlined uppercase, bold italics was created at the FatA1 intron/reversed first exon junction to aid in RNA splicing in these vectors. The inverted first exon of FatA1 is indicated by uppercase. The *C. vulgaris* nitrate reductase 3' UTR is again indicated by lowercase underlined text followed by the S1920 6S genomic region indicated by bold, lowercase text. The sequences of the FATA portions of this RNAi construct is listed as SEQ ID NO: 110.

(SEQ ID NO: 113)

gctcttcgccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc -continued cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaacccccttgcgcgttagtgttgccatcctttgcagaccggtgag agccgacttgttgtgcgccaccccccacaccacctcctcccagaccaattctgtcaccttttttggcgaaggcatcggcctcggcc tgcagagaggacagcagtgvvvagccgctgggggttggcggatgcacgctcaggtacc|ctttcttgcgctatgacacttccagca aaaggtagggcgggctgcgagacggcttcccggcgctgcatgcaacaccgatgatgcttcgaccccccgaagctccttcggggctg catgggcgctccgatgccgctccagggcgagcgctgtttaaatagccaggccccgattgcaaagacattatagcgagctaccaaag ccatattcaaacacctagatcactaccacttctacacaggccactcgagcttgtgatcgcactccgctaaggggggcgcctcttcctcttc gtttcagtcacaacccgcaaac|tctagaatatca*ATG*ctgctgcaggccttcctgttcctgctggccggcttcgccgccaagatcag cgcctccatgacgaagagacgtccgaccgcccctggtgcacttcaccccaacaagggctggatgaacgacccaaggcc tgtggtacgacgagaaggacgccaagtggcacctgtacttccagtacaacccgaacgacaccgtctggggacgcccttgttctg gggccacgccacgtccgacgacctgaccaactgggaggaccagcccatcgccatcgcccgaagcgcaacgactccggcgc cttctccggctccatggtggtggactacaacaacacctccggcttcttcaacgacaccatcgacccgcgccagcgctgcgtggcca tctggacctacaacacccggagtccgaggagcagtacatctcctacagcctggacggcggctacaccttcaccgagtaccaga agaacccgtgctggccgccaactccacccagttccgcgacccgaaggtcttctggtacgagccctcccagaagtggatcatgac cgcggccaagtccaggactacaagatcgagatctactcctccgacgacctgaagtcctggaagctggagtccgcgttcgccaa cgagggcttcctcggctaccagtacgagtgccccggcctgatcgaggtccccaccgagcaggaccccagcaagtcctactgggt gatgttcatctccatcaaccccggcgcccccggccggcggctccttcaaccagtacttcgtcggagcttcaaggcacccacttcg aggccttcgacaaccagtcccgcgtggtggacttcggcaaggactactacgcctgcagaccttcttcaacaccgacccgaccta cgggagcgccctgggcatcgcgtgggcctccaactgggagtactccgccttcgtgcccaccaacccctggtcgctcctccatgtccc tcgtgcgcaagttctccctcaacaccgagtaccaggccaacccggagacggagctgatcaacctgaaggccgagccgatcctg aacatcagcaacgccggccctggagccggttcgccaccaacaccacgttgacgaaggccaacagctacaagtcgacctgtc caacagcaccggcaccctggagttcgagctggtgtacgccgtcaacaccacccagacgatctccaagtccgtgttcgcggacctc tccctctggttcaagggcctggaggaccccgaggagtacctccgcatgggcttcgaggtgtccgcgttcctccttctttcctggaccgc gggaacagcaaggtgaagttcgtgaaggagaaccctacttcaccaaccgcatgagcgtgaacaaccagccccttcaagagcg agaacgacctgtcctactacaaggtgtacggcttgctggaccagaacatcctggagctgtacttcaacgacggcgacgtcgtgtcc accaacacctacttcatgaccaccgggaacgccctgggctccgtgaacatgacgacggggtggacaacctgttctacatcgac aagttccaggtgcgcgaggtcaag*TGA*caattggcagcagcagctcggatagtatcgacacactctggacgctggtcgtgtgat ggactgttgccgccacacttgctgccttgacctgtgaatatccctgccgcttttatcaaacagcctcagtgtgtttgatcttgtgtgtttgatcttgtgtgtacgc cttttgcgagttgctagctgcttgtgctatttgcgaataccaccccagcatccccttcctcgtttcatatcgcttgcatcccaaccgcaac ttatctacgctgtcctgctatccctcagcgctgctcctgctcctgctcactgccctcgcacagccttggtttgggctccgcctgtattctcc tggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg -continued cttggttcttcgtccattagcgaagcgtccggttcacacacgtgccacgttggcgaggtggcaggtgacaatgatcggtggagctgatg gtcgaaacgttcacagcctagggatatcgaattcctttcttgcgctatgacacttccagcaaaaggtagggcgggctgcgagacgg cttcccggcgctgcatgcaacaccgatgatgcttcgaccccccgaagctccttcggggctgcatgggcgctccgatgccgctccag ggcgagcgctgtttaaatagccaggccccgattgcaaagacattatagcgagctaccaaagccatattcaaacacctagatca ctaccacttctacacaggccactcgagcttgtgatcgcactccgctaagggggcgcctcttcctcttcgtttcagtcacaacccgcaa acactagtATGGCACCGACCAGCCTGCTTGCCAGTACTGGCGTCTCTTCCGCTTCTCT

GTGGTCCTCTGCGCGCTCCAGCGCGTGCGCTTTTCCGGTGGATCATGCGGTCCGT

GGCGCACCGCAGCGGCCGCTGCCCATGCAGCGCCGCTGCTTCCGAACAGTGGCG

GTCAGGGCCGCACCCGCGGTAGCCGTCCGTCCGGAACCCGCCCAAGAGTTTTGG

GAGCAGCTTGAGCCCTGCAAGATGGCGGAGGACAAGCGCATCTTCCTGGAGGAG

CACCGGTGCGTGGAGGTCCGGGGCTGACCGGCCGTCGCATTCAACGTAATCAAT

CGCATGATGATCAGAGGACACGAAGTCTTGGTGGCGGTGGCCAGAAACACTGTC

CATTGCAAGGGCATAGGGATGCGTTCCTTCACCTCTCATTTCTCATTTCTGAATCC

CTCCCTGCTCACTCTTTCTCCTCCTCCTTCCCGTTCACGCAG*ATTCGGGGCAACG*

*AGGTGGGCCC*GTGCTCCTCCAGGAAGATGCGCTTGTCCTCCGCCATCTTGCAGGG

CTCAAGCTGCTCCCAAAACTCTTGGGCGGGTTCCGGACGGACGGCTACCGCGGGT

GCGGCCCTGACCGCCACTGTTCGGAAGCAGCGGCGCTGCATGGGCAGCGGCCGC

TGCGGTGCGCCACGGACCGCATGATCCACCGGAAAAGCGCACGCGCTGGAGCGC

GCAGAGGACCACAGAGAAGCGGAAGAGACGCCAGTACTGGCAAGCAAGCAGGCTGGT

CGGTGCCATatcgatagatctcttaaggcagcagcagctcggatagtatcgacacactctggacgctggtcgtgtgatggact gttgccgccacacttgctgccttgacctgtgaatatccctgccgcttttatcaaacagcctcagtgtgtttgatcttgtgtgtacgcgcttttg cgagttgctagctgcttgtgctatttgcgaataccaccccagcatccccttccctcgtttcatatcgcttgcatcccaaccgcaacttatct acgctgtcctgctatccctcagcgctgctcctgctcctgctcactgcccctcgcacagccttggtttgggctccgcctgtattctcctggta ctgcaacctgtaaaccagcactgcaatgctgatgcacgggaagtagtgggatgggaacacaaatggaaagcttaattaagagctctt gttttccagaaggagttgctccttgagcctttcattctcagcctcgataacctccaaagccgctctaattgtggaggggggttcgaa tttaaaagcttggaatgttggttcgtgcgtctggaacaagcccagacttgttgctcactgggaaaaggaccatcagctccaaaa aacttgccgctcaaaccgcgtacctctgctttcgcgcaatctgccctgttgaaatcgccaccacattcatattgtgacgcttgagc agtctgtaattgcctcagaatgtggaatcatctgcccctgtgcgagcccatgccaggcatgtcgcgggcgaggacacccgcc actcgtacagcagaccattatgctacctcacaatagttcataacagtgaccatatttctcgaagctccccaacgagcacctccat gctctgagtggccaccccggccctggtgcttgcggagggcaggtcaaccggcatggggctaccgaaatccccgaccggat cccaccaccccgcgatgggaagaatctctccccgggatgtgggcccaccaccagcacaacctgctggcccaggcgagcgtc aaaccataccacacaaatatccttggcatcggccctgaattccttctgccgctctgctacccggtgcttctgtccgaagcagggg ttgctagggatcgctccgagtccgcaaacccttgtcgcgtggcggggcttgttgagcttgaagagc

Expression of 6S::β-Tub:suc2:nr::β-tub:hairpin FatA:nr::6S leads to the formation of a hairpin RNA to silence the target FatA genes. Upon its transformation into S1920, primary transformants were clonally purified and grown under standard lipid production conditions at pH 5.0. The resulting profiles from representative transformant clones are listed in Table 31.

TABLE 31

Fatty acid profiles of *Prototheca moriformis* cells containing a hairpin RNA construct to down-regulate the expression of FATA.

| Transformant | % C10:0 | % C12:0 | % C14:0 | % C16:0 | % C16:1 | % C18:0 | % C18:1 | % C18:2 |
|---|---|---|---|---|---|---|---|---|
| Wildtype | 0.01 | 0.03 | 1.23 | 25.68 | 0.96 | 2.83 | 60.54 | 7.52 |
| pSZ1773 Transformant 1 | 0.01 | 0.03 | 0.71 | 15.10 | 1.05 | 1.67 | 72.08 | 8.27 |
| pSZ1773 Transformant 2 | 0.01 | 0.03 | 0.81 | 15.66 | 1.16 | 1.56 | 70.03 | 9.61 |
| pSZ1773 Transformant 3 | 0.01 | 0.03 | 1.09 | 22.67 | 1.05 | 2.12 | 63.18 | 8.66 |
| pSZ1773 Transformant 4 | 0.01 | 0.04 | 1.14 | 23.31 | 1.01 | 2.23 | 62.83 | 8.26 |

The above results show that the FATA hairpin construct yielded expected phenotypes: a reduction in C16 fatty acid levels and an increase in C18:1 fatty acid levels as compared to the wildtype, untransformed control.

Although this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

All references cited herein, including patents, patent applications, and publications, including Genbank Accession numbers, are hereby incorporated by reference in their entireties, whether previously specifically incorporated or not. The publications mentioned herein are cited for the purpose of describing and disclosing reagents, methodologies and concepts that may be used in connection with the present invention. Nothing herein is to be construed as an admission that these references are prior art in relation to the inventions described herein. In particular, the following patent applications are hereby incorporated by reference in their entireties for all purposes: PCT Application No. PCT/US2009/066142, filed Nov. 30, 2009, entitled "Production of Tailored Oils in Heterotrophic Microorganisms"; PCT Application No. PCT/US2009/066141, filed Nov. 30, 2009, entitled "Production of Tailored Oils in Heterotrophic Microorganisms"; and PCT Application No. PCT/US2010/31108 filed Apr. 14, 2010, entitled "Methods of Microbial Oil Extraction and Separation."

What is claimed is:

1. A recombinant *Chlorella* or *Prototheca* cell engineered to ablate or downregulate expression of an endogenous fatty acyl-ACP thioesterase gene.

2. The cell of claim 1, wherein the endogenous fatty acyl-ACP thioesterase gene is downregulated by an inhibitory RNA.

3. The cell of claim 1, wherein the *Prototheca* or *Chlorella* cell is of the species *Prototheca moriformis* or *Chlorella protothecoides*.

4. The cell of claim 1, wherein the *Chlorella* or *Prototheca* cell further comprises one or more exogenous genes that encode a sucrose invertase, a fatty acyl-ACP thioesterase, a desaturase, or an inhibitory RNA that targets an endogenous desaturase.

5. The cell of claim 4, wherein the one or more expressed exogenous genes encode(s) an inhibitory RNA that targets an endogenous desaturase.

6. The cell of claim 4, wherein the one or more exogenous genes encode(s) sucrose invertase, fatty acyl-ACP thioesterase or desaturase.

7. The Cell of claim 6, wherein the *Prototheca* or *Chlorella* is of the species *Prototheca moriformis* or *Chlorella protothecoides*.

* * * * *

SEQUENCE LISTING

<160> NUMBER OF SEQ ID NOS: 113

<210> SEQ ID NO 1
<211> LENGTH: 1187
<212> TYPE: DNA
<213> ORGANISM: Unknown
<220> FEATURE:
<223> OTHER INFORMATION: HUP promoter from Chlorella

<400> SEQUENCE: 1

```
gatcagacgg gcctgacctg cgagataatc aagtgctcgt aggcaaccaa ctcagcagct      60
gcttggtgtt gggtctgcag gatagtgttg cagggcccca aggacagcag gggaacttac     120
accttgtccc cgacccagtt ttatggagtg cattgcctca agagcctagc cggagcgcta     180
ggctacatac ttgccgcacc ggtatgaggg gatatagtac tcgcactgcg ctgtctagtg     240
agatgggcag tgctgcccat aaacaactgg ctgctcagcc atttgttggc ggaccattct     300 ggggggggcca gcaatgcctg actttcgggt agggtgaaaa ctgaacaaag actaccaaaa     360
cagaatttct tcctccttgg aggtaagcgc aggccggccc gcctgcgccc acatggcgct     420
ccgaacacct ccatagctgt aagggcgcaa acatggccgg actgttgtca gcactctttc     480
atggccatac aaggtcatgt cgagattagt gctgagtaag acactatcac cccatgttcg     540
attgaagccg tgacttcatg ccaacctgcc cctgggcgta gcagacgtat gccatcatga     600
ccactagccg acatgcgctg tcttttgcca ccaaaacaac tggtacaccg ctcgaagtcg     660
tgccgcacac ctccgggagt gagtccggcg actcctcccc ggcgggccgc ggccctacct     720
gggtagggtc gccatacgcc cacgaccaaa cgacgcagga ggggattggg gtagggaatc     780
ccaaccagcc taaccaagac ggcacctata ataaggtg gggggactaa cagccctata     840
tcgcaagctt tgggtgccta tcttgagaag cacgagttgg agtggctgtg tacggtcgac     900
```

-continued

```
cctaaggtgg gtgtgccgca gcctgaaaca aagcgtctag cagctgcttc tataatgtgt    960
cagccgttgt gtttcagtta tattgtatgc tattgtttgt tcgtgctagg gtggcgcagg   1020
cccacctact gtggcgggcc attggttggt gcttgaattg cctcaccatc taaggtctga   1080
acgctcactc aaacgccttt gtacaactgc agaactttcc ttggcgctgc aactacagtg   1140
tgcaaaccag cacatagcac tcccttacat cacccagcag tacaaca               1187
```

<210> SEQ ID NO 2
<211> LENGTH: 1414
<212> TYPE: DNA
<213> ORGANISM: Chlorella ellipsoidea

<400> SEQUENCE: 2

```
cgctgcgcac cagggccgcc agctcgctga tgtcgctcca aatgcggtcc cccgattttt    60
tgttcttcat cttctccacc ttggtggcct tcttggccag ggccttcagc tgcatgcgca   120
cagaccgttg agctcctgat cagcatcctc aggaggcccc ttgacaagca agccctgtg   180 caagcccatt cacggggtac cagtggtgct gaggtagatg ggtttgaaaa ggattgctcg   240
gtcgattgct gctcatggaa ttggcatgtg catgcatgtt cacaatatgc caccaggctt   300
tggagcaaga gagcatgaat gccttcaggc aggttgaaag ttcctggggg tgaagaggca   360
gggccgagga ttgaggagg aaagcatcaa gtcgtcgctc atgctcatgt tttcagtcag   420
agtttgccaa gctcacagga gcagagacaa gactggctgc tcaggtgttg catcgtgtgt   480
gtggtggggg ggggggggtt aatacggtac gaaatgcact tggaattccc acctcatgcc   540
agcggaccca catgcttgaa ttcgaggcct gtggggtgag aaatgctcac tctgccctcg   600
ttgctgaggt acttcaggcc gctgagctca aagtcgatgc cctgctcgtc tatcagggcc   660
tgcacctctg ggctgaccgg ctcagcctcc ttcgcgggca tggagtaggc gccggcagcg   720
ttcatgtccg ggcccagggc agcggtggtg ccataaatgt cggtgatggt ggggaggggg   780
gccgtcgcca caccattgcc gttgctggct gacgcatgca catgtggcct ggctggcacc   840
ggcagcactg gtctccagcc agccagcaag tggctgttca ggaaagcggc catgttgttg   900
gtccctgcgc atgtaattcc ccagatcaaa ggagggaaca gcttggattt gatgtagtgc   960
ccaaccggac tgaatgtgcg atggcaggtc cctttgagtc tcccgaatta ctagcagggc   1020
actgtgacct aacgcagcat gccaaccgca aaaaaatgat tgcagaaaaa tgaagcggtg   1080
tgtcaatatt tgctgtattt attcgtttta atcagcaacc aagttcgaaa cgcaactatc   1140
gtggtgatca agtgaaccct catcagactta cctcgttcgg caaggaaacg gaggcaccaa   1200
attccaattt gatattatcg cttgccaagc tagagctgat cttttgggaaa ccaactgcca   1260 gacagtggac tgtgatggag tgccccgagt ggtggagcct cttcgattcg gttagtcatt   1320
actaacgtga accctcagtg aagggaccat cagaccagaa agaccagatc tcctcctcga   1380
caccgagaga gtgttgcggc agtaggacga caag                               1414
```

<210> SEQ ID NO 3
<211> LENGTH: 512
<212> TYPE: PRT
<213> ORGANISM: Unknown
<220> FEATURE:
<223> OTHER INFORMATION: Yeast sucrose invertase

<400> SEQUENCE: 3

```
Met Thr Asn Glu Thr Ser Asp Arg Pro Leu Val His Phe Thr Pro Asn
1               5                   10                  15
```

```
Lys Gly Trp Met Asn Asp Pro Asn Gly Leu Trp Tyr Asp Glu Lys Asp
             20                  25                  30

Ala Lys Trp His Leu Tyr Phe Gln Tyr Asn Pro Asn Asp Thr Val Trp
         35                  40                  45

Gly Thr Pro Leu Phe Trp Gly His Ala Thr Ser Asp Asp Leu Thr Asn
     50                  55                  60

Trp Glu Asp Gln Pro Ile Ala Ile Ala Pro Lys Arg Asn Asp Ser Gly
 65                  70                  75                  80

Ala Phe Ser Gly Ser Met Val Val Asp Tyr Asn Asn Thr Ser Gly Phe
                 85                  90                  95

Phe Asn Asp Thr Ile Asp Pro Arg Gln Arg Cys Val Ala Ile Trp Thr
             100                 105                 110

Tyr Asn Thr Pro Glu Ser Glu Glu Gln Tyr Ile Ser Tyr Ser Leu Asp
         115                 120                 125

Gly Gly Tyr Thr Phe Thr Glu Tyr Gln Lys Asn Pro Val Leu Ala Ala
     130                 135                 140

Asn Ser Thr Gln Phe Arg Asp Pro Lys Val Phe Trp Tyr Glu Pro Ser
145                 150                 155                 160

Gln Lys Trp Ile Met Thr Ala Ala Lys Ser Gln Asp Tyr Lys Ile Glu
                 165                 170                 175

Ile Tyr Ser Ser Asp Asp Leu Lys Ser Trp Lys Leu Glu Ser Ala Phe
             180                 185                 190

Ala Asn Glu Gly Phe Leu Gly Tyr Gln Tyr Glu Cys Pro Gly Leu Ile
         195                 200                 205

Glu Val Pro Thr Glu Gln Asp Pro Ser Lys Ser Tyr Trp Val Met Phe
     210                 215                 220

Ile Ser Ile Asn Pro Gly Ala Pro Ala Gly Gly Ser Phe Asn Gln Tyr
225                 230                 235                 240

Phe Val Gly Ser Phe Asn Gly Thr His Phe Glu Ala Phe Asp Asn Gln
                 245                 250                 255

Ser Arg Val Val Asp Phe Gly Lys Asp Tyr Tyr Ala Leu Gln Thr Phe
             260                 265                 270

Phe Asn Thr Asp Pro Thr Tyr Gly Ser Ala Leu Gly Ile Ala Trp Ala
         275                 280                 285

Ser Asn Trp Glu Tyr Ser Ala Phe Val Pro Thr Asn Pro Trp Arg Ser
     290                 295                 300

Ser Met Ser Leu Val Arg Lys Phe Ser Leu Asn Thr Glu Tyr Gln Ala
305                 310                 315                 320

Asn Pro Glu Thr Glu Leu Ile Asn Leu Lys Ala Glu Pro Ile Leu Asn
                 325                 330                 335

Ile Ser Asn Ala Gly Pro Trp Ser Arg Phe Ala Thr Asn Thr Thr Leu
             340                 345                 350

Thr Lys Ala Asn Ser Tyr Asn Val Asp Leu Ser Asn Ser Thr Gly Thr
         355                 360                 365

Leu Glu Phe Glu Leu Val Tyr Ala Val Asn Thr Thr Gln Thr Ile Ser
     370                 375                 380

Lys Ser Val Phe Ala Asp Leu Ser Leu Trp Phe Lys Gly Leu Glu Asp
385                 390                 395                 400

Pro Glu Glu Tyr Leu Arg Met Gly Phe Glu Val Ser Ala Ser Ser Phe
                 405                 410                 415

Phe Leu Asp Arg Gly Asn Ser Lys Val Lys Phe Val Lys Glu Asn Pro
             420                 425                 430
```

-continued

Tyr Phe Thr Asn Arg Met Ser Val Asn Asn Gln Pro Phe Lys Ser Glu
            435                 440                 445

Asn Asp Leu Ser Tyr Tyr Lys Val Tyr Gly Leu Leu Asp Gln Asn Ile
450                 455                 460

Leu Glu Leu Tyr Phe Asn Asp Gly Asp Val Val Ser Thr Asn Thr Tyr
465                 470                 475                 480

Phe Met Thr Thr Gly Asn Ala Leu Gly Ser Val Asn Met Thr Thr Gly
                485                 490                 495

Val Asp Asn Leu Phe Tyr Ile Asp Lys Phe Gln Val Arg Glu Val Lys
            500                 505                 510

<210> SEQ ID NO 4
<211> LENGTH: 20
<212> TYPE: PRT
<213> ORGANISM: Unknown
<220> FEATURE:
<223> OTHER INFORMATION: Yeast secretion signal

<400> SEQUENCE: 4

Met Leu Leu Gln Ala Phe Leu Phe Leu Leu Ala Gly Phe Ala Ala Lys
1               5                   10                  15

Ile Ser Ala Ser
            20

<210> SEQ ID NO 5
<211> LENGTH: 18
<212> TYPE: PRT
<213> ORGANISM: Unknown
<220> FEATURE:
<223> OTHER INFORMATION: higher plants secretion signal

<400> SEQUENCE: 5

Met Ala Asn Lys Ser Leu Leu Leu Leu Leu Leu Leu Gly Ser Leu Ala
1               5                   10                  15

Ser Gly

<210> SEQ ID NO 6
<211> LENGTH: 10
<212> TYPE: PRT
<213> ORGANISM: Unknown
<220> FEATURE:
<223> OTHER INFORMATION: consensus eukaryotic secretion signal

<400> SEQUENCE: 6

Met Ala Arg Leu Pro Leu Ala Ala Leu Gly
1               5                   10

<210> SEQ ID NO 7
<211> LENGTH: 20
<212> TYPE: PRT
<213> ORGANISM: Unknown
<220> FEATURE:
<223> OTHER INFORMATION: combination higher plants / eukaryotic
      secretion signal

<400> SEQUENCE: 7

Met Ala Asn Lys Leu Leu Leu Leu Leu Leu Leu Leu Leu Pro Leu
1               5                   10                  15

Ala Ala Ser Gly
            20

<210> SEQ ID NO 8
<211> LENGTH: 2615

<212> TYPE: DNA
<213> ORGANISM: Saccharomyces cerevisiae

<400> SEQUENCE: 8

| | | | | | |
|---|---|---|---|---|---|
| gaattcccca | acatggtgga | gcacgacact | ctcgtctact | ccaagaatat | caaagataca | 60 |
| gtctcagaag | accaagggc | tattgagact | tttcaacaaa | gggtaatatc | gggaaacctc | 120 |
| ctcggattcc | attgcccagc | tatctgtcac | ttcatcaaaa | ggacagtaga | aaaggaaggt | 180 |
| ggcacctaca | aatgccatca | ttgcgataaa | ggaaaggcta | tcgttcaaga | tgcctctgcc | 240 |
| gacagtggtc | ccaaagatgg | accccaccc | acgaggagca | tcgtggaaaa | agaagacgtt | 300 |
| ccaaccacgt | cttcaaagca | agtggattga | tgtgaacatg | gtggagcacg | acactctcgt | 360 |
| ctactccaag | aatatcaaag | atacagtctc | agaagaccaa | agggctattg | agactttca | 420 |
| acaaaggta | atatcgggaa | acctcctcgg | attccattgc | ccagctatct | gtcacttcat | 480 |
| caaaaggaca | gtagaaaagg | aaggtggcac | ctacaaatgc | catcattgcg | ataaggaaa | 540 |
| ggctatcgtt | caagatgcct | ctgccgacag | tggtcccaaa | gatggacccc | cacccacgag | 600 |
| gagcatcgtg | gaaaagaag | acgttccaac | cacgtcttca | aagcaagtgg | attgatgtga | 660 |
| tatctccact | gacgtaaggg | atgacgcaca | atcccactat | ccttcgcaag | acccttcctc | 720 |
| tatataagga | agttcatttc | atttggagag | acacgctga | aatcaccagt | ctctctctac | 780 |
| aaatctatct | ctggcgcgcc | atatcaatgc | ttcttcaggc | ctttcttttt | cttcttgctg | 840 |
| gttttgctgc | caagatcagc | gcctctatga | cgaacgaaac | ctcggataga | ccacttgtgc | 900 |
| actttacacc | aaacaagggc | tggatgaatg | accccaatgg | actgtggtac | gacgaaaaag | 960 |
| atgccaagtg | gcatctgtac | tttcaataca | acccgaacga | tactgtctgg | gggacgccat | 1020 |
| tgttttgggg | ccacgccacg | tccgacgacc | tgaccaattg | ggaggaccaa | ccaatagcta | 1080 |
| tcgctccgaa | gaggaacgac | tccggagcat | tctcgggttc | catggtggtt | gactacaaca | 1140 |
| atacttccgg | cttttcaac | gataccattg | accgagaca | acgctgcgtg | gccatatgga | 1200 |
| cttacaacac | accggagtcc | gaggagcagt | acatctcgta | tagcctggac | ggtggataca | 1260 |
| cttttacaga | gtatcagaag | aaccctgtgc | ttgctgcaaa | ttcgactcag | ttccgagatc | 1320 |
| cgaaggtctt | ttggtacgag | ccctcgcaga | agtggatcat | gacagcggca | aagtcacagg | 1380 |
| actacaagat | cgaaatttac | tcgtctgacg | accttaaatc | ctggaagctc | gaatccgcgt | 1440 |
| tcgcaaacga | gggctttctc | ggctaccaat | acgaatgccc | aggcctgata | gaggtcccaa | 1500 |
| cagagcaaga | tcccagcaag | tcctactggg | tgatgtttat | ttccattaat | ccaggagcac | 1560 |
| cggcaggagg | ttcttttaat | cagtacttcg | tcggaagctt | taacggaact | catttcgagg | 1620 |
| catttgataa | ccaatcaaga | gtagttgatt | ttggaaagga | ctactatgcc | ctgcagactt | 1680 |
| tcttcaatac | tgacccgacc | tatgggagcg | ctcttggcat | tgcgtgggct | tctaactggg | 1740 |
| agtattccgc | attcgttcct | acaaacccctt | ggaggtcctc | catgtcgctc | gtgaggaaat | 1800 |
| tctctctcaa | cactgagtac | caggccaacc | cggaaaccga | actcataaac | ctgaaagccg | 1860 |
| aaccgatcct | gaacattagc | aacgctggcc | cctggagccg | gtttgcaacc | aacaccacgt | 1920 |
| tgacgaaagc | caacagctac | aacgtcgatc | tttcgaatag | caccggtaca | cttgaatttg | 1980 |
| aactggtgta | tgccgtcaat | accacccaaa | cgatctcgaa | gtcggtgttc | gcggacctct | 2040 |
| ccctctggtt | taaaggcctg | gaagaccccg | aggagtacct | cagaatgggt | ttcgaggttt | 2100 |
| ctgcgtcctc | cttcttcctt | gatcgcggga | acagcaaagt | aaaatttgtt | aaggagaacc | 2160 |
| catattttac | caacaggatg | agcgttaaca | accaaccatt | caagagcgaa | aacgacctgt | 2220 |

```
cgtactacaa agtgtatggt ttgcttgatc aaaatatcct ggaactctac ttcaacgatg   2280
gtgatgtcgt gtccaccaac acatacttca tgacaaccgg gaacgcactg ggctccgtga   2340
acatgacgac gggtgtggat aacctgttct acatcgacaa attccaggtg agggaagtca   2400
agtgagatct gtcgatcgac aagctcgagt ttctccataa taatgtgtga gtagttccca   2460
gataagggaa ttagggttcc tatagggttt cgctcatgtg ttgagcatat aagaaaccct   2520
tagtatgtat ttgtatttgt aaaatacttc tatcaataaa atttctaatt cctaaaacca   2580
aaatccagta ctaaaatcca gatcccccga attaa                              2615
```

<210> SEQ ID NO 9
<211> LENGTH: 22
<212> TYPE: DNA
<213> ORGANISM: Unknown
<220> FEATURE:
<223> OTHER INFORMATION: primer

<400> SEQUENCE: 9

```
tgttgaagaa tgagccggcg ac                                              22
```

<210> SEQ ID NO 10
<211> LENGTH: 20
<212> TYPE: DNA
<213> ORGANISM: Unknown
<220> FEATURE:
<223> OTHER INFORMATION: primer

<400> SEQUENCE: 10

```
cagtgagcta ttacgcactc                                                 20
```

<210> SEQ ID NO 11
<211> LENGTH: 541
<212> TYPE: DNA
<213> ORGANISM: Prototheca kruegani

<400> SEQUENCE: 11

```
tgttgaagaa tgagccggcg agttaaaaag agtggcatgg ttaaagaaaa tactctggag     60
ccatagcgaa agcaagttta gtaagcttag gtcattcttt ttagacccga aaccgagtga   120
tctacccatg atcagggtga agtgttagta aaataacatg gaggcccgaa ccgactaatg   180
ttgaaaaatt agcggatgaa ttgtgggtag gggcgaaaaa ccaatcgaac tcggagttag   240
ctggttctcc ccgaaatgcg tttaggcgca gcagtagcag tacaaataga ggggtaaagc   300
actgtttctt ttgtgggctt cgaaagttgt acctcaaagt ggcaaactct gaatactcta   360
tttagatatc tactagtgag accttggggg ataagctcct tggtcaaaag ggaaacagcc   420
cagatcacca gttaaggccc caaaatgaaa atgatagtga ctaaggatgt gggtatgtca   480
aaacctccag caggttagct tagaagcagc aatcctttca agagtgcgta atagctcact   540
g                                                                    541
```

<210> SEQ ID NO 12
<211> LENGTH: 573
<212> TYPE: DNA
<213> ORGANISM: Prototheca wickerhamii

<400> SEQUENCE: 12

```
tgttgaagaa tgagccggcg acttaaaata aatggcaggc taagagattt ataaactcga    60
aacctaagcg aaagcaagtc ttaatagggc gtcaatttaa caaaacttta aataaattat   120
aaagtcattt attttagacc cgaacctgag tgatctaacc atggtcagga tgaaacttgg   180
```

```
gtgacaccaa gtggaagtcc gaaccgaccg atgttgaaaa atcggcggat gaactgtggt      240
tagtggtgaa ataccagtcg aactcagagc tagctggttc tccccgaaat gcgttgaggc      300
gcagcaatat atctcgtcta tctaggggta aagcactgtt tcggtgcggg ctatgaaaat      360
ggtaccaaat cgtggcaaac tctgaatact agaaatgacg atatattagt gagactatgg      420
gggataagct ccatagtcga gagggaaaca gcccagacca ccagttaagg ccccaaaatg      480
ataatgaagt ggtaaaggag gtgaaaatgc aaatacaacc aggaggttgg cttagaagca      540
gccatccttt aaagagtgcg taatagctca ctg                                   573
```

<210> SEQ ID NO 13
<211> LENGTH: 541
<212> TYPE: DNA
<213> ORGANISM: Prototheca stagnora

<400> SEQUENCE: 13

```
tgttgaagaa tgagccggcg agttaaaaaa aatggcatgg ttaaagatat ttctctgaag       60
ccatagcgaa agcaagtttt acaagctata gtcattttt ttagacccga aaccgagtga      120
tctacccatg atcagggtga agtgttggtc aaataacatg gaggcccgaa ccgactaatg      180
gtgaaaaatt agcggatgaa ttgtgggtag gggcgaaaaa ccaatcgaac tcggagttag      240
ctggttctcc ccgaaatgcg tttaggcgca gcagtagcaa cacaaataga ggggtaaagc      300
actgtttctt ttgtgggctt cgaaagttgt acctcaaagt ggcaaactct gaatactcta      360
tttagatatc tactagtgag accttggggg ataagctcct tggtcaaaag ggaaacagcc      420
cagatcacca gttaaggccc caaaatgaaa atgatagtga ctaaggacgt gagtatgtca      480
aaacctccag caggttagct tagaagcagc aatcctttca agagtgcgta atagctcact      540
g                                                                      541
```

<210> SEQ ID NO 14
<211> LENGTH: 541
<212> TYPE: DNA
<213> ORGANISM: Prototheca moriformis

<400> SEQUENCE: 14

```
tgttgaagaa tgagccggcg agttaaaaag agtggcatgg ttaaagataa ttctctggag       60
ccatagcgaa agcaagttta acaagctaaa gtcaccctt ttagacccga aaccgagtga      120
tctacccatg atcagggtga agtgttggta aaataacatg gaggcccgaa ccgactaatg      180
gtgaaaaatt agcggatgaa ttgtgggtag gggcgaaaaa ccaatcgaac tcggagttag      240
ctggttctcc ccgaaatgcg tttaggcgca gcagtagcaa cacaaataga ggggtaaagc      300
actgtttctt ttgtgggctt cgaaagttgt acctcaaagt ggcaaactct gaatactcta      360
tttagatatc tactagtgag accttggggg ataagctcct tggtcaaaag ggaaacagcc      420
cagatcacca gttaaggccc caaaatgaaa atgatagtga ctaaggatgt gggtatgtta      480
aaacctccag caggttagct tagaagcagc aatcctttca agagtgcgta atagctcact      540
g                                                                      541
```

<210> SEQ ID NO 15
<211> LENGTH: 573
<212> TYPE: DNA
<213> ORGANISM: Prototheca moriformis

<400> SEQUENCE: 15

```
tgttgaagaa tgagccggcg acttaaaata aatggcaggc taagagaatt ataactcga      60 aacctaagcg aaagcaagtc ttaatagggc gctaatttaa caaaacatta aataaaatct    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573
```

```
<210> SEQ ID NO 16
<211> LENGTH: 573
<212> TYPE: DNA
<213> ORGANISM: Prototheca wickerhamii

<400> SEQUENCE: 16
tgttgaagaa tgagccgtcg acttaaaata aatggcaggc taagagaatt ataactcga      60 aacctaagcg aaagcaagtc ttaatagggc gctaatttaa caaaacatta aataaaatct    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573
```

```
<210> SEQ ID NO 17
<211> LENGTH: 541
<212> TYPE: DNA
<213> ORGANISM: Prototheca moriformis

<400> SEQUENCE: 17
tgttgaagaa tgagccggcg agttaaaaag agtggcgtgg ttaaagaaaa ttctctggaa      60
ccatagcgaa agcaagttta acaagcttaa gtcactttt ttagacccga aaccgagtga     120
tctacccatg atcagggtga agtgttggta aaataacatg gaggcccgaa ccgactaatg    180
gtgaaaaatt agcggatgaa ttgtgggtag gggcgaaaaa ccaatcgaac tcggagttag    240
ctggttctcc ccgaaatgcg tttaggcgca gcagtagcaa cacaaataga ggggtaaagc    300
actgtttctt ttgtgggctc cgaaagttgt acctcaaagt ggcaaactct gaatactcta    360
tttagatatc tactagtgag accttggggg ataagctcct tggtcgaaag ggaaacagcc    420
cagatcacca gttaaggccc caaaatgaaa atgatagtga ctaaggatgt gagtatgtca    480
aaacctccag caggttagct tagaagcagc aatccttca agagtgcgta atagctcact    540
g                                                                    541
```

```
<210> SEQ ID NO 18
<211> LENGTH: 541
```

```
<212> TYPE: DNA
<213> ORGANISM: Prototheca zopfii

<400> SEQUENCE: 18
tgttgaagaa tgagccggcg agttaaaaag agtggcatgg ttaaagaaaa ttctctggag      60
ccatagcgaa agcaagttta acaagcttaa gtcactttt ttagacccga aaccgagtga     120
tctacccatg atcagggtga agtgttggta aaataacatg gaggcccgaa ccgactaatg     180
gtgaaaaatt agcggatgaa ttgtgggtag gggcgaaaaa ccaatcgaac tcggagttag     240
ctggttctcc ccgaaatgcg tttaggcgca gcagtagcaa cacaaataga ggggtaaagc     300
actgtttctt tcgtgggctt cgaaagttgt acctcaaagt ggcaaactct gaatactcta     360
tttagatatc tactagtgag accttggggg ataagctcct tggtcaaaag ggaaacagcc     420
cagatcacca gttaaggccc caaaatgaaa atgatagtga ctaaggatgt gagtatgtca     480
aaacctccag caggttagct tagaagcagc aatcctttca agagtgcgta atagctcact     540
g                                                                    541

<210> SEQ ID NO 19
<211> LENGTH: 565
<212> TYPE: DNA
<213> ORGANISM: Prototheca moriformis

<400> SEQUENCE: 19
tgttgaagaa tgagccggcg acttagaaaa ggtggcatgg ttaaggaaat attccgaagc      60
cgtagcaaaa gcgagtctga ataggggcgat aaaatatatt aatatttaga atctagtcat    120
tttttctaga cccgaacccg ggtgatctaa ccatgaccag gatgaagctt gggtgatacc     180
aagtgaaggt ccgaaccgac cgatgttgaa aaatcggcgg atgagttgtg gttagcggtg     240
aaataccagt cgaacccgga gctagctggt tctccccgaa atgcgttgag gcgcagcagt     300
acatctagtc tatctagggg taaagcactg tttcggtgcg ggctgtgaga acggtaccaa     360
atcgtggcaa actctgaata ctagaaatga cgatgtagta gtgagactgt gggggataag     420
ctccattgtc aagagggaaa cagcccagac caccagctaa ggccccaaaa tggtaatgta     480
gtgacaaagg aggtgaaaat gcaaatacaa ccaggaggtt ggcttagaag cagccatcct     540
ttaaagagtg cgtaatagct cactg                                          565

<210> SEQ ID NO 20
<211> LENGTH: 550
<212> TYPE: PRT
<213> ORGANISM: Chicorium intybus

<400> SEQUENCE: 20

Met Ser Asn Ser Ser Asn Ala Ser Glu Ser Leu Phe Pro Ala Thr Ser
1               5                   10                  15

Glu Gln Pro Tyr Arg Thr Ala Phe His Phe Gln Pro Gln Asn Trp
            20                  25                  30

Met Asn Asp Pro Asn Gly Pro Met Cys Tyr Asn Gly Val Tyr His Leu
        35                  40                  45

Phe Tyr Gln Tyr Asn Pro Phe Gly Pro Leu Trp Asn Leu Arg Met Tyr
    50                  55                  60

Trp Ala His Ser Val Ser His Asp Leu Ile Asn Trp Ile His Leu Asp
65                  70                  75                  80

Leu Ala Phe Ala Pro Thr Glu Pro Phe Asp Ile Asn Gly Cys Leu Ser
                85                  90                  95
```

```
Gly Ser Ala Thr Val Leu Pro Gly Asn Lys Pro Ile Met Leu Tyr Thr
            100                 105                 110
Gly Ile Asp Thr Glu Asn Arg Gln Val Gln Asn Leu Ala Val Pro Lys
        115                 120                 125
Asp Leu Ser Asp Pro Tyr Leu Arg Glu Trp Val Lys His Thr Gly Asn
    130                 135                 140
Pro Ile Ile Ser Leu Pro Glu Glu Ile Gln Pro Asp Asp Phe Arg Asp
145                 150                 155                 160
Pro Thr Thr Thr Trp Leu Glu Glu Asp Gly Thr Trp Arg Leu Leu Val
                165                 170                 175
Gly Ser Gln Lys Asp Lys Thr Gly Ile Ala Phe Leu Tyr His Ser Gly
            180                 185                 190
Asp Phe Val Asn Trp Thr Lys Ser Asp Ser Pro Leu His Lys Val Ser
        195                 200                 205
Gly Thr Gly Met Trp Glu Cys Val Asp Phe Phe Pro Val Trp Val Asp
    210                 215                 220
Ser Thr Asn Gly Val Asp Thr Ser Ile Ile Asn Pro Ser Asn Arg Val
225                 230                 235                 240
Lys His Val Leu Lys Leu Gly Ile Gln Asp His Gly Lys Asp Cys Tyr
                245                 250                 255
Leu Ile Gly Lys Tyr Ser Ala Asp Lys Glu Asn Tyr Val Pro Glu Asp
            260                 265                 270
Glu Leu Thr Leu Ser Thr Leu Arg Leu Asp Tyr Gly Met Tyr Tyr Ala
        275                 280                 285
Ser Lys Ser Phe Phe Asp Pro Val Lys Asn Arg Arg Ile Met Thr Ala
    290                 295                 300
Trp Val Asn Glu Ser Asp Ser Glu Ala Asp Val Ile Ala Arg Gly Trp
305                 310                 315                 320
Ser Gly Val Gln Ser Phe Pro Arg Ser Leu Trp Leu Asp Lys Asn Gln
                325                 330                 335
Lys Gln Leu Leu Gln Trp Pro Ile Glu Glu Ile Glu Met Leu His Gln
            340                 345                 350
Asn Glu Val Ser Phe His Asn Lys Lys Leu Asp Gly Gly Ser Ser Leu
        355                 360                 365
Glu Val Leu Gly Ile Thr Ala Ser Gln Ala Asp Val Lys Ile Ser Phe
    370                 375                 380
Lys Leu Ala Asn Leu Glu Ala Glu Leu Asp Pro Ser Trp Val
385                 390                 395                 400
Asp Pro Gln Leu Ile Cys Ser Glu Asn Asp Ala Ser Lys Lys Gly Lys
                405                 410                 415
Phe Gly Pro Phe Gly Leu Leu Ala Leu Ala Ser Ser Asp Leu Arg Glu
            420                 425                 430
Gln Thr Ala Ile Phe Phe Arg Val Phe Arg Lys Asn Gly Arg Tyr Val
        435                 440                 445
Val Leu Met Cys Ser Asp Gln Ser Arg Ser Met Lys Asn Gly Ile
    450                 455                 460
Glu Lys Arg Thr Tyr Gly Ala Phe Val Asp Ile Asp Pro Gln Gln Asp
465                 470                 475                 480
Glu Ile Ser Leu Arg Thr Leu Ile Asp His Ser Ile Val Glu Ser Phe
                485                 490                 495
Gly Gly Arg Gly Lys Thr Cys Ile Thr Thr Arg Val Tyr Pro Thr Leu
            500                 505                 510
Ala Ile Gly Glu Gln Ala Arg Leu Phe Ala Phe Asn His Gly Thr Glu
```

-continued

```
                515                 520                 525
Ser Val Glu Ile Ser Glu Leu Ser Ala Trp Ser Met Lys Lys Ala Gln
            530                 535                 540

Met Lys Val Glu Glu Pro
545                 550

<210> SEQ ID NO 21
<211> LENGTH: 581
<212> TYPE: PRT
<213> ORGANISM: Schizosaccharomyces pombe

<400> SEQUENCE: 21

Met Phe Leu Lys Tyr Ile Leu Ala Ser Gly Ile Cys Leu Val Ser Leu
1               5                   10                  15

Leu Ser Ser Thr Asn Ala Ala Pro Arg His Leu Tyr Val Lys Arg Tyr
            20                  25                  30

Pro Val Ile Tyr Asn Ala Ser Asn Ile Thr Glu Val Ser Asn Ser Thr
        35                  40                  45

Thr Val Pro Pro Pro Phe Val Asn Thr Thr Ala Pro Asn Gly Thr
    50                  55                  60

Cys Leu Gly Asn Tyr Asn Glu Tyr Leu Pro Ser Gly Tyr Tyr Asn Ala
65                  70                  75                  80

Thr Asp Arg Pro Lys Ile His Phe Thr Pro Ser Ser Gly Phe Met Asn
                85                  90                  95

Asp Pro Asn Gly Leu Val Tyr Thr Gly Gly Val Tyr His Met Phe Phe
            100                 105                 110

Gln Tyr Ser Pro Lys Thr Leu Thr Ala Gly Glu Val His Trp Gly His
        115                 120                 125

Thr Val Ser Lys Asp Leu Ile His Trp Glu Asn Tyr Pro Ile Ala Ile
    130                 135                 140

Tyr Pro Asp Glu His Glu Asn Gly Val Leu Ser Leu Pro Phe Ser Gly
145                 150                 155                 160

Ser Ala Val Val Asp Val His Asn Ser Ser Gly Leu Phe Ser Asn Asp
                165                 170                 175

Thr Ile Pro Glu Glu Arg Ile Val Leu Ile Tyr Thr Asp His Trp Thr
            180                 185                 190

Gly Val Ala Glu Arg Gln Ala Ile Ala Tyr Thr Thr Asp Gly Gly Tyr
        195                 200                 205

Thr Phe Lys Lys Tyr Ser Gly Asn Pro Val Leu Asp Ile Asn Ser Leu
    210                 215                 220

Gln Phe Arg Asp Pro Lys Val Ile Trp Asp Phe Asp Ala Asn Arg Trp
225                 230                 235                 240

Val Met Ile Val Ala Met Ser Gln Asn Tyr Gly Ile Ala Phe Tyr Ser
                245                 250                 255

Ser Tyr Asp Leu Ile His Trp Thr Glu Leu Ser Val Phe Ser Thr Ser
            260                 265                 270

Gly Tyr Leu Gly Leu Gln Tyr Glu Cys Pro Gly Met Ala Arg Val Pro
        275                 280                 285

Val Glu Gly Thr Asp Glu Tyr Lys Trp Val Leu Phe Ile Ser Ile Asn
    290                 295                 300

Pro Gly Ala Pro Leu Gly Gly Ser Val Val Gln Tyr Phe Val Gly Asp
305                 310                 315                 320

Trp Asn Gly Thr Asn Phe Val Pro Asp Asp Gly Gln Thr Arg Phe Val
                325                 330                 335
```

```
Asp Leu Gly Lys Asp Phe Tyr Ala Ser Ala Leu Tyr His Ser Ser Ser
                340                 345                 350

Ala Asn Ala Asp Val Ile Gly Val Gly Trp Ala Ser Asn Trp Gln Tyr
            355                 360                 365

Thr Asn Gln Ala Pro Thr Gln Val Phe Arg Ser Ala Met Thr Val Ala
        370                 375                 380

Arg Lys Phe Thr Leu Arg Asp Val Pro Gln Asn Pro Met Thr Asn Leu
385                 390                 395                 400

Thr Ser Leu Ile Gln Thr Pro Leu Asn Val Ser Leu Leu Arg Asp Glu
                405                 410                 415

Thr Leu Phe Thr Ala Pro Val Ile Asn Ser Ser Ser Leu Ser Gly
            420                 425                 430

Ser Pro Ile Thr Leu Pro Ser Asn Thr Ala Phe Glu Phe Asn Val Thr
            435                 440                 445

Leu Ser Ile Asn Tyr Thr Glu Gly Cys Thr Thr Gly Tyr Cys Leu Gly
        450                 455                 460

Arg Ile Ile Ile Asp Ser Asp Pro Tyr Arg Leu Gln Ser Ile Ser
465                 470                 475                 480

Val Asp Val Asp Phe Ala Ala Ser Thr Leu Val Ile Asn Arg Ala Lys
                485                 490                 495

Ala Gln Met Gly Trp Phe Asn Ser Leu Phe Thr Pro Ser Phe Ala Asn
            500                 505                 510

Asp Ile Tyr Ile Tyr Gly Asn Val Thr Leu Tyr Gly Ile Val Asp Asn
        515                 520                 525

Gly Leu Leu Glu Leu Tyr Val Asn Asn Gly Glu Lys Thr Tyr Thr Asn
530                 535                 540

Asp Phe Phe Leu Gln Gly Ala Thr Pro Gly Gln Ile Ser Phe Ala
545                 550                 555                 560

Ala Phe Gln Gly Val Ser Phe Asn Asn Val Thr Val Thr Pro Leu Lys
                565                 570                 575

Thr Ile Trp Asn Cys
            580

<210> SEQ ID NO 22
<211> LENGTH: 550
<212> TYPE: PRT
<213> ORGANISM: Picha anomala

<400> SEQUENCE: 22

Met Ile Gln Leu Ser Pro Leu Leu Leu Pro Leu Phe Ser Val Phe
1               5                   10                  15

Asn Ser Ile Ala Asp Ala Ser Thr Glu Tyr Leu Arg Pro Gln Ile His
                20                  25                  30

Leu Thr Pro Asp Gln Gly Trp Met Asn Asp Pro Asn Gly Met Phe Tyr
            35                  40                  45

Asp Arg Lys Asp Lys Leu Trp His Val Tyr Phe Gln His Asn Pro Asp
        50                  55                  60

Lys Lys Ser Ile Trp Ala Thr Pro Val Thr Trp Gly His Ser Thr Ser
65                  70                  75                  80

Lys Asp Leu Leu Thr Trp Asp Tyr His Gly Asn Ala Leu Glu Pro Glu
                85                  90                  95

Asn Asp Asp Glu Gly Ile Phe Ser Gly Ser Val Val Asp Arg Asn
            100                 105                 110

Asn Thr Ser Gly Phe Phe Asn Asp Ser Thr Asp Pro Glu Gln Arg Ile
        115                 120                 125
```

```
Val Ala Ile Tyr Thr Asn Asn Ala Gln Leu Gln Thr Gln Glu Ile Ala
    130                 135                 140

Tyr Ser Leu Asp Lys Gly Tyr Ser Phe Ile Lys Tyr Asp Gln Asn Pro
145                 150                 155                 160

Val Ile Asn Val Asn Ser Ser Gln Gln Arg Asp Pro Lys Val Leu Trp
                165                 170                 175

His Asp Glu Ser Asn Gln Trp Ile Met Val Val Ala Lys Thr Gln Glu
            180                 185                 190

Phe Lys Val Gln Ile Tyr Gly Ser Pro Asp Leu Lys Lys Trp Asp Leu
        195                 200                 205

Lys Ser Asn Phe Thr Ser Asn Gly Tyr Leu Gly Phe Gln Tyr Glu Cys
    210                 215                 220

Pro Gly Leu Phe Lys Leu Pro Ile Glu Asn Pro Leu Asn Asp Thr Val
225                 230                 235                 240

Thr Ser Lys Trp Val Leu Leu Ala Ile Asn Pro Gly Ser Pro Leu
                245                 250                 255

Gly Gly Ser Ile Asn Glu Tyr Phe Ile Gly Asp Phe Asp Gly Thr Thr
            260                 265                 270

Phe His Pro Asp Asp Gly Ala Thr Arg Phe Met Asp Ile Gly Lys Asp
        275                 280                 285

Phe Tyr Ala Phe Gln Ser Phe Asp Asn Thr Glu Pro Glu Asp Gly Ala
    290                 295                 300

Leu Gly Leu Ala Trp Ala Ser Asn Trp Gln Tyr Ala Asn Thr Val Pro
305                 310                 315                 320

Thr Glu Asn Trp Arg Ser Ser Met Ser Leu Val Arg Asn Tyr Thr Leu
                325                 330                 335

Lys Tyr Val Asp Val Asn Pro Glu Asn Tyr Gly Leu Thr Leu Ile Gln
            340                 345                 350

Lys Pro Val Tyr Asp Thr Lys Glu Thr Arg Leu Asn Glu Thr Leu Lys
        355                 360                 365

Thr Leu Glu Thr Ile Asn Glu Tyr Glu Val Asn Asp Leu Lys Leu Asp
    370                 375                 380

Lys Ser Ser Phe Val Ala Thr Asp Phe Asn Thr Glu Arg Asn Ala Thr
385                 390                 395                 400

Gly Val Phe Glu Phe Asp Leu Lys Phe Thr Gln Thr Asp Leu Lys Met
                405                 410                 415

Gly Tyr Ser Asn Met Thr Thr Gln Phe Gly Leu Tyr Ile His Ser Gln
            420                 425                 430

Thr Val Lys Gly Ser Gln Glu Thr Leu Gln Leu Val Phe Asp Thr Leu
        435                 440                 445

Ser Thr Thr Trp Tyr Ile Asp Arg Thr Gln His Ser Phe Gln Arg
    450                 455                 460

Asn Ser Pro Val Phe Thr Glu Arg Ile Ser Thr Tyr Val Glu Lys Ile
465                 470                 475                 480

Asp Thr Thr Asp Gln Gly Asn Val Tyr Thr Leu Tyr Gly Val Val Asp
                485                 490                 495

Arg Asn Ile Leu Glu Leu Tyr Phe Asn Asp Gly Ser Ile Ala Met Thr
            500                 505                 510

Asn Thr Phe Phe Phe Arg Glu Gly Lys Ile Pro Thr Ser Phe Glu Val
        515                 520                 525

Val Cys Asp Ser Glu Lys Ser Phe Ile Thr Ile Asp Glu Leu Ser Val
530                 535                 540
```

Arg Glu Leu Ala Arg Lys
545                 550

<210> SEQ ID NO 23
<211> LENGTH: 533
<212> TYPE: PRT
<213> ORGANISM: Debaryomyces occidentalis

<400> SEQUENCE: 23

Met Val Gln Val Leu Ser Val Leu Val Ile Pro Leu Leu Thr Leu Phe
1               5                   10                  15

Phe Gly Tyr Val Ala Ser Ser Ile Asp Leu Ser Val Asp Thr Ser
            20                  25                  30

Glu Tyr Asn Arg Pro Leu Ile His Phe Thr Pro Glu Lys Gly Trp Met
            35                  40                  45

Asn Asp Pro Asn Gly Leu Phe Tyr Asp Lys Thr Ala Lys Leu Trp His
        50                  55                  60

Leu Tyr Phe Gln Tyr Asn Pro Asn Ala Thr Ala Trp Gly Gln Pro Leu
65                  70                  75                  80

Tyr Trp Gly His Ala Thr Ser Asn Asp Leu Val His Trp Asp Glu His
                85                  90                  95

Glu Ile Ala Ile Gly Pro Glu His Asp Asn Glu Gly Ile Phe Ser Gly
            100                 105                 110

Ser Ile Val Val Asp His Asn Asn Thr Ser Gly Phe Phe Asn Ser Ser
            115                 120                 125

Ile Asp Pro Asn Gln Arg Ile Val Ala Ile Tyr Thr Asn Asn Ile Pro
        130                 135                 140

Asp Leu Gln Thr Gln Asp Ile Ala Phe Ser Leu Asp Gly Gly Tyr Thr
145                 150                 155                 160

Phe Thr Lys Tyr Glu Asn Asn Pro Val Ile Asp Val Ser Ser Asn Gln
                165                 170                 175

Phe Arg Asp Pro Lys Val Phe Trp His Glu Arg Phe Lys Ser Met Asp
            180                 185                 190

His Gly Cys Ser Glu Ile Ala Arg Val Lys Ile Gln Ile Phe Gly Ser
        195                 200                 205

Ala Asn Leu Lys Asn Trp Val Leu Asn Ser Asn Phe Ser Ser Gly Tyr
    210                 215                 220

Tyr Gly Asn Gln Tyr Gly Met Ser Arg Leu Ile Glu Val Pro Ile Glu
225                 230                 235                 240

Asn Ser Asp Lys Ser Lys Trp Val Met Phe Leu Ala Ile Asn Pro Gly
                245                 250                 255

Ser Pro Leu Gly Gly Ser Ile Asn Gln Tyr Phe Val Gly Asp Phe Asp
            260                 265                 270

Gly Phe Gln Phe Val Pro Asp Asp Ser Gln Thr Arg Phe Val Asp Ile
        275                 280                 285

Gly Lys Asp Phe Tyr Ala Phe Gln Thr Phe Ser Glu Val Glu His Gly
    290                 295                 300

Val Leu Gly Leu Ala Trp Ala Ser Asn Trp Gln Tyr Ala Asp Gln Val
305                 310                 315                 320

Pro Thr Asn Pro Trp Arg Ser Ser Thr Ser Leu Ala Arg Asn Tyr Thr
                325                 330                 335

Leu Arg Tyr Val Ile Gln Met Leu Lys Leu Thr Ala Asn Ile Asp Lys
            340                 345                 350

Ser Val Leu Pro Asp Ser Ile Asn Val Val Asp Lys Leu Lys Lys Lys
        355                 360                 365

```
Asn Val Lys Leu Thr Asn Lys Pro Ile Lys Thr Asn Phe Lys Gly
        370                 375                 380

Ser Thr Gly Leu Phe Asp Phe Asn Ile Thr Phe Lys Val Leu Asn Leu
385                 390                 395                 400

Asn Val Ser Pro Gly Lys Thr His Phe Asp Ile Leu Ile Asn Ser Gln
            405                 410                 415

Glu Leu Asn Ser Ser Val Asp Ser Ile Lys Ile Gly Phe Asp Ser Ser
            420                 425                 430

Gln Ser Leu Phe Tyr Ile Asp Arg His Ile Pro Asn Val Glu Phe Pro
                435                 440                 445

Arg Lys Gln Phe Phe Thr Asp Lys Leu Ala Ala Tyr Leu Glu Pro Leu
        450                 455                 460

Asp Tyr Asp Gln Asp Leu Arg Val Phe Ser Leu Tyr Gly Ile Val Asp
465                 470                 475                 480

Lys Asn Ile Ile Glu Leu Tyr Phe Asn Asp Gly Thr Val Ala Met Thr
                485                 490                 495

Asn Thr Phe Phe Met Gly Glu Gly Lys Tyr Pro His Asp Ile Gln Ile
                500                 505                 510

Val Thr Asp Thr Glu Glu Pro Leu Phe Glu Leu Glu Ser Val Ile Ile
            515                 520                 525

Arg Glu Leu Asn Lys
        530

<210> SEQ ID NO 24
<211> LENGTH: 654
<212> TYPE: PRT
<213> ORGANISM: Oryza sativa

<400> SEQUENCE: 24

Met Ala Thr Ser Arg Leu Thr Pro Ala Tyr Asp Leu Lys Asn Ala Ala
1               5                   10                  15

Ala Ala Val Tyr Thr Pro Leu Pro Glu Gln Pro His Ser Ala Glu Val
            20                  25                  30

Glu Ile Arg Asp Arg Lys Pro Phe Lys Ile Ile Ser Ala Ile Ile Leu
        35                  40                  45

Ser Ser Leu Leu Leu Leu Ala Leu Ile Leu Val Ala Val Asn Tyr Gln
    50                  55                  60

Ala Pro Pro Ser His Ser Ser Gly Asp Asn Ser Gln Pro Ala Ala Val
65                  70                  75                  80

Met Pro Pro Ser Arg Gly Val Ser Gln Gly Val Ser Glu Lys Ala Phe
                85                  90                  95

Arg Gly Ala Ser Gly Ala Gly Asn Gly Val Ser Phe Ala Trp Ser Asn
            100                 105                 110

Leu Met Leu Ser Trp Gln Arg Thr Ser Tyr His Phe Gln Pro Val Lys
        115                 120                 125

Asn Trp Met Asn Asp Pro Asn Gly Pro Leu Tyr Tyr Lys Gly Trp Tyr
    130                 135                 140

His Leu Phe Tyr Gln Tyr Asn Pro Asp Ser Ala Val Trp Gly Asn Ile
145                 150                 155                 160

Thr Trp Gly His Ala Val Ser Thr Asp Leu Ile Asn Trp Leu His Leu
                165                 170                 175

Pro Phe Ala Met Val Pro Asp Gln Trp Tyr Asp Val Asn Gly Val Trp
            180                 185                 190

Thr Gly Ser Ala Thr Ile Leu Pro Asp Gly Arg Ile Val Met Leu Tyr
```

```
            195                 200                 205
Thr Gly Asp Thr Asp Tyr Val Gln Asp Gln Asn Leu Ala Phe Pro
210                 215                 220

Ala Asn Leu Ser Asp Pro Leu Leu Val Asp Trp Val Lys Tyr Pro Asn
225                 230                 235                 240

Asn Pro Val Ile Tyr Pro Pro Gly Ile Gly Val Lys Asp Phe Arg
                245                 250                 255

Asp Pro Thr Thr Ala Gly Thr Ala Gly Met Gln Asn Gly Gln Arg Leu
                260                 265                 270

Val Thr Ile Gly Ser Lys Val Gly Lys Thr Gly Ile Ser Leu Val Tyr
            275                 280                 285

Glu Thr Thr Asn Phe Thr Thr Phe Lys Leu Leu Tyr Gly Val Leu His
290                 295                 300

Ala Val Pro Gly Thr Gly Met Trp Glu Cys Val Asp Leu Tyr Pro Val
305                 310                 315                 320

Ser Thr Thr Gly Glu Asn Gly Leu Asp Thr Ser Val Asn Gly Leu Gly
                325                 330                 335

Val Lys His Val Leu Lys Thr Ser Leu Asp Asp Lys His Asp Tyr
            340                 345                 350

Tyr Ala Leu Gly Thr Tyr Asp Pro Val Lys Asn Lys Trp Thr Pro Asp
                355                 360                 365

Asn Pro Asp Leu Asp Val Gly Ile Gly Leu Arg Leu Asp Tyr Gly Lys
370                 375                 380

Tyr Tyr Ala Ala Arg Thr Phe Tyr Asp Gln Asn Lys Gln Arg Arg Ile
385                 390                 395                 400

Leu Trp Gly Trp Ile Gly Glu Thr Asp Leu Glu Ala Val Asp Leu Met
                405                 410                 415

Lys Gly Trp Ala Ser Leu Gln Ala Ile Pro Arg Thr Ile Val Phe Asp
                420                 425                 430

Lys Lys Thr Gly Thr Asn Val Leu Gln Arg Pro Glu Glu Glu Val Glu
            435                 440                 445

Ser Trp Ser Ser Gly Asp Pro Ile Thr Gln Arg Arg Ile Phe Glu Pro
450                 455                 460

Gly Ser Val Val Pro Ile His Val Ser Gly Ala Thr Gln Leu Asp Ile
465                 470                 475                 480

Thr Ala Ser Phe Glu Val Asp Glu Thr Leu Leu Glu Thr Thr Ser Glu
                485                 490                 495

Ser His Asp Ala Gly Tyr Asp Cys Ser Asn Ser Gly Ala Gly Thr
                500                 505                 510

Arg Gly Ser Leu Gly Pro Phe Gly Leu Leu Val Val Ala Asp Glu Lys
            515                 520                 525

Leu Ser Glu Leu Thr Pro Val Tyr Leu Tyr Val Ala Lys Gly Gly Asp
            530                 535                 540

Gly Lys Ala Lys Ala His Leu Cys Ala Tyr Gln Thr Arg Ser Ser Met
545                 550                 555                 560

Ala Ser Gly Val Glu Lys Glu Val Tyr Gly Ser Ala Val Pro Val Leu
                565                 570                 575

Asp Gly Glu Asn Tyr Ser Ala Arg Ile Leu Ile Asp His Ser Ile Val
                580                 585                 590

Glu Ser Phe Ala Gln Ala Gly Arg Thr Cys Val Arg Ser Arg Asp Tyr
            595                 600                 605

Pro Thr Lys Asp Ile Tyr Gly Ala Ala Arg Cys Phe Phe Asn Asn
610                 615                 620
```

```
Ala Thr Glu Ala Ser Val Arg Ala Ser Leu Lys Ala Trp Gln Met Lys
625                 630                 635                 640

Ser Phe Ile Arg Pro Tyr Pro Phe Ile Pro Asp Gln Lys Ser
                645                 650

<210> SEQ ID NO 25
<211> LENGTH: 690
<212> TYPE: PRT
<213> ORGANISM: Allium cepa

<400> SEQUENCE: 25

Met Ser Ser Asp Asp Leu Glu Ser Pro Pro Ser Ser Tyr Leu Pro Ile
1               5                   10                  15

Pro Pro Ser Asp Glu Phe His Asp Gln Pro Pro Leu Arg Ser Trp
            20                  25                  30

Leu Arg Leu Leu Ser Ile Pro Leu Ala Leu Met Phe Leu Leu Phe Leu
            35                  40                  45

Ala Thr Phe Leu Ser Asn Leu Glu Ser Pro Pro Ser Asp Ser Gly Leu
50                  55                  60

Val Ser Asp Pro Val Thr Phe Asp Val Asn Pro Ala Val Val Arg Arg
65                  70                  75                  80

Gly Lys Asp Ala Gly Val Ser Asp Lys Thr Ser Gly Val Asp Ser Gly
                85                  90                  95

Phe Val Leu Asp Pro Val Ala Val Asp Ala Asn Ser Val Val His
                100                 105                 110

Arg Gly Lys Asp Ala Gly Val Ser Asp Lys Thr Ser Gly Val Asp Ser
            115                 120                 125

Gly Leu Leu Lys Asp Ser Pro Leu Gly Pro Tyr Pro Trp Thr Asn Gln
    130                 135                 140

Met Leu Ser Trp Gln Arg Thr Gly Phe His Phe Gln Pro Val Lys Asn
145                 150                 155                 160

Trp Met Asn Asp Pro Asn Gly Pro Leu Tyr Tyr Lys Gly Trp Tyr His
                165                 170                 175

Phe Phe Tyr Gln Tyr Asn Pro Glu Gly Ala Val Trp Gly Asn Ile Ala
                180                 185                 190

Trp Gly His Ala Val Ser Arg Asp Leu Val His Trp Thr His Leu Pro
            195                 200                 205

Leu Ala Met Val Pro Asp Gln Trp Tyr Asp Ile Asn Gly Val Trp Thr
    210                 215                 220

Gly Ser Ala Thr Ile Leu Pro Asp Gly Gln Ile Val Met Leu Tyr Thr
225                 230                 235                 240

Gly Ala Thr Asn Glu Ser Val Gln Val Gln Asn Leu Ala Val Pro Ala
                245                 250                 255

Asp Gln Ser Asp Thr Leu Leu Leu Arg Trp Lys Lys Ser Glu Ala Asn
                260                 265                 270

Pro Ile Leu Val Pro Pro Gly Ile Gly Asp Lys Asp Phe Arg Asp
            275                 280                 285

Pro Thr Thr Ala Trp Tyr Glu Pro Ser Asp Thr Trp Arg Ile Val
    290                 295                 300

Ile Gly Ser Lys Asp Ser Ser His Ser Gly Ile Ala Ile Val Tyr Ser
305                 310                 315                 320

Thr Lys Asp Phe Ile Asn Tyr Lys Leu Ile Pro Gly Ile Leu His Ala
                325                 330                 335

Val Glu Arg Val Gly Met Trp Glu Cys Val Asp Phe Tyr Pro Val Ala
```

340                 345                 350

Thr Ala Asp Ser Ser His Ala Asn His Gly Leu Asp Pro Ser Ala Arg
            355                 360                 365

Pro Ser Pro Ala Val Lys His Val Leu Lys Ala Ser Met Asp Asp Asp
        370                 375                 380

Arg His Asp Tyr Tyr Ala Ile Gly Thr Tyr Asp Pro Ala Gln Asn Thr
385                 390                 395                 400

Trp Val Pro Asp Asp Ala Ser Val Asp Val Gly Ile Gly Leu Arg Tyr
                405                 410                 415

Asp Trp Gly Lys Phe Tyr Ala Ser Lys Thr Phe Tyr Asp His Ala Lys
            420                 425                 430

Lys Arg Arg Ile Leu Trp Ser Trp Ile Gly Glu Thr Asp Ser Glu Thr
        435                 440                 445

Ala Asp Ile Ala Lys Gly Trp Ala Ser Leu Gln Gly Val Pro Arg Thr
    450                 455                 460

Val Leu Leu Asp Val Lys Thr Gly Ser Asn Leu Ile Thr Trp Pro Val
465                 470                 475                 480

Val Glu Ile Glu Ser Leu Arg Thr Arg Pro Arg Asp Phe Ser Gly Ile
                485                 490                 495

Thr Val Asp Ala Gly Ser Thr Phe Lys Leu Asp Val Gly Gly Ala Ala
            500                 505                 510

Gln Leu Asp Ile Glu Ala Glu Phe Lys Ile Ser Ser Glu Glu Leu Glu
        515                 520                 525

Ala Val Lys Glu Ala Asp Val Ser Tyr Asn Cys Ser Ser Ser Gly Gly
    530                 535                 540

Ala Ala Glu Arg Gly Val Leu Gly Pro Phe Gly Leu Leu Val Leu Ala
545                 550                 555                 560

Asn Gln Asp Leu Thr Glu Gln Thr Ala Thr Tyr Phe Tyr Val Ser Arg
                565                 570                 575

Gly Met Asp Gly Gly Leu Asn Thr His Phe Cys Gln Asp Glu Lys Arg
            580                 585                 590

Ser Ser Lys Ala Ser Asp Ile Val Lys Arg Ile Val Gly His Ser Val
        595                 600                 605

Pro Val Leu Asp Gly Glu Ser Phe Ala Leu Arg Ile Leu Val Asp His
    610                 615                 620

Ser Ile Val Glu Ser Phe Ala Gln Gly Gly Arg Ala Ser Ala Thr Ser
625                 630                 635                 640

Arg Val Tyr Pro Thr Glu Ala Ile Tyr Asn Asn Ala Arg Val Phe Val
                645                 650                 655

Phe Asn Asn Ala Thr Gly Ala Lys Val Thr Ala Gln Ser Leu Lys Val
            660                 665                 670

Trp His Met Ser Thr Ala Ile Asn Glu Ile Tyr Asp Pro Ala Thr Ser
        675                 680                 685

Val Met
    690

<210> SEQ ID NO 26
<211> LENGTH: 501
<212> TYPE: PRT
<213> ORGANISM: Beta vulgaris
<220> FEATURE:
<221> NAME/KEY: misc_feature
<222> LOCATION: (382)..(382)
<223> OTHER INFORMATION: Xaa can be any naturally occurring amino acid

<400> SEQUENCE: 26

```
Leu Phe Tyr Gln Tyr Asn Pro Asn Gly Val Ile Trp Gly Pro Val
1               5                   10                  15

Trp Gly His Ser Thr Ser Lys Asp Leu Val Asn Trp Val Pro Gln Pro
                20                  25                  30

Leu Thr Met Glu Pro Glu Met Ala Ala Asn Ile Asn Gly Ser Trp Ser
        35                  40                  45

Gly Ser Ala Thr Ile Leu Pro Gly Asn Lys Pro Ala Ile Leu Phe Thr
    50                  55                  60

Gly Leu Asp Pro Lys Tyr Glu Gln Val Gln Val Leu Ala Tyr Pro Lys
65                  70                  75                  80

Asp Thr Ser Asp Pro Asn Leu Lys Glu Trp Phe Leu Ala Pro Gln Asn
                85                  90                  95

Pro Val Met Phe Pro Thr Pro Gln Asn Gln Ile Asn Ala Thr Ser Phe
            100                 105                 110

Arg Asp Pro Thr Thr Ala Trp Arg Leu Pro Asp Gly Val Trp Arg Leu
            115                 120                 125

Leu Ile Gly Ser Lys Arg Gly Gln Arg Gly Leu Ser Leu Leu Phe Arg
    130                 135                 140

Ser Arg Asp Phe Val His Trp Val Gln Ala Lys His Pro Leu Tyr Ser
145                 150                 155                 160

Asp Lys Leu Ser Gly Met Trp Glu Cys Pro Asp Phe Phe Pro Val Tyr
                165                 170                 175

Ala Asn Gly Asp Gln Met Gly Val Asp Thr Ser Ile Ile Gly Ser His
            180                 185                 190

Val Lys His Val Leu Lys Asn Ser Leu Asp Ile Thr Lys His Asp Ile
        195                 200                 205

Tyr Thr Ile Gly Asp Tyr Asn Ile Lys Lys Asp Ala Tyr Thr Pro Asp
    210                 215                 220

Ile Gly Tyr Met Asn Asp Ser Ser Leu Arg Tyr Asp Tyr Gly Lys Tyr
225                 230                 235                 240

Tyr Ala Ser Lys Thr Phe Phe Asp Asp Ala Lys Lys Glu Arg Ile Leu
                245                 250                 255

Leu Gly Trp Ala Asn Glu Ser Ser Val Gly Asp Asp Ile Lys Lys
            260                 265                 270

Gly Trp Ser Gly Ile His Thr Ile Pro Arg Lys Ile Trp Leu Asp Lys
            275                 280                 285

Leu Gly Lys Gln Leu Ile Gln Trp Pro Ile Ala Asn Ile Glu Lys Leu
    290                 295                 300

Arg Gln Lys Pro Val Asn Ile Tyr Arg Lys Val Leu Lys Gly Gly Ser
305                 310                 315                 320

Gln Ile Glu Val Ser Gly Ile Thr Ala Ala Gln Ala Asp Val Glu Ile
                325                 330                 335

Ser Phe Lys Ile Lys Asp Leu Lys Asn Val Glu Lys Phe Asp Ala Ser
            340                 345                 350

Trp Thr Ser Pro Gln Leu Leu Cys Ser Lys Lys Gly Ala Ser Val Lys
            355                 360                 365

Gly Gly Leu Gly Pro Phe Gly Leu Leu Thr Leu Ala Ser Xaa Gly Leu
    370                 375                 380

Glu Glu Tyr Thr Ala Val Phe Phe Arg Ile Phe Lys Ala Tyr Asp Asn
385                 390                 395                 400

Lys Phe Val Val Leu Met Cys Ser Asp Gln Ser Arg Ser Ser Leu Asn
                405                 410                 415
```

```
Pro Thr Asn Asp Lys Thr Thr Tyr Gly Thr Phe Val Asp Val Asn Pro
                420                 425                 430

Ile Arg Glu Gly Leu Ser Leu Arg Val Leu Ile Asp His Ser Val Val
            435                 440                 445

Glu Ser Phe Gly Ala Lys Gly Lys Asn Val Ile Thr Ala Arg Val Tyr
        450                 455                 460

Pro Thr Leu Ala Ile Asn Glu Lys Ala His Leu Tyr Val Phe Asn Arg
465                 470                 475                 480

Gly Thr Ser Asn Val Glu Ile Thr Gly Leu Thr Ala Trp Ser Met Lys
                485                 490                 495

Lys Ala Asn Ile Ala
            500

<210> SEQ ID NO 27
<211> LENGTH: 518
<212> TYPE: PRT
<213> ORGANISM: Bifidobacterium breve

<400> SEQUENCE: 27

Met Thr Asp Phe Thr Pro Glu Thr Pro Val Leu Thr Pro Ile Arg Asp
1               5                   10                  15

His Ala Ala Glu Leu Ala Lys Ala Glu Ala Gly Val Ala Glu Met Ala
                20                  25                  30

Ala Lys Arg Asn Asn Arg Trp Tyr Pro Lys Tyr His Ile Ala Ser Asn
            35                  40                  45

Gly Gly Trp Ile Asn Asp Pro Asn Gly Leu Cys Phe Tyr Lys Gly Arg
        50                  55                  60

Trp His Val Phe Tyr Gln Leu His Pro Tyr Gly Thr Gln Trp Gly Pro
65                  70                  75                  80

Met His Trp Gly His Val Ser Ser Thr Asp Met Leu Asn Trp Lys Arg
                85                  90                  95

Glu Pro Ile Met Phe Ala Pro Ser Leu Glu Gln Glu Lys Asp Gly Val
            100                 105                 110

Phe Ser Gly Ser Ala Val Ile Asp Asp Asn Gly Asp Leu Arg Phe Tyr
        115                 120                 125

Tyr Thr Gly His Arg Trp Ala Asn Gly His Asp Asn Thr Gly Gly Asp
    130                 135                 140

Trp Gln Val Gln Met Thr Ala Leu Pro Asp Asn Asp Glu Leu Thr Ser
145                 150                 155                 160

Ala Thr Lys Gln Gly Met Ile Ile Asp Cys Pro Thr Asp Lys Val Asp
                165                 170                 175

His His Tyr Arg Asp Pro Lys Val Trp Lys Thr Gly Asp Thr Trp Tyr
            180                 185                 190

Met Thr Phe Gly Val Ser Ser Glu Asp Lys Arg Gly Gln Met Trp Leu
        195                 200                 205

Phe Ser Ser Lys Asp Met Val Arg Trp Glu Tyr Glu Arg Val Leu Phe
    210                 215                 220

Gln His Pro Asp Pro Asp Val Phe Met Leu Glu Cys Pro Asp Phe Phe
225                 230                 235                 240

Pro Ile Lys Asp Lys Asp Gly Asn Glu Lys Trp Val Ile Gly Phe Ser
                245                 250                 255

Ala Met Gly Ser Lys Pro Ser Gly Phe Met Asn Arg Asn Val Asn Asn
            260                 265                 270

Ala Gly Tyr Met Ile Gly Thr Trp Glu Pro Gly Gly Glu Phe Lys Pro
        275                 280                 285
```

-continued

```
Glu Thr Glu Phe Arg Leu Trp Asp Cys Gly His Asn Tyr Tyr Ala Pro
    290                 295                 300

Gln Ser Phe Asn Val Asp Gly Arg Gln Ile Val Tyr Gly Trp Met Ser
305                 310                 315                 320

Pro Phe Val Gln Pro Ile Pro Met Glu Asp Asp Gly Trp Cys Gly Gln
                325                 330                 335

Leu Thr Leu Pro Arg Glu Ile Thr Leu Asp Asp Gly Asp Val Val
            340                 345                 350

Thr Ala Pro Val Ala Glu Met Glu Gly Leu Arg Glu Asp Thr Leu Asp
        355                 360                 365

His Gly Ser Ile Thr Leu Asp Met Asp Gly Glu Gln Val Ile Ala Asp
    370                 375                 380

Asp Ala Glu Ala Val Glu Ile Glu Met Thr Ile Asp Leu Ala Ala Ser
385                 390                 395                 400

Thr Ala Asp Arg Ala Gly Leu Lys Ile His Ala Thr Glu Asp Gly Ala
                405                 410                 415

Tyr Thr Tyr Val Ala Tyr Asp Asp Gln Ile Gly Arg Val Val Val Asp
            420                 425                 430

Arg Gln Ala Met Ala Asn Gly Asp His Gly Tyr Arg Ala Ala Pro Leu
        435                 440                 445

Thr Asp Ala Glu Leu Ala Ser Gly Lys Leu Asp Leu Arg Val Phe Val
    450                 455                 460

Asp Arg Gly Ser Val Glu Val Tyr Val Asn Gly Gly His Gln Val Leu
465                 470                 475                 480

Ser Ser Tyr Ser Tyr Ala Ser Glu Gly Pro Arg Ala Ile Lys Leu Val
                485                 490                 495

Ala Glu Phe Gly Asn Leu Lys Val Glu Ser Leu Lys Leu His His Met
            500                 505                 510

Lys Ser Ile Gly Leu Glu
        515
```

<210> SEQ ID NO 28
<211> LENGTH: 532
<212> TYPE: PRT
<213> ORGANISM: Saccharomyces cerevisiae

<400> SEQUENCE: 28

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
```

```
          130                 135                 140
Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
                180                 185                 190

Tyr Lys Ile Glu Ile Tyr Ser Ser Asp Asp Leu Lys Ser Trp Lys Leu
                195                 200                 205

Glu Ser Ala Phe Ala Asn Glu Gly Phe Leu Gly Tyr Gln Tyr Glu Cys
                210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
                260                 265                 270

Phe Asp Asn Gln Ser Arg Val Val Asp Phe Gly Lys Asp Tyr Tyr Ala
                275                 280                 285

Leu Gln Thr Phe Phe Asn Thr Asp Pro Thr Tyr Gly Ser Ala Leu Gly
                290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
                340                 345                 350

Pro Ile Leu Asn Ile Ser Asn Ala Gly Pro Trp Ser Arg Phe Ala Thr
                355                 360                 365

Asn Thr Thr Leu Thr Lys Ala Asn Ser Tyr Asn Val Asp Leu Ser Asn
                370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
                420                 425                 430

Ala Ser Ser Phe Phe Leu Asp Arg Gly Asn Ser Lys Val Lys Phe Val
                435                 440                 445

Lys Glu Asn Pro Tyr Phe Thr Asn Arg Met Ser Val Asn Asn Gln Pro
450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
                500                 505                 510

Met Thr Thr Gly Val Asp Asn Leu Phe Tyr Ile Asp Lys Phe Gln Val
                515                 520                 525

Arg Glu Val Lys
        530

<210> SEQ ID NO 29
```

-continued

```
<211> LENGTH: 512
<212> TYPE: PRT
<213> ORGANISM: Zymomonas mobilis

<400> SEQUENCE: 29
```

| | | | | | | | | | | | | | | |
|---|---|---|---|---|---|---|---|---|---|---|---|---|---|---|
| Met | Glu | Ser | Pro | Ser | Tyr | Lys | Asn | Leu | Ile | Lys | Ala | Glu | Asp | Ala | Gln |
| 1 | | | | 5 | | | | | 10 | | | | | 15 | |
| Lys | Lys | Ala | Gly | Lys | Arg | Leu | Leu | Ser | Ser | Glu | Trp | Tyr | Pro | Gly | Phe |
| | | | 20 | | | | | 25 | | | | | 30 | | |
| His | Val | Thr | Pro | Leu | Thr | Gly | Trp | Met | Asn | Asp | Pro | Asn | Gly | Leu | Ile |
| | | 35 | | | | | 40 | | | | | 45 | | | |
| Phe | Phe | Lys | Gly | Glu | Tyr | His | Leu | Phe | Tyr | Gln | Tyr | Tyr | Pro | Phe | Ala |
| 50 | | | | | 55 | | | | | 60 | | | | | |
| Pro | Val | Trp | Gly | Pro | Met | His | Trp | Gly | His | Ala | Lys | Ser | Arg | Asp | Leu |
| 65 | | | | | 70 | | | | | 75 | | | | | 80 |
| Val | His | Trp | Glu | Thr | Leu | Pro | Val | Ala | Leu | Ala | Pro | Gly | Asp | Leu | Phe |
| | | | | 85 | | | | | 90 | | | | | 95 | |
| Asp | Arg | Asp | Gly | Cys | Phe | Ser | Gly | Cys | Ala | Val | Asp | Asn | Asn | Gly | Val |
| | | | 100 | | | | | 105 | | | | | 110 | | |
| Leu | Thr | Leu | Ile | Tyr | Thr | Gly | His | Ile | Val | Leu | Ser | Asn | Asp | Ser | Pro |
| | | 115 | | | | | 120 | | | | | 125 | | | |
| Asp | Ala | Ile | Arg | Glu | Val | Gln | Cys | Met | Ala | Thr | Ser | Ile | Asp | Gly | Ile |
| 130 | | | | | 135 | | | | | 140 | | | | | |
| His | Phe | Gln | Lys | Glu | Gly | Ile | Val | Leu | Glu | Lys | Ala | Pro | Met | Pro | Gln |
| 145 | | | | | 150 | | | | | 155 | | | | | 160 |
| Val | Ala | His | Phe | Arg | Asp | Pro | Arg | Val | Trp | Lys | Glu | Asn | Asp | His | Trp |
| | | | | 165 | | | | | 170 | | | | | 175 | |
| Phe | Met | Val | Val | Gly | Tyr | Arg | Thr | Asp | Asp | Glu | Lys | His | Gln | Gly | Ile |
| | | | 180 | | | | | 185 | | | | | 190 | | |
| Gly | His | Val | Ala | Leu | Tyr | Arg | Ser | Glu | Asn | Leu | Lys | Asp | Trp | Ile | Phe |
| | | 195 | | | | | 200 | | | | | 205 | | | |
| Val | Lys | Thr | Leu | Leu | Gly | Asp | Asn | Ser | Gln | Leu | Pro | Leu | Gly | Lys | Arg |
| | 210 | | | | | 215 | | | | | 220 | | | | |
| Ala | Phe | Met | Trp | Glu | Cys | Pro | Asp | Phe | Phe | Ser | Leu | Gly | Asn | Arg | Ser |
| 225 | | | | | 230 | | | | | 235 | | | | | 240 |
| Val | Leu | Met | Phe | Ser | Pro | Gln | Gly | Leu | Lys | Ala | Ser | Gly | Tyr | Lys | Asn |
| | | | | 245 | | | | | 250 | | | | | 255 | |
| Arg | Asn | Leu | Phe | Gln | Asn | Gly | Tyr | Ile | Leu | Gly | Lys | Trp | Gln | Ala | Pro |
| | | | 260 | | | | | 265 | | | | | 270 | | |
| Gln | Phe | Thr | Pro | Glu | Thr | Ser | Phe | Gln | Glu | Leu | Asp | Tyr | Gly | His | Asp |
| | | 275 | | | | | 280 | | | | | 285 | | | |
| Phe | Tyr | Ala | Ala | Gln | Arg | Phe | Glu | Ala | Lys | Asp | Gly | Arg | Gln | Ile | Leu |
| | 290 | | | | | 295 | | | | | 300 | | | | |
| Ile | Ala | Trp | Phe | Asp | Met | Trp | Glu | Asn | Gln | Lys | Pro | Ser | Gln | Arg | Asp |
| 305 | | | | | 310 | | | | | 315 | | | | | 320 |
| Gly | Trp | Ala | Gly | Cys | Met | Thr | Leu | Pro | Arg | Lys | Leu | Asp | Leu | Ile | Asp |
| | | | | 325 | | | | | 330 | | | | | 335 | |
| Asn | Lys | Ile | Val | Met | Thr | Pro | Val | Arg | Glu | Met | Glu | Ile | Leu | Arg | Gln |
| | | | 340 | | | | | 345 | | | | | 350 | | |
| Ser | Glu | Lys | Ile | Glu | Ser | Val | Val | Thr | Leu | Ser | Asp | Ala | Glu | His | Pro |
| | | 355 | | | | | 360 | | | | | 365 | | | |
| Phe | Thr | Met | Asp | Ser | Pro | Leu | Gln | Glu | Ile | Glu | Leu | Ile | Phe | Asp | Leu |
| | 370 | | | | | 375 | | | | | 380 | | | | |
| Glu | Lys | Ser | Ser | Ala | Tyr | Gln | Ala | Gly | Leu | Ala | Leu | Arg | Cys | Asn | Gly |

```
                385                 390                 395                 400
Lys Gly Gln Glu Thr Leu Leu Tyr Ile Asp Arg Ser Gln Asn Arg Ile
                    405                 410                 415

Ile Leu Asp Arg Asn Arg Ser Gly Gln Asn Val Lys Gly Ile Arg Ser
                420                 425                 430

Cys Pro Leu Pro Asn Thr Ser Lys Val Arg Leu His Ile Phe Leu Asp
            435                 440                 445

Arg Ser Ser Ile Glu Ile Phe Val Gly Asp Gln Thr Gln Gly Leu
        450                 455                 460

Tyr Ser Ile Ser Ser Arg Ile Phe Pro Asp Lys Asp Ser Leu Lys Gly
465                 470                 475                 480

Arg Leu Phe Ala Ile Glu Gly Tyr Ala Val Phe Asp Ser Phe Lys Arg
                485                 490                 495

Trp Thr Leu Gln Asp Ala Asn Leu Ala Ala Phe Ser Ser Asp Ala Cys
            500                 505                 510
```

<210> SEQ ID NO 30
<211> LENGTH: 1092
<212> TYPE: DNA
<213> ORGANISM: Artificial Sequence
<220> FEATURE:
<223> OTHER INFORMATION: synthetic construct

<400> SEQUENCE: 30

```
gctcttcggg tttgctcacc cgcgaggtcg acgcccagca tggctatcaa gacgaacagg      60
cagcctgtgg agaagcctcc gttcacgatc gggacgctgc gcaaggccat ccccgcgcac     120
tgtttcgagc gctcggcgct tcgtagcagc atgtacctgg cctttgacat cgcggtcatg     180
tccctgctct acgtcgcgtc gacgtacatc gaccctgcgc cggtgcctac gtgggtcaag     240
tatgcgtca tgtggccgct ctactggttc ttccaggtgt gtgtgagggt gtggttgcc      300
cgtatcgagg tcctggtggc gcgcatgggg agaaggcgc ctgtcccgct gacccccccg      360
gctaccctcc cggcaccttc cagggcgcct tcggcacggg tgtctgggtg tgcgcgcacg     420
agtgcggcca ccaggccttt tcctccagcc aggccatcaa cgacggcgtg ggcctggtgt     480
tccacagcct gctgctggtg ccctactact cctggaagca ctcgcaccgc cgccaccact     540
ccaacacggg gtgcctggac aaggacgagg tgtttgtgcc gccgcaccgc gcagtggcgc     600
acgagggcct ggagtgggag gagtggctgc ccatccgcat gggcaaggtg ctggtcaccc     660
tgaccctggg ctggccgctg tacctcatgt tcaacgtcgc ctcgcggccg tacccgcgct     720
cgccaacca ctttgacccg tggtcgccca tcttcagcaa gcgcgaggta cccttttctg     780
cgctatgaca cttccagcaa aaggtagggc gggctgcgag acggcttccc ggcgctgcat     840
gcaacaccga tgatgcttcg acccccgaa gctccttcgg ggctgcatgg gcgctccgat      900
gccgctccag ggcgagcgct gtttaaatag ccaggccccc gattgcaaag acattatagc     960
gagctaccaa agccatattc aaacacctag atcactacca cttctacaca ggccactcga    1020
gcttgtgatc gcactccgct aagggggcgc ctcttcctct tcgtttcagt cacaacccgc    1080
aaacggcgcg cc                                                         1092
```

<210> SEQ ID NO 31
<211> LENGTH: 1400
<212> TYPE: DNA
<213> ORGANISM: Prototheca moriformis

<400> SEQUENCE: 31

```
caattggcag cagcagctcg atagtatcg acacactctg gacgctggtc gtgtgatgga      60
ctgttgccgc cacacttgct gccttgacct gtgaatatcc ctgccgcttt tatcaaacag     120
cctcagtgtg tttgatcttg tgtgtacgcg cttttgcgag ttgctagctg cttgtgctat    180
ttgcgaatac caccccagc atcccttcc ctcgtttcat atcgcttgca tcccaaccgc      240
aacttatcta cgctgtcctg ctatccctca gcgctgctcc tgctcctgct cactgcccct    300
cgcacagcct tggtttgggc tccgcctgta ttctcctggt actgcaacct gtaaaccagc    360
actgcaatgc tgatgcacgg gaagtagtgg gatgggaaca caaatggagc atcgaggtgg    420
tcatctccga cctcgcgttg gtggcggtgc tcagcgggct cagcgtgctg ggccgcacca    480
tgggctgggc ctggctggtc aagacctacg tggtgcccta catgatcgtg aacatgtggc    540
tggtgctcat cacgctgctc cagcacacgc acccggccct gccgcactac ttcgagaagg    600
actgggactg gctacgcggc gccatggcca ccgtcgaccg ctccatgggc ccgcccttca    660
tggacagcat cctgcaccac atctccgaca cccacgtgct gcaccacctc ttcagcacca    720
tcccgcacta ccacgccgag gaggcctccg ccgccatccg gccatcctg ggcaagtact    780
accaatccga cagccgctgg gtcggccgcg ccctgtggga ggactggcgc gactgccgct    840
acgtcgtccc cgacgcgccc gaggacgact ccgcgctctg gttccacaag tgagcgcgcc    900
tgcgcgagga cgcagaacaa cgctgccgcc gtgtcttttg cacgcgcgac tccggcgctt    960
cgctggtggc acccccataa agaaaccctc aattctgttt gtggaagaca cggtgtaccc   1020
ccacccaccc acctgcacct ctattattgg tattattgac gcgggagtgg gcgttgtacc   1080
ctacaacgta gcttctctag ttttcagctg gctcccacca ttgtaaagag cctctagagt   1140
cgacctgcag gcatgcaagc ttggcgtaat catggtcata gctgtttcct gtgtgaaatt   1200
gttatccgct cacaattcca cacaacatac gagccggaag cataaagtgt aaagcctggg   1260
gtgcctaatg agtgagctaa ctcacattaa ttgcgttgcg ctcactgccc gctttccagt   1320
cgggaaacct gtcgtgccag ctgcattaat gaatcggcca acgcgcgggg agaggcggtt   1380
tgcgtattgg gcgctcttcc                                               1400

<210> SEQ ID NO 32
<211> LENGTH: 4091
<212> TYPE: DNA
<213> ORGANISM: Prototheca moriformis

<400> SEQUENCE: 32
gctcttcggg tttgctcacc cgcgaggtcg acgcccagca tggctatcaa gacgaacagg     60
cagcctgtgg agaagcctcc gttcacgatc gggacgctgc gcaaggccat ccccgcgcac    120
tgtttcgagc gctcggcgct tcgtagcagc atgtacctgg cctttgacat cgcggtcatg    180
tccctgctct acgtcgcgtc gacgtacatc gaccctgcgc cggtgcctac gtgggtcaag    240
tatggcgtca tgtggccgct ctactggttc ttccaggtgt gtgtgagggt gtgggttgcc    300
cgtatcgagg tcctggtggc gcgcatgggg gagaaggcgc ctgtcccgct gaccccccg    360
gctaccctcc cggcaccttc cagggcgcct tcggcacggg tgtctgggtg tgcgcgcacg    420
agtgcggcca ccaggccttt tcctccagcc aggccatcaa cgacgcgtg ggcctggtgt    480
tccacagcct gctgctggtg ccctactact cctggaagca ctcgcaccgc cgccaccact    540
ccaaacacgg gtgcctggac aaggacgagg tgtttgtgcc gccgcaccgc gcagtggcgc    600
acgagggcct ggagtgggag gagtggctgc ccatccgcat gggcaaggtg ctggtcaccc    660
tgaccctggg cctggccgct gtacctcatg tcaacgtcgc ctcgcggccg tacccgcgct    720
```

```
tcgccaacca ctttgacccg tggtcgccca tcttcagcaa gcgcgaggta ccctttcttg     780
cgctatgaca cttccagcaa aaggtagggc gggctgcgag acggcttccc ggcgctgcat     840
gcaacaccga tgatgcttcg accccccgaa gctccttcgg ggctgcatgg gcgctccgat     900
gccgctccag ggcgagcgct gtttaaatag ccaggccccc gattgcaaag acattatagc     960
gagctaccaa agccatattc aaacacctag atcactacca cttctacaca ggccactcga    1020
gcttgtgatc gcactccgct aagggggcgc ctcttcctct tcgtttcagt cacaacccgc    1080
aaacggcgcg ccatgctgct gcaggccttc ctgttcctgc tggccggctt cgccgccaag    1140
atcagcgcct ccatgacgaa cgagacgtcc gaccgccccc tggtgcactt caccccaac    1200
aagggctgga tgaacgaccc caacggcctg tggtacgacg agaaggacgc caagtggcac    1260
ctgtacttcc agtacaaccc gaacgacacc gtctggggga cgcccttgtt ctggggccac    1320
gccacgtccg acgacctgac caactgggag gaccagccca tcgccatcgc cccgaagcgc    1380
aacgactccg gcgccttctc cggctccatg gtggtggact acaacaacac ctccggcttc    1440
ttcaacgaca ccatcgaccc gcgccagcgc tgcgtggcca tctggaccta caacaccccg    1500
gagtccgagg agcagtacat ctcctacagc ctggacggcg gctacacctt caccgagtac    1560
cagaagaacc ccgtgctggc cgccaactcc acccagttcc gcgacccgaa ggtcttctgg    1620
tacgagccct cccagaagtg gatcatgacc gcggccaagt cccaggacta caagatcgag    1680
atctactcct ccgacgacct gaagtcctgg aagctggagt ccgcgttcgc caacgagggc    1740
ttcctcggct accagtacga gtgccccggc ctgatcgagg tccccaccga gcaggacccc    1800
agcaagtcct actgggtgat gttcatctcc atcaaccccg gcgccccggc cggcggctcc    1860
ttcaaccagt acttcgtcgg cagcttcaac ggcacccact tcgaggcctt cgacaaccag    1920
tcccgcgtgg tggacttcgg caaggactac tacgccctgc agaccttctt caacaccgac    1980
ccgacctacg ggagcgccct gggcatcgcg tgggcctcca actgggagta ctccgccttc    2040
gtgcccacca cccctggcg ctcctccatg tccctcgtgc gcaagttctc cctcaacacc    2100
gagtaccagg ccaacccgga gacggagctg atcaacctga aggccgagcc gatcctgaac    2160
atcagcaacg ccggcccctg gagccggttc gccaccaaca ccacgttgac gaaggccaac    2220
agctacaacg tcgacctgtc caacagcacc ggcacctgg agttcgagct ggtgtacgcc    2280
gtcaacacca cccagacgat ctccaagtcc gtgttcgcgg acctctcct ctggttcaag    2340
ggcctggagg accccgagga gtacctccgc atgggcttcg aggtgtccgc gtcctccttc    2400
ttcctggacc gcgggaacag caaggtgaag ttcgtgaagg agaaccccta cttcaccaac    2460
cgcatgagcg tgaacaacca gcccttcaag agcgagaacg acctgtccta ctacaaggtg    2520
tacggcttgc tggaccagaa catcctggag ctgtacttca cgacggcga cgtcgtgtcc    2580
accaacacct acttcatgac caccgggaac gccctgggct ccgtgaacat gacgacgggg    2640
gtggacaacc tgttctacat cgacaagttc caggtgcgcg aggtcaagtg acaattggca    2700
gcagcagctc ggatagtatc gacacactct ggacgctggt cgtgtgatgg actgttgccg    2760
ccacacttgc tgccttgacc tgtgaatatc cctgccgctt ttatcaaaca gcctcagtgt    2820
gtttgatctt gtgtgtacgc gcttttgcga gttgctagct gcttgtgcta tttgcgaata    2880
ccacccccag catccccttc cctcgtttca tatcgcttgc atcccaaccg caacttatct    2940
acgctgtcct gctatccctc agcgctgctc ctgctcctgc tcactgcccc tcgcacagcc    3000
ttggtttggg ctccgcctgt attctcctgg tactgcaacc tgtaaaccag cactgcaatg    3060
```

| | |
|---|---|
| ctgatgcacg ggaagtagtg ggatgggaac acaaatggag catcgaggtg gtcatctccg | 3120 |
| acctcgcgtt ggtggcggtg ctcagcgggc tcagcgtgct gggccgcacc atgggctggg | 3180 |
| cctggctggt caagacctac gtggtgccct acatgatcgt gaacatgtgg ctggtgctca | 3240 |
| tcacgctgct ccagcacacg cacccggccc tgccgcacta cttcgagaag gactgggact | 3300 |
| ggctacgcgg cgccatggcc accgtcgacc gctccatggg cccgcccttc atggacagca | 3360 |
| tcctgcacca catctccgac acccacgtgc tgcaccacct cttcagcacc atccgcgcact | 3420 |
| accacgccga ggaggcctcc gccgccatcc ggcccatcct gggcaagtac taccaatccg | 3480 |
| acagccgctg ggtcggccgc gccctgtggg aggactggcg cgactgccgc tacgtcgtcc | 3540 |
| ccgacgcgcc cgaggacgac tccgcgctct ggttccacaa gtgagcgcgc ctgcgcgagg | 3600 |
| acgcagaaca acgctgccgc cgtgtctttt gcacgcgcga ctccggcgct tcgctggtgg | 3660 |
| caccccata aagaaaccct caattctgtt tgtggaagac acggtgtacc cccacccacc | 3720 |
| cacctgcacc tctattattg gtattattga cgcgggagtg ggcgttgtac cctacaacgt | 3780 |
| agcttctcta gttttcagct ggctcccacc attgtaaaga gcctctagag tcgacctgca | 3840 |
| ggcatgcaag cttggcgtaa tcatggtcat agctgtttcc tgtgtgaaat tgttatccgc | 3900 |
| tcacaattcc acacaacata cgagccggaa gcataaagtg taaagcctgg ggtgcctaat | 3960 |
| gagtgagcta actcacatta attgcgttgc gctcactgcc cgctttccag tcgggaaacc | 4020 |
| tgtcgtgcca gctgcattaa tgaatcggcc aacgcgcggg gagaggcggt ttgcgtattg | 4080 |
| ggcgctcttc c | 4091 |

<210> SEQ ID NO 33
<211> LENGTH: 510
<212> TYPE: DNA
<213> ORGANISM: Prototheca moriformis

<400> SEQUENCE: 33

| | |
|---|---|
| gctcttccgc ctggagctgg tgcagagcat gggtcagttt gcggaggaga gggtgctccc | 60 |
| cgtgctgcac cccgtggaca agctgtggca gccgcaggac ttcctgcccg accccgagtc | 120 |
| gcccgacttc gaggaccagg tggcggagct gcgcgcgcgc gccaaggacc tgcccgacga | 180 |
| gtactttgtg gtgctggtgg cgacatgat cacggaggag gcgctgccga cctacatggc | 240 |
| catgctcaac accttggacg gtgtgcgcga cgacacgggc gcggctgacc acccgtgggc | 300 |
| gcgctggacg cggcagtggg tggccgagga gaaccggcac ggcgacctgc tgaacaagta | 360 |
| ctgttggctg acggggcgcg tcaacatgcg ggccgtggag gtgaccatca acaacctgat | 420 |
| caagagcggc atgaacccgc agacggacaa caacccttac ttgggcttcg tctacaccctc | 480 |
| cttccaggag cgcgccacca agtaggtacc | 510 |

<210> SEQ ID NO 34
<211> LENGTH: 1186
<212> TYPE: DNA
<213> ORGANISM: Prototheca moriformis

<400> SEQUENCE: 34

| | |
|---|---|
| caattggcag cagcagctcg gatagtatcg acacactctg gacgctggtc gtgtgatgga | 60 |
| ctgttgccgc cacacttgct gccttgacct gtgaatatcc ctgccgcttt tatcaaacag | 120 |
| cctcagtgtg tttgatcttg tgtgtacgcg cttttgcgag ttgctagctg cttgtgctat | 180 |
| ttgcgaatac caccccagc atccccttcc ctcgttcat atcgcttgca tcccaaccgc | 240 |
| aacttatcta cgctgtcctg ctatccctca gcgctgctcc tgctcctgct cactgccct | 300 |

```
cgcacagcct tggtttgggc tccgcctgta ttctcctggt actgcaacct gtaaaccagc    360
actgcaatgc tgatgcacgg gaagtagtgg gatgggaaca caaatggaag gatcgtagag    420
ctccagccac ggcaacaccg cgcgcctggc ggccgagcac ggcgacaagg gcctgagcaa    480
gatctgcggg ctgatcgcca gcgacgaggg ccggcacgag atcgcctaca cgcgcatcgt    540
ggacgagttc ttccgcctcg accccgaggg cgccgtcgcc gcctacgcca acatgatgcg    600
caagcagatc accatgcccg cgcacctcat ggacgacatg ggccacggcg aggccaaccc    660
gggccgcaac ctcttcgccg acttctccgc cgtcgccgag aagatcgacg tctacgacgc    720
cgaggactac tgccgcatcc tggagcacct caacgcgcgc tggaaggtgg acgagcgcca    780
ggtcagcggc caggccgccg cggaccagga gtacgttctg ggcctgcccc agcgcttccg    840
gaaactcgcc gagaagaccg ccgccaagcg caagcgcgtc gcgcgcaggc ccgtcgcctt    900
ctcctggaga gaagagcctc tagagtcgac ctgcaggcat gcaagcttgg cgtaatcatg    960
gtcatagctg tttcctgtgt gaaattgtta tccgctcaca attccacaca acatacgagc   1020
cggaagcata aagtgtaaag cctggggtgc ctaatgagtg agctaactca cattaattgc   1080
gttgcgctca ctgcccgctt tccagtcggg aaacctgtcg tgccagctgc attaatgaat   1140
cggccaacgc gcggggagag gcggtttgcg tattgggcgc tcttcc              1186
```

<210> SEQ ID NO 35
<211> LENGTH: 3615
<212> TYPE: DNA
<213> ORGANISM: Prototheca moriformis

<400> SEQUENCE: 35

```
gctcttccgc ctggagctgg tgcagagcat gggtcagttt gcggaggaga gggtgctccc     60
cgtgctgcac cccgtggaca gctgtggca gccgcaggac ttcctgcccg accccgagtc    120
gcccgacttc gaggaccagg tggcggagct gcgcgcgcgc gccaaggacc tgcccgacga    180
gtactttgtg gtgctggtgg cgacatgat cacgaggag gcgctgccga cctacatggc    240
catgctcaac accttggacg gtgtgcgcga cgacacgggc gcggctgacc acccgtgggc    300
gcgctggacg cggcagtggg tggccgagga gaaccggcac ggcgacctgc tgaacaagta    360
ctgttggctg acggggcgcg tcaacatgcg ggccgtggag gtgaccatca acaacctgat    420
caagagcggc atgaacccgc agacggacaa caacccttac ttgggcttcg tctacacctc    480
cttccaggag cgcgccacca agtaggtacc ctttcttgcg ctatgacact tccagcaaaa    540
ggtagggcgg gctgcgagac ggcttccctg gcgctgcatgc aacaccgatg atgcttcgac    600
cccccgaagc tccttcgggg ctgcatgggc gctccgatgc cgctccaggg cgagcgctgt    660
ttaaatagcc aggcccccga ttgcaaagac attatagcga gctaccaaag ccatattcaa    720
acacctagat cactaccact tctacacagg ccactcgagc ttgtgatcgc actccgctaa    780
gggggcgcct cttcctcttc gtttcagtca caacccgcaa acggcgcgcc atgctgctgc    840
aggccttcct gttcctgctg gccggcttcg ccgccaagat cagcgcctcc atgacgaacg    900
agacgtccga ccgccccctg gtgcacttca ccccccaacaa gggctggatg aacgaccccca    960 acggcctgtg gtacgacgag aaggacgcca agtggcacct gtacttccag tacaacccga   1020
acgacaccgt ctgggggacg cccttgttct ggggccacgc cacgtccgac gacctgacca   1080
actgggagga ccagcccatc gccatcgccc cgaagcgcaa cgactccggc gccttctccg   1140
gctccatggt ggtggactac aacaacacct ccggcttctt caacgacacc atcgaccgc   1200
```

```
gccagcgctg cgtggccatc tggacctaca acaccccgga gtccgaggag cagtacatct    1260
cctacagcct ggacggcggc tacaccttca ccgagtacca aagaaccccc gtgctggccg    1320
ccaactccac ccagttccgc gacccgaagg tcttctggta cgagccctcc cagaagtgga    1380
tcatgaccgc ggccaagtcc caggactaca agatcgagat ctactcctcc gacgacctga    1440
agtcctggaa gctggagtcc gcgttcgcca acgagggctt cctcggctac cagtacgagt    1500
gccccggcct gatcgaggtc cccaccgagc aggaccccag caagtcctac tgggtgatgt    1560
tcatctccat caacccoggc gccccggccg gcggctcctt caaccagtac ttcgtcggca    1620
gcttcaacgg cacccacttc gaggccttcg acaaccagtc ccgcgtggtg gacttcggca    1680
aggactacta cgccctgcag accttcttca acaccgaccc gacctacggg agcgccctgg    1740
gcatcgcgtg ggcctccaac tgggagtact ccgccttcgt gcccaccaac ccctggcgct    1800
cctccatgtc cctcgtgcgc aagttctccc tcaacaccga gtaccaggcc aacccggaga    1860
cggagctgat caacctgaag gccgagccga tcctgaacat cagcaacgcc ggcccctgga    1920
gccggttcgc caccaacacc acgttgacga aggccaacag ctacaacgtc gacctgtcca    1980
acagcaccgg caccctggag ttcgagctgg tgtacgccgt caacaccacc cagacgatct    2040
ccaagtccgt gttcgcggac ctctccctct ggttcaaggg cctggaggac cccgaggagt    2100
acctccgcat gggcttcgag gtgtccgcgt cctccttctt cctggaccgc gggaacagca    2160
aggtgaagtt cgtgaaggag aaccoctact tcaccaaccg catgagcgtg aacaaccagc    2220
ccttcaagag cgagaacgac ctgtcctact acaaggtgta cggcttgctg gaccagaaca    2280
tcctggagct gtacttcaac gacggcgacg tcgtgtccac caacacctac ttcatgacca    2340
ccgggaacgc cctgggctcc gtgaacatga cgacggggt ggacaacctg ttctacatcg    2400
acaagttcca ggtgcgcgag gtcaagtgac aattggcagc agcagctcgg atagtatcga    2460
cacactctgg acgctggtcg tgtgatggac tgttgccgcc acacttgctg ccttgacctg    2520
tgaatatccc tgccgctttt atcaaacagc ctcagtgtgt tgatcttgt gtgtacgcgc    2580 ttttgcgagt tgctagctgc ttgtgctatt tgcgaatacc acccccagca tccccttccc    2640
tcgtttcata tcgcttgcat cccaaccgca acttatctac gctgtcctgc tatccctcag    2700
cgctgctcct gctcctgctc actgcccctc gcacagcctt ggtttgggct ccgcctgtat    2760
tctcctggta ctgcaacctg taaaccagca ctgcaatgct gatgcacggg aagtagtggg    2820
atgggaacac aaatggaagg atcgtagagc tccagccacg gcaacaccgc gcgcctggcg    2880
gccgagcacg gcgacaaggg cctgagcaag atctgcgggc tgatcgccag cgacgagggc    2940
cggcacgaga tcgcctacac gcgcatcgtg gacgagttct tccgcctcga ccccgagggc    3000
gccgtcgccg cctacgccaa catgatgcgc aagcagatca ccatgcccgc gcacctcatg    3060
gacgacatgg ccacggcga ggccaacccg ggccgcaacc tcttcgccga cttctccgcc    3120
gtcgccgaga gatcgacgt ctacgacgcc gaggactact gccgcatcct ggagcacctc    3180
aacgcgcgct ggaaggtgga cgagcgccag gtcagcggcc aggccgccgc ggaccaggag    3240
tacgttctgg gcctgcccca gcgcttccgg aaactcgccg agaagaccgc cgccaagcgc    3300
aagcgcgtcg cgcgcaggcc cgtcgccttc tcctggagag aagagcctct agagtcgacc    3360
tgcaggcatg caagcttggc gtaatcatgg tcatagctgt ttcctgtgtg aaattgttat    3420
ccgctcacaa ttccacacaa catacgagcc ggaagcataa agtgtaaagc ctggggtgcc    3480
taatgagtga gctaactcac attaattgcg ttgcgctcac tgcccgcttt ccagtcggga    3540
aacctgtcgt gccagctgca ttaatgaatc ggccaacgcg cggggagagg cggtttgcgt    3600
```

```
attgggcgct cttcc                                                   3615

<210> SEQ ID NO 36
<211> LENGTH: 511
<212> TYPE: DNA
<213> ORGANISM: Prototheca moriformis

<400> SEQUENCE: 36
gctcttcccg cctggagctg gtgcagagca tggggcagtt tgcggaggag agggtgctcc    60
ccgtgctgca ccccgtggac aagctgtggc agccgcagga cttcctgccc gaccccgagt   120
cgcccgactt cgaggaccag gtggcggagc tgcgcgcgcg cgccaaggac ctgcccgacg   180
agtactttgt ggtgctggtg ggcgacatga tcacggagga ggcgctgccg acctacatgg   240
ccatgctcaa caccttggac ggtgtgcgcg acgacacggg cgcggctgac cacccgtggg   300
cgcgctggac gcggcagtgg gtggccgagg agaaccggca cggcgacctg ctgaacaagt   360
actgttggct gacggggcgc gtcaacatgc gggccgtgga ggtgaccatc aacaacctga   420
tcaagagcgg catgaacccg cagacggaca caaccccta cttgggcttc gtctacacct   480
ccttccagga gcgcgccacc aagtaggtac c                                   511

<210> SEQ ID NO 37
<211> LENGTH: 761
<212> TYPE: DNA
<213> ORGANISM: Prototheca moriformis

<400> SEQUENCE: 37
cagccacggc aacaccgcgc gccttgcggc cgagcacggc gacaagaacc tgagcaagat    60
ctgcgggctg atcgccagcg acgagggccg cacgagatc gcctacacgc gcatcgtgga   120
cgagttcttc cgcctcgacc ccgagggcgc cgtcgccgcc tacgccaaca tgatgcgcaa   180
gcagatcacc atgcccgcgc acctcatgga cgacatgggc cacggcgagg ccaacccggg   240
ccgcaacctc ttcgccgact tctccgcggt cgccgagaag atcgacgtct acgacgccga   300
ggactactgc cgcatcctgg agcacctcaa cgcgcgctgg aaggtggacg agcgccaggt   360
cagcggccag gccgccgcgg accaggagta cgtcctgggc ctgccccagc gcttccggaa   420
actcgccgag aagaccgccg ccaagcgcaa gcgcgtcgcg cgcaggcccg tcgccttctc   480
ctggagaaga gcctctagag tcgacctgca ggcatgcaag cttggcgtaa tcatggtcat   540
agctgtttcc tgtgtgaaat tgttatccgc tcacaattcc acacaacata cgagccggaa   600
gcataaagtg taaagcctgg ggtgcctaat gagtgagcta actcacatta attgcgttgc   660
gctcactgcc cgctttccag tcgggaaacc tgtcgtgcca gctgcattaa tgaatcggcc   720
aacgcgcggg gagaggcggt ttgcgtattg ggcgctcttc c                       761

<210> SEQ ID NO 38
<211> LENGTH: 3599
<212> TYPE: DNA
<213> ORGANISM: Prototheca moriformis

<400> SEQUENCE: 38
gctcttcccg cctggagctg gtgcagagca tggggcagtt tgcggaggag agggtgctcc    60
ccgtgctgca ccccgtggac aagctgtggc agccgcagga cttcctgccc gaccccgagt   120
cgcccgactt cgaggaccag gtggcggagc tgcgcgcgcg cgccaaggac ctgcccgacg   180
agtactttgt ggtgctggtg ggcgacatga tcacggagga ggcgctgccg acctacatgg   240
```

```
ccatgctcaa caccttggac ggtgtgcgcg acgacacggg cgcggctgac cacccgtggg    300
cgcgctggac gcggcagtgg gtggccgagg agaaccggca cggcgacctg ctgaacaagt    360
actgttggct gacggggcgc gtcaacatgc gggccgtgga ggtgaccatc aacaacctga    420
tcaagagcgg catgaacccg cagacggaca caaccctta cttgggcttc gtctacacct    480
ccttccagga gcgcgccacc aagtaggtac cctttcttgc gctatgacac ttccagcaaa    540
aggtagggcg ggctgcgaga cggcttcccg gcgctgcatg caacaccgat gatgcttcga    600
ccccccgaag ctccttcggg gctgcatggg cgctccgatg ccgctccagg gcgagcgctg    660
tttaaatagc caggccccccg attgcaaaga cattatagcg agctaccaaa gccatattca    720
aacacctaga tcactaccac ttctacacag gccactcgag cttgtgatcg cactccgcta    780
aggggggcgcc tcttcctctt cgtttcagtc acaacccgca aacggcgcgc catgctgctg    840
caggccttcc tgttcctgct ggccggcttc gccgccaaga tcagcgcctc catgacgaac    900
gagacgtccg accgcccct ggtgcacttc acccccaaca agggctggat gaacgacccc    960
aacggcctgt ggtacgacga gaaggacgcc aagtggcacc tgtacttcca gtacaacccg    1020
aacgacaccg tctggggac gcccttgttc tggggccacg ccacgtccga cgacctgacc    1080
aactgggagg accagcccat cgccatcgcc ccgaagcgca acgactccgg cgccttctcc    1140
ggctccatgg tggtggacta caacaacacc tccggcttct tcaacgacac catcgacccg    1200
cgccagcgct gcgtggccat ctggacctac aacaccccgg agtccgagga gcagtacatc    1260
tcctacagcc tggacggcgg ctacaccttc accgagtacc agaagaaccc cgtgctggcc    1320
gccaactcca cccagttccg cgacccgaag gtcttctggt acgagccctc ccagaagtgg    1380
atcatgaccg cggccaagtc ccaggactac aagatcgaga tctactcctc cgacgacctg    1440
aagtcctgga gctggagtc cgcgttcgcc aacgagggct cctcggcta ccagtacgag    1500
tgccccggcc tgatcgaggt ccccaccgag caggacccca gcaagtccta ctgggtgatg    1560
ttcatctcca tcaaccccgg cgccccggcc ggcggctcct tcaaccagta cttcgtcggc    1620
agcttcaacg gcacccactt cgaggccttc gacaaccagt cccgcgtggt ggacttcggc    1680
aaggactact acgccctgca gaccttcttc aacaccgacc cgacctacgg gagcgccctg    1740
ggcatcgcgt gggcctccaa ctgggagtac tccgccttcg tgcccaccaa ccctggcgc    1800
tcctccatgt ccctcgtgcg caagttctcc ctcaacaccg agtaccaggc caacccggag    1860
acggagctga tcaacctgaa ggccgagccg atcctgaaca tcagcaacgc cggccctgg    1920
agccggttcg ccaccaacac cacgttgacg aaggccaaca gctacaacgt cgacctgtcc    1980
aacagcaccg gcaccctgga gttcgagctg gtgtacgccg tcaacaccac ccagacgatc    2040
tccaagtccg tgttcgcgga cctctccctc tggttcaagg gcctggagga ccccgaggag    2100
tacctccgca tgggcttcga ggtgtccgcg tcctccttct cctggaccg cgggaacagc    2160
aaggtgaagt tcgtgaagga gaaccctac ttcaccaacc gcatgagcgt gaacaaccag    2220
cccttcaaga gcgagaacga cctgtcctac tacaaggtgt acggcttgct ggaccagaac    2280
atcctggagc tgtacttcaa cgacggcgac gtcgtgtcca ccaacaccta cttcatgacc    2340
accgggaacg ccctgggctc cgtgaacatg acgacggggg tggacaacct gttctacatc    2400
gacaagttcc aggtgcgcga ggtcaagtga caattggcag cagcagctcg gatagtatcg    2460
acacactctg gacgctggtc gtgtgatgga ctgttgccgc cacacttgct gccttgacct    2520
gtgaatatcc ctgccgcttt tatcaaacag ccctcagtgt ttttgatcttg tgtgtacgcg    2580
cttttgcgag ttgctagctg cttgtgctat ttgcgaatac cacccccagc atccccttcc    2640
```

```
ctcgtttcat atcgcttgca tcccaaccgc aacttatcta cgctgtcctg ctatccctca    2700
gcgctgctcc tgctcctgct cactgcccct cgcacagcct tggtttgggc tccgcctgta    2760
ttctcctggt actgcaacct gtaaaccagc actgcaatgc tgatgcacgg gaagtagtgg    2820
gatgggaaca caaatggaca gccacggcaa caccgcgcgc cttgcggccg agcacggcga    2880
caagaacctg agcaagatct gcgggctgat cgccagcgac gagggccggc acgagatcgc    2940
ctacacgcgc atcgtggacg agttcttccg cctcgacccc gagggcgccg tcgccgccta    3000
cgccaacatg atgcgcaagc agatcaccat gcccgcgcac ctcatggacg acatgggcca    3060
cggcgaggcc aacccgggcc gcaacctctt cgccgacttc tccgcggtcg ccgagaagat    3120
cgacgtctac gacgccgagg actactgccg catcctggag cacctcaacg cgcgctggaa    3180
ggtggacgag cgccaggtca gcggccaggc cgccgcggac caggagtacg tcctgggcct    3240
gccccagcgc ttccggaaac tcgccgagaa gaccgccgcc aagcgcaagc gcgtcgcgcg    3300
caggcccgtc gccttctcct ggagaagagc ctctagagtc gacctgcagg catgcaagct    3360
tggcgtaatc atggtcatag ctgtttcctg tgtgaaattg ttatccgctc acaattccac    3420
acaacatacg agccggaagc ataaagtgta aagcctgggg tgcctaatga gtgagctaac    3480
tcacattaat tgcgttgcgc tcactgcccg ctttccagtc gggaaacctg tcgtgccagc    3540
tgcattaatg aatcggccaa cgcgcgggga gaggcggttt gcgtattggg cgctcttcc     3599
```

<210> SEQ ID NO 39
<211> LENGTH: 21
<212> TYPE: DNA
<213> ORGANISM: Unknown
<220> FEATURE:
<223> OTHER INFORMATION: primer

<400> SEQUENCE: 39

```
gtccctgccc tttgtacaca c                                                21
```

<210> SEQ ID NO 40
<211> LENGTH: 23
<212> TYPE: DNA
<213> ORGANISM: Unknown
<220> FEATURE:
<223> OTHER INFORMATION: primer

<400> SEQUENCE: 40

```
ttgatatgct taagttcagc ggg                                              23
```

<210> SEQ ID NO 41
<211> LENGTH: 710
<212> TYPE: DNA
<213> ORGANISM: Rhodotorula glutini

<400> SEQUENCE: 41

```
cgcccgtcgc tactaccgat tgaatggctt agtgaggcct ccggattggc tattgggagc      60
tcgcgagagc acctgactgc cgagaagttg tacgaacttg gtcatttaga ggaagtaaaa     120
gtcgtaacaa ggtttccgta ggtgaacctg cggaaggatc attagtgaat attagggtgt     180
ccaacttaac ttggagcccg accctcactt tctaaccctg tgcatttgtc ttgggtagta     240
gcttgcgtca gcgagcgaat cccatttcac ttacaaacac aaagtctatg aatgtaacaa     300
atttataaca aaacaaaaact ttcaacaacg gatctcttgg ctctcgcatc gatgaagaac     360
gcagcgaaat gcgatacgta atgtgaattg cagaattcag tgaatcatcg aatctttgaa     420
```

```
cgcaccttgc gctccatggt attccgtgga gcatgcctgt ttgagtgtca tgaattcttc    480
aacccacctc tttcttagtg aatcaggcgg tgtttggatt ctgagcgctg ctggcttcgc    540
ggcctagctc gctcgtaatg cattagcatc cgcaatcgaa cttcggattg actcggcgta    600
atagactatt cgttgaggat tctggtctct gactggagcc gggtaaggtt aaagggagct    660
actaatcctc atgtctatct tgagattaga cctcaaatca ggtaggacta               710
```

```
<210> SEQ ID NO 42
<211> LENGTH: 707
<212> TYPE: DNA
<213> ORGANISM: Rhodotorula glutini

<400> SEQUENCE: 42
cgcccgtcgc tactaccgat tgaatggctt agtgaggcct ccggattggc tattgggagc     60
tcgcgagagc acccgactgc cgagaagttg tacgaacttg gtcatttaga ggaagtaaaa    120
gtcgtaacaa ggtttccgta ggtgaacctg cggaaggatc attagtgaat attagggcgt    180
ccaacttaac ttggagcccg aactctcact ttctaaccct gtgcatctgt ttctggtcag    240
tagctctctc gggagtgaac gccattcact aaaacacaa agtctatgaa tgtataaaat     300
ttataacaaa acaaaacttt caacaacgga tctcttggct ctcgcatcga tgaagaacgc    360
agcgaaatgc gataagtaat gtgaattgca gaattcagtg aatcatcgaa tctttgaacg    420
caccttgcgc tctctggtat tccggagagc atgcctgttt gagtgtcatg aaatcttcaa    480
ccctctcttt tcttaatgaa tcgagaggtg cttggatcct gagcgctgct ggcttcggcc    540
tagctcgttc gtaatgcatt agcatccgca atcgaacttc ggattgactt ggcgtaatag    600
actattcgct gaggattctg gtctcgtacc agagccgggt tgggttaaag gaagcttcta    660
atcctaaaag tctaactttt gattagatct caaatcaggt aggacta                  707
```

```
<210> SEQ ID NO 43
<211> LENGTH: 630
<212> TYPE: DNA
<213> ORGANISM: Lipomyces tetrasporu

<400> SEQUENCE: 43
cgcccgtcgc tactaccgat tgaatggctt agtgaggcct tcggactggc tccagaaaat     60
gggaaaccat tatcaggagc tggaaagttg gtcaaacttg gtcatttaga ggaagtaaaa    120
gtcgtaacaa ggtttccgta ggtgaacctg cggaaggatc attactgagt atttgtcttt    180
taaagacatc tctctatcca taaactcttt tttctaaaaa gacatgattt acacaattag    240
tctgaatgat tatataaaaa tcttcaaaac tttcaacaac ggatctcttg gttctcgcat    300
cgatgaagaa cgcagcaaaa tgcgataagt attgtgaatt gcaggatttt gtgaatcatc    360 gaattttga acgcacattg caccttctgg tattccggag ggtatacctg tttgagcgtc    420
atttatatac tcaaaacttt gttttggtga tgggcacata tctggtgaga gctagatttg    480
cctgaaatat agtggtagag attgctacga gttatgcaag ttagccaatg ctattaagtt    540
aattcgttgg tgaagcatgc ggagctttag cggtcgcctt ccttaactat tggaatttt    600 ctaatttga cctcaaatca ggcaggagta                                     630
```

```
<210> SEQ ID NO 44
<211> LENGTH: 641
<212> TYPE: DNA
<213> ORGANISM: Lipomyces starkeyi

<400> SEQUENCE: 44
```

```
cgcccgtcgc tactaccgat tgaatggctt agtgagaccc tcggattggc gttaggaagc      60
cggcaacggc atcctttggc cgagaagttg gtcaaacttg gtcatttaga ggaagtaaaa     120
gtcgtaacaa ggtttccgta ggtgaacctg cggaaggatc attagtgatt gcctttatag     180
gcttataact atatccactt acacctgtga actgttctat tacttgacgc aagtcgagta     240
tttttacaaa caatgtgtaa tgaacgtcgt tttattataa caaataaaa ctttcaacaa      300 cggatctctt ggctctcgca tcgatgaaga acgcagcgaa ttgcgataag taatgtgaat     360
tgcagaattc agtgaatcat cgaatctttg aacgcagctt gcgctctctg gtattccgga     420
gagcatgcct gtttcagtgt catgaaatcct caaccactag ggtttcctaa tggattggat     480
ttgggcgtct gcgatctctg atcgctcgcc ttaaaagagt tagcaagttt gacattaatg     540
tctggtgtaa taagtttcac tgggtccatt gtgttgaagc gtgcttctaa tcgtccgcaa     600
ggacaattac tttgactctg gcctgaaatc aggtaggact a                          641
```

<210> SEQ ID NO 45
<211> LENGTH: 456
<212> TYPE: DNA
<213> ORGANISM: Yarrowia lipolytica

<400> SEQUENCE: 45

```
cgcccgtcgc tactaccgat tgaatggttt agtgagacct tgggagggcg agatgagggg      60
ggcaacccct tttgaacatc caaacttggt caaacttgat tatttagagg aagtaaaagt     120
cgtaacaagg tttccgtagg tgaacctgcg aaggatcat tattgatttt atctatttct      180
gtggatttct ggtatattac agcgtcattt tatctcaatt ataactatca acaacggatc     240
tcttggctct cacatcgatg aagaacgcag cgaaccgcga tatttttgt gacttgcaga      300 tgtgaatcat caatctttga acgcacattg cgcggtatgg cattccgtac cgcacggatg     360
gaggagcgtg ttccctctgg gatcgcattg ctttcttgaa atggatttt taaactctca      420 attattacgt catttcacct ccttcatccg agatta                                456
```

<210> SEQ ID NO 46
<211> LENGTH: 628
<212> TYPE: DNA
<213> ORGANISM: Cryptococcus curvatus

<400> SEQUENCE: 46

```
cgcccgtcgc tactaccgat tgaatggctt agtgagattt ctggattggc gttaggaagc      60
cggcaacggc atcctttggc tgagaagtta ctcaaacttg gtcatttaga ggaagtaaaa     120
gtcgtaacaa ggtttccgta ggtgaacctg cggaaggatc attagtgatt tgccttcggg     180
ctaaactata tccataacac ctgtgaactg ttgattgact tcggtcaata tttttacaaa     240
cattgtgtaa tgaacgtcat gttataataa caaatataac tttcaacaac ggatctcttg     300
gctctcgcat cgatgaagaa cgcagcgaaa tgcgataag aatgtgaatt gcagaattca      360
gtgaatcatc gaatctttga acgcaacttg cgctctctgg tattccggag agcatgcctg     420
tttgagtgtc atgaaatctc aaccattagg gtttcttaat ggcttggatt tggacgtttg     480
ccagtcaaat ggctcgtctt aaaagagtta gtgaatttaa catttgtctt ctggcgtaat     540
aagtttcgct gggctgatag tgtgaagttt gcttctaatc gtccgcaagg acaattcttg     600
aactctggcc tcaaatcagg taggacta                                         628
```

<210> SEQ ID NO 47

<211> LENGTH: 628
<212> TYPE: DNA
<213> ORGANISM: Unknown
<220> FEATURE:
<223> OTHER INFORMATION: Trichosporon sp. CBS 7617

<400> SEQUENCE: 47

| cgcccgtcgc tactaccgat tgaatggctt agtgagaccc tcggattggc gttaagaagc | 60 |
| cggcaacggc atcttttggc cgagaagttg gtcaaacttg gtcatttaga ggaagtaaaa | 120 |
| gtcgtaacaa ggtttccgta ggtgaacctg cggaaggatc attagtgaat tgctctttga | 180 |
| gcgttaaact atatccatct acacctgtga acttgttgatt gacttcggtc aattactttt | 240 |
| acaaacattg tgtaatgaac gtcatgttat tataacaaaa ataactttca acaacggatc | 300 |
| tcttggctct cgcatcgatg aagaacgcag cgaaatgcga taagtaatgt gaattgcaga | 360 |
| attcagtgaa tcatcgaatc tttgaacgca acttgcgctc tctggtattc cggagagcat | 420 |
| gcctgtttga gtatcatgaa atctcaacca ttagggtttc ttaatggctt ggatttgggc | 480 |
| gctgccactt gcctggctcg ccttaaaaga gttagcgtat taacttgtcg atctggcgta | 540 |
| ataagtttcg ctggtgtaga cttgagaagt gcgcttctaa tcgtcctcgg acaattcttg | 600 |
| aactctggtc tcaaatcagg taggacta | 628 |

<210> SEQ ID NO 48
<211> LENGTH: 716
<212> TYPE: DNA
<213> ORGANISM: Sporobolomyces alborubescens

<400> SEQUENCE: 48

| cgcccgtcgc tactaccgat tgaatggctt agtgaggcct ccggattggc tattgggagc | 60 |
| tcgcgagagc acccgactgc cgagaagttg tacgaacttg gtcatttaga ggaagtaaaa | 120 |
| gtcgtaacaa ggtttccgta ggtgaacctg cggaaggatc attagtgaat ataggacgtc | 180 |
| caacttaact tggagtccga actctcactt tctaaccctg tgcacttgtt tgggatagta | 240 |
| actctcgcaa gagagcgaac tcctattcac ttataaacac aaagtctatg aatgtattaa | 300 |
| attttataac aaaataaaac tttcaacaac ggatctcttg gctctcgcat cgatgaagaa | 360 |
| cgcagcgaaa tgcgataagt aatgtgaatt gcagaattca gtgaatcatc gaatctttga | 420 |
| acgcaccttg cgctccatgg tattccgtgg agcatgcctg tttgagtgtc atgaatactt | 480 |
| caaccctcct ctttcttaat gattgaagag gtgtttggtt tctgagcgct gctggccttt | 540 |
| acggtctagc tcgttcgtaa tgcattagca tccgcaatcg aatttcggat tgacttggcg | 600 |
| taatagacta ttcgctgagg aattctagtc ttcggattag agccgggttg ggttaaagga | 660 |
| agcttctaat cagaatgtct acattttaag attagatctc aaatcaggta ggacta | 716 |

<210> SEQ ID NO 49
<211> LENGTH: 718
<212> TYPE: DNA
<213> ORGANISM: Rhodotorula glutinis

<400> SEQUENCE: 49

| cgcccgtcgc tactaccgat tgaatggctt agtgaggcct ccggattggc tattgggagc | 60 |
| tcgcgagagc acccgactgc cgagaagttg tacgaacttg gtcatttaga ggaagtaaaa | 120 |
| gtcgtaacaa ggtttccgta ggtgaacctg cggaaggatc attagtgaat ctaggacgtc | 180 |
| caacttaact tggagtccga actctcactt tctaaccctg tgcatctgtt ttaaaattgg | 240 |
| ctagtagctc ttcggagcga accaccattt ttcacttata caaacacaaa gtctatgaat | 300 |

```
gtaaacaaat ttataacaaa acaaaacttt caacaacgga tctcttggct ctcgcatcga    360
tgaagaacgc agcgaaatgc gatacgtaat gtgaattgca gaattcagtg aatcatcgaa    420
tctttgaacg caccttgcgc tccttggtat tccgaggagc atgcctgttt gagtgtcatg    480
aaatcttcaa cccacctctt tcttagtgaa tctggtggtg cttggtttct gagcgctgct    540
ctgcttcggc ttagctcgtt cgtaatgcat tagcatccgc aaccgaaact tcggattgac    600
ttggcgtaat agactattcg ctgaggattc cagacttgtt ctggagccga gttgggttaa    660
aggaagcttc taatcctaaa gtctattttt tgattagatc tcaaatcagg taggacta     718

<210> SEQ ID NO 50
<211> LENGTH: 693
<212> TYPE: DNA
<213> ORGANISM: Rhodotorula glutinis

<400> SEQUENCE: 50
cgcccgtcgc tactaccgat tgaatggctt agtgagggct ccggattggc ttctgggagc     60
cggcaacggc acctagtcgc tgagaagttg gacgaacttg gtcatttaga ggaagtaaaa    120
gtcgtaacaa ggtttccgta ggtgaacctg cggaaggatc attaatgaaa tgcaaggacg    180
ctctttttag aggtccgacc caattcattt tctcacactg tgcacacact acttttttaca   240 ccatttttaa cacttgaagt ctaagaatgt aaacagtctc ttaattgagc ataaaattta    300
aacaaaactt tcagcaacgg atctcttggc tctcccatcg atgaagaacg cagcgaaatg    360
cgatacgtaa tgtgaattgc agaattcagt gaatcatcga atctttgaac gcaccttgca    420
ctctttggta ttccgaagag tatgtctgtt tgagtgtcat gaaactctca accccctgt    480 tttgtaatga accaggcgtg ggcttggatt atggctgctg ccggcgtaat tgtcgactcg    540
gctgaaatac acgagctacc catttcataa gaaatagacg gtttgactcg gcgtaataac    600
atatttcgct gaggacgtca cattcttttac ctagtggtgc ttctaatgcg acatctaaac    660
tttaagcttt agacctcaaa tcagtcagga cta                                 693

<210> SEQ ID NO 51
<211> LENGTH: 640
<212> TYPE: DNA
<213> ORGANISM: Trichosporon behrend

<400> SEQUENCE: 51
cgcccgtcgc tactaccgat tgaatggctt agtgagaccc tcggattggc gttaggaagc     60
cggcaacggc atcctttggc cgagaagttg gtcaaacttg gtcatttaga ggaagtaaaa    120
gtcgtaacaa ggtttccgta ggtgaacctg cggaaggatc attagtgatt gccttcatag    180
gcttaaacta tatccacata cacctgtgaa ctgttccacc acttgacgca agtcgagtgt    240
ttttacaaac aatgtgtaat gaacgtcgtt ttattataac aaaataaaac tttcaacaac    300
ggatctcttg gctctcgcat cgatgaagaa cgcagcgaat tgcgataagt aatgtgaatt    360
gcagaattca gtgaatcatc gaatctttga acgcagcttg cgctctctgg tattccggag    420
agcatgcctg tttcagtgtc atgaaatctc aaccactagg gtttcctaat ggattggatt    480
tgggcgtctg cgatctctga tcgctcgcct taaaagagtt agcaagtttg acattaatgt    540
ctggtgtaat aagtttcact gggtccattg tgttgaagcg tgcttctaat cgtccgcaag    600
gacaattact ttgactctgg cctgaaatca ggtaggacta                          640

<210> SEQ ID NO 52
```

<211> LENGTH: 476
<212> TYPE: DNA
<213> ORGANISM: Geotrichum histeridarum

<400> SEQUENCE: 52

```
cgcccgtcgc tactaccgat cgaatggctt agtgaggctt ccggattgat ttgggagaga    60
gggcgacttt tttcctggaa cgagaagcta gtcaaacttg gtcatttaga ggaagtaaaa   120
gtcgtaacaa ggtttccgta ggtgaacctg cggaaggatc attagaaaaa tgcgatatta   180
gtggtttatt ttgctcgccg aaaggcaaac ttttaacata cctacctttt tttaactata   240
aaaacttttta acaacggatc tcttggttct cgcatcgatg aagaacgcag cgaattgcga   300
tacgttttgt gaattgcaga agtgaatcat caatctttga acgcacattg cgcctggtgg   360
tattccgcca ggcatacctg tttgagcgtt gttctctctg ggattgtcta ctttcctcaa   420
agaaattaaa caaacaagtt tgacacaaca cctcaacctc agatcaggta ggacta       476
```

<210> SEQ ID NO 53
<211> LENGTH: 687
<212> TYPE: DNA
<213> ORGANISM: Rhodotorula aurantiaca

<400> SEQUENCE: 53

```
cgcccgtcgc tactaccgat tgaatggctt agtgaggcct tcggattggc ttctgggagc    60
cggcaacggc acctagtcgc tgagaagttt gacgaacttg gtcatttaga ggaagtaaaa   120
gtcgtaacaa ggtttccgta ggtgaacctg cggaaggatc attaatgaat tttaggacgt   180
tcttttttaga agtccgaccc tttcatttc ttacactgtg cacacacttc tttttttacac   240
acacttttaa caccttagta taagaatgta atagtctctt aattgagcat aaataaaaac   300
aaaactttca gcaacggatc tcttggctct cgcatcgatg aagaacgcag cgaattgcga   360
taagtaatgt gaattgcaga attcagtgaa tcatcgaatc tttgaacgca ccttgcactc   420
tttggtattc cgaagagtat gtctgtttga gtgtcatgaa actctcaacc cccctatttt   480
gtaatgagat gggtgtgggc ttggattatg gttgtctgtc ggcgtaattg ccggctcaac   540
tgaaatacac gagcaaccct attgaaataa acggtttgac ttggcgtaat aattatttcg   600
ctaaggacgc tttcttcaaa tataagaggt gcttctaatt cgcttctaat agcatttaag   660
ctttagacct caaatcagtc aggacta                                      687
```

<210> SEQ ID NO 54
<211> LENGTH: 636
<212> TYPE: DNA
<213> ORGANISM: Trichosporon domesticum

<400> SEQUENCE: 54

```
cgcccgtcgc tactaccgat tgaatggctt agtgagacct ccggattggc gttgagaagc    60
cggcaacggc atctcttggc tgagaagttg gtcaaacttg gtcatttaga ggaagtaaaa   120
gtcgtaacaa ggtttccgta ggtgaacctg cggaaggatc attagtgatt gccttaattg   180
gcttaaacta tatccatcta cacctgtgaa ctgtttgatt gaatcttcgg attcgatttt   240
atacaaacat tgtgtaatga acgtcattat attataacaa aaaaaaaact ttcaacaacg   300
gatctcttgg ctctcgcatc gatgaagaac gcagcgaaat gcgataagta atgtgaattg   360
cagaattcag tgaatcatcg aatctttgaa cgcaacttgc gctctctggt attccggaga   420
gcatgcctgt ttgagtgtca tgaaatctca accattaggg tttcttaatg gcttggattt   480
ggaggtttgc cagtctgact ggctcctctt aaaagagtta gcaagttgaa ctattgctat   540
```

```
ctggcgtaat aagtttcgct ggaatggtat tgtgaagcgt gcttctaatc gtcttcggac    600 aatttttga ctctggcctc aaatcaggta ggacta                              636

<210> SEQ ID NO 55
<211> LENGTH: 711
<212> TYPE: DNA
<213> ORGANISM: Rhodotorula toruloides

<400> SEQUENCE: 55
cgcccgtcgc tactaccgat tgaatggctt agtgaggcct ccggattggc tatcgggagc     60
tcgcgagagc acctgactgc cgagaagttg tacgaacttg gtcatttaga ggaagtaaaa    120
gtcgtaacaa ggtttccgta ggtgaacctg cggaaggatc attagtgaat attagggtgt    180
ccaacttaac ttggagcccg accctcactt tctaaccctg tgcatttgtc ttgggtagta    240
gctcgtgtca gcgagcgaat cccatttcac ttacaaacac aaagtctatg aatgtaacaa    300
atttataaca aacaaaactt tcaacaacgg atctcttggc tctcgcatcg atgaagaacg    360
cagcgaaatg cgatacgtaa tgtgaattgc agaattcagt gaatcatcga atctttgaac    420
gcaccttgcg ctccatggta ttccgtggag catgcctgtt tgagtgtcat gaattcttca    480
acccacctct ttcttagtga atcaggcggt gtttggattc tgagcgttgc tggcttcgcg    540
gcctagctcg ctcgtaatgc attagcatcc gcaatcgaac ttcggattga ctcggcgtaa    600
tagactattc gctgaggatt ctggtctctg actggagccg ggtaagatta aggaagcta    660 ctaatcctca tgtctatctt ttgagattag acctcaaatc aggtaggact a            711

<210> SEQ ID NO 56
<211> LENGTH: 753
<212> TYPE: DNA
<213> ORGANISM: Rhodotourula terpendoidalis

<400> SEQUENCE: 56
cgcccgtcgc tactaccgat tgaatggctt agtgaggcct ccggactggc tattgggatc     60
tcgcgagaga acctgactgc tgggaagttg tacgaacttg gtcatttaga ggaagtaaaa    120
gtcgtaacaa ggtttccgta ggtgaacctg cggaaggatc attaatgaat attagggtgc    180
tcttttcatc aaagaggcct gaccttcatt cttctaccct gtgcactatt caaacattcg    240
gcagttggta atttggcttg taaaagagcc agacgactct gctgaattca ctcttaaact    300
ctaaagtata agaatgttac aaataaaaca aataaaactt tcaacaacgg atctcttggc    360
tctcgcatcg atgaagaacg cagcgaaatg cgataagtaa tgtgaattgc agaattcagt    420
gaatcatcga atctttgaac gcaccttgcg ctcgctggta ttccggcgag catgcctgtt    480
tgagtgtcat gaaaacctca acccttcaat tccttgttga attgtaaggt gtttggattc    540
tgaatgtttg ctggcttgaa gggcccttgg ctacttcaaa agcgaagctc attcgtaata    600
cattagcatc tcaatttcga atattcggat tgactcggcg taatagactt tattcgctga    660
ggacaccttc acaaggtggc cgaatttcga ggtagaagct tccaattcga tcaaaagtca    720
ctcttagttt agacctcaga tcaggcagga cta                                 753

<210> SEQ ID NO 57
<211> LENGTH: 456
<212> TYPE: DNA
<213> ORGANISM: Yarrowia lipolytica

<400> SEQUENCE: 57
```

```
cgcccgtcgc tactaccgat tgaatggttt agtgagacct tgggagggcg agatgagggg      60
ggcaacccct tttgaacatc caaacttggt caaacttgat tatttagagg aagtaaaagt     120
cgtaacaagg tttccgtagg tgaacctgcg aaggatcat tattgatttt atctatttct     180
gtggatttct ggtatattac agcgtcattt tatctcaatt ataactatca acaacggatc     240
tcttggctct cacatcgatg aagaacgcag cgaaccgcga tattttttgt gacttgcaga     300
tgtgaatcat caatctttga acgcacattg cgcggtatgg tattccgtac cgcacggatg     360
gaggagcgtg ttccctctgg gatcgcattg cttttcttgaa atggattttt taaactctca     420
attattacgt catttcacct ccttcatccg agatta                                456

<210> SEQ ID NO 58
<211> LENGTH: 709
<212> TYPE: DNA
<213> ORGANISM: Rhodotorula glutinis

<400> SEQUENCE: 58
cgcccgtcgc tactaccgat tgaatggctt agtgaggcct ccggattggc tattgggagc      60
tcgcgagagc acctgactgc cgagaagttg tacgaacttg gtcatttaga ggaagtaaaa     120
gtcgtaacaa ggtttccgta ggtgaacctg cggaaggatc attagtgaat attagggtgt     180
ccaacttaac ttggaacccg accctcactt tctaaccctg tgcatttgtc ttgggtagta     240
gcttgcgtcg gcgagcgaat cccatttcac ttacaaacac aaagtctatg aatgtaacaa     300
atttataaca aacaaaactt tcaacaacgg atctcttggc tctcgcatcg atgaagaacg     360
cagcgaaatg cgatacgtaa tgtgaattgc agaattcagt gaatcatcga atctttgaac     420
gcaccttgcg ctccatggta ttccgtggag catgcctgtt tgagtgtcat gaattcttca     480
acccacctat ttcttagtga atcaggcggt gtttggattc tgagcgctgc tggcctcacg     540
gcctagctcg ctcgtaatgc attagcatcc gcaatcgaac ttcggattga ctcggcgtaa     600
tagactattc gctgaggatt ctggtctctg actggagccg ggtgagatta aaggaagcta     660
ctaatcctca tgtctatctt gagattagac ctcaaatcag gtaggacta                  709

<210> SEQ ID NO 59
<211> LENGTH: 500
<212> TYPE: DNA
<213> ORGANISM: Yarrowia lipolytica

<400> SEQUENCE: 59
gtccctgccc tttgtacaca ccgcccgtcg ctactaccga ttgaatggtt tagtgagacc      60
ttgggagggc gagatgaggg gggcaacccc ttctgaacat ccaaacttgg tcaaacttga     120
ttatttagag gaagtaaaag tcgtaacaag gtttccgtag gtgaacctgc ggaaggatca     180
ttattgattt tatctatttc tgtggatttc tattctatta cagcgtcatt ttatctcaat     240
tataactatc aacaacggat ctcttggctc tcacatcgat gaagaacgca gcgaaccgcg     300 atatttttg tgacttgcag atgtgaatca tcaatctttg aacgcacatt gcgcggtatg     360
gcattccgta ccgcacggat ggaggagcgt gttccctctg gatcgcatt gctttcttga     420 aatggatttt ttaaactctc aattattacg tcatttcacc tccttcatcc gagattaccc     480
gctgaactta agcatatcaa                                                  500

<210> SEQ ID NO 60
<211> LENGTH: 707
<212> TYPE: DNA
<213> ORGANISM: Lipomyces tetrasporus
```

<400> SEQUENCE: 60

```
cgcccgtcgc tactaccgat tgaatggctt agtgaggcct ccggattggc tattgggagc    60
tcgcgagagc acctgactgc tgagaagttg tacgaacttg gtcatttaga ggaagtaaaa   120
gtcgtaacaa ggtttccgta ggtgaacctg cggaaggatc attagtgaat ctaggacgtc   180
caacttaact tggagtccga atctcacttt ctaaccctg  tgcatctgtt aattggaata   240
gtagctcttc ggagtgaacc accattcact tataaaacac aaagtctatg aatgtataca   300
aatttataac aaaacaaaac tttcaacaac ggatctcttg gctctcgcat cgatgaagaa   360
cgcagcgaaa tgcgatacgt aatgtgaatt gcagaattca gtgaatcatc gaatctttga   420
acgcaccttg cgctccttgg tattccgagg agcatgcctg tttgagtgtc atgaaatctt   480
caacccacct ctttcttagt gaatctggtg gtgcttggtt tctgagcgct gctctgcttc   540
ggcttagctc gttcgtaatg cattagcatc cgcaaccgaa cttcggattg acttggcgta   600
atagactatt cgctgaggat tctagtttac tagagccgag ttgggttaaa ggaagctcct   660
aatcctaaag tctattttttt gattagatct caaatcaggt aggacta              707
```

<210> SEQ ID NO 61
<211> LENGTH: 457
<212> TYPE: DNA
<213> ORGANISM: Yarrowia lipolytica

<400> SEQUENCE: 61

```
cgcccgtcgc tactaccgat tgaatggttt agtgagacct tgggagggcg agatgagggg    60
ggcaacccct tctgaacatc caaacttggt caaacttgat tatttagagg aagtaaaagt   120
cgtaacaagg tttccgtagg tgaacctgcg aaggatcat  tattgatttt atctatttct   180
gtggatttct attctattac agcgtcattt tatctcaatt ataactatca acaacggatc   240
tcttggctct cacatcgatg aagaacgcag cgaaccgcga tatttttgt  gacttgcaga   300
tgtgaatcat caatctttga acgcacattg cgcggtatgg cattccgtac cgcacggatg   360
gaggagcgtg ttccctctgg gatcgcattg ctttcttgaa atggattttt ttaaactctc   420
aattattacg tcatttcacc tccttcatcc gagatta                            457
```

<210> SEQ ID NO 62
<211> LENGTH: 1022
<212> TYPE: DNA
<213> ORGANISM: Lipomyces tetraspo

<400> SEQUENCE: 62

```
cgcccgtcgc tactaccgat tgaatggctt agtgaggcct tcggactggc tccagaaaat    60
gggaaaccat tatcaggagc tggaaagttg gtcaaacttg gtcatttaga ggaagtaaaa   120
gtcgtaacaa ggtttccttc cgtagcactt actgaagctt tagcagcccg aaaaggcgaa   180
tgctagcgac tataaataaa tatggcgttc ttaaatgcta gtctctgatt agaggcgaca   240
ttgccaaatt gcggggacat cctaaagatc ttgataccaa gctggtagtc gaaagacgcc   300
agtggccgag ctaacagccc tgggtatggt aataattcaa gatatggaac aatgggtaat   360
ccgcagccaa gtcctaaact acgcaagtag catggatgca gttcacaggc caaatggtga   420
tgggtagatt actaaatctg cttaagatat ggtcggtccc gctgtgagag cagatgggaa   480
gctacaaagc agactcgtga gtttgcgcaa acgtaactaa aaacgttccg taggtgaacc   540
tgcggaagga tcattactga gtatttgtct tttaaagaca tctctctatc cataaactct   600
```

```
tttttctaaa aagacatgat ttacacaatt agtctgaatg attatataaa aatcttcaaa    660
actttcaaca acggatctct tggttctcgc atcgatgaag aacgcagcaa aatgcgataa    720
gtattgtgaa ttgcaggatt tgtgaatca tcgaattttt gaacgcacat tgcaccttct    780
ggtattccgg agggtatacc tgtttgagcg tcatttatat actcaaaact tcgttttggt    840
gatgggcaca tatctggtga gagctagatt tgcctgaaat atagtggtag agattgctac    900
gagttatgca agttagccaa tgctattaag ttaattcgtt ggtgaagcat gcggagcttt    960
agtgatcgcc ttccttaact attggaattt ttctaatttt gacctcaaat caggcaggag   1020
ta                                                                  1022
```

<210> SEQ ID NO 63
<211> LENGTH: 712
<212> TYPE: DNA
<213> ORGANISM: Rhodosporidium sphaerocarpum

<400> SEQUENCE: 63

```
cgcccgtcgc tactaccgat tgaatggctt agtgaggcct ccggaccggc tattgggagc     60
tcgcgagagc acccgactgc tgggaagttg tacgaacttg gtcatttaga ggaagtaaaa    120
gtcgtaacaa ggtttccgta ggtgaacctg cggaaggatc attagtgaat ataggacgtc    180
caacttaact tggagtccga actctcactt tctaaccctg tgcatttgtt tgggatagta    240
gcctctcggg gtgaactcct attcactcat aaacacaaag tctatgaatg tatttaattt    300
ataacaaaat aaaactttca acaacggatc tcttggctct cgcatcgatg aagaacgcag    360
cgaaatgcga taagtaatgt gaattgcaga attcagtgaa tcatcgaatc tttgaacgca    420
ccttgcgctc catggtattc cgtggagcat gcctgtttga gtgtcatgaa tacttcaacc    480
ctcctctttt ctagtgaaag agaaggtgct tggtttctga gcgttttgct ggcctcacgg    540
tcgagctcgc tcgtaatgca ttagcatccg caatcgaact tcggattgac ttggcgtaat    600
agactattcg ctgaggaatt ctaatcttcg gattagagcc gggttgggtt aaaggaagct    660
tctaatccta atgtctatat ttttagatta gatctcaaat caggtaggac ta            712
```

<210> SEQ ID NO 64
<211> LENGTH: 631
<212> TYPE: DNA
<213> ORGANISM: Trichosporon brassicae

<400> SEQUENCE: 64

```
cgcccgtcgc tactaccgat tgaatggctt agtgagacct ccggattggc gttgagaagc     60
cggcaacggc atctcttggc cgagaagttg gtcaaacttg gtcatttaga ggaagtaaaa    120
gtcgtaacaa ggtttccgta ggtgaacctg cggaaggatc attagtgatt gccttaattg    180
gcttaaacta tatccaacta cacctgtgaa ctgttcgatt gaatcttcga ttcaattttta    240 caaacattgt gtaaagaacg tcattagatc ataacaaaaa aaactttta acaacggatc    300 tcttggctct cgcatcgatg aagaacgcag cgaaatgcga taagtaatgt gaattgcaga    360
attcagtgaa tcatcgaatc tttgaacgca acttgcgctc tctggtattc cggagagcat    420
gcctgtttga gtgtcatgaa atctcacaca tcaaggtttc ttgatgaagt ggatttggag    480
gttgccagtc taactggctc ctcttaaagg agttagcata tttgattatt gctgtctggc    540
gtaataagtt tcgctagttt ggcattttga agtgtgcttc taatcgtctt cggacaattt    600
tttgactctg gcctcaaatc aggtaggact a                                   631
```

<210> SEQ ID NO 65
<211> LENGTH: 627
<212> TYPE: DNA
<213> ORGANISM: Cryptococcus curvatus

<400> SEQUENCE: 65

| | | | | |
|---|---|---|---|---|
| cgcccgtcgc | tactaccgat | tgaatggctt | agtgagattt | ccggattggc | gttaggaagc | 60 |
| cggcaacggc | atcctttggc | tgagaagcta | ctcaaacttg | gtcatttaga | ggaagtaaaa | 120 |
| gtcgtaacaa | ggtttccgta | ggtgaacctg | cggaaggatc | attagtgatt | tgccttcggg | 180 |
| ctaactatat | ccataacacc | tgtgaactgt | tgattgactt | cggtcaatat | ttttacaaac | 240 |
| attgtgtaat | gaacgtcatg | ttataataac | aaatataact | ttcaacaacg | gatctcttgg | 300 |
| ctctcgcatc | gatgaagaac | gcagcgaaat | gcgataagta | atgtgaattg | cagaattcag | 360 |
| tgaatcatcg | aatctttgaa | cgcaacttgc | gctctctggt | attccggaga | gcatgcctgt | 420 |
| ttgagtgtca | tgaaatctca | accattaggg | tttcttaatg | gcttggattt | ggacgtttgc | 480 |
| cagtcaaatg | gctcgtctta | aaagagttag | tgaatttaac | atttgtcttc | tggcgtaata | 540 |
| agtttcgctg | ggctgatagt | gtgaagtttg | cttctaatcg | tccgcaagga | caattcttga | 600 |
| actctggcct | caaatcaggt | aggacta | | | | 627 |

<210> SEQ ID NO 66
<211> LENGTH: 637
<212> TYPE: DNA
<213> ORGANISM: Lipomyces starkeyi

<400> SEQUENCE: 66

| | | | | | | |
|---|---|---|---|---|---|---|
| cgcccgtcgc | tactaccgat | tgaatggctt | agtgaggcct | tcggactggc | tccagaaaat | 60 |
| gggaaaccat | tatcaggagc | tggaaagttg | gtcaaacttg | gtcatttaga | ggaagtaaaa | 120 |
| gtcgtaacaa | ggtttccgta | ggtgaacctg | cggaaggatc | attactgagt | atttgtcttt | 180 |
| tcaagacatc | tctctatcca | taaactcttt | tttttaaaaa | gacatgattt | ataacaatta | 240 |
| gtctgaatga | ttatttttaa | atcttcaaaa | ctttcaacaa | cggatctctt | ggttctcgca | 300 |
| tcgatgaaga | acgcagcaaa | ttgcgataag | taatgtgaat | tgcaggattt | tgtgaatcat | 360 |
| cgaattttg | aacgcacatt | gcaccttctg | gtattccgga | gggtatacct | gtttgagcgt | 420 |
| catttatata | ctcaaaactt | acgttttggt | gatgggcacg | tatctggctt | ctaagttaga | 480 |
| tttgcctgaa | atatagcggt | agaggtcgct | agaagcgatg | caagttagcc | aatgctatta | 540 |
| aagttaattc | gttggtgacg | catgttgagc | ttttggtgaa | gtcttcctta | attattggaa | 600 |
| ttttttttcta | attttgacct | caaatcaggc | aggagta | | | 637 |

<210> SEQ ID NO 67
<211> LENGTH: 457
<212> TYPE: DNA
<213> ORGANISM: Yarrowia lipolytica

<400> SEQUENCE: 67

| | | | | | | |
|---|---|---|---|---|---|---|
| cgcccgtcgc | tactaccgat | tgaatggttt | agtgagacct | tgggagggcg | agatgagggg | 60 |
| ggcaaccct | tttgaacatc | caaacttggt | caaacttgat | tatttagagg | aagtaaaagt | 120 |
| cgtaacaagg | tttccgtagg | tgaacctgcg | gaaggatcat | tattgatttt | atctatttct | 180 |
| gtggatttct | attctattac | agcgtcattt | tatctcaatt | ataactatca | caacggatc | 240 |
| tcttggctct | cacatcgatg | aagaacgcag | cgaaccgcga | tattttttgt | gacttgcaga | 300 |
| tgtgaatcat | caatctttga | acgcacattg | cgcggtatgg | cattccgtac | cgcacggatg | 360 |

```
gaggagcgtg ttccctctgg gatcgcattg ctttcttgaa atggattttt ttaaactctc      420
aattattacg tcatttcacc tccttcatcc gagatta                              457
```

<210> SEQ ID NO 68
<211> LENGTH: 631
<212> TYPE: DNA
<213> ORGANISM: Trichosporon loubieri

<400> SEQUENCE: 68

```
cgcccgtcgc tactaccgat tgaatggctt agtgagacct ccggattggc gttgagaagc       60
cggcaacggc atctcttggc cgagaagttg gtcaaacttg gtcatttaga ggaagtaaaa      120
gtcgtaacaa ggtttccgta ggtgaacctg cggaaggatc attagtgatt gccatcttgg      180
cttaaactat atccatctac acctgtgaac cgtttgattg aatcttctga ttcaatttta      240
caaacattgt gtaatgaacg tcattagatc ataataagaa aaaactttca acaacggatc      300
tcttggctct cgcatcgatg aagaacgcag cgaaatgcga taagtaatgt gaattgcaga      360
attcagtgaa tcatcgaatc tttgaacgca acttgcgctc tctggtattc cggagagcat      420
gcctgtttga gtgtcatgaa atctcaacca ttagggtttc ttaatggctt ggatttggag      480
gttgccattc taaatggctc ctcttaaaag agttagcgag tttaactatt gctatctggc      540
gtaataagtt tcgctggaat ggtattgtga agcgcgcttc taatcgtctt cggacaattt      600
tttgactctg gcctcaaatc aggtaggact a                                    631
```

<210> SEQ ID NO 69
<211> LENGTH: 476
<212> TYPE: DNA
<213> ORGANISM: Geotrichum vulgare

<400> SEQUENCE: 69

```
cgcccgtcgc tactaccgat tgaatggctt agtgaggctt ccggattgat tagttggaga       60
gggagacttt tctgactgaa cgagaagcta gtcaaacttg gtcatttaga ggaagtaaaa      120
gtcgtaacaa ggtttccgta ggtgaacctg cggaaggatc attaaagatt taatattaat      180
tgtgaaatta aaacgatatt aacaaaaaat catacaatca attataaaaa aaatcaaaac      240
ttttaacaat ggatctcttg gttctcgtat cgatgaagaa cgcagcgaaa cgcgatattt      300
cttgtgaatt gcagaagtga atcatcagtt tttgaacgca cattgcactt tggggtatcc      360
cccaaagtat acttgtttga gcgttgtttc tctcttggaa ttgcattgct tttctaaaaa      420
atcgaatcaa attcgtttga acatccatt cttcaacctc agatcaagta ggatta          476
```

<210> SEQ ID NO 70
<211> LENGTH: 710
<212> TYPE: DNA
<213> ORGANISM: Rhodosporidium toruloides

<400> SEQUENCE: 70

```
cgcccgtcgc tactaccgat tgaatggctt agtgaggcct ccggattggc tattgggagc       60
tcgcgagagc acctgactgc cgagaagttg tacgaacttg gtcatttaga ggaagtaaaa      120
gtcgtaacaa ggtttccgta ggtgaacctg cggaaggatc attagtgaat attagggtgt      180
ccaacttaac ttggagcccg accctcactt tctaaccctg tgcatttgtc ttgggtagta      240
gcttgcgtca gcgagcgaat cccatttcac ttacaaacac aaagtctatg aatgtaacaa      300
atttataaca aaacaaaaact ttcaacaacg gatctcttgg ctctcgcatc gatgaagaac      360
gcagcgaaat gcgatacgta atgtgaattg cagaattcag tgaatcatcg aatctttgaa      420
```

```
cgcaccttgc gctccatggt attccgtgga gcatgcctgt ttgagtgtca tgaattcttc      480
aacccacctc tttcttagtg aatcaggcgg tgtttggatt ctgagcgctg ctggcttcgc      540
ggcctagctc gctcgtaatg cattagcatc cgcaatcgaa cttcggattg actcggcgta      600
atagactatt cgctgaggat tctggtctct gactggagcc gggtaaggtt aaagggagct      660
actaatcctc atgtctatct tgagattaga cctcaaatca ggtaggacta                 710

<210> SEQ ID NO 71
<211> LENGTH: 707
<212> TYPE: DNA
<213> ORGANISM: Rhodotorula glutinis

<400> SEQUENCE: 71
cgcccgtcgc tactaccgat tgaatggctt agtgaggcct ccggattggc tattgggagc       60
tcgcgagagc acctgactgc tgagaagttg tacgaacttg gtcatttaga ggaagtaaaa      120
gtcgtaacaa ggtttccgta ggtgaacctg cggaaggatc attagtgaat ctaggacgtc      180
caacttaact tggagtccga actctcactt tctaaccctg tgcatctgtt aattggaata      240
gtagctcttc ggagtgaacc accattcact tataaaacac aaagtctatg aatgtataca      300
aatttataac aaaacaaaac tttcaacaac ggatctcttg gctctcgcat cgatgaagaa      360
cgcagcgaaa tgcgatacgt aatgtgaatt gcagaattca gtgaatcatc gaatctttga      420
acgcaccttg cgctccttgg tattccgagg agcatgcctg tttgagtgtc atgaaatctt      480
caacccacct ctttcttagt gaatctggtg gtgcttggtt tctgagcgct gctctgcttc      540
ggcttagctc gttcgtaatg cattagcatc cgcaccgaa cttcggattg acttggcgta       600
atagactatt cgctgaggat tctagtttac tagagccgag ttgggttaaa ggaagctcct      660
aatcctaaag tctatttttt gattagatct caaatcaggt aggacta                    707

<210> SEQ ID NO 72
<211> LENGTH: 627
<212> TYPE: DNA
<213> ORGANISM: Rhodotorula aurantiaca

<400> SEQUENCE: 72
cgcccgtcgc tactaccgat tgaatggctt agtgagattt ccggattggc gttaggaagc       60
cggcaacggc atcctttggc tgagaagcta ctcaaacttg gtcatttaaa ggaagtaaaa      120
gtcgtaacaa ggtttccgta ggtgaacctg cggaaggatc attagtgatt tgccttcggg      180
ctaactatat ccataacacc tgtgaactgt tgattgactt cggtcaatat ttttacaaac      240
attgtgtaat gaacgtcatg ttataataac aaatataact ttcaacaacg gatctcttgg      300
ctctcgcatc gatgaagaac gcagcgaaat gcgataagta atgtgaattg cagaattcag      360
tgaatcatcg aatctttgaa cgcaacttgc gctctctggt attccggaga gcatgcctgt      420
ttgagtgtca tgaaatctca accattaggg tttcttaatg gcttgatttt ggacgtttgc      480
cagtcaaatg gctcgtctta aaagagttag tgaatttaac atttgtcttc tggcgtaata      540
agtttcgctg ggctgatagt gtgaagtttg cttctaatcg tccgcaagga caattcttga      600
actctggcct caaatcaggt aggacta                                          627

<210> SEQ ID NO 73
<211> LENGTH: 899
<212> TYPE: DNA
<213> ORGANISM: Torulaspora delbrueckii
```

<400> SEQUENCE: 73

```
cgcccgtcgc tagtaccgat tgaatggctt agtgaggcct caggatctgc ttagagaagg      60
gggcaactcc atctcagagc ggagaatctg gtcaaacttg gtcatttaga ggaactaaaa     120
gtcgtaacaa ggtttccgta ggtgaacctg cggaaggatc attagagaaa tctatatgaa     180
tgaagttaga ggacgtctaa agatactgta agagaggatc aggttcaaga ccagcgctta     240
attgcgcggt tgcggcttgg ttcgccttt gcggaacatg tcttttctcg ttgttaactc      300
tacttcaact tctacaacac tgtggagttt tctacacaac ttttcttctt tgggaagata     360
cgtcttgtgc gtgcttccca gaggtgacaa acacaaacaa cttttttatta ttataaacca    420
gtcaaaacca atttcgttat gaaattaaaa atatttaaaa ctttcaacaa cggatctctt     480
ggttctcgca tcgatgaaga acgcagcgaa atgcgatacg taatgtgaat tgcagaattc     540
cgtgaatcat cgaatctttg aacgcacatt gcgccccttg gtattccagg gggcatgcct     600
gtttgagcgt catttccttc tcaaacaatc atgtttggta gtgagtgata ctctgtcaag     660
ggttaacttg aaattgctag cctgttattt ggttgtgatt ttgctggctt ggatgacttt     720
gtccagtcta gctaataccg aattgtcgta ttaggtttta ccaacttcgg cagactgtgt     780
gttggctcgg gcgctttaaa gactttgtcg taaacgattt atcgtttgtt tgagcttttc     840
gcatacgcaa tccgggcgaa caatactctc aaagtttgac ctcaaatcag gtaggaata     899
```

<210> SEQ ID NO 74
<211> LENGTH: 20
<212> TYPE: DNA
<213> ORGANISM: Prototheca moriformis

<400> SEQUENCE: 74

```
tcacttcatg ccggcggtcc                                                  20
```

<210> SEQ ID NO 75
<211> LENGTH: 20
<212> TYPE: DNA
<213> ORGANISM: Prototheca moriformis

<400> SEQUENCE: 75

```
gcgctcctgc ttggctcgaa                                                  20
```

<210> SEQ ID NO 76
<211> LENGTH: 733
<212> TYPE: DNA
<213> ORGANISM: Artificial Sequence
<220> FEATURE:
<223> OTHER INFORMATION: gene targeting sequence

<400> SEQUENCE: 76

```
gctcttcgag acgtggtctg aatcctccag gcgggtttcc ccgagaaaga aagggtgccg      60
atttcaaagc agagccatgt gccgggccct gtggcctgtg ttggcgccta tgtagtcacc     120
cccctcacc caattgtcgc cagtttgcgc aatccataaa ctcaaaactg cagcttctga      180
gctgcgctgt tcaagaacac ctctgggggtt tgctcacccg cgaggtcgac gcccagcatg    240
gctatcaaga cgaacaggca gcctgtggag aagcctccgt tcacgatcgg gacgctgcgc    300
aaggccatcc ccgcgcactg tttcgagcgc tcggcgcttc gtagcagcat gtacctggcc    360
tttgacatcg cggtcatgtc cctgctctac gtcgcgtcga cgtacatcga ccctgcgccg    420
gtgcctacgt gggtcaagta tggcgtcatg tggccgctct actggttctt ccaggtgtgt    480
gtgagggttg tggttgcccg tatcgaggtc ctggtggcgc gcatggggga aaggcgcct    540
```

```
gtcccgctga cccccccggc taccctcccg gcaccttcca gggcgccttc ggcacgggtg    600
tctgggtgtg cgcgcacgag tgcggccacc aggccttttc ctccagccag ccatcaacg     660 acggcgtggg cctggtgttc cacagcctgc tgctggtgcc ctactactcc tggaagcact    720
cgcaccgggt acc                                                        733

<210> SEQ ID NO 77
<211> LENGTH: 739
<212> TYPE: DNA
<213> ORGANISM: Artificial Sequence
<220> FEATURE:
<223> OTHER INFORMATION: gene targeting sequence

<400> SEQUENCE: 77
ccgccaccac tccaacacgg ggtgcctgga caaggacgag gtgtttgtgc cgccgcaccg     60
cgcagtggcg cacgagggcc tggagtggga ggagtggctg cccatccgca tgggcaaggt    120
gctggtcacc ctgaccctgg gctggccgct gtacctcatg ttcaacgtcg cctcgcggcc    180
gtacccgcgc ttcgccaacc actttgaccc gtggtcgccc atcttcagca agcgcgagcg    240
catcgaggtg gtcatctccg acctggcgct ggtggcggtg ctcagcgggc tcagcgtgct    300
gggccgcacc atgggctggg cctggctggt caagacctac gtggtgccct acctgatcgt    360
gaacatgtgg ctcgtgctca tcacgctgct ccagcacacg cacccggcgc tgccgcacta    420
cttcgagaag gactgggact ggctgcgcgg cgccatggcc accgtggacc gctccatggg    480
cccgcccttc atggacaaca tcctgcacca catctccgac acccacgtgc tgcaccacct    540
cttcagcacc atcccgcact accacgccga ggaggcctcc gccgccatca ggcccatcct    600
gggcaagtac taccagtccg cacagccgct ggtcggccgc gccctgtggg aggactggcg    660
cgactgccgc tacgtcgtcc cggacgcgcc cgaggacgac tccgcgctct ggttccacaa    720
gtgagtgagt gagaagagc                                                  739

<210> SEQ ID NO 78
<211> LENGTH: 2327
<212> TYPE: DNA
<213> ORGANISM: Saccharomyces cerevisiae

<400> SEQUENCE: 78 cttcttgcg ctatgacact tccagcaaaa ggtagggcgg gctgcgagac ggcttcccgg      60
cgctgcatgc aacaccgatg atgcttcgac cccccgaagc tccttcgggg ctgcatgggc    120
gctccgatgc cgctccaggg cgagcgctgt ttaaatagcc aggcccccga ttgcaaagac    180
attatagcga gctaccaaag ccatattcaa acacctagat cactaccact tctacacagg    240
ccactcgagc ttgtgatcgc actccgctaa ggggcgcct cttcctcttc gtttcagtca     300
caacccgcaa acggcgcgcc atgctgctgc aggccttcct gttcctgctg ccggcttcg     360 ccgccaagat cagcgcctcc atgacgaacg agacgtccga ccgcccctg gtgcacttca     420 cccccaacaa gggctggatg aacgaccca acggcctgtg gtacgacgag aaggacgcca     480
agtggcacct gtacttccag tacaacccga acgacaccgt ctgggggacg cccttgttct    540
ggggccacgc cacgtccgac gacctgacca actggggagga ccagcccatc gccatcgccc    600
cgaagcgcaa cgactccggc gccttctccg gctccatggt ggtggactac aacaacacct    660
ccggcttctt caacgacacc atcgaccgc gccagcgctg cgtggccatc tggacctaca    720
acaccccgga gtccgaggag cagtacatct cctacagcct ggacgggcgc tacacctcta    780
```

```
ccgagtacca agaaccccc gtgctggccg ccaactccac ccagttccgc gacccgaagg      840
tcttctggta cgagccctcc cagaagtgga tcatgaccgc ggccaagtcc caggactaca      900
agatcgagat ctactcctcc gacgacctga agtcctggaa gctggagtcc gcgttcgcca      960
acgagggctt cctcggctac cagtacgagt gccccggcct gatcgaggtc cccaccgagc     1020 aggacccag caagtcctac tgggtgatgt tcatctccat caaccccggc gccccggccg      1080
gcggctcctt caaccagtac ttcgtcggca gcttcaacgg cacccacttc gaggccttcg     1140
acaaccagtc ccgcgtggtg gacttcggca aggactacta cgccctgcag accttcttca     1200
acaccgaccc gacctacggg agcgccctgg gcatcgcgtg ggcctccaac tgggagtact     1260
ccgccttcgt gcccaccaac ccctggcgct cctccatgtc cctcgtgcgc aagttctccc     1320
tcaacaccga gtaccaggcc aacccggaga cggagctgat caacctgaag gccgagccga     1380
tcctgaacat cagcaacgcc ggcccctgga gccggttcgc caccaacacc acgttgacga     1440
aggccaacag ctacaacgtc gacctgtcca acagcaccgg cacccctgag ttcgagctgg     1500
tgtacgccgt caacaccacc cagacgatct ccaagtccgt gttcgcggac ctctccctct     1560
ggttcaaggg cctggaggac cccgaggagt acctccgcat gggcttcgag gtgtccgcgt     1620
cctccttctt cctggaccgc gggaacagca aggtgaagtt cgtgaaggag aacccctact     1680
tcaccaaccg catgagcgtg aacaaccagc ccttcaagag cgagaacgac ctgtcctact     1740
acaaggtgta cggcttgctg gaccagaaca tcctggagct gtacttcaac gacggcgacg     1800
tcgtgtccac caacacctac ttcatgacca ccgggaacgc cctgggctcc gtgaacatga     1860 cgacggggt ggacaacctg ttctacatcg acaagttcca ggtgcgcgag gtcaagtgac     1920
aattggcagc agcagctcgg atagtatcga cacactctgg acgctggtcg tgtgatggac     1980
tgttgccgcc acacttgctg ccttgacctg tgaatatccc tgccgctttt atcaaacagc     2040
ctcagtgtgt ttgatcttgt gtgtacgcgc ttttgcgagt tgctagctgc ttgtgctatt     2100
tgcgaatacc ccccccagca tcccttccc tcgtttcata tcgcttgcat cccaaccgca     2160
acttatctac gctgtcctgc tatccctcag cgctgctcct gctcctgctc actgccctc     2220 gcacagcctt ggtttgggct ccgcctgtat tctcctggta ctgcaacctg taaaccagca     2280
ctgcaatgct gatgcacggg aagtagtggg atgggaacac aaatgga                  2327
```

<210> SEQ ID NO 79
<211> LENGTH: 735
<212> TYPE: DNA
<213> ORGANISM: Artificial Sequence
<220> FEATURE:
<223> OTHER INFORMATION: gene targeting sequence

<400> SEQUENCE: 79

```
gctcttcgag gggctggtct gaatccttca ggcgggtgtt acccgagaaa gaaagggtgc       60
cgatttcaaa gcagacccat gtgccgggcc ctgtggcctg tgttggcgcc tatgtagtca      120
ccccccctca cccaattgtc gccagtttgc gcactccata aactcaaaac agcagcttct      180
gagctgcgct gttcaagaac acctctgggg tttgctcacc cgcgaggtcg acgcccagca      240
tggctatcaa gacgaacagg cagcctgtgg agaagcctcc gttcacgatc gggacgctgc      300
gcaaggccat ccccgcgcac tgtttcgagc gctcggcgct tcgtagcagc atgtacctgg      360
cctttgacat cgcggtcatg tccctgctct acgtcgcgtc gacgtacatc gaccctgcac      420
cggtgcctac gtgggtcaag tacggcatca tgtggccgct ctactggttc ttccaggtgt      480
gtttgagggt tttggttgcc cgtattgagg tcctggtggc gcgcatggag gagaaggcgc      540
```

```
ctgtcccgct gaccccccg gctaccctcc cggcaccttc cagggcgcct tcggcacggg        600
tgtctgggtg tgcgcgcacg agtgcggcca ccaggccttt tcctccagcc aggccatcaa        660
cgacggcgtg ggcctggtgt tccacagcct gctgctggtg ccctactact cctggaagca        720
ctcgcaccgg gtacc                                                          735
```

<210> SEQ ID NO 80
<211> LENGTH: 739
<212> TYPE: DNA
<213> ORGANISM: Artificial Sequence
<220> FEATURE:
<223> OTHER INFORMATION: gene targeting sequence

<400> SEQUENCE: 80

```
ccgccaccac tccaacacgg ggtgcctgga caaggacgag gtgtttgtgc cgccgcaccg        60
cgcagtggcg cacgagggcc tggagtggga ggagtggctg cccatccgca tgggcaaggt       120
gctggtcacc ctgaccctgg gctggccgct gtacctcatg ttcaacgtcg cctcgcggcc       180 gtaccgcgc ttcgccaacc actttgaccc gtggtcgccc atcttcagca agcgcgagcg        240
catcgaggtg gtcatctccg acctggcgct ggtggcggtg ctcagcgggc tcagcgtgct       300
gggccgcacc atgggctggg cctggctggt caagacctac gtggtgccct acctgatcgt       360
gaacatgtgg ctcgtgctca tcacgctgct ccagcacacg cacccggcgc tgccgcacta       420
cttcgagaag gactgggact ggctgcgcgg cgccatggcc accgtggacc gctccatggg       480
cccgcccttc atggacaaca tcctgcacca catctccgac acccacgtgc tgcaccacct       540
cttcagcacc atcccgcact accacgccga ggaggcctcc gccgccatca ggcccatcct       600
gggcaagtac taccagtccg acagccgctg ggtcggccgc gccctgtggg aggactggcg       660
cgactgccgc tacgtcgtcc cggacgcgcc cgaggacgac tccgcgctct ggttccacaa       720
gtgagtgagt gagaagagc                                                    739
```

<210> SEQ ID NO 81
<211> LENGTH: 726
<212> TYPE: DNA
<213> ORGANISM: Artificial Sequence
<220> FEATURE:
<223> OTHER INFORMATION: genomic donor sequence

<400> SEQUENCE: 81

```
gctcttcgcc gccgccactc ctgctcgagc gcgcccgcgc gtgcgccgcc agcgccttgg        60 cctttttcgcc gcgctcgtgc gcgtcgctga tgtccatcac caggtccatg aggtctgcct      120
tgcgccggct gagccactgc ttcgtccggg cggccaagag gagcatgagg gaggactcct       180
ggtccagggt cctgacgtgg tcgcggctct gggagcgggc cagcatcatc tggctctgcc       240
gcaccgaggc cgcctccaac tggtcctcca gcagccgcag tcgccgccga ccctggcaga       300
ggaagacagg tgagggggt atgaattgta cagaacaacc acgagcctig tctaggcaga        360 atccctacca gtcatggctt tacctggatg acggcctgcg aacagctgtc cagcgaccct       420
cgctgccgcc gcttctcccg cacgcttctt tccagcaccg tgatggcgcg agccagcgcc       480
gcacgctggc gctgcgcttc gccgatctga ggacagtcgg ggaactctga tcagtctaaa       540
cccccttgcg cgttagtgtt gccatccttt gcagaccggt gagagccgac ttgttgtgcg       600 ccaccccca caccacctcc tcccagacca attctgtcac cttttttggcg aaggcatcgg       660 cctcggcctg cagagaggac agcagtgccc agccgctggg ggttggcgga tgcacgctca      720
``` ggtacc 726

<210> SEQ ID NO 82
<211> LENGTH: 3635
<212> TYPE: DNA
<213> ORGANISM: Artificial Sequence
<220> FEATURE:
<223> OTHER INFORMATION: relevant expression construct

<400> SEQUENCE: 82

| | |
|---|---|
| ctttcttgcg ctatgacact tccagcaaaa ggtagggcgg gctgcgagac ggcttcccgg | 60 |
| cgctgcatgc aacaccgatg atgcttcgac cccccgaagc tccttcgggg ctgcatgggc | 120 |
| gctccgatgc cgctccaggg cgagcgctgt ttaaatagcc aggcccccga ttgcaaagac | 180 |
| attatagcga gctaccaaag ccatattcaa acacctagat cactaccact tctacacagg | 240 |
| ccactcgagc ttgtgatcgc actccgctaa gggggcgcct cttcctcttc gtttcagtca | 300 |
| caacccgcaa actctagaat atcaatgatc gagcaggacg gcctccacgc cggctccccc | 360 |
| gccgcctggg tggagcgcct gttcggctac gactgggccc agcagaccat cggctgctcc | 420 |
| gacgccgccg tgttccgcct gtccgcccag gccgcccccg tgctgttcgt gaagaccgac | 480 |
| ctgtccggcc cctgaacga gctgcaggac gaggccgccc gctgtcctg gctggccacc | 540 |
| accggcgtgc cctgcgccgc cgtgctggac gtggtgaccg aggccggccg cgactggctg | 600 |
| ctgctgggcg aggtgcccgg ccaggacctg ctgtcctccc acctggcccc cgccgagaag | 660 |
| gtgtccatca tggccgacgc catgcgccgc ctgcacaccc tggacccgc cacctgcccc | 720 |
| ttcgaccacc aggccaagca ccgcatcgag cgcgcccgca cccgcatgga ggccggcctg | 780 |
| gtggaccagg acgacctgga cgaggagcac cagggcctgg cccccgccga gctgttcgcc | 840 |
| cgcctgaagg cccgcatgcc cgacggcgag gacctggtgg tgacccacgg cgacgcctgc | 900 |
| ctgcccaaca tcatggtgga aaacggccgc ttctccggct catcgactg cggccgcctg | 960 |
| ggcgtggccg accgctacca ggacatcgcc ctggccaccc gcgacatcgc cgaggagctg | 1020 |
| ggcggcgagt gggccgaccg cttcctggtg ctgtacggca tcgccgcccc cgactcccag | 1080 |
| cgcatcgcct tctaccgcct gctggacgag ttcttctgac aattggcagc agcagctcgg | 1140 |
| atagtatcga cacactctgg acgctggtcg tgtgatggac tgttgccgcc acacttgctg | 1200 |
| ccttgacctg tgaatatccc tgccgctttt atcaaacagc ctcagtgtgt ttgatcttgt | 1260 |
| gtgtacgcgc ttttgcgagt tgctagctgc ttgtgctatt tgcgaatacc accccagca | 1320 |
| tccccttccc tcgtttcata tcgcttgcat cccaaccgca acttatctac gctgtcctgc | 1380 |
| tatccctcag cgctgctcct gctcctgctc actgcccctc gcacagcctt ggtttgggct | 1440 |
| ccgcctgtat tctcctggta ctgcaacctg taaaccagca ctgcaatgct gatgcacggg | 1500 |
| aagtagtggg atgggaacac aaatggagga tcccgcgtct cgaacagagc gcgcagagga | 1560 |
| acgctgaagg tctcgcctct gtcgcacctc agcgcggcat acaccacaat aaccacctga | 1620 |
| cgaatgcgct tggttcttcg tccattagcg aagcgtccgg ttcacacacg tgccacgttg | 1680 |
| gcgaggtggc aggtgacaat gatcggtgga gctgatggtc gaaacgttca cagcctaggg | 1740 |
| atatcgaatt cctttcttgc gctatgacac ttccagcaaa aggtagggcg gctgcgaga | 1800 |
| cggcttcccg gcgctgcatg caacaccgat gatgcttcga ccccccgaag ctccttcggg | 1860 |
| gctgcatggg cgctccgatg ccgctccagg gcgagcgctg tttaaatagc caggcccccg | 1920 |
| attgcaaaga cattatagcg agctaccaaa gccatattca aacacctaga tcactaccac | 1980 |
| ttctacacag gccactcgag cttgtgatcg cactccgcta agggggcgcc tcttcctctt | 2040 |

```
cgtttcagtc acaacccgca aacactagta tggccaccgc atccactttc tcggcgttca    2100
atgcccgctg cggcgacctg cgtcgctcgg cgggctccgg gccccggcgc ccagcgaggc    2160
ccctccccgt gcgcgggcgc gcccccgact ggtccatgct gttcgccgtg atcaccacca    2220
tcttctccgc cgccgagaag cagtggacca acctggagtg gaagcccaag cccaaccccc    2280
cccagctgct ggacgaccac ttcggccccc acggcctggt gttccgccgc accttcgcca    2340
tccgcagcta cgaggtgggc cccgaccgct ccaccagcat cgtggccgtg atgaaccacc    2400
tgcaggaggc cgccctgaac cacgccaagt ccgtgggcat cctgggcgac ggcttcggca    2460
ccaccctgga gatgtccaag cgcgacctga tctgggtggt gaagcgcacc cacgtggccg    2520
tggagcgcta ccccgcctgg ggcgacaccg tggaggtgga gtgctgggtg gcgcctccg    2580
gcaacaacgg ccgccgccac gacttcctgg tgcgcgactg caagaccggc gagatcctga    2640
cccgctgcac ctccctgagc gtgatgatga cacccgcac ccgccgcctg agcaagatcc    2700
ccgaggaggt gcgcggcgag atcggcccg ccttcatcga caacgtggcc gtgaaggacg    2760
aggagatcaa gaagccccag aagctgaacg actccaccgc cgactacatc cagggcggcc    2820
tgacccccg ctggaacgac ctggacatca accagcacgt gaacaacatc aagtacgtgg    2880
actggatcct ggagaccgtg cccgacagca tcttcgagag ccaccacatc tcctccttca    2940
ccatcgagta ccgccgcgag tgcaccatgg acagcgtgct gcagtccctg accaccgtga    3000
gcggcggctc ctccgaggcc ggcctggtgt gcgagcacct gctgcagctg agggcggca    3060
gcgaggtgct gcgcgccaag accgagtggc gccccaagct gaccgactcc ttccgcggca    3120
tcagcgtgat ccccgccgag tccagcgtga tggactacaa ggaccacgac ggcgactaca    3180
aggaccacga catcgactac aaggacgacg acgacaagtg actcgaggca gcagcagctc    3240
ggatagtatc gacacactct ggacgctggt cgtgtgatgg actgttgccg ccacacttgc    3300
tgccttgacc tgtgaatatc cctgccgctt ttatcaaaca gcctcagtgt gtttgatctt    3360
gtgtgtacgc gcttttgcga gttgctagct gcttgtgcta tttgcgaata ccaccccag    3420
catcccttc cctcgtttca tatcgcttgc atcccaaccg caacttatct acgctgtcct    3480
gctatccctc agcgctgctc ctgctcctgc tcactgcccc tcgcacagcc ttggtttggg    3540
ctccgcctgt attctcctgg tactgcaacc tgtaaaccag cactgcaatg ctgatgcacg    3600
ggaagtagtg ggatgggaac acaaatggaa agctt                              3635

<210> SEQ ID NO 83
<211> LENGTH: 1096
<212> TYPE: DNA
<213> ORGANISM: Prototheca moriformis

<400> SEQUENCE: 83
ccaggcaggc ggtagggttg ccgattgctt gagcgaattg gaagatataa ttttttgtgg      60
tgtccctgga cgctgtttgt ggcgctcctt tttggagaag attgcgtggg ggagctttcc     120
atgtaccacg cttccttctg aaaggattct ggccgagtcc tgatgagccc aaagaaaaca     180
cctgcctttc agtgctggca ctctgaaaac gtcaacagat gattatacat gtcacaaaag     240
gcagccgatt aggaacggga gctctggccg ttcgtttggc tgcctgggct gattgaagtg     300
atccaccctg ttcgaatgaa ggcggtcgag tcgaattatc gaccggagct gtcgggaagg     360
cgtccggggc agagtgaggt gctgcggcct ggttgtcgtt caaaaagacc ccggtagccc     420
aacaatcacg aacgaaagga atataattgc ttgcatacta tacattcagt ttctatgtgg     480
```

| | |
|---|---|
| cgggtagaca agtctcatgg gcttctaaag gctgtcccttt gaaggctact tataaaaact | 540 |
| tgctgcgcca tggcacggat cgcgcttgcg caggctgcaa ccctgcgcgc aaggtcaaat | 600 |
| acacagcaaa agatactaac agaatttcta aaaacattta aatatttgtt tcgaccagcc | 660 |
| aattgtggtc gtaggcacgc aaaagacttt gttttgcgcc caccgagcat ccacgctggc | 720 |
| agtcaagcca gtccgatgtg cattgcgtgg cagcatcgag gagcatcaaa aacctcgtgc | 780 |
| acgcttttct gtcaatcatc atcaaccact ccaccatgta tacccgatgc atcgcggtgc | 840 |
| gcagcgcgcc acgcgtccca gacccgccca aaaacccagc agcggcgaaa gcaaatcttc | 900 |
| acttgcccga aaccccgagc agcggcattc acacgtgggc gaaaacccca cttgccctaa | 960 |
| caggcgtatg tctgctgtca cgatgcctga caacggtatt atagatatac actgattaat | 1020 |
| gtttgagtgt gtgcgagtcg cgaatcagga atgaattgct agtaggcact ccgaccgggc | 1080 |
| gggggccgag ggacca | 1096 |

<210> SEQ ID NO 84
<211> LENGTH: 1065
<212> TYPE: DNA
<213> ORGANISM: Prototheca moriformis

<400> SEQUENCE: 84

| | |
|---|---|
| ggccgacagg acgcgcgtca aaggtgctgg tcgtgtatgc cctggccggc aggtcgttgc | 60 |
| tgctgctggt tagtgattcc gcaaccctga ttttggcgtc ttattttggc gtggcaaacg | 120 |
| ctggcgcccg cgagccgggc cggcggcgat gcggtgcccc acggctgccg gaatccaagg | 180 |
| gaggcaagag cgcccgggtc agttgaaggg ctttacgcgc aaggtacagc cgctcctgca | 240 |
| aggctgcgtg gtggaattgg acgtgcaggt cctgctgaag ttcctccacc gcctcaccag | 300 |
| cggacaaagc accggtgtat caggtccgtg tcatccactc taaagagctc gactacgacc | 360 |
| tactgatggc cctagattct tcatcaaaaa cgcctgagac acttgcccag gattgaaact | 420 |
| ccctgaaggg accaccaggg gccctgagtt gttccttccc ccgtggcga gctgccagcc | 480 |
| aggctgtacc tgtgatcgag gctggcggga aaataggctt cgtgtgctca ggtcatggga | 540 |
| ggtgcaggac agctcatgaa acgccaacaa tcgcacaatt catgtcaagc taatcagcta | 600 |
| tttcctcttc acgagctgta attgtcccaa aattctggtc taccgggggt gatccttcgt | 660 |
| gtacgggccc ttccctcaac cctaggtatg cgcgcatgcg gtcgccgcgc aactcgcgcg | 720 |
| agggccgagg gtttgggacg ggccgtcccg aaatgcagtt gcacccggat gcgtggcacc | 780 |
| ttttttgcga taatttatgc aatggactgc tctgcaaaat tctggctctg tcgccaaccc | 840 |
| taggatcagc ggcgtaggat ttcgtaatca ttcgtcctga tggggagcta ccgactaccc | 900 |
| taatatcagc ccgactgcct gacgccagcg tccacttttg tgcacacatt ccattcgtgc | 960 |
| ccaagacatt tcattgtggt gcgaagcgtc cccagttacg ctcacctgtt tcccgacctc | 1020 |
| cttactgttc tgtcgacaga gcgggcccac aggccggtcg cagcc | 1065 |

<210> SEQ ID NO 85
<211> LENGTH: 408
<212> TYPE: DNA
<213> ORGANISM: Chlorella vulgaris

<400> SEQUENCE: 85

| | |
|---|---|
| gcagcagcag ctcggatagt atcgacacac tctggacgct ggtcgtgtga tggactgttg | 60 |
| ccgccacact tgctgccttg acctgtgaat atccctgccg cttttatcaa acagcctcag | 120 |
| tgtgtttgat cttgtgtgta cgcgcttttg cgagttgcta gctgcttgtg ctatttgcga | 180 |

```
ataccacccc cagcatcccc ttccctcgtt tcatatcgct tgcatcccaa ccgcaactta      240
tctacgctgt cctgctatcc ctcagcgctg ctcctgctcc tgctcactgc ccctcgcaca      300
gccttggttt gggctccgcc tgtattctcc tggtactgca acctgtaaac cagcactgca      360
atgctgatgc acgggaagta gtgggatggg aacacaaatg aggatcc                    408

<210> SEQ ID NO 86
<211> LENGTH: 120
<212> TYPE: DNA
<213> ORGANISM: Artificial Sequence
<220> FEATURE:
<223> OTHER INFORMATION: synthetic construct

<400> SEQUENCE: 86
actagtatgg ccaccgcatc cactttctcg gcgttcaatg cccgctgcgg cgacctgcgt       60
cgctcggcgg gctccgggcc ccggcgccca gcgaggcccc tccccgtgcg cgggcgcgcc      120

<210> SEQ ID NO 87
<211> LENGTH: 1038
<212> TYPE: DNA
<213> ORGANISM: Artificial Sequence
<220> FEATURE:
<223> OTHER INFORMATION: synthetic construct

<400> SEQUENCE: 87
actagtatgg ccaccgcatc cactttctcg gcgttcaatg cccgctgcgg cgacctgcgt       60
cgctcggcgg gctccgggcc ccggcgccca gcgaggcccc tccccgtgcg cgggcgcgcc      120
cgctcctacg aggtgggcat caacaagacc gccaccgtgg agaccatcgc caacctgctg      180
caggaggtgg gctgcaacca cgcccagtcc gtgggcttct ccaccgacgg cttcgccacc      240
accacctcca tgcgcaagat gcacctgatc tgggtgaccg cccgcatgca catcgagatc      300
tacaagtacc ccgcctggtc cgacgtggtg gaggtggaga cctggtgcca gtccgagggc      360
cgcatcggca cccgccgcga ctggatcctg accgactacg ccaccggcca gatcatcggc      420
cgcgccacct ccaagtgggt gatgatgaac caggacaccc gccgcctgca gaaggtgacc      480
gacgacgtgc gcgaggagta cctggtgttc tgccccccgcg agctgcgcct ggccttcccc      540
gaggagaaca accgctcctc caagaagatc tccaagctgg aggaccccgc ccagtactcc      600
aagctgggcc tggtgccccg ccgcgccgac ctggacatga ccagcacgt gaacaacgtg       660 acctacatcg gctgggtgct ggagtccatc ccccaggaga tcatcgacac ccacgagctg      720
cagaccatca ccctggacta ccgccgcgag tgccagcacg acgacatcgt ggactccctg      780
acctccgtgg agccctccga gaacctggag gccgtgtccg agctgcgcgg caccaacggc      840
tccgccacca ccaccgccgg cgacgaggac tgccgcaact tcctgcacct gctgcgcctg      900
tccggcgacg gcctggagat caaccgcggc cgcaccgagt ggcgcaagaa gtccgcccgc      960
atggactaca aggaccacga cggcgactac aaggaccacg acatcgacta caaggacgac     1020
gacgacaagt gaatcgat                                                   1038

<210> SEQ ID NO 88
<211> LENGTH: 371
<212> TYPE: PRT
<213> ORGANISM: Ricinus communis

<400> SEQUENCE: 88

Met Leu Lys Val Pro Cys Cys Asn Ala Thr Asp Pro Ile Gln Ser Leu
1               5                   10                  15
```

Ser Ser Gln Cys Arg Phe Leu Thr His Phe Asn Asn Arg Pro Tyr Phe
    20                  25                  30

Thr Arg Arg Pro Ser Ile Pro Thr Phe Phe Ser Ser Lys Asn Ser Ser
        35                  40                  45

Ala Ser Leu Gln Ala Val Val Ser Asp Ile Ser Ser Val Glu Ser Ala
 50                  55                  60

Ala Cys Asp Ser Leu Ala Asn Arg Leu Arg Leu Gly Lys Leu Thr Glu
 65                  70                  75                  80

Asp Gly Phe Ser Tyr Lys Glu Lys Phe Ile Val Arg Ser Tyr Glu Val
                85                  90                  95

Gly Ile Asn Lys Thr Ala Thr Val Glu Thr Ile Ala Asn Leu Leu Gln
            100                 105                 110

Glu Val Gly Cys Asn His Ala Gln Ser Val Gly Phe Ser Thr Asp Gly
            115                 120                 125

Phe Ala Thr Thr Thr Ser Met Arg Lys Met His Leu Ile Trp Val Thr
130                 135                 140

Ala Arg Met His Ile Glu Ile Tyr Lys Tyr Pro Ala Trp Ser Asp Val
145                 150                 155                 160

Val Glu Val Glu Thr Trp Cys Gln Ser Glu Gly Arg Ile Gly Thr Arg
                165                 170                 175

Arg Asp Trp Ile Leu Thr Asp Tyr Ala Thr Gly Gln Ile Ile Gly Arg
            180                 185                 190

Ala Thr Ser Lys Trp Val Met Met Asn Gln Asp Thr Arg Arg Leu Gln
            195                 200                 205

Lys Val Thr Asp Asp Val Arg Glu Glu Tyr Leu Val Phe Cys Pro Arg
210                 215                 220

Glu Leu Arg Leu Ala Phe Pro Glu Glu Asn Asn Arg Ser Ser Lys Lys
225                 230                 235                 240

Ile Ser Lys Leu Glu Asp Pro Ala Gln Tyr Ser Lys Leu Gly Leu Val
                245                 250                 255

Pro Arg Arg Ala Asp Leu Asp Met Asn Gln His Val Asn Asn Val Thr
            260                 265                 270

Tyr Ile Gly Trp Val Leu Glu Ser Ile Pro Gln Glu Ile Ile Asp Thr
            275                 280                 285

His Glu Leu Gln Thr Ile Thr Leu Asp Tyr Arg Arg Glu Cys Gln His
290                 295                 300

Asp Asp Ile Val Asp Ser Leu Thr Ser Val Glu Pro Ser Glu Asn Leu
305                 310                 315                 320

Glu Ala Val Ser Glu Leu Arg Gly Thr Asn Gly Ser Ala Thr Thr Thr
                325                 330                 335

Ala Gly Asp Glu Asp Cys Arg Asn Phe Leu His Leu Arg Leu Arg Leu Ser
            340                 345                 350

Gly Asp Gly Leu Glu Ile Asn Arg Gly Arg Thr Glu Trp Arg Lys Lys
            355                 360                 365

Ser Ala Arg
    370

<210> SEQ ID NO 89
<211> LENGTH: 312
<212> TYPE: DNA
<213> ORGANISM: Chlamydomonas reinhardtii

<400> SEQUENCE: 89
ctttcttgcg ctatgacact tccagcaaaa ggtagggcgg gctgcgagac ggcttcccgg      60

```
cgctgcatgc aacaccgatg atgcttcgac cccccgaagc tccttcgggg ctgcatgggc    120
gctccgatgc cgctccaggg cgagcgctgt ttaaatagcc aggccccccga ttgcaaagac    180 attatagcga gctaccaaag ccatattcaa acacctagat cactaccact tctacacagg    240
ccactcgagc ttgtgatcgc actccgctaa gggggcgcct cttcctcttc gtttcagtca    300
caacccgcaa ac                                                        312
```

<210> SEQ ID NO 90
<211> LENGTH: 595
<212> TYPE: DNA
<213> ORGANISM: Artificial Sequence
<220> FEATURE:
<223> OTHER INFORMATION: construct FADc portion of the hairpin RNA
      expression cassette

<400> SEQUENCE: 90

```
actagtatgg ctatcaagac gaacaggcag cctgtggaga agcctccgtt cacgatcggg     60
acgctgcgca aggccatccc cgcgcactgt ttcgagcgct cggcgcttcg tagcagcatg    120
tacctggcct ttgacatcgc ggtcatgtcc ctgctctacg tcgcgtcgac gtacatcgac    180
cctgcaccgg tgcctacgtg ggtcaagtac ggcatcatgt ggccgctcta ctggttcttc    240
caggtgtgtt tgagggtttt ggttgcccgt attgaggtcc tggtggcgcg catggaggag    300
aaggcgcctg tcccgctgac cccccggct acctcccgg caccttccag ggcgcgtacg    360
ggaagaacca gtagagcggc cacatgatgc cgtacttgac ccacgtaggc accggtgcag    420
ggtcgatgta cgtcgacgcg acgtagagca gggacatgac cgcgatgtca aaggccaggt    480
acatgctgct acgaagcgcc gagcgctcga acagtgcgc ggggatggcc ttgcgcagcg    540
tcccgatcgt gaacggaggc ttctccacag gctgcctgtt cgtcttgata gccat         595
```

<210> SEQ ID NO 91
<211> LENGTH: 6101
<212> TYPE: DNA
<213> ORGANISM: Artificial Sequence
<220> FEATURE:
<223> OTHER INFORMATION: construct FADc hairpin RNA expression cassette

<400> SEQUENCE: 91

```
gctcttcgcc gccgccactc ctgctcgagc gcgcccgcgc gtgcgccgcc agcgccttgg     60 cctttcgcc gcgctcgtgc gcgtcgctga tgtccatcac caggtccatg aggtctgcct    120
tgcgccggct gagccactgc ttcgtccggg cggccaagag gagcatgagg gaggactcct    180
ggtccagggt cctgacgtgg tcgcggctct gggagcgggc cagcatcatc tggctctgcc    240
gcaccgaggc cgcctccaac tggtcctcca gcagccgcag tcgccgccga ccctggcaga    300
ggaagacagg tgagggggggt atgaattgta cagaacaacc acgagccttg tctaggcaga    360
atccctacca gtcatggctt tacctggatg acggcctgcg aacagctgtc cagcgaccct    420
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540 ccccccttgcg cgttagtgtt gccatccttt gcagaccggt gagagccgac ttgttgtgcg    600
ccacccccca caccacctcc tcccagacca attctgtcac cttttggcg aaggcatcgg    660 cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
```

```
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaacgg cgcgccatgc tgctgcaggc cttcctgttc ctgctggccg   1080
gcttcgccgc caagatcagc gcctccatga cgaacgagac gtccgaccgc cccctggtgc   1140
acttcacccc caacaagggc tggatgaacg accccaacgg cctgtggtac gacgagaagg   1200
acgccaagtg gcacctgtac ttccagtaca cccgaacga caccgtctgg gggacgccct   1260
tgttctgggg ccacgccacg tccgacgacc tgaccaactg ggaggaccag cccatcgcca   1320
tcgccccgaa gcgcaacgac tccggcgcct ctccggctc catggtggtg gactacaaca   1380
acacctccgg cttcttcaac gacaccatcg acccgcgcca gcgctgcgtg gccatctgga   1440
cctacaacac cccggagtcc gaggagcagt acatctccta cagcctggac ggcggctaca   1500
ccttcaccga gtaccagaag aaccccgtgc tggccgccaa ctccacccag ttccgcgacc   1560
cgaaggtctt ctggtacgag ccctcccaga gtggatcat gaccgcggcc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtcccca   1740
ccgagcagga ccccagcaag tcctactggg tgatgttcat ctccatcaac cccgcgccc   1800 cggccggcgg ctccttcaac cagtacttcg tcggcagctt caacggcacc cacttcgagg   1860
ccttcgacaa ccagtcccgc gtggtggact cggcaagga ctactacgcc ctgcagacct   1920
tcttcaacac cgacccgacc tacggagcg ccctgggcat cgcgtgggcc tccaactggg   1980
agtactccgc cttcgtgccc accaacccct ggcgctcctc catgtccctc gtgcgcaagt   2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accacccaga cgatctccaa gtccgtgttc gcggacctct   2280
ccctctggtt caagggcctg gaggacccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca accagcccct caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg gctccgtga   2580 acatgacgac gggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg aacacaaat ggaggatccc   3060 gcgtctcgaa cagagcgcgc agaggaacgc tgaaggtctc gcctctgtcg cacctcagcg   3120
cggcatacac cacaataacc acctgacgaa tgcgcttggt tcttcgtcca ttagcgaagc   3180
```

-continued

```
gtccggttca cacacgtgcc acgttggcga ggtggcaggt gacaatgatc ggtggagctg    3240
atggtcgaaa cgttcacagc ctagggatat cgaattcggc cgacaggacg cgcgtcaaag    3300
gtgctggtcg tgtatgccct ggccggcagg tcgttgctgc tgctggttag tgattccgca    3360
accctgattt tggcgtctta ttttggcgtg gcaaacgctg gcgcccgcga gccgggccgg    3420
cggcgatgcg gtgccccacg gctgccggaa tccaagggag gcaagagcgc ccgggtcagt    3480
tgaagggctt tacgcgcaag gtacagccgc tcctgcaagg ctgcgtggtg gaattggacg    3540
tgcaggtcct gctgaagttc ctccaccgcc tcaccagcgg acaaagcacc ggtgtatcag    3600
gtccgtgtca tccactctaa agagctcgac tacgacctac tgatggccct agattcttca    3660
tcaaaaacgc ctgagacact tgcccaggat tgaaactccc tgaagggacc accaggggcc    3720
ctgagttgtt ccttcccccc gtggcgagct gccagccagg ctgtacctgt gatcgaggct    3780
ggcgggaaaa taggcttcgt gtgctcaggt catgggaggt gcaggacagc tcatgaaacg    3840
ccaacaatcg cacaattcat gtcaagctaa tcagctattt cctcttcacg agctgtaatt    3900
gtcccaaaat tctggtctac cggggtgat ccttcgtgta cgggcccttc cctcaaccct    3960
aggtatgcgc gcatgcggtc gccgcgcaac tcgcgcgagg gccgagggtt tgggacgggc    4020
cgtcccgaaa tgcagttgca cccggatgcg tggcacctt tttgcgataa tttatgcaat    4080
ggactgctct gcaaaattct ggctctgtcg ccaaccctag gatcagcggc gtaggatttc    4140
gtaatcattc gtcctgatgg ggagctaccg actaccctaa tatcagcccg actgcctgac    4200
gccagcgtcc acttttgtgc acacattcca ttcgtgccca agacatttca ttgtggtgcg    4260
aagcgtcccc agtacgctc acctgtttcc cgacctcctt actgttctgt cgacagagcg    4320
ggcccacagg ccggtcgcag ccactagtat ggctatcaag acgaacaggc agcctgtgga    4380
gaagcctccg ttcacgatcg ggacgctgcg caaggccatc cccgcgcact gtttcgagcg    4440
ctcggcgctt cgtagcagca tgtacctggc cttTGACATc gcggtcatgt ccctgctcta    4500
cgtcgcgtcg acgtacatcg accctgcacc ggtgcctacg tgggtcaagt acggcatcat    4560
gtggccgctc tactggttct ccaggtgtg tttgagggtt ttggttgccc gtattgaggt    4620
cctggtggcg cgcatggagg agaaggcgcc tgtcccgctg accccccgg ctaccctccc    4680
ggcaccttcc agggcgcgta cgggaagaac cagtagagcg gccacatgat gccgtacttg    4740
acccacgtag gcaccggtgc agggtcgatg tacgtcgacg cgacgtagag cagggacatg    4800
accgcgatgt caaaggccag gtacatgctg ctacgaagcg ccgagcgctc gaaacagtgc    4860
gcggggatgg ccttgcgcag cgtcccgatc gtgaacggag gcttctccac aggctgcctg    4920
ttcgtcttga tagccatctc gaggcagcag cagctcggat agtatcgaca cactctggac    4980
gctggtcgtg tgatggactg ttgccgccac acttgctgcc ttgacctgtg aatatccctg    5040
ccgcttttat caaacagcct cagtgtgttt gatcttgtgt gtacgcgctt ttgcgagttg    5100
ctagctgctt gtgctatttg cgaataccac ccccagcatc cccttccctc gtttcatatc    5160
gcttgcatcc caaccgcaac ttatctacgc tgtcctgcta tccctcagcg ctgctcctgc    5220
tcctgctcac tgcccctcgc acagccttgg tttgggctcc gcctgtattc tcctggtact    5280
gcaacctgta aaccagcact gcaatgctga tgcacgggaa gtagtgggat gggaacacaa    5340
atggaaagct gtagagctct tgttttccag aaggagttgc tccttgagcc tttcattctc    5400
agcctcgata acctccaaag ccgctctaat tgtggagggg gttcgaattt aaaagcttgg    5460
aatgttggtt cgtgcgtctg gaacaagccc agacttgttg ctcactggga aaaggaccat    5520
cagctccaaa aaacttgccg ctcaaaccgc gtacctctgc tttcgcgcaa tctgccctgt    5580
```

```
tgaaatcgcc accacattca tattgtgacg cttgagcagt ctgtaattgc ctcagaatgt    5640
ggaatcatct gccccctgtg cgagcccatg ccaggcatgt cgcgggcgag acacccgcc     5700 actcgtacag cagaccatta tgctacctca caatagttca taacagtgac catatttctc    5760
gaagctcccc aacgagcacc tccatgctct gagtggccac ccccggccc tggtgcttgc    5820 ggagggcagg tcaaccggca tggggctacc gaaatcccg accggatccc accaccccg     5880 cgatgggaag aatctctccc cgggatgtgg cccaccacc agcacaacct gctggcccag   5940
gcgagcgtca aaccatacca cacaaatatc cttggcatcg ccctgaatt ccttctgccg    6000 ctctgctacc cggtgcttct gtccgaagca ggggttgcta gggatcgctc cgagtccgca   6060
aacccttgtc gcgtggcggg gcttgttcga gcttgaagag c                      6101
```

<210> SEQ ID NO 92
<211> LENGTH: 595
<212> TYPE: DNA
<213> ORGANISM: Artificial Sequence
<220> FEATURE:
<223> OTHER INFORMATION: construct FADc portion of the hairpin RNA
      expression cassette

<400> SEQUENCE: 92

```
actagtatgg ctatcaagac gaacaggcag cctgtggaga agcctccgtt cacgatcggg    60
acgctgcgca aggccatccc cgcgcactgt ttcgagcgct cggcgcttcg tagcagcatg   120
tacctggcct ttgacatcgc ggtcatgtcc ctgctctacg tcgcgtcgac gtacatcgac   180
cctgcaccgg tgcctacgtg ggtcaagtac ggcatcatgt ggccgctcta ctggttcttc   240
caggtgtgtt tgagggtttt ggttgcccgt attgaggtcc tggtggcgcg catggaggag   300
aaggcgcctg tcccgctgac cccccggct accctcccgg caccttccag ggcgcgtacg   360
ggaagaacca gtagagcggc cacatgatgc cgtacttgac ccacgtaggc accggtgcag   420
ggtcgatgta cgtcgacgcg acgtagagca gggacatgac cgcgatgtca aaggccaggt   480
acatgctgct acgaagcgcc gagcgctcga aacagtgcgc ggggatggcc ttgcgcagcg   540
tcccgatcgt gaacggaggc ttctccacag gctgcctgtt cgtcttgata gccat        595
```

<210> SEQ ID NO 93
<211> LENGTH: 5348
<212> TYPE: DNA
<213> ORGANISM: Artificial Sequence
<220> FEATURE:
<223> OTHER INFORMATION: construct FADc hairpin RNA expression cassette

<400> SEQUENCE: 93

```
gctcttcgcc gccgccactc ctgctcgagc gcgcccgcgc gtgcgccgcc agcgccttgg    60
ccttttcgcc gcgctcgtgc gcgtcgctga tgtccatcac caggtccatg aggtctgcct   120
tgcgccggct gagccactgc ttcgtccggg cggccaagag gagcatgagg gaggactcct   180
ggtccagggt cctgacgtgg tcgcggctct gggagcgggc cagcatcatc tggctctgcc   240
gcaccgaggc cgcctccaac tggtcctcca gcagccgcag tcgccgccga ccctggcaga   300
ggaagacagg tgaggggggt atgaattgta cagaacaacc acgagccttg tctaggcaga   360
atccctacca gtcatggctt tacctggatg acggcctgcg aacagctgtc cagcgaccct   420
cgctgccgcc gcttctcccg cacgcttctt tccagcaccg tgatggcgcg agccagcgcc   480
gcacgctggc gctgcgcttc gccgatctga ggacagtcgg ggaactctga tcagtctaaa   540 ccccccttgcg cgttagtgtt gccatccttt gcagaccggt gagagccgac ttgttgtgcg   600
```

```
ccaccccca caccacctcc tcccagacca attctgtcac ctttttggcg aaggcatcgg      660
cctcggcctg cagagaggac agcagtgccc agccgctggg ggttggcgga tgcacgctca      720
ggtaccdttt cttgcgctat gacacttcca gcaaaaggta gggcgggctg cgagacggct      780
tcccggcgct gcatgcaaca ccgatgatgc ttcgaccccc cgaagctcct tcggggctgc      840
atgggcgctc cgatgccgct ccagggcgag cgctgtttaa atagccaggc ccccgattgc      900
aaagacatta tagcgagcta ccaaaagccat attcaaacac ctagatcact accacttcta     960
cacaggccac tcgagcttgt gatcgcactc cgctaagggg gcgcctcttc ctcttcgttt     1020
cagtcacaac ccgcaaacgg cgcgccatgc tgctgcaggc cttcctgttc ctgctggccg     1080
gcttcgccgc caagatcagc gcctccatga cgaacgagac gtccgaccgc ccctggtgc      1140 acttcacccc caacaagggc tggatgaacg accccaacgg cctgtggtac gacgagaagg     1200
acgccaagtg gcacctgtac ttccagtaca acccgaacga caccgtctgg gggacgccct     1260
tgttctgggg ccacgccacg tccgacgacc tgaccaactg ggaggaccag cccatcgcca     1320
tcgccccgaa gcgcaacgac tccggcgcct ctccggctc catggtggtg gactacaaca     1380
acacctccgg cttcttcaac gacaccatcg accgcgcca gcgctgcgtg gccatctgga     1440
cctacaacac cccggagtcc gaggagcagt acatctccta cagcctggac ggcggctaca     1500
ccttcaccga gtaccagaag aacccgtgc tggccgccaa ctccacccag ttccgcgacc      1560
cgaaggtctt ctggtacgag ccctcccaga agtggatcat gaccgcggcc aagtcccagg    1620
actacaagat cgagatctac tcctccgacg acctgaagtc ctggaagctg gagtccgcgt    1680
tcgccaacga gggcttcctc ggctaccagt acagtgccc cggcctgatc gaggtcccca    1740
ccgagcagga ccccagcaag tcctactggg tgatgttcat ctccatcaac cccggcgccc    1800
cggccggcgg ctccttcaac cagtacttcg tcggcagctt caacggcacc cacttcgagg    1860
ccttcgacaa ccagtcccgc gtggtggact tcggcaagga ctactacgcc ctgcagacct    1920
tcttcaacac cgacccgacc tacgggagcg ccctgggcat cgcgtgggcc tccaactggg   1980
agtactccgc cttcgtgccc accaaccct ggcgctcctc catgtccctc gtgcgcaagt     2040
tctccctcaa caccgagtac caggccaacc cggagacgga gctgatcaac ctgaaggccg    2100
agccgatcct gaacatcagc aacgccggcc cctggagccg gttcgccacc aacaccacgt    2160
tgacgaaggc caacagctac aacgtcgacc tgtccaacag caccgcacc ctggagttcg    2220 agctggtgta cgccgtcaac accacccaga cgatctccaa gtccgtgttc gcggacctct    2280
ccctctggtt caagggcctg gaggacccccg aggagtacct ccgcatgggc ttcgaggtgt   2340
ccgcgtcctc cttcttcctg gaccgcggga acagcaaggt gaagttcgtg aaggagaacc   2400
cctacttcac caaccgcatg agcgtgaaca ccagcccctt caagagcgag aacgacctgt    2460
cctactacaa ggtgtacggc ttgctggacc agaacatcct ggagctgtac ttcaacgacg    2520
gcgacgtcgt gtccaccaac acctacttca tgaccaccgg gaacgccctg gctccgtga    2580 acatgacgac gggggtggac aacctgttct acatcgacaa gttccaggtg cgcgaggtca    2640
agtgacaatt ggcagcagca gctcggatag tatcgacaca ctctggacgc tggtcgtgtg    2700
atggactgtt gccgccacac ttgctgcctt gacctgtgaa tatccctgcc gcttttatca    2760
aacagcctca gtgtgtttga tcttgtgtgt acgcgctttt gcgagttgct agctgcttgt    2820
gctatttgcg aataccaccc ccagcatccc cttccctcgt ttcatatcgc ttgcatccca    2880
accgcaactt atctacgctg tcctgctatc cctcagcgct gctcctgctc ctgctcactg    2940
```

```
cccctcgcac agccttggtt tgggctccgc ctgtattctc ctggtactgc aacctgtaaa      3000
ccagcactgc aatgctgatg cacgggaagt agtgggatgg aaacacaaat ggaggatccc      3060
gcgtctcgaa cagagcgcgc agaggaacgc tgaaggtctc gcctctgtcg caccctcagcg     3120
cggcatacac cacaataacc acctgacgaa tgcgcttggt tcttcgtcca ttagcgaagc      3180
gtccggttca cacacgtgcc acgttggcga ggtggcaggt gacaatgatc ggtggagctg      3240
atggtcgaaa cgttcacagc ctagggatat cgaattcctt tcttgcgcta tgacacttcc      3300
agcaaaaggt agggcgggct gcgagacggc ttcccggcgc tgcatgcaac accgatgatg      3360
cttcgacccc ccgaagctcc ttcggggctg catgggcgct ccgatgccgc tccagggcga      3420
gcgctgttta aatagccagg ccccgattg caaagacatt atagcgagct accaaagcca       3480
tattcaaaca cctagatcac taccacttct acacaggcca ctcgagcttg tgatcgcact      3540
ccgctaaggg ggcgcctctt cctcttcgtt tcagtcacaa cccgcaaaca ctagtatggc      3600
tatcaagacg aacaggcagc ctgtggagaa gcctccgttc acgatcggga cgctgcgcaa      3660
ggccatcccc gcgcactgtt tcgagcgctc ggcgcttcgt agcagcatgt acctggcctt      3720
tgacatcgcg gtcatgtccc tgctctacgt cgcgtcgacg tacatcgacc ctgcaccggt      3780
gcctacgtgg gtcaagtacg gcatcatgtg gccgctctac tggttcttcc aggtgtgttt      3840
gagggttttg gttgcccgta ttgaggtcct ggtggcgcgc atggaggaga aggcgcctgt      3900
cccgctgacc ccccggcta ccctcccggc accttccagg gcgcgtacgg gaagaaccag       3960
tagagcggcc acatgatgcc gtacttgacc cacgtaggca ccggtgcagg gtcgatgtac      4020
gtcgacgcga cgtagagcag ggacatgacc gcgatgtcaa aggccaggta catgctgcta      4080
cgaagcgccg agcgctcgaa acagtgcgcg gggatggcct tgcgcagcgt cccgatcgtg      4140
aacggaggct tctccacagg ctgcctgttc gtcttgatag ccatctcgag gcagcagcag      4200
ctcggatagt atcgacacac tctggacgct ggtcgtgtga tggactgttg ccgccacact      4260
tgctgccttg acctgtgaat atccctgccg ctttatcaa acagcctcag tgtgtttgat       4320
cttgtgtgta cgcgcttttg cgagttgcta gctgcttgtg ctatttgcga ataccacccc      4380
cagcatcccc ttccctcgtt tcatatcgct tgcatcccaa ccgcaactta tctacgctgt      4440
cctgctatcc ctcagcgctg ctcctgctcc tgctcactgc ccctcgcaca gccttggttt      4500
gggctccgcc tgtattctcc tggtactgca acctgtaaac cagcactgca atgctgatgc      4560
acgggaagta gtgggatggg aacacaaatg gaaagctgta gagctcttgt tttccagaag      4620
gagttgctcc ttgagccttt cattctcagc ctcgataacc tccaaagccg ctctaattgt      4680
ggagggggtt cgaatttaaa agcttggaat gttggttcgt gcgtctggaa caagcccaga      4740
cttgttgctc actgggaaaa ggaccatcag ctccaaaaaa cttgccgctc aaaccgcgta      4800
cctctgcttt cgcgcaatct gccctgttga aatcgccacc acattcatat tgtgacgctt      4860
gagcagtctg taattgcctc agaatgtgga atcatctgcc cctgtgcga gcccatgcca       4920
ggcatgtcgc gggcgaggac acccgccact cgtacagcag accattatgc tacctcacaa      4980
tagttcataa cagtgaccat atttctcgaa gctccccaac gagcacctcc atgctctgag      5040
tggccacccc ccgccctgg tgcttgcgga ggcaggtca accggcatgg gctaccgaa         5100
atccccgacc ggatcccacc accccgcga tgggaagaat ctctcccggg gatgtgggcc       5160
caccaccagc acaacctgct ggcccaggcg agcgtcaaac catacccacac aaatatcctt     5220
ggcatcggcc ctgaattcct tctgccgctc tgctacccgg tgcttctgtc cgaagcaggg      5280
gttgctaggg atcgctccga gtccgcaaac ccttgtcgcg tggcggggct tgttcgagct      5340
```

<210> SEQ ID NO 94
<211> LENGTH: 1220
<212> TYPE: DNA
<213> ORGANISM: Artificial Sequence
<220> FEATURE:
<223> OTHER INFORMATION: construct FADc portion of the hairpin RNA expression cassette

<400> SEQUENCE: 94

```
actagttcac ttgtggaacc agagcgcgga gtcgtcctcg ggcgcgtccg ggacgacgta      60
gcggcagtcg cgccagtcct cccacagggc gcggccgacc cagcggctgt cggactggta     120
gtacttgccc aggatgggcc tgatggcggc ggaggcctcc tcggcgtggt agtgcgggat     180
ggtgctgaag aggtggtgca gcacgtgggt gtcggagatg tggtgcagga tgttgtccat     240
gaagggcggg cccatggagc ggtccacggt ggccatggcg ccgcgcagcc agtcccagtc     300
cttctcgaag tagtgcggca cgccgggtg cgtgtgctgg agcagcgtga tgagcacgag      360
ccacatgttc acgatcaggt agggcaccac gtaggtcttg accagccagg cccagcccat     420
ggtgcggccc agcacgctga gcccgctgag caccgccacc agcgccaggt cggagatgac     480
cacctcgatg cgctcgcgct tgctgaagat gggcgaccac gggtcaaagt ggttggcgaa     540
gcgcgggtac ggccgcgagg cgacgttgaa catgaggtac agcggccagc ccagggtcag     600
ggtgaccagc accttgccca tgcggatggg cagccactcc tcccactcca ggccctcgtg     660
cgccactgcg cggtgcggcg gcacaaacac ctcgtccttg tccaggcacc ccgtgttgga     720
gtggtggcgg cggtgcgagt gcttccagga gtagtagggc accagcagca ggctgtggaa     780
caccaggccc acgccgtcgt tgatggcctg gctggaggaa aaggcctggt ggccgcactc     840
gtgcgcgcac acccagacac ccgtgccgaa ggcgccctgg aagtgccgg gagggtagcc       900
gggggggtca gcgggacagg cgccttctcc tccatgcgcg ccaccaggac ctcaatacgg     960
gcaaccaaaa ccctcaaaca cacctggaag aaccagtaga gcggccacat gatgccgtac    1020
ttgacccacg taggcaccgg tgcagggtcg atgtacgtcg acgcgacgta gagcagggac    1080
atgaccgcga tgtcaaaggc caggtacatg ctgctacgaa gcgccgagcg ctcgaaacag    1140
tgcgcgggga tggccttgcg cagcgtcccg atcgtgaacg gaggcttctc cacaggctgc    1200
ctgttcgtct tgatagccat                                                1220
```

<210> SEQ ID NO 95
<211> LENGTH: 6726
<212> TYPE: DNA
<213> ORGANISM: Artificial Sequence
<220> FEATURE:
<223> OTHER INFORMATION: construct FADc hairpin RNA expression cassette

<400> SEQUENCE: 95

```
gctcttcgcc gccgccactc ctgctcgagc gcgcccgcgc gtgcgccgcc agcgccttgg      60
cctttttcgcc gcgctcgtgc gcgtcgctga tgtccatcac caggtccatg aggtctgcct    120
tgcgccggct gagccactgc ttcgtccggg cggccaagag gagcatgagg gaggactcct    180
ggtccagggt cctgacgtgg tcgcggctct gggagcgggc cagcatcatc tggctctgcc    240
gcaccgaggc cgcctccaac tggtcctcca gcagccgcag tcgccgccga ccctggcaga    300
ggaagacagg tgaggggggt atgaattgta cagaacaacc acgagccttg tctaggcaga    360
atccctacca gtcatggctt tacctggatg acggcctgcg aacagctgtc cagcgaccct    420
```

-continued

```
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
cccccttgcg cgttagtgtt gccatccttt gcagaccggt gagagccgac ttgttgtgcg    600
ccacccccca caccacctcc tcccagacca attctgtcac cttttttggcg aaggcatcgg   660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg cgcctcttc ctcttcgttt    1020
cagtcacaac ccgcaaacgg cgcgccatgc tgctgcaggc cttcctgttc ctgctggccg   1080
gcttcgccgc caagatcagc gcctccatga cgaacgagac gtccgaccgc ccctggtgc    1140
acttcacccc caacaagggc tggatgaacg accccaacgg cctgtggtac gacgagaagg   1200
acgccaagtg gcacctgtac ttccagtaca cccgaacga caccgtctgg gggacgccct    1260
tgttctgggg ccacgccacg tccgacgacc tgaccaactg ggaggaccag cccatcgcca   1320
tcgccccgaa gcgcaacgac tccggcgcct ctctccggctc catggtggtg gactacaaca   1380
acacctccgg cttcttcaac gacaccatcg acccgcgcca gcgctgcgtg gccatctgga   1440
cctacaacac cccggagtcc gaggagcagt acatctccta cagcctggac ggcggctaca   1500
ccttcaccga gtaccagaag aaccccgtgc tggccgccaa ctccacccag ttccgcgacc   1560
cgaaggtctt ctggtacgag ccctcccaga agtggatcat gaccgcgccc aagtcccagg   1620
actacaagat cgagatctac tcctccgacg acctgaagtc ctggaagctg gagtccgcgt   1680
tcgccaacga gggcttcctc ggctaccagt acgagtgccc cggcctgatc gaggtccca    1740
ccgagcagga ccccagcaag tcctactggg tgatgttcat ctccatcaac cccggcgccc   1800
cggccggcgg ctccttcaac cagtactcg tcggcagctt caacggcacc cacttcgagg   1860
ccttcgacaa ccagtcccgc gtggtggact cggcaagga ctactacgcc ctgcagacct   1920
tcttcaacac cgacccgacc tacgggagcg ccctgggcat cgcgtgggcc tccaactggg   1980
agtactccgc cttcgtgccc accaaccct ggcgctcctc catgtccctc gtgcgcaagt    2040
tctccctcaa caccgagtac caggccaacc cggagacgga gctgatcaac ctgaaggccg   2100
agccgatcct gaacatcagc aacgccggcc cctggagccg gttcgccacc aacaccacgt   2160
tgacgaaggc caacagctac aacgtcgacc tgtccaacag caccggcacc ctggagttcg   2220
agctggtgta cgccgtcaac accaccccaga cgatctccaa gtccgtgttc gcggacctct   2280
ccctctggtt caagggcctg gaggacccg aggagtacct ccgcatgggc ttcgaggtgt    2340
ccgcgtcctc cttcttcctg gaccgcggga acagcaaggt gaagttcgtg aaggagaacc   2400
cctacttcac caaccgcatg agcgtgaaca accagcccct caagagcgag aacgacctgt   2460
cctactacaa ggtgtacggc ttgctggacc agaacatcct ggagctgtac ttcaacgacg   2520
gcgacgtcgt gtccaccaac acctacttca tgaccaccgg gaacgccctg gctccgtga    2580
acatgacgac ggggggtggac aacctgttct acatcgacaa gttccaggtg cgcgaggtca   2640
agtgacaatt ggcagcagca gctcggatag tatcgacaca ctctggacgc tggtcgtgtg   2700
atggactgtt gccgccacac ttgctgcctt gacctgtgaa tatccctgcc gcttttatca   2760
```

```
aacagcctca gtgtgtttga tcttgtgtgt acgcgctttt gcgagttgct agctgcttgt   2820
gctatttgcg aataccaccc ccagcatccc cttccctcgt ttcatatcgc ttgcatccca   2880
accgcaactt atctacgctg tcctgctatc cctcagcgct gctcctgctc ctgctcactg   2940
cccctcgcac agccttggtt tgggctccgc ctgtattctc ctggtactgc aacctgtaaa   3000
ccagcactgc aatgctgatg cacgggaagt agtgggatgg aaacacaaat ggaggatccc   3060
gcgtctcgaa cagagcgcgc agaggaacgc tgaaggtctc gcctctgtcg cacctcagcg   3120
cggcatacac cacaataacc acctgacgaa tgcgcttggt tcttcgtcca ttagcgaagc   3180
gtccggttca cacacgtgcc acgttggcga ggtggcaggt gacaatgatc ggtggagctg   3240
atggtcgaaa cgttcacagc ctagggatat cgaattcggc cgacaggacg cgcgtcaaag   3300
gtgctggtcg tgtatgccct ggccggcagg tcgttgctgc tgctggttag tgattccgca   3360
accctgattt tggcgtctta ttttggcgtg caaacgctg gcgcccgcga gccgggccgg   3420
cggcgatgcg gtgccccacg gctgccggaa tccaagggag gcaagagcgc ccgggtcagt   3480
tgaagggctt tacgcgcaag gtacagccgc tcctgcaagg ctgcgtggtg gaattggacg   3540
tgcaggtcct gctgaagttc ctccaccgcc tcaccagcgg acaaagcacc ggtgtatcag   3600
gtccgtgtca tccactctaa agagctcgac tacgacctac tgatggccct agattcttca   3660
tcaaaaacgc ctgagacact tgcccaggat tgaaactccc tgaagggacc accggggcc    3720 ctgagttgtt ccttccccc gtggcgagct gccagccagg ctgtacctgt gatcgaggct   3780
ggcgggaaaa taggcttcgt gtgctcaggt catgggaggt gcaggacagc tcatgaaacg   3840
ccaacaatcg cacaattcat gtcaagctaa tcagctattt cctcttcacg agctgtaatt   3900
gtcccaaaat tctggtctac cggggtgat ccttcgtgta cgggcccttc cctcaaccct    3960
aggtatgcgc gcatgcggtc gccgcgcaac tcgcgcgagg gccgagggtt tgggacgggc   4020
cgtcccgaaa tgcagttgca cccggatgcg tggcacctttt tttgcgataa tttatgcaat   4080
ggactgctct gcaaaattct ggctctgtcg ccaacccctag gatcagcggc gtaggatttc   4140
gtaatcattc gtcctgatgg ggagctaccg actaccctaa tatcagcccg actgcctgac   4200
gccagcgtcc acttttgtgc acacattcca ttcgtgccca agacatttca ttgtggtgcg   4260
aagcgtcccc agttacgctc acctgtttcc cgacctcctt actgttctgt cgacagagcg   4320
ggcccacagg ccggtcgcag ccactagttc acttgtggaa ccagagcgcg gagtcgtcct   4380
cgggcgcgtc cgggacgacg tagcggcagt cgcgccagtc ctcccacagg gcgcggccga   4440
cccagcggct gtcggactgg tagtacttgc ccaggatggg cctgatgcg gcggaggcct    4500 cctcggcgtg gtagtgcggg atggtgctga agaggtggtg cagcacgtgg gtgtcggaga   4560
tgtggtgcag gatgttgtcc atgaagggcg ggcccatgga gcggtccacg gtggccatgg   4620
cgccgcgcag ccagtcccag tccttctcga agtagtgcgg cagcgccggg tgcgtgtgct   4680
ggagcagcgt gatgagcacg agccacatgt tcacgatcag gtagggcacc acgtaggtct   4740
tgaccagcca ggcccagccc atggtgcggc ccagcacgct gagcccgctg agcaccgcca   4800
ccagcgccag gtcggagatg accacctcga tgcgctcgcg cttgctgaag atgggcgacc   4860
acgggtcaaa gtggttggcg aagcgcgggt acggccgcga ggcgacgttg aacatgaggt   4920
acagcggcca gcccagggtc agggtgacca gcaccttgcc catgcggatg ggcagccact   4980
cctcccactc caggccctcg tgcgccactg cgcggtgcgg cggcacaaac acctcgtcct   5040
tgtccaggca ccccgtgttg gagtggtggc ggcggtgcga gtgcttccag gagtagtagg   5100
gcaccagcag caggctgtgg aacaccaggc ccacgccgtc gttgatggcc tggctggagg   5160
```

```
aaaaggcctg gtggccgcac tcgtgcgcgc acacccagac acccgtgccg aaggcgccct    5220
ggaaggtgcc gggagggtag ccgggggggt cagcgggaca ggcgccttct cctccatgcg    5280
cgccaccagg acctcaatac gggcaaccaa aaccctcaaa cacacctgga agaaccagta    5340
gagcggccac atgatgccgt acttgaccca cgtaggcacc ggtgcagggt cgatgtacgt    5400
cgacgcgacg tagagcaggg acatgaccgc gatgtcaaag gccaggtaca tgctgctacg    5460
aagcgccgag cgctcgaaac agtgcgcggg gatggccttg cgcagcgtcc cgatcgtgaa    5520
cggaggcttc tccacaggct gcctgttcgt cttgatagcc atctcgaggc agcagcagct    5580
cggatagtat cgacacactc tggacgctgg tcgtgtgatg gactgttgcc gccacacttg    5640
ctgccttgac ctgtgaatat ccctgccgct tttatcaaac agcctcagtg tgtttgatct    5700
tgtgtgtacg cgcttttgcg agttgctagc tgcttgtgct atttgcgaat accaccccca    5760
gcatcccctt ccctcgtttc atatcgcttg catcccaacc gcaacttatc tacgctgtcc    5820
tgctatccct cagcgctgct cctgctcctg ctcactgccc ctcgcacagc cttggtttgg    5880
gctccgcctg tattctcctg gtactgcaac ctgtaaacca gcactgcaat gctgatgcac    5940
gggaagtagt gggatgggaa cacaaatgga aagctgtaga gctcttgttt tccagaagga    6000
gttgctcctt gagcctttca ttctcagcct cgataacctc caaagccgct ctaattgtgg    6060 aggggggttcg aatttaaaag cttggaatgt tggttcgtgc gtctggaaca gcccagact     6120 tgttgctcac tgggaaaagg accatcagct ccaaaaaact tgccgctcaa accgcgtacc    6180 tctgcttcg cgcaatctgc cctgttgaaa tcgccaccac attcatattg tgacgcttga    6240
gcagtctgta attgcctcag aatgtggaat catctgcccc ctgtgcgagc ccatgccagg    6300
catgtcgcgg gcgaggacac ccgccactcg tacagcagac cattatgcta cctcacaata    6360
gttcataaca gtgaccatat ttctcgaagc tccccaacga gcacctccat gctctgagtg    6420
gccacccccc ggccctggtg cttgcggagg gcaggtcaac cggcatgggg ctaccgaaat    6480
ccccgaccgg atcccaccac ccccgcgatg ggaagaatct ctccccggga tgtgggccca    6540
ccaccagcac aacctgctgg cccaggcgag cgtcaaacca taccacacaa atatccttgg    6600
catcggccct gaattccttc tgccgctctg ctacccggtg cttctgtccg aagcagggt    6660 tgctagggat cgctccgagt ccgcaaaccc ttgtcgcgtg gcggggcttg ttcgagcttg    6720
aagagc                                                              6726
```

<210> SEQ ID NO 96
<211> LENGTH: 1220
<212> TYPE: DNA
<213> ORGANISM: Artificial Sequence
<220> FEATURE:
<223> OTHER INFORMATION: construct FADc portion of the hairpin RNA
     expression cassette

<400> SEQUENCE: 96

```
actagttcac ttgtggaacc agagcgcgga gtcgtcctcg ggcgcgtccg ggacgacgta      60
gcggcagtcg cgccagtcct cccacagggc gcggccgacc cagcggctgt cggactggta     120
gtacttgccc aggatgggcc tgatggcggc ggaggcctcc tcggcgtggt agtgcgggat     180
ggtgctgaag aggtggtgca gcacgtgggt gtcggagatg tggtgcagga tgttgtccat     240
gaagggcggg cccatggagc ggtccacggt ggccatggcg ccgcgcagcc agtcccagtc     300
cttctcgaag tagtgcggca gcgccgggtg cgtgtgctgg agcagcgtga tgagcacgag    360
ccacatgttc acgatcaggt agggcaccac gtaggtcttg accagccagg cccagcccat    420
```

```
ggtgcggccc agcacgctga gcccgctgag caccgccacc agcgccaggt cggagatgac    480
cacctcgatg cgctcgcgct tgctgaagat gggcgaccac gggtcaaagt ggttggcgaa    540
gcgcgggtac ggccgcgagg cgacgttaa catgaggtac agcggccagc ccagggtcag     600
ggtgaccagc accttgccca tgcggatggg cagccactcc tcccactcca ggccctcgtg    660
cgccactgcg cggtgcggcg gcacaaacac ctcgtccttg tccaggcacc ccgtgttgga    720
gtggtggcgg cggtgcgagt gcttccagga gtagtagggc accagcagca ggctgtggaa    780
caccaggccc acgccgtcgt tgatggcctg gctggaggaa aaggcctggt ggccgcactc    840
gtgcgcgcac acccagacac ccgtgccgaa ggcgccctgg aaggtgccgg agggtagcc    900 gggggggtca gcgggacagg cgccttctcc tccatgcgcg ccaccaggac ctcaatacgg   960
gcaaccaaaa ccctcaaaca cacctggaag aaccagtaga gcggccacat gatgccgtac   1020
ttgacccacg taggcaccgg tgcagggtcg atgtacgtcg acgcgacgta gagcagggac   1080
atgaccgcga tgtcaaaggc caggtacatg ctgctacgaa gcgccgagcg ctcgaaacag   1140
tgcgcgggga tggccttgcg cagcgtcccg atcgtgaacg gaggcttctc cacaggctgc   1200
ctgttcgtct tgatagccat                                              1220

<210> SEQ ID NO 97
<211> LENGTH: 5973
<212> TYPE: DNA
<213> ORGANISM: Artificial Sequence
<220> FEATURE:
<223> OTHER INFORMATION: construct FADc hairpin RNA expression cassette

<400> SEQUENCE: 97
gctcttcgcc gccgccactc ctgctcgagc gcgcccgcgc gtgcgccgcc agcgccttgg    60
ccttttcgcc gcgctcgtgc gcgtcgctga tgtccatcac caggtccatg aggtctgcct   120
tgcgccggct gagccactgc ttcgtccggg cggccaagag gagcatgagg gaggactcct   180
ggtccagggt cctgacgtgg tcgcggctct gggagcgggc cagcatcatc tggctctgcc   240
gcaccgaggc cgcctccaac tggtcctcca gcagccgcag tcgccgccga ccctggcaga   300
ggaagacagg tgaggggggt atgaattgta cagaacaacc acgagcctttg tctaggcaga   360 atccctacca gtcatggctt tacctggatg acggcctgcg aacagctgtc cagcgaccct   420
cgctgccgcc gcttctcccg cacgcttctt tccagcaccg tgatggcgcg agccagcgcc   480
gcacgctggc gctgcgcttc gccgatctga ggacagtcgg ggaactctga tcagtctaaa   540
cccccttgcg cgttagtgtt gccatccttt gcagaccggt gagagccgac ttgttgtgcg   600 ccaccccca caccacctcc tcccagacca attctgtcac cttttttggcg aaggcatcgg   660 cctcggcctg cagagaggac agcagtgccc agccgctggg ggttggcgga tgcacgctca   720 ggtaccctttt cttgcgctat gacacttcca gcaaaaggta gggcgggctg cgagacggct   780
tcccggcgct gcatgcaaca ccgatgatgc ttcgaccccc cgaagctcct tcggggctgc   840
atgggcgctc cgatgccgct ccagggcgag cgctgtttaa atagccaggc cccgattgc    900 aaagacatta tagcgagcta ccaaagccat attcaaacac ctagatcact accacttcta   960
cacaggccac tcgagcttgt gatcgcactc cgctaagggg gcgcctcttc ctcttcgttt   1020
cagtcacaac ccgcaaacgg cgcgccatgc tgctgcaggc cttcctgttc ctgctggccg   1080
gcttcgccgc caagatcagc gcctccatga cgaacgagac gtccgaccgc ccctggtgc    1140 acttcacccc caacaagggc tggatgaacg accccaacgg cctgtggtac gacgagaagg   1200
```

```
acgccaagtg gcacctgtac ttccagtaca acccgaacga caccgtctgg gggacgccct    1260
tgttctgggg ccacgccacg tccgacgacc tgaccaactg ggaggaccag cccatcgcca    1320
tcgccccgaa gcgcaacgac tccggcgcct tctccggctc catggtggtg gactacaaca    1380
acacctccgg cttcttcaac gacaccatcg acccgcgcca gcgctgcgtg ccatctggaa    1440
cctacaacac cccggagtcc gaggagcagt acatctccta cagcctggac ggcggctaca    1500
ccttcaccga gtaccagaag aaccccgtgc tggccgccaa ctccacccag ttccgcgacc    1560
cgaaggtctt ctggtacgag ccctcccaga gtggatcat gaccgcggcc aagtcccagg     1620
actacaagat cgagatctac tcctccgacg acctgaagtc ctggaagctg gagtccgcgt    1680
tcgccaacga gggcttcctc ggctaccagt acgagtgccc cggcctgatc gaggtcccca    1740
ccgagcagga ccccagcaag tcctactggg tgatgttcat ctccatcaac cccgcgccc    1800
cggccggcgg ctccttcaac cagtacttcg tcggcagctt caacggcacc cacttcgagg    1860
ccttcgacaa ccagtcccgc gtggtggact tcggcaagga ctactacgcc ctgcagacct    1920
tcttcaacac cgacccgacc tacgggagcg ccctgggcat cgcgtgggcc tccaactggg    1980
agtactccgc cttcgtgccc accaacccct ggcgctcctc catgtccctc gtgcgcaagt    2040
tctccctcaa caccgagtac caggccaacc cggagacgga gctgatcaac ctgaaggccg    2100
agccgatcct gaacatcagc aacgccggcc cctggagccg gttcgccacc aacaccacgt    2160
tgacgaaggc caacagctac aacgtcgacc tgtccaacag caccggcacc ctggagttcg    2220
agctggtgta cgccgtcaac accacccaga cgatctccaa gtccgtgttc gcggacctct    2280
ccctctggtt caagggcctg gaggaccccg aggagtacct ccgcatgggc ttcgaggtgt    2340
ccgcgtcctc cttcttcctg gaccgcggga acagcaaggt gaagttcgtg aaggagaacc    2400
cctacttcac caaccgcatg agcgtgaaca accagcccct caagagcgag aacgacctgt    2460
cctactacaa ggtgtacggc ttgctggacc agaacatcct ggagctgtac ttcaacgacg    2520
gcgacgtcgt gtccaccaac acctacttca tgaccaccgg gaacgccctg ggctccgtga    2580
acatgacgac gggggtggac aacctgttct acatcgacaa gttccaggtg cgcgaggtca    2640
agtgacaatt ggcagcagca gctcggatag tatcgacaca ctctggacgc tggtcgtgtg    2700
atggactgtt gccgccacac ttgctgcctt gacctgtgaa tatccctgcc gcttttatca    2760
aacagcctca gtgtgtttga tcttgtgtgt acgcgctttt gcgagttgct agctgcttgt    2820
gctatttgcg aataccaccc ccagcatccc cttccctcgt ttcatatcgc ttgcatccca    2880
accgcaactt atctacgctg tcctgctatc cctcagcgct gctcctgctc ctgctcactg    2940
cccctcgcac agccttggtt tgggctccgc ctgtattctc ctggtactgc aacctgtaaa    3000
ccagcactgc aatgctgatg cacgggaagt agtgggatgg gaacacaaat ggaggatccc    3060
gcgtctcgaa cagagcgcgc agaggaacgc tgaaggtctc gcctctgtcg cacctcagcg    3120
cggcatacac cacaataacc acctgacgaa tgcgcttggt tcttcgtcca ttagcgaagc    3180
gtccggttca cacacgtgcc acgttggcga ggtggcaggt gacaatgatc ggtggagctg    3240
atggtcgaaa cgttcacagc ctagggatat cgaattcctt tcttgcgcta tgacacttcc    3300
agcaaaaggt agggcgggct gcgagacggc ttcccggcgc tgcatgcaac accgatgatg    3360
cttcgacccc ccgaagctcc ttcggggctg catgggcgct ccgatgccgc tccagggcga    3420
gcgctgttta aatagccagg ccccgattg caaagacatt atagcgagct accaaagcca    3480
tattcaaaca cctagatcac taccacttct acacaggcca ctcgagcttg tgatcgcact    3540
ccgctaaggg ggcgcctctt cctcttcgtt tcagtcacaa cccgcaaaca ctagttcact    3600
```

```
tgtggaacca gagcgcggag tcgtcctcgg gcgcgtccgg gacgacgtag cggcagtcgc    3660
gccagtcctc ccacagggcg cggccgaccc agcggctgtc ggactggtag tacttgccca    3720
ggatgggcct gatggcggcg gaggcctcct cggcgtggta gtgcgggatg gtgctgaaga    3780
ggtggtgcag cacgtgggtg tcggagatgt ggtgcaggat gttgtccatg aagggcgggc    3840
ccatggagcg gtccacggtg gccatggcgc cgcgcagcca gtcccagtcc ttctcgaagt    3900
agtgcggcag cgccgggtgc gtgtgctgga gcagcgtgat gagcacgagc acatgttca     3960 cgatcaggta gggcaccacg taggtcttga ccagccaggc ccagcccatg gtgcggccca    4020
gcacgctgag cccgctgagc accgccacca gcgccaggtc ggagatgacc acctcgatgc    4080
gctcgcgctt gctgaagatg ggcgaccacg ggtcaaagtg gttggcgaag cgcgggtacg    4140
gccgcgaggc gacgttgaac atgaggtaca cggccagcc cagggtcagg gtgaccagca     4200
ccttgcccat gcggatgggc agccactcct cccactccag gccctcgtgc gccactgcgc    4260
ggtgcggcgc cacaaacacc tcgtccttgt ccaggcaccc cgtgttggag tggtggcggc    4320
ggtgcgagtg cttccaggag tagtagggca ccagcagcag gctgtggaac accaggccca    4380
cgccgtcgtt gatggcctgg ctggaggaaa aggcctggtg gccgcactcg tgcgcgcaca    4440
cccagacacc cgtgccgaag gcgccctgga aggtgccggg agggtagccg gggggtcag     4500 cgggacaggc gccttctcct ccatgcgcgc caccaggacc tcaatacggg caaccaaaac    4560
cctcaaacac acctggaaga accagtagag cggccacatg atgccgtact tgacccacgt    4620
aggcaccggt gcagggtcga tgtacgtcga cgcgacgtag agcagggaca tgaccgcgat    4680
gtcaaaggcc aggtacatgc tgctacgaag cgccgagcgc tcgaaacagt gcgcggggat    4740
ggccttgcgc agcgtcccga tcgtgaacgg aggcttctcc acaggctgcc tgttcgtctt    4800
gatagccatc tcgaggcagc agcagctcgg atagtatcga cacactctgg acgctggtcg    4860
tgtgatggac tgttgccgcc acacttgctg ccttgacctg tgaatatccc tgccgctttt    4920
atcaaacagc ctcagtgtgt ttgatcttgt gtgtacgcgc ttttgcgagt tgctagctgc    4980
ttgtgctatt tgcgaatacc cccccagca tcccctt ccc tcgtttcata tcgcttgcat    5040
cccaaccgca acttatctac gctgtcctgc tatccctcag cgctgctcct gctcctgctc    5100
actgcccctc gcacagcctt ggtttgggct ccgcctgtat tctcctggta ctgcaacctg    5160
taaaccagca ctgcaatgct gatgcacggg aagtagtggg atgggaacac aaatggaaag    5220
ctgtagagct cttgttttcc agaaggagtt gctccttgag cctttcattc tcagcctcga    5280
taacctccaa agccgctcta attgtggagg gggttcgaat ttaaaagctt ggaatgttgg    5340
ttcgtgcgtc tggaacaagc ccagacttgt tgctcactgg gaaaaggacc atcagctcca    5400
aaaaacttgc cgctcaaacc gcgtacctct gctttcgcgc aatctgccct gttgaaatcg    5460
ccaccacatt catattgtga cgcttgagca gtctgtaatt gcctcagaat gtggaatcat    5520 ctgcccctg tgcgagccca tgccaggcat gtcgcgggcg aggacacccg ccactcgtac    5580
agcagaccat tatgctacct cacaatagtt cataacagtg accatatttc tcgaagctcc    5640
ccaacgagca cctccatgct ctgagtggcc accccccggc cctggtgctt gcggagggca    5700
ggtcaaccgg catgggcta ccgaaatccc cgaccggatc ccaccacccc cgcgatggga     5760
agaatctctc cccgggatgt gggcccacca ccagcacaac ctgctggccc aggcgagcgt    5820
caaaccatac cacacaaata tccttggcat cggccctgaa ttccttctgc cgctctgcta    5880
cccggtgctt ctgtccgaag caggggttgc tagggatcgc tccgagtccg caaacccttg    5940
```

```
tcgcgtggcg gggcttgttc gagcttgaag agc                              5973
```

<210> SEQ ID NO 98
<211> LENGTH: 1221
<212> TYPE: DNA
<213> ORGANISM: Artificial Sequence
<220> FEATURE:
<223> OTHER INFORMATION: codon-optimized construct

<400> SEQUENCE: 98

```
actagtatgg ccaccgcatc cactttctcg gcgttcaatg cccgctgcgg cgacctgcgt    60
cgctcggcgg gctccgggcc ccggcgccca gcgaggcccc tccccgtgcg cgggcgcgcc   120
gaggtgcacg tgcaggtgac ccactccctg gcccccgaga agcgcgagat cttcaactcc   180
ctgaacaact gggcccagga gaacatcctg gtgctgctga aggacgtgga caagtgctgg   240
cagccctccg acttcctgcc cgactccgcc tccgagggct cgacgagca ggtgatggag    300
ctgcgcaagc gctgcaagga gatccccgac gactacttca tcgtgctggt gggcgacatg   360
atcaccgagg aggccctgcc cacctaccag accatgctga cacccctgga cggcgtgcgc   420
gacgagaccg cgcctccct gaccccctgg gccatctgga cccgcgcctg accgccgag    480
gagaaccgcc acgcgacct gctgaacaag tacctgtacc tgtccggccg cgtggacatg   540
aagcagatcg agaagaccat ccagtacctg atcggctccg gcatggaccc ccgcaccgag   600
aacaaccccct acctgggctt catctacacc tccttccagg agcgcgccac cttcatctcc   660
cacggcaaca ccgcccgcct ggccaaggag cacggcgacc tgaagctggc ccagatctgc   720
ggcatcatcg ccgccgacga aagcgccac gagaccgcct acaccaagat cgtggagaag   780
ctgttcgaga tcgaccccga cggcaccgtg ctggccctgg ccgacatgat gcgcaagaag   840
gtgtccatgc ccgccacct gatgtacgac ggccaggacg acaacctgtt cgagaacttc   900
tcctccgtgg cccagcgcct gggcgtgtac accgccaagg actacgccga catcctggag   960
ttcctggtgg ccgctgggga catcgagaag ctgaccggcc tgtccggcga gggccgcaag   1020
gcccaggact acgtgtgcac cctgcccccc cgcatccgcc gcctggagga gcgcgcccag  1080
tcccgcgtga gaaggcctc cgccacccc ttctcctgga tcttcggccg cgagatcaac   1140
ctgatggact acaaggacca cgacggcgac tacaaggacc acgacatcga ctacaaggac   1200
gacgacgaca agtgaatcga t                                             1221
```

<210> SEQ ID NO 99
<211> LENGTH: 390
<212> TYPE: PRT
<213> ORGANISM: Olea europae

<400> SEQUENCE: 99

```
Met Ala Leu Lys Leu Cys Phe Pro Pro His Lys Met Pro Ser Phe Pro
1               5                  10                  15

Asp Ala Arg Ile Arg Ser His Arg Val Phe Met Ala Ser Thr Ile His
            20                  25                  30

Ser Pro Ser Met Glu Val Gly Lys Val Lys Lys Pro Phe Thr Pro Pro
        35                  40                  45

Arg Glu Val His Val Gln Val Thr His Ser Leu Ala Pro Glu Lys Arg
    50                  55                  60

Glu Ile Phe Asn Ser Leu Asn Asn Trp Ala Gln Glu Asn Ile Leu Val
65                  70                  75                  80

Leu Leu Lys Asp Val Asp Lys Cys Trp Gln Pro Ser Asp Phe Leu Pro
                85                  90                  95
```

Asp Ser Ala Ser Glu Gly Phe Asp Glu Gln Val Met Glu Leu Arg Lys
            100                 105                 110

Arg Cys Lys Glu Ile Pro Asp Tyr Phe Ile Val Leu Val Gly Asp
            115                 120                 125

Met Ile Thr Glu Glu Ala Leu Pro Thr Tyr Gln Thr Met Leu Asn Thr
130                 135                 140

Leu Asp Gly Val Arg Asp Glu Thr Gly Ala Ser Leu Thr Pro Trp Ala
145                 150                 155                 160

Ile Trp Thr Arg Ala Trp Thr Ala Glu Glu Asn Arg His Gly Asp Leu
                165                 170                 175

Leu Asn Lys Tyr Leu Tyr Leu Ser Gly Arg Val Asp Met Lys Gln Ile
            180                 185                 190

Glu Lys Thr Ile Gln Tyr Leu Ile Gly Ser Gly Met Asp Pro Arg Thr
        195                 200                 205

Glu Asn Asn Pro Tyr Leu Gly Phe Ile Tyr Thr Ser Phe Gln Glu Arg
    210                 215                 220

Ala Thr Phe Ile Ser His Gly Asn Thr Ala Arg Leu Ala Lys Glu His
225                 230                 235                 240

Gly Asp Leu Lys Leu Ala Gln Ile Cys Gly Ile Ile Ala Ala Asp Glu
                245                 250                 255

Lys Arg His Glu Thr Ala Tyr Thr Lys Ile Val Glu Lys Leu Phe Glu
            260                 265                 270

Ile Asp Pro Asp Gly Thr Val Leu Ala Leu Ala Asp Met Met Arg Lys
        275                 280                 285

Lys Val Ser Met Pro Ala His Leu Met Tyr Asp Gly Gln Asp Asp Asn
    290                 295                 300

Leu Phe Glu Asn Phe Ser Ser Val Ala Gln Arg Leu Gly Val Tyr Thr
305                 310                 315                 320

Ala Lys Asp Tyr Ala Asp Ile Leu Glu Phe Leu Val Gly Arg Trp Asp
                325                 330                 335

Ile Glu Lys Leu Thr Gly Leu Ser Gly Glu Gly Arg Lys Ala Gln Asp
            340                 345                 350

Tyr Val Cys Thr Leu Pro Pro Arg Ile Arg Arg Leu Glu Glu Arg Ala
        355                 360                 365

Gln Ser Arg Val Lys Lys Ala Ser Ala Thr Pro Phe Ser Trp Ile Phe
    370                 375                 380

Gly Arg Glu Ile Asn Leu
385                 390

<210> SEQ ID NO 100
<211> LENGTH: 726
<212> TYPE: DNA
<213> ORGANISM: Prototheca moriformis

<400> SEQUENCE: 100
gctcttcgcc gccgccactc ctgctcgagc gcgcccgcgc gtgcgccgcc agcgccttgg    60
ccttttcgcc gcgctcgtgc gcgtcgctga tgtccatcac caggtccatg aggtctgcct   120
tgcgccggct gagccactgc ttcgtccggg cggccaagag gagcatgagg gaggactcct   180
ggtccagggt cctgacgtgg tcgcggctct gggagcgggc cagcatcatc tggctctgcc   240
gcaccgaggc cgcctccaac tggtcctcca gcagccgcag tcgccgccga ccctggcaga   300
ggaagacagg tgaggggggt atgaattgta cagaacaacc acgagccttg tctaggcaga   360
atccctacca gtcatggctt tacctggatg acggcctgcg aacagctgtc cagcgaccct   420

```
cgctgccgcc gcttctcccg cacgcttctt tccagcaccg tgatggcgcg agccagcgcc    480
gcacgctggc gctgcgcttc gccgatctga ggacagtcgg ggaactctga tcagtctaaa    540
cccccttgcg cgttagtgtt gccatccttt gcagaccggt gagagccgac ttgttgtgcg    600
ccacccccca caccacctcc tcccagacca attctgtcac cttttttggcg aaggcatcgg   660
```

```
cctcggcctg cagagaggac agcagtgccc agccgctggg ggttggcgga tgcacgctca    720
ggtacc                                                               726

<210> SEQ ID NO 101
<211> LENGTH: 749
<212> TYPE: DNA
<213> ORGANISM: Prototheca moriformis

<400> SEQUENCE: 101
gagctccttg ttttccagaa ggagttgctc cttgagcctt tcattctcag cctcgataac     60
ctccaaagcc gctctaattg tggagggggt tcgaatttaa aagcttggaa tgttggttcg    120
tgcgtctgga acaagcccag acttgttgct cactgggaaa aggaccatca gctccaaaaa    180
acttgccgct caaaccgcgt acctctgctt tcgcgcaatc tgccctgttg aaatcgccac    240
cacattcata ttgtgacgct tgagcagtct gtaattgcct cagaatgtgg aatcatctgc    300 ccctgtgcg agcccatgcc aggcatgtcg cgggcgagga cacccgccac tcgtacagca    360
gaccattatg ctacctcaca atagttcata acagtgacca tatttctcga agctccccaa    420
cgagcacctc catgctctga gtggccaccc cccggccctg gtgcttgcgg agggcaggtc    480
aaccggcatg gggctaccga aatccccgac cggatcccac caccccgcg atgggaagaa     540 tctctccccg ggatgtgggc ccaccaccag cacaacctgc tggcccaggc gagcgtcaaa    600
ccataccaca caaatatcct tggcatcggc cctgaattcc ttctgccgct ctgctacccg    660
gtgcttctgt ccgaagcagg ggttgctagg gatcgctccg agtccgcaaa cccttgtcgc    720
gtggcggggc ttgttcgagc ttgaagagc                                      749

<210> SEQ ID NO 102
<211> LENGTH: 719
<212> TYPE: DNA
<213> ORGANISM: Artificial Sequence
<220> FEATURE:
<223> OTHER INFORMATION: synthetic construct

<400> SEQUENCE: 102
gggctggtct gaatccttca ggcgggtgtt acccgagaaa gaaagggtgc cgatttcaaa     60
gcagacccat gtgccgggcc ctgtggcctg tgttggcgcc tatgtagtca ccccccctca    120
cccaattgtc gccagtttgc gcactccata aactcaaaac agcagcttct gagctgcgct    180
gttcaagaac acctctgggg tttgctcacc cgcgaggtcg acgcccagca tggctatcaa    240
gacgaacagg cagcctgtgg agaagcctcc gttcacgatc gggacgctgc gcaaggccat    300
ccccgcgcac tgtttcgagc gctcggcgct tcgtagcagc atgtacctgg cctttgacat    360
cgcggtcatg tccctgctct acgtcgcgtc gacgtacatc gaccctgcac cggtgcctac    420
gtgggtcaag tacggcatca tgtggccgct ctactggttc ttccaggtgt gtttgagggt    480
tttggttgcc cgtattgagg tcctggtggc gcgcatggag gagaaggcgc ctgtcccgct    540 gaccccccg gctaccctcc cggcaccttc cagggcgcct tcggcacggg tgtctgggtg    600
tgcgcgcacg agtgcggcca ccaggccttt tcctccagca aggccatcaa cgacggcgtg    660
```

```
ggcctggtgt tccacagcct gctgctggtg ccctactact cctggaagca ctcgcaccg    719
```

<210> SEQ ID NO 103
<211> LENGTH: 732
<212> TYPE: DNA
<213> ORGANISM: Artificial Sequence
<220> FEATURE:
<223> OTHER INFORMATION: synthetic construct

<400> SEQUENCE: 103

```
ccgccaccac tccaacacgg ggtgcctgga caaggacgag gtgtttgtgc cgccgcaccg     60
cgcagtggcg cacgagggcc tggagtggga ggagtggctg cccatccgca tgggcaaggt    120
gctggtcacc ctgaccctgg gctggccgct gtacctcatg ttcaacgtcg cctcgcggcc    180
gtacccgcgc ttcgccaacc actttgaccc gtggtcgccc atcttcagca agcgcgagcg    240
catcgaggtg gtcatctccg acctggcgct ggtggcggtg ctcagcgggc tcagcgtgct    300
gggccgcacc atgggctggg cctggctggt caagacctac gtggtgccct acctgatcgt    360
gaacatgtgg ctcgtgctca tcacgctgct ccagcacacg cacccggcgc tgccgcacta    420
cttcgagaag gactgggact ggctgcgcgg cgccatggcc accgtggacc gctccatggg    480
cccgcccttc atggacaaca tcctgcacca catctccgac acccacgtgc tgcaccacct    540
cttcagcacc atcccgcact accacgccga ggaggcctcc gccgccatca ggcccatcct    600
gggcaagtac taccagtccg acagccgctg ggtcggccgc gccctgtggg aggactggcg    660
cgactgccgc tacgtcgtcc cggacgcgcc cgaggacgac tccgcgctct ggttccacaa    720
gtgagtgagt ga                                                        732
```

<210> SEQ ID NO 104
<211> LENGTH: 384
<212> TYPE: PRT
<213> ORGANISM: Carthamus tinctorius

<400> SEQUENCE: 104

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Thr Gly Glu Gln Pro Ser Gly Val Ala
        35                  40                  45

Ser Leu Arg Glu Ala Asp Lys Glu Lys Ser Leu Gly Asn Arg Leu Arg
    50                  55                  60

Leu Gly Ser Leu Thr Glu Asp Gly Leu Ser Tyr Lys Glu Lys Phe Val
65                  70                  75                  80

Ile Arg Cys Tyr Glu Val Gly Ile Asn Lys Thr Ala Thr Ile Glu Thr
                85                  90                  95

Ile Ala Asn Leu Leu Gln Glu Val Gly Gly Asn His Ala Gln Gly Val
            100                 105                 110

Gly Phe Ser Thr Asp Gly Phe Ala Thr Thr Thr Met Arg Lys Leu
            115                 120                 125

His Leu Ile Trp Val Thr Ala Arg Met His Ile Glu Ile Tyr Arg Tyr
        130                 135                 140

Pro Ala Trp Ser Asp Val Ile Glu Ile Glu Thr Trp Val Gln Gly Glu
145                 150                 155                 160

Gly Lys Val Gly Thr Arg Arg Asp Trp Ile Leu Lys Asp Tyr Ala Asn
                165                 170                 175
```

Gly Glu Val Ile Gly Arg Ala Thr Ser Lys Trp Val Met Met Asn Glu
                180                 185                 190

Asp Thr Arg Arg Leu Gln Lys Val Ser Asp Val Arg Glu Glu Tyr
            195                 200                 205

Leu Val Phe Cys Pro Arg Thr Leu Arg Leu Ala Phe Pro Glu Glu Asn
        210                 215                 220

Asn Asn Ser Met Lys Lys Ile Pro Lys Leu Glu Asp Pro Ala Glu Tyr
225                 230                 235                 240

Ser Arg Leu Gly Leu Val Pro Arg Arg Ser Asp Leu Asp Met Asn Lys
                245                 250                 255

His Val Asn Asn Val Thr Tyr Ile Gly Trp Ala Leu Glu Ser Ile Pro
            260                 265                 270

Pro Glu Ile Ile Asp Thr His Glu Leu Gln Ala Ile Thr Leu Asp Tyr
        275                 280                 285

Arg Arg Glu Cys Gln Arg Asp Asp Ile Val Asp Ser Leu Thr Ser Arg
        290                 295                 300

Glu Pro Leu Gly Asn Ala Ala Gly Val Lys Phe Lys Glu Ile Asn Gly
305                 310                 315                 320

Ser Val Ser Pro Lys Lys Asp Glu Gln Asp Leu Ser Arg Phe Met His
                325                 330                 335

Leu Leu Arg Ser Ala Gly Ser Gly Leu Glu Ile Asn Arg Cys Arg Thr
            340                 345                 350

Glu Trp Arg Lys Lys Pro Ala Lys Arg Met Asp Tyr Lys Asp His Asp
        355                 360                 365

Gly Asp Tyr Lys Asp His Asp Ile Asp Tyr Lys Asp Asp Asp Asp Lys
        370                 375                 380

<210> SEQ ID NO 105
<211> LENGTH: 408
<212> TYPE: PRT
<213> ORGANISM: Cuphea wrightii

<400> SEQUENCE: 105

Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
                20                  25                  30

Leu Ser Gln Pro Phe Lys Pro Lys Ser Asn Pro Asn Gly Arg Phe Gln
            35                  40                  45

Val Lys Ala Asn Val Ser Pro His Pro Lys Ala Asn Gly Ser Ala Val
        50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
        130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Glu Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Phe Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405

<210> SEQ ID NO 106
<211> LENGTH: 1155
<212> TYPE: DNA
<213> ORGANISM: Artificial Sequence
<220> FEATURE:
<223> OTHER INFORMATION: Codon optimized sequence

<400> SEQUENCE: 106
atggccaccg catccacttt ctcggcgttc aatgcccgct gcggcgacct gcgtcgctcg    60
gcgggctccg ggccccggcg cccagcgagg cccctccccg tgcgcgggcg cgccgccacc   120
ggcgagcagc cctccggcgt ggcctccctg cgcgaggccg acaaggagaa gtccctgggc   180
aaccgcctgc gcctgggctc cctgaccgag gacggcctgt cctacaagga gaagttcgtg   240
atccgctgct acgaggtggg catcaacaag accgccacca tcgagaccat cgccaacctg   300
ctgcaggagg tgggcggcaa ccacgcccag ggcgtgggct ctccaccga cggcttcgcc   360 accaccacca ccatgcgcaa gctgcacctg atctgggtga ccgcccgcat gcacatcgag   420
atctaccgct accccgcctg gtccgacgtg atcgagatcg agacctgggt gcagggcgag   480
ggcaaggtgg gcacccgccg cgactggatc ctgaaggact acgccaacgg cgaggtgatc   540
ggccgcgcca cctccaagtg ggtgatgatg aacgaggaca cccgccgcct gcagaaggtg   600
tccgacgacg tgcgcgagga gtacctggtg ttctgccccc gcaccctgcg cctggccttc   660
cccgaggaga caacaactc catgaagaag atccccaagc tggaggaccc cgccgagtac   720

```
tcccgcctgg gcctggtgcc ccgccgctcc gacctggaca tgaacaagca cgtgaacaac    780
gtgacctaca tcggctgggc cctggagtcc atcccccccg agatcatcga cacccacgag    840
ctgcaggcca tcaccctgga ctaccgccgc gagtgccagc gcgacgacat cgtggactcc    900
ctgacctccc gcgagcccct gggcaacgcc gccggcgtga agttcaagga gatcaacggc    960
tccgtgtccc ccaagaagga cgagcaggac ctgtcccgct tcatgcacct gctgcgctcc   1020
gccggctccg gcctggagat caaccgctgc cgcaccgagt ggcgcaagaa gcccgccaag   1080
cgcatggact acaaggacca cgacggcgac tacaaggacc acgacatcga ctacaaggac   1140
gacgacgaca agtga                                                    1155

<210> SEQ ID NO 107
<211> LENGTH: 1236
<212> TYPE: DNA
<213> ORGANISM: Artificial Sequence
<220> FEATURE:
<223> OTHER INFORMATION: codon optimized sequence

<400> SEQUENCE: 107
atggtggtgg ccgccgccgc cagcagcgcc ttcttccccg tgcccgcccc ccgccccacc     60
cccaagcccg gcaagttcgg caactggccc agcagcctga ccagcccctt caagcccaag    120
agcaacccca cggccgcctt ccaggtgaag gccaacgtga gccccacggg cgcgcccccc    180
aaggccaacg gcagcgccgt gagcctgaag tccggcagcc tgaacaccct ggaggacccc    240
cccagcagcc ccccccccg caccttcctg aaccagctgc ccgactggag ccgcctgcgc    300
accgccatca ccaccgtgtt cgtggccgcc gagaagcagt tcacccgcct ggaccgcaag    360
agcaagcgcc ccgacatgct ggtggactgg ttcggcagcg agaccatcgt gcaggacggc    420
ctggtgttcc gcgagcgctt cagcatccgc agctacgaga tcggcgccga ccgcaccgcc    480
agcatcgaga ccctgatgaa ccacctgcag gacaccagcc tgaaccactg caagagcgtg    540
ggcctgctga cgacggcctt cggccgcacc ccgagatgt gcacccgcga cctgatctgg    600
gtgctgacca agatgcagat cgtggtgaac cgctacccca cctggggcga caccgtggag    660
atcaacagct ggttcagcca gagcggcaag atcggcatgg ccgcgagtg gctgatcagc    720 gactgcaaca ccggcgagat cctggtgcgc gccaccagcg cctgggccat gatgaaccag    780
aagacccgcc gcttcagcaa gctgcccctgc gaggtgcgcc aggagatcgc ccccccacttc    840 gtggacgccc ccccgtgat cgaggacaac gaccgcaagc tgcacaagtt cgacgtgaag    900
accggcgaca gcatctgcaa gggcctgacc ccggctgga cgacttcga cgtgaaccag    960 cacgtgagca acgtgaagta catcggctgg attctggaga gcatgccac cgaggtgctg   1020 gagacccagg agctgtgcag cctgacctg gagtaccgcc gcgagtgcgg ccgcgagagc   1080
gtggtggaga gcgtgaccag catgaacccc agcaaggtgg gcgaccgcag ccagtaccag   1140
cacctgctgc gcctggagga cggcgccgac atcatgaagg gccgcaccga gtggcgcccc   1200
aagaacgccg gcaccaaccg cgccatcagc acctga                            1236

<210> SEQ ID NO 108
<211> LENGTH: 612
<212> TYPE: DNA
<213> ORGANISM: Artificial Sequence
<220> FEATURE:
<223> OTHER INFORMATION: construct 5' donor DNA sequence of Prototheca
      moriformis FATA1 knockout homologous recombination targeting
      construct
```

<400> SEQUENCE: 108

```
gctcttcgga gtcactgtgc cactgagttc gactggtagc tgaatggagt cgctgctcca        60
ctaaacgaat tgtcagcacc gccagccggc cgaggacccg agtcatagcg agggtagtag       120
cgcgccatgg caccgaccag cctgcttgcc agtactggcg tctcttccgc ttctctgtgg       180
tcctctgcgc gctccagcgc gtgcgctttt ccggtggatc atgcggtccg tggcgcaccg       240
cagcggccgc tgcccatgca gcgccgctgc ttccgaacag tggcggtcag ggccgcaccc       300
gcggtagccg tccgtccgga acccgcccaa gagttttggg agcagcttga gccctgcaag       360
atggcggagg acaagcgcat cttcctggag gagcaccggt gcgtggaggt ccggggctga       420
ccggccgtcg cattcaacgt aatcaatcgc atgatgatca gaggacacga agtcttggtg       480
gcggtggcca gaaacactgt ccattgcaag ggcatcggga tgcgttcctt cacctctcat       540
ttctcatttc tgaatccctc cctgctcact ctttctcctc ctccttcccg ttcacgcagc       600
attcggggta cc                                                           612
```

<210> SEQ ID NO 109
<211> LENGTH: 528
<212> TYPE: DNA
<213> ORGANISM: Artificial Sequence
<220> FEATURE:
<223> OTHER INFORMATION: construct 3' donor DNA sequence of Prototheca moriformis FATA1 knockout homologous recombination targeting construct

<400> SEQUENCE: 109

```
gacagggtgg ttggctggat ggggaaacgc tggtcgcggg attcgatcct gctgcttata        60
tcctccctgg aagcacaccc acgactctga agaagaaaac gtgcacacac acaacccaac       120
cggccgaata tttgcttcct tatcccgggt ccaagagaga ctgcgatgcc ccctcaatc        180
agcatcctcc tccctgccgc ttcaatcttc cctgcttgcc tgcgcccgcg gtgcgccgtc       240
tgcccgccca gtcagtcact cctgcacagg ccccttgtgc gcagtgctcc tgtacccttt       300
accgctcctt ccattctgcg aggcccccta ttgaatgtat tcgttgcctg tgtggccaag       360
cgggctgctg ggcgcgccgc cgtcgggcag tgctcggcga cttttggcgga agccgattgt      420
tcttctgtaa gccacgcgct tgctgctttg ggaagagaag ggggggggta ctgaatggat       480
gaggaggaga aggaggggta ttggtattat ctgagttggg tgaagagc                    528
```

<210> SEQ ID NO 110
<211> LENGTH: 767
<212> TYPE: DNA
<213> ORGANISM: Artificial Sequence
<220> FEATURE:
<223> OTHER INFORMATION: construct FATA portion of the hairpin RNA expression cassette

<400> SEQUENCE: 110

```
atggcaccga ccagcctgct tgccagtact ggcgtctctt ccgcttctct gtggtcctct        60
gcgcgctcca gcgcgtgcgc ttttccggtg gatcatgcgg tccgtggcgc accgcagcgg       120
ccgctgccca tgcagcgccg ctgcttccga acagtggcgg tcaggccgc acccgcggta       180
gccgtccgtc cggaacccgc ccaagagttt tgggagcagc ttgagccctg caagatggcg       240
gaggacaagc gcatcttcct ggaggagcac cggtgcgtgg aggtccgggg ctgaccggcc       300
gtcgcattca acgtaatcaa tcgcatgatg atcagaggac acgaagtctt ggtggcggtg       360
gccagaaaca ctgtccattg caagggcata gggatgcgtt ccttcacctc tcatttctca       420
```

| | |
|---|---|
| tttctgaatc cctccctgct cactctttct cctcctcctt cccgttcacg cagcattcgg | 480 |
| ggcaacgagg tgggcccgtg ctcctccagg aagatgcgct tgtcctccgc catcttgcag | 540 |
| ggctcaagct gctcccaaaa ctcttgggcg ggttccggac ggacggctac cgcgggtgcg | 600 |
| gccctgaccg ccactgttcg gaagcagcgg cgctgcatgg gcagcggccg ctgcggtgcg | 660 |
| ccacggaccg catgatccac cggaaaagcg cacgcgctgg agcgcgcaga ggaccacaga | 720 |
| gaagcggaag agacgccagt actggcaagc aggctggtcg gtgccat | 767 |

<210> SEQ ID NO 111
<211> LENGTH: 3499
<212> TYPE: DNA
<213> ORGANISM: Artificial Sequence
<220> FEATURE:
<223> OTHER INFORMATION: synthetic construct

<400> SEQUENCE: 111

| | |
|---|---|
| gctcttcgga gtcactgtgc cactgagttc gactggtagc tgaatggagt cgctgctcca | 60 |
| ctaaacgaat tgtcagcacc gccagccggc cgaggacccg agtcatagcg agggtagtag | 120 |
| cgcgccatgg caccgaccag cctgcttgcc agtactggcg tctcttccgc ttctctgtgg | 180 |
| tcctctgcgc gctccagcgc gtgcgctttt ccggtggatc atgcggtccg tggcgcaccg | 240 |
| cagcggccgc tgcccatgca gcgccgctgc ttccgaacag tggcggtcag ggccgcaccc | 300 |
| gcggtagccg tccgtccgga acccgcccaa gagttttggg agcagcttga gccctgcaag | 360 |
| atggcggagg acaagcgcat cttcctggag gagcaccggt gcgtggaggt ccggggctga | 420 |
| ccggccgtcg cattcaacgt aatcaatcgc atgatgatca gaggacacga agtcttggtg | 480 |
| gcggtggcca gaaacactgt ccattgcaag ggcatagggga tgcgttcctt cacctctcat | 540 |
| ttctcatttc tgaatccctc cctgctcact ctttctcctc ctccttcccg ttcacgcagc | 600 |
| attcggggta ccctttcttg cgctatgaca cttccagcaa aaggtagggc gggctgcgag | 660 |
| acggcttccc ggcgctgcat gcaacaccga tgatgcttcg acccccgaa gctccttcgg | 720 |
| ggctgcatgg gcgctccgat gccgctccag ggcgagcgct gtttaaatag ccaggcccc | 780 |
| gattgcaaag acattatagc gagctaccaa agccatattc aaacacctag atcactacca | 840 |
| cttctacaca ggccactcga gcttgtgatc gcactccgct aaggggggcgc ctcttcctct | 900 |
| tcgtttcagt cacaacccgc aaacggcgcg ccatgctgct gcaggccttc ctgttcctgc | 960 |
| tggccggctt cgccgccaag atcagcgcct ccatgacgaa cgagacgtcc gaccgccccc | 1020 |
| tggtgcactt cacccccaac aagggctgga tgaacgaccc caacggcctg tggtacgacg | 1080 |
| agaaggacgc caagtggcac ctgtacttcc agtacaaccc gaacgacacc gtctggggga | 1140 |
| cgcccttgtt ctggggccac gccacgtccg acgacctgac caactgggag gaccagccca | 1200 |
| tcgccatcgc cccgaagcgc aacgactccg gcgccttctc cggctccatg gtggtggact | 1260 |
| acaacaacac ctccggcttc ttcaacgaca ccatcgaccc gcgccagcgc tgcgtggcca | 1320 |
| tctggaccta caacaccccg gagtccgagg agcagtacat ctcctacagc ctggacggcg | 1380 |
| gctacacctt caccgagtac cagaagaacc ccgtgctggc cgccaactcc acccagttcc | 1440 |
| gcgacccgaa ggtcttctgg tacgagcccc ccagaagtg gatcatgacc gcggccaagt | 1500 |
| cccaggacta caagatcgag atctactcct ccgacgacct gaagtcctgg aagctggagt | 1560 |
| ccgcgttcgc caacgagggc ttcctcggct accagtacga gtgccccggc ctgatcgagg | 1620 |
| tccccaccga gcaggacccc agcaagtcct actgggtgat gttcatctcc atcaaccccg | 1680 |
| gcgccccggc cggcggctcc ttcaaccagt acttcgtcgg cagcttcaac ggcacccact | 1740 |

```
tcgaggcctt cgacaaccag tcccgcgtgg tggacttcgg caaggactac tacgccctgc    1800
agaccttctt caacaccgac ccgacctacg ggagcgccct gggcatcgcg tgggcctcca    1860
actgggagta ctccgccttc gtgcccacca acccctggcg ctcctccatg tccctcgtgc    1920
gcaagttctc cctcaacacc gagtaccagg ccaacccgga gacggagctg atcaacctga    1980
aggccgagcc gatcctgaac atcagcaacg ccggcccctg gagccggttc gccaccaaca    2040
ccacgttgac gaaggccaac agctacaacg tcgacctgtc caacagcacc ggcaccctgg    2100
agttcgagct ggtgtacgcc gtcaacacca cccagacgat ctccaagtcc gtgttcgcgg    2160
acctctccct ctggttcaag ggcctggagg accccgagga gtacctccgc atgggcttcg    2220
aggtgtccgc gtcctccttc ttcctggacc gcgggaacag caaggtgaag ttcgtgaagg    2280 agaacccta cttcaccaac cgcatgagcg tgaacaacca gcccttcaag agcgagaacg    2340
acctgtccta ctacaaggtg tacggcttgc tggaccagaa catcctggag ctgtacttca    2400
acgacggcga cgtcgtgtcc accaacacct acttcatgac caccgggaac gccctgggct    2460
ccgtgaacat gacgacgggg gtggacaacc tgttctacat cgacaagttc caggtgcgcg    2520
aggtcaagtg acaattggca gcagcagctc ggatagtatc gacacactct ggacgctggt    2580
cgtgtgatgg actgttgccg ccacacttgc tgccttgacc tgtgaatatc cctgccgctt    2640
ttatcaaaca gcctcagtgt gtttgatctt gtgtgtacgc gcttttgcga gttgctagct    2700
gcttgtgcta tttgcgaata ccaccccag catcccttc cctcgtttca tatcgcttgc    2760
atcccaaccg caacttatct acgctgtcct gctatccctc agcgctgctc ctgctcctgc    2820
tcactgcccc tcgcacagcc ttggtttggg ctccgcctgt attctcctgg tactgcaacc    2880
tgtaaaccag cactgcaatg ctgatgcacg ggaagtagtg ggatgggaac acaaatggag    2940
gatcgtagag ctcactagta tcgatttcga agacagggtg gttggctgga tggggaaacg    3000
ctggtcgcgg gattcgatcc tgctgcttat atcctccctg gaagcacacc cacgactctg    3060
aagaagaaaa cgtgcacaca cacaacccaa ccggccgaat atttgcttcc ttatcccggg    3120
tccaagagag actgcgatgc cccctcaat cagcatcctc ctccctgccg cttcaatctt    3180
ccctgcttgc ctgcgcccgc ggtgcgccgt ctgcccgccc agtcagtcac tcctgcacag    3240 gcccctgtg cgcagtgctc ctgtaccctt taccgctcct tccattctgc gaggcccct    3300 attgaatgta ttcgttgcct gtgtggccaa gcgggctgct gggcgcgccg ccgtcgggca    3360
gtgctcggcg actttggcgg aagccgattg ttcttctgta agccacgcgc ttgctgcttt    3420
gggaagagaa gggggggggt actgaatgga tgaggaggag aaggagggt attggtatta    3480 tctgagttgg gtgaagagc                                                3499
```

<210> SEQ ID NO 112
<211> LENGTH: 6514
<212> TYPE: DNA
<213> ORGANISM: Artificial Sequence
<220> FEATURE:
<223> OTHER INFORMATION: synthetic construct

<400> SEQUENCE: 112

```
gctcttcgga gtcactgtgc cactgagttc gactggtagc tgaatggagt cgctgctcca      60
ctaaacgaat tgtcagcacc gccagccggc cgaggacccg agtcatagcg agggtagtag     120
cgcgccatgg caccgaccag cctgcttgcc agtactggcg tctcttccgc ttctctgtgg     180
tcctctgcgc gctccagcgc gtgcgctttt ccggtggatc atgcggtccg tggcgcaccg     240
```

-continued

| | | | | | |
|---|---|---|---|---|---|
| cagcggccgc | tgcccatgca | gcgccgctgc | ttccgaacag | tggcggtcag | ggccgcaccc | 300 |
| gcggtagccg | tccgtccgga | acccgcccaa | gagttttggg | agcagcttga | gccctgcaag | 360 |
| atggcggagg | acaagcgcat | cttcctggag | gagcaccggt | gcgtggaggt | ccggggctga | 420 |
| ccggccgtcg | cattcaacgt | aatcaatcgc | atgatgatca | gaggacacga | agtcttggtg | 480 |
| gcggtggcca | gaaacactgt | ccattgcaag | gcatagggat | gcgttcctt | cacctctcat | 540 |
| ttctcatttc | tgaatccctc | cctgctcact | ctttctcctc | ctccttcccg | ttcacgcagc | 600 |
| attcggggta | ccctttcttg | cgctatgaca | cttccagcaa | aaggtagggc | gggctgcgag | 660 |
| acggcttccc | ggcgctgcat | gcaacaccga | tgatgcttcg | acccccgaa | gctccttcgg | 720 |
| ggctgcatgg | gcgctccgat | gccgctccag | ggcgagcgct | gtttaaatag | ccaggccccc | 780 |
| gattgcaaag | acattatagc | gagctaccaa | agccatattc | aaacacctag | atcactacca | 840 |
| cttctacaca | ggccactcga | gcttgtgatc | gcactccgct | aaggggggcgc | ctcttcctct | 900 |
| tcgtttcagt | cacaacccgc | aaacggcgcg | ccatgctgct | gcaggccttc | ctgttcctgc | 960 |
| tggccggctt | cgccgccaag | atcagcgcct | ccatgacgaa | cgagacgtcc | gaccgccccc | 1020 |
| tggtgcactt | cacccccaac | aagggctgga | tgaacgaccc | caacggcctg | tggtacgacg | 1080 |
| agaaggacgc | caagtggcac | ctgtacttcc | agtacaaccc | gaacgacacc | gtctggggga | 1140 |
| cgccccttgtt | ctgggccac | gccacgtccg | acgacctgac | caactgggag | gaccagccca | 1200 |
| tcgccatcgc | cccgaagcgc | aacgactccg | gcgccttctc | cggctccatg | gtggtggact | 1260 |
| acaacaacac | ctccggcttc | ttcaacgaca | ccatcgaccc | gcgccagcgc | tgcgtggcca | 1320 |
| tctggaccta | caacacccg | gagtccgagg | agcagtacat | ctcctacagc | ctggacggcg | 1380 |
| gctacacctt | caccgagtac | cagaagaacc | ccgtgctggc | cgccaactcc | acccagttcc | 1440 |
| gcgaccgaa | ggtcttctgg | tacgagccct | cccagaagtg | gatcatgacc | gcggccaagt | 1500 |
| cccaggacta | caagatcgag | atctactcct | ccgacgacct | gaagtcctgg | aagctggagt | 1560 |
| ccgcgttcgc | caacgagggc | ttcctcggct | accagtacga | gtgccccggc | ctgatcgagg | 1620 |
| tccccaccga | gcaggacccc | agcaagtcct | actgggtgat | gttcatctcc | atcaaccccg | 1680 |
| gcgcccggc | cggcggctcc | ttcaaccagt | acttcgtcgg | cagcttcaac | ggcacccact | 1740 |
| tcgaggcctt | cgacaaccag | tcccgcgtgg | tggacttcgg | caaggactac | tacgccctgc | 1800 |
| agaccttctt | caacaccgac | ccgacctacg | ggagcgccct | gggcatcgcg | tgggcctcca | 1860 |
| actgggagta | ctccgccttc | gtgcccacca | acccctggcg | ctcctccatg | tccctcgtgc | 1920 |
| gcaagttctc | cctcaacacc | gagtaccagg | ccaacccgga | gacggagctg | atcaacctga | 1980 |
| aggccgagcc | gatcctgaac | atcagcaacg | ccggcccctg | gagccggttc | gccaccaaca | 2040 |
| ccacgttgac | gaaggccaac | agctacaacg | tcgacctgtc | caacagcacc | ggcacccctgg | 2100 |
| agttcgagct | ggtgtacgcc | gtcaacacca | cccagacgat | ctccaagtcc | gtgttcgcgg | 2160 |
| acctctcccct | ctggttcaag | ggcctggagg | accccgagga | gtacctccgc | atgggcttcg | 2220 |
| aggtgtccgc | gtcctcctttc | ttcctggacc | gcggaacag | caaggtgaag | ttcgtgaagg | 2280 |
| agaaccccta | cttcaccaac | cgcatgagcg | tgaacaacca | gcccttcaag | agcgagaacg | 2340 |
| acctgtccta | ctacaaggtg | tacgcttgc | tggaccagaa | catcctggag | ctgtacttca | 2400 |
| acgacggcga | cgtcgtgtcc | accaacacct | acttcatgac | caccgggaac | gccctgggct | 2460 |
| ccgtgaacat | gacgacgggg | gtggacaacc | tgttctacat | cgacaagttc | caggtgcgcg | 2520 |
| aggtcaagtg | acaattggca | gcagcagctc | ggatagtatc | gacacactct | ggacgctggt | 2580 |
| cgtgtgatgg | actgttgccg | ccacacttgc | tgccttgacc | tgtgaatatc | cctgccgctt | 2640 |

-continued

```
ttatcaaaca gcctcagtgt gtttgatctt gtgtgtacgc gcttttgcga gttgctagct      2700
gcttgtgcta tttgcgaata ccaccccccag catccccttc cctcgtttca tatcgcttgc     2760
atcccaaccg caacttatct acgctgtcct gctatccctc agcgctgctc ctgctcctgc      2820
tcactgcccc tcgcacagcc ttggtttggg ctccgcctgt attctcctgg tactgcaacc      2880
tgtaaaccag cactgcaatg ctgatgcacg ggaagtagtg ggatgggaac acaaatggag      2940
gatcccgcgt ctcgaacaga gcgcgcagag gaacgctgaa ggtctcgcct ctgtcgcacc      3000
tcagcgcggc atacaccaca ataaccacct gacgaatgcg cttggttctt cgtccattag      3060
cgaagcgtcc ggttcacaca cgtgccacgt tggcgaggtg gcaggtgaca atgatcggtg      3120
gagctgatgg tcgaaacgtt cacagcctag ggatatcgaa ttcggccgac aggacgcgcg      3180
tcaaaggtgc tggtcgtgta tgccctggcc ggcaggtcgt tgctgctgct ggttagtgat      3240
tccgcaaccc tgattttggc gtcttatttt ggcgtggcaa acgctggcgc ccgcgagccg      3300
ggccggcggc gatgcggtgc cccacggctg ccggaatcca agggaggcaa gagcgcccgg      3360
gtcagttgaa gggctttacg cgcaaggtac agccgctcct gcaaggctgc gtggtggaat      3420
tggacgtgca ggtcctgctg aagttcctcc accgcctcac cagcggacaa agcaccggtg      3480
tatcaggtcc gtgtcatcca ctctaaagag ctcgactacg acctactgat ggccctagat      3540
tcttcatcaa aaacgcctga gacacttgcc caggattgaa actccctgaa gggaccacca      3600
ggggccctga gttgttcctt cccccgtgg cgagctgcca gccaggctgt acctgtgatc      3660
gaggctggcg ggaaaatagg cttcgtgtgc tcaggtcatg ggaggtgcag gacagctcat      3720
gaaacgccaa caatcgcaca attcatgtca agctaatcag ctatttcctc ttcacgagct      3780
gtaattgtcc caaaattctg gtctaccggg ggtgatcctt cgtgtacggg cccttccctc      3840
aaccctaggt atgcgcgcat gcggtcgccg cgcaactcgc gcgagggccg agggtttggg      3900
acgggccgtc ccgaaatgca gttgcacccg gatgcgtggc acctttttttg cgataattta      3960
tgcaatggac tgctctgcaa aattctggct ctgtcgccaa ccctaggatc agcggcgtag      4020
gatttcgtaa tcattcgtcc tgatgggag ctaccgacta ccctaatatc agcccgactg      4080
cctgacgcca gcgtccactt ttgtgcacac attccattcg tgcccaagac atttcattgt      4140
ggtgcgaagc gtccccagtt acgctcacct gtttcccgac ctccttactg ttctgtcgac      4200
agagcgggcc cacaggccgg tcgcagccac tagtatggtg gtggccgccg ccgccagcag      4260
cgccttcttc cccgtgcccg ccccccgccc cacccccaag cccggcaagt tcggcaactg      4320
gcccagcagc ctgagccagc ccttcaagcc caagagcaac cccaacgccc gcttccaggt      4380
gaaggccaac gtgagccccc acgggcgcgc cccaaggcc aacggcagcg ccgtgagcct      4440
gaagtccggc agcctgaaca ccctggagga cccccccagc agcccccccc ccgcaccctt      4500
cctgaaccag ctgcccgact ggagccgcct gcgcaccgcc atcaccaccg tgttcgtggc      4560
cgccgagaag cagttcaccc gcctggaccg caagagcaag cgccccgaca tgctggtgga      4620
ctggttcggc agcgagacca tcgtgcagga cggcctggtg ttccgcgagc gcttcagcat      4680
ccgcagctac gagatcggcg ccgaccgcac cgccagcatc gagaccctga tgaaccacct      4740
gcaggacacc agcctgaacc actgcaagag cgtgggcctg ctgaacgacg gcttcggccg      4800
caccccccgag atgtgcaccc gcgacctgat ctgggtgctg accaagatgc agatcgtggt      4860
gaaccgctac cccaccctggg gcgacaccgt ggagatcaac agctggttca gccagagcgg      4920
caagatcggc atgggccgcg agtggctgat cagcgactgc aacaccggcg agatcctggt      4980
```

| | |
|---|---:|
| gcgcgccacc agcgcctggg ccatgatgaa ccagaagacc cgccgcttca gcaagctgcc | 5040 |
| ctgcgaggtg cgccaggaga tcgcccccca cttcgtggac gccccccccg tgatcgagga | 5100 |
| caacgaccgc aagctgcaca agttcgacgt gaagaccggc gacagcatct gcaagggcct | 5160 |
| gaccccggc tggaacgact tcgacgtgaa ccagcacgtg agcaacgtga agtacatcgg | 5220 |
| ctggattctg gagagcatgc ccaccgaggt gctggagacc caggagctgt gcagcctgac | 5280 |
| cctggagtac cgccgcgagt gcggccgcga gagcgtggtg gagagcgtga ccagcatgaa | 5340 |
| ccccagcaag gtgggcgacc gcagccagta ccagcacctg ctgcgcctgg aggacggcgc | 5400 |
| cgacatcatg aagggccgca ccgagtggcg ccccaagaac gccggcacca accgcgccat | 5460 |
| cagcacctga ttaattaact cgaggcagca gcagctcgga tagtatcgac acactctgga | 5520 |
| cgctggtcgt gtgatggact gttgccgcca cacttgctgc cttgacctgt gaatatccct | 5580 |
| gccgctttta tcaaacagcc tcagtgtgtt tgatcttgtg tgtacgcgct tttgcgagtt | 5640 |
| gctagctgct tgtgctattt gcgaatacca ccccagcat ccccttccct cgtttcatat | 5700 |
| cgcttgcatc ccaaccgcaa cttatctacg ctgtcctgct atccctcagc gctgctcctg | 5760 |
| ctcctgctca ctgcccctcg cacagccttg gtttgggctc cgcctgtatt ctcctggtac | 5820 |
| tgcaacctgt aaaccagcac tgcaatgctg atgcacggga agtagtggga tgggaacaca | 5880 |
| aatggaaagc ttgagctctt gttttccaga aggagttgct ccttgagcct ttcattctca | 5940 |
| gcctcgataa cctccaaagc cgctctaatt gtggaggggg ttcgaagaca gggtggttgg | 6000 |
| ctggatgggg aaacgctggt cgcgggattc gatcctgctg cttatatcct ccctggaagc | 6060 |
| acacccacga ctctgaagaa gaaaacgtgc acacacacaa cccaaccggc cgaatatttg | 6120 |
| cttccttatc ccgggtccaa gagagactgc gatgcccccc tcaatcagca tcctcctccc | 6180 |
| tgccgcttca atcttccctg cttgcctgcg cccgcggtgc gccgtctgcc cgcccagtca | 6240 |
| gtcactcctg cacaggcccc ttgtgcgcag tgctcctgta ccctttaccg ctccttccat | 6300 |
| tctgcgaggc cccctattga atgtattcgt tgcctgtgtg gccaagcggg ctgctgggcg | 6360 |
| cgccgccgtc gggcagtgct cggcgacttt ggcggaagcc gattgttctt ctgtaagcca | 6420 |
| cgcgcttgct gctttgggaa gagaagggggg ggggtactga atggatgagg aggagaagga | 6480 |
| ggggtattgg tattatctga gttgggtgaa gagc | 6514 |

<210> SEQ ID NO 113
<211> LENGTH: 5546
<212> TYPE: DNA
<213> ORGANISM: Artificial Sequence
<220> FEATURE:
<223> OTHER INFORMATION: synthetic construct

<400> SEQUENCE: 113

| | |
|---|---:|
| gctcttcgcc gccgccactc ctgctcgagc gcgcccgcgc gtgcgccgcc agcgccttgg | 60 |
| ccttttcgcc gcgctcgtgc gcgtcgctga tgtccatcac caggtccatg aggtctgcct | 120 |
| tgcgccggct gagccactgc ttcgtccggg cggccaagag gagcatgagg gaggactcct | 180 |
| ggtccagggt cctgacgtgg tcgcggctct gggagcgggc cagcatcatc tggctctgcc | 240 |
| gcaccgaggc cgcctccaac tggtcctcca gcagccgcag tcgccgccga ccctggcaga | 300 |
| ggaagacagg tgagggggt atgaattgta cagaacaacc acgagccttg tctaggcaga | 360 |
| atccctacca gtcatggctt tacctggatg acggcctgcg aacagctgtc cagcgaccct | 420 |
| cgctgccgcc gcttctcccg cacgcttctt tccagcaccg tgatgcgcg agccagcgcc | 480 |
| gcacgctggc gctgcgcttc gccgatctga ggacagtcgg ggaactctga tcagtctaaa | 540 |

```
cccccttgcg cgttagtgtt gccatccttt gcagaccggt gagagccgac ttgttgtgcg    600 ccaccccca caccacctcc tcccagacca attctgtcac cttttggcg aaggcatcgg      660 cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt    1020
cagtcacaac ccgcaaactc tagaatatca atgctgctgc aggccttcct gttcctgctg    1080
gccggcttcg ccgccaagat cagcgcctcc atgacgaacg agacgtccga ccgcccctg     1140 gtgcacttca ccccaacaa gggctggatg aacgacccca acggcctgtg gtacgacgag     1200
aaggacgcca gtggcacct gtacttccag tacaacccga acgacaccgt ctgggggacg     1260
cccttgttct ggggccacgc cacgtccgac gacctgacca actgggagga ccagcccatc    1320
gccatcgccc cgaagcgcaa cgactccggc gccttctccg gctccatggt ggtggactac    1380
aacaacacct ccggcttctt caacgacacc atcgaccccg ccagcgctg cgtggccatc     1440 tggacctaca cacccggga gtccgaggag cagtacatct cctacagcct ggacggcggc     1500
tacaccttca ccgagtacca gaagaacccc gtgctggccg ccaactccac ccagttccgc    1560
gacccgaagg tcttctggta cgagccctcc cagaagtgga tcatgaccgc ggccaagtcc    1620
caggactaca agatcgagat ctactcctcc gacgacctga agtcctggaa gctggagtcc    1680
gcgttcgcca acgagggctt cctcggctac cagtacgagt gccccggcct gatcgaggtc    1740
cccaccgagc aggaccccag caagtcctac tgggtgatgt tcatctccat caaccccggc    1800
gccccggccg gcggctcctt caaccagtac ttcgtcggca gcttcaacgg cacccacttc    1860
gaggccttcg acaaccagtc ccgcgtggtg gacttcggca aggactacta cgccctgcag    1920
accttcttca caccgaccc gacctacggg agcgccctgg catcgcgtg ggcctccaac      1980 tgggagtact ccgccttcgt gcccaccaac ccctggcgct cctccatgtc cctcgtgcgc    2040
aagttctccc tcaacaccga gtaccaggcc aacccggaga cggagctgat caacctgaag    2100
gccgagccga tcctgaacat cagcaacgcc ggccccctgga gccggttcgc caccaacacc    2160
acgttgacga aggccaacag ctacaacgtc gacctgtcca acagcaccgg cacccctggag   2220 ttcgagctgg tgtacgccgt caacaccacc agacgatct ccagtccgt gttcgcggac      2280 ctctcccctct ggttcaaggg cctggaggac cccgaggagt acctccgcat gggcttcgag   2340
gtgtccgcgt cctccttctt cctggaccgc gggaacagca aggtgaagtt cgtgaaggag    2400
aacccctact tcaccaaccg catgagcgtg aacaaccagc ccttcaagag cgagaacgac    2460
ctgtcctact acaaggtgta cggcttgctg gaccagaaca tcctggagct gtacttcaac    2520
gacggcgacg tcgtgtccac caacacctac ttcatgacca ccgggaacgc cctgggctcc    2580
gtgaacatga cgacggggt ggacaacctg ttctacatcg acaagttcca ggtgcgcgag     2640
gtcaagtgac aattggcagc agcagctcgg atagtatcga cacactctgg acgctggtcg    2700
tgtgatggac tgttgccgcc acacttgctg ccttgacctg tgaatatccc tgccgctttt    2760
atcaaacagc ctcagtgtgt ttgatcttgt gtgtacgcgc ttttgcgagt tgctagctgc    2820
ttgtgctatt tgcgaatacc accccagca tccccttccc tcgtttcata tcgcttgcat     2880
```

```
cccaaccgca acttatctac gctgtcctgc tatccctcag cgctgctcct gctcctgctc    2940
actgcccctc gcacagcctt ggtttgggct ccgcctgtat tctcctggta ctgcaacctg    3000
taaaccagca ctgcaatgct gatgcacggg aagtagtggg atgggaacac aaatggagga    3060
tcccgcgtct cgaacagagc gcgcagagga acgctgaagg tctcgcctct gtcgcacctc    3120
agcgcggcat acaccacaat aaccacctga cgaatgcgct tggttcttcg tccattagcg    3180
aagcgtccgg ttcacacacg tgccacgttg gcgaggtggc aggtgacaat gatcggtgga    3240
gctgatggtc gaaacgttca cagcctaggg atatcgaatt cctttcttgc gctatgacac    3300
ttccagcaaa aggtagggcg ggctgcgaga cggcttcccg gcgctgcatg caacaccgat    3360
gatgcttcga cccccgaag ctccttcggg gctgcatggg cgctccgatg ccgctccagg    3420
gcgagcgctg tttaaatagc caggcccccg attgcaaaga cattatagcg agctaccaaa    3480
gccatattca aacacctaga tcactaccac ttctacacag gccactcgag cttgtgatcg    3540
cactccgcta agggggcgcc tcttcctctt cgtttcagtc acaacccgca aacactagta    3600
tggcaccgac cagcctgctt gccagtactg gcgtctcttc cgcttctctg tggtcctctg    3660
cgcgctccag cgcgtgcgct tttccggtgg atcatgcggt ccgtggcgca ccgcagcggc    3720
cgctgcccat gcagcgccgc tgcttccgaa cagtggcggt cagggccgca cccgcggtag    3780
ccgtccgtcc ggaacccgcc caagagtttt gggagcagct tgagccctgc aagatggcgg    3840
aggacaagcg catcttcctg gaggagcacc ggtgcgtgga ggtccggggc tgaccggccg    3900
tcgcattcaa cgtaatcaat cgcatgatga tcagaggaca cgaagtcttg gtggcggtgg    3960
ccagaaacac tgtccattgc aagggcatag ggatgcgttc cttcacctct catttctcat    4020
ttctgaatcc ctccctgctc actctttctc ctcctccttc ccgttcacgc agcattcggg    4080
gcaacgaggt gggcccgtgc tcctccagga agatgcgctt gtcctccgcc atcttgcagg    4140
gctcaagctg ctcccaaaac tcttgggcgg gttccggacg gacggctacc gcgggtgcgg    4200
ccctgaccgc cactgttcgg aagcagcggc gctgcatggg cagcggccgc tgcggtgcgc    4260
cacggaccgc atgatccacc ggaaaagcgc acgcgctgga gcgcgcagag gaccacagag    4320
aagcggaaga gacgccagta ctggcaagca ggctggtcgg tgccatatcg atagatctct    4380
taaggcagca gcagctcgga tagtatcgac acactctgga cgctggtcgt gtgatggact    4440
gttgccgcca cacttgctgc cttgacctgt gaatatccct gccgctttta tcaaacagcc    4500
tcagtgtgtt tgatcttgtg tgtacgcgct tttgcgagtt gctagctgct tgtgctattt    4560
gcgaatacca cccccagcat ccccttccct cgtttcatat cgcttgcatc ccaaccgcaa    4620
cttatctacg ctgtcctgct atccctcagc gctgctcctg ctcctgctca ctgcccctcg    4680
cacagccttg gtttgggctc cgcctgtatt ctcctggtac tgcaacctgt aaaccagcac    4740
tgcaatgctg atgcacggga agtagtggga tgggaacaca aatggaaagc ttaattaaga    4800
gctcttgttt tccagaagga gttgctcctt gagccttca ttctcagcct cgataacctc    4860
caaagccgct ctaattgtgg aggggttcg aatttaaaag cttggaatgt tggttcgtgc    4920
gtctggaaca agcccagact tgttgctcac tgggaaaagg accatcagct ccaaaaaact    4980
tgccgctcaa accgcgtacc tctgctttcg cgcaatctgc cctgttgaaa tcgccaccac    5040
attcatattg tgacgcttga gcagtctgta attgcctcag aatgtggaat catctgcccc    5100
ctgtgcgagc ccatgccagg catgtcgcgg gcgaggacac ccgccactcg tacagcagac    5160
cattatgcta cctcacaata gttcataaca gtgaccatat ttctcgaagc tccccaacga    5220
gcacctccat gctctgagtg gccaccccc ggccctggtg cttgcggagg gcaggtcaac    5280
```

```
cggcatgggg ctaccgaaat ccccgaccgg atcccaccac ccccgcgatg ggaagaatct    5340
ctccccggga tgtgggccca ccaccagcac aacctgctgg cccaggcgag cgtcaaacca    5400
taccacacaa atatccttgg catcggccct gaattccttc tgccgctctg ctacccggtg    5460
cttctgtccg aagcaggggt tgctagggat cgctccgagt ccgcaaaccc ttgtcgcgtg    5520
gcggggcttg ttcgagcttg aagagc                                        5546
```